(12) United States Patent
Huang et al.

(10) Patent No.: US 7,772,444 B2
(45) Date of Patent: Aug. 10, 2010

(54) METHOD FOR THE PRODUCTION OF RESVERATROL IN A RECOMBINANT OLEAGINOUS MICROORGANISM

(75) Inventors: Lixuan Lisa Huang, Hockessin, DE (US); Zhixiong Xue, Chadds Ford, PA (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1051 days.

(21) Appl. No.: 11/436,182

(22) Filed: May 17, 2006

(65) Prior Publication Data

US 2009/0082286 A1    Mar. 26, 2009

Related U.S. Application Data

(60) Provisional application No. 60/682,651, filed on May 19, 2005.

(51) Int. Cl.
*A61K 31/7034* (2006.01)
*A61K 31/05* (2006.01)
*C07C 39/04* (2006.01)
*C07H 15/203* (2006.01)

(52) U.S. Cl. .................. 568/729; 514/25; 514/733; 536/4.1

(58) Field of Classification Search .................. None
See application file for complete search history.

(56) References Cited

U.S. PATENT DOCUMENTS

| 6,368,837 | B1 | 4/2002 | Gatenby et al. |
| 6,521,748 | B2 | 2/2003 | Tang |
| 6,974,895 | B1 | 12/2005 | Paiva et al. |
| 2005/0208643 | A1* | 9/2005 | Schmidt-Dannert et al. ...... 435/252.31 |

FOREIGN PATENT DOCUMENTS

WO    2006089898 A1    8/2006

OTHER PUBLICATIONS

Alvarez et al., "Triacylglycerols in prokaryotic microorganisms" Appl. Microbiol. Biotechnol. (2002) vol. 60 pp. 367-376.*
U.S. Appl. No. 10/138,970, filed May 3, 2002, Wei Wei Qi et. al.
U.S. Appl. No. 10/439,479, filed May 16, 2003, Sabine Breinig et. al.
U.S. Appl. No. 10/621,826, filed Jul. 17, 2003, Zhixiong Xue et. al.
Manna et. al., Resveratrol Suppresses TNF-Induced Activation of Nuclear Transcription Factors NF-KB, Activator Protein-1, and Apoptosis: Potential Role of Reactive Oxygen Intermediates and Lipid Peroxidation, J. Immunol., 2000, vol. 164:6509-6519.
Bradamante et. al., Cardiovascular Protective Effects of Resveratrol, Cardiovascular Drug. Reviews, 2004, vol. 22:169-188.
J. Schultz, Resveratrol May Be a Powerful Cancer-Fighting Ally, J. Natl. Cancer Inst., 2004, vol. 96:1497-1498.
Scifo et. al., Resveratrol and Propolis as Necrosis or Apoptosis Inducers in Human Prostate Carcinoma Cells, Oncol. Res., 2004, vol. 14:415-426.
J. Kundu et. al., Molecular Basis of Chemprevention by Resveratrol: NF-Kb and AP-1 as Potential Targets, Mutat. Res., 2004, vol. 555:65-80.
Gonzalez-Urena et. al., Improving Postharvest Resistance in Fruits by External Application of Trans-Resveratrol, J. Agric. Food Chem., 2003, vol. 51:82-89.
Davis et. al., Overproduction of Acetyl-CoA Carboxylase Activity Increases the Rate of Fatty Acid Biosynthesis in *Escherichia coli*, J. Biol. Chem., 2000, vol. 275:28593-28598.
S. Subrahmanyam et. al., Overproduction of a Functional Fatty Acid Biosynthetic Enzyme Blocks Fatty Acid Synthesis in *Escherichia coli*, J. Bacteriol., 1998, vol. 180:4596-4602.
Kaneko et. al., Cinnamate:: Coenzyme A Ligase From the Filamentous Bacterium *Streptomyces coelicolor* A3(2), J. Bacteriol., 2003, vol. 185:20-27.
Becker et. al., Metabolic Engineering of *Saccharomyces cerevisiae* for the Synthesis of the Wine-Related Antioxidant Resveratrol, FEMS Yeast Research, 2003, vol. 4:79-85.
Watts et. al., Exploring Recombinant Flavonoid Biosynthesis in Metabolically Engineered *Escherichia coli*, Chembiochem., 2004,vol. 5:500-507.
Hwang et. al., Production of Plant-Specific Flavanones by *Escherichia coli* Containing an Artificial Gene Cluster, Appl. Environ. Microbiol., 2003, vol. 69:2699-2706.
J. Schroder et. al., Stilbene and Chalcone: Synthases: Related Enzymes With Key Functions in Plant-Specific Pathways, Z. Naturforsch, 1990, vol. 45:1-8.
Beekwilder, Jules et al., Production of Resveratrol in Recombinant Microorganisms, Applied and Environmental Microbiology, Aug. 2006, 5670-5672, vol. 72, No. 8 American Society for Microbiology.
Neidleman, S. et al., Advances in Applied Microbiology, 1997, 254 pages, Academic Press, at pp. 197-198.
Kamisaka et al., "DGA1 (diacylglycerol acyltransferase gene) overexpression and leucine biosynthesis significantly significantly increase lipid accumulation in the deltasnf2 disruptant of *Saccharomyces cerevisiae*"; Biochem J, 2007, vol. 408, pp. 61-68.

* cited by examiner

*Primary Examiner*—Eric S Olson

(57) ABSTRACT

Methods to produce resveratrol and/or resveratrol glucoside in a recombinant oleaginous microorganism are provided. Expression of a resveratrol synthase gene in combination with genes involved in the phenylpropanoid pathway enabled recombinant microbial production of resveratrol in significant amounts.

30 Claims, 6 Drawing Sheets

Figure 1:
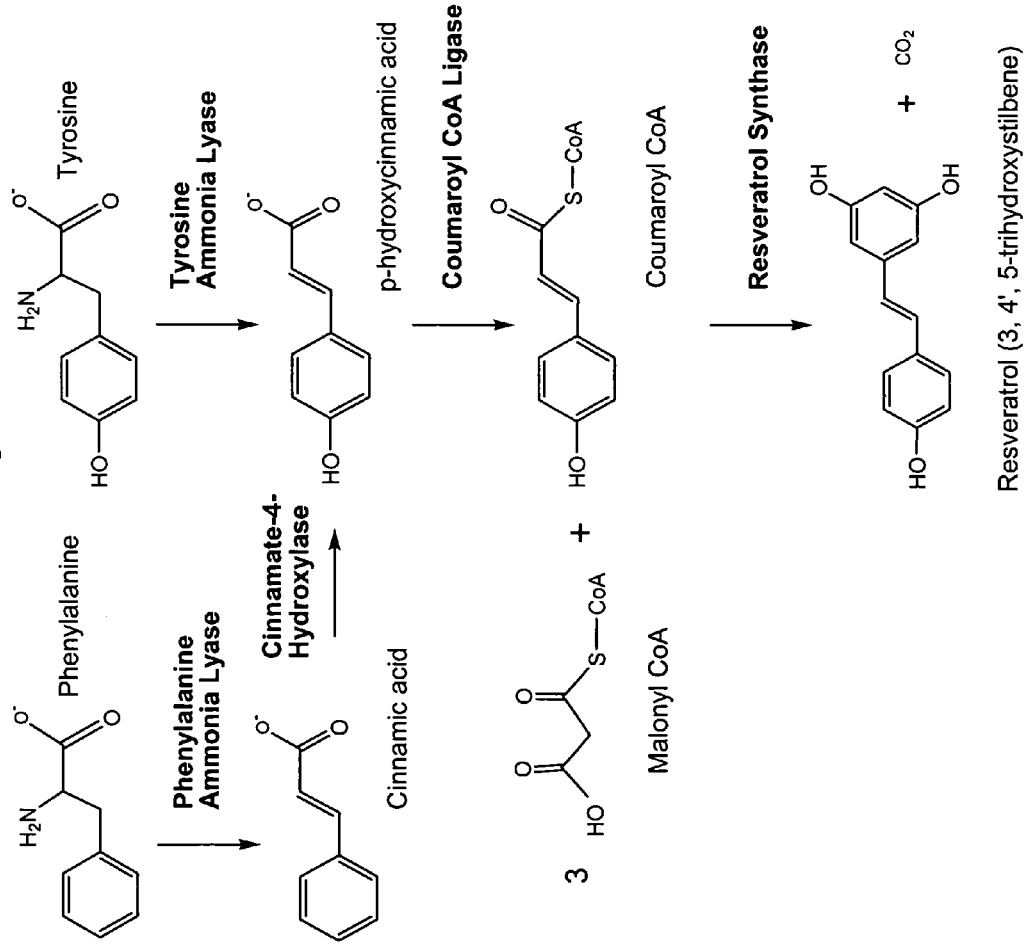

```
                          SEQUENCE LISTING

<160> NUMBER OF SEQ ID NOS: 139

<210> SEQ ID NO 1
<211> LENGTH: 2151
<212> TYPE: DNA
<213> ORGANISM: Rhodotorula glutinis
<220> FEATURE:
<221> NAME/KEY: CDS
<222> LOCATION: (1)..(2151)

<400> SEQUENCE: 1 atg gca ccc tcg ctc gac tcg atc tcg cac tcg ttc gca aac ggc gtc         48
Met Ala Pro Ser Leu Asp Ser Ile Ser His Ser Phe Ala Asn Gly Val
1               5                   10                  15 gca tcc gca aag cag gct gtc aat ggc gcc tcg acc aac ctc gca gtc         96
Ala Ser Ala Lys Gln Ala Val Asn Gly Ala Ser Thr Asn Leu Ala Val
            20                  25                  30 gca ggc tcg cac ctg ccc aca acc cag gtc acg cag gtc gac atc gtc        144
Ala Gly Ser His Leu Pro Thr Thr Gln Val Thr Gln Val Asp Ile Val
        35                  40                  45 gag aag atg ctc gcc gcg ccg acc gac tcg acg ctc gaa ctc gac ggc        192
Glu Lys Met Leu Ala Ala Pro Thr Asp Ser Thr Leu Glu Leu Asp Gly
    50                  55                  60 tac tcg ctc aac ctc gga gac gtc gtc tcg gcc gcg agg aag ggc agg        240
Tyr Ser Leu Asn Leu Gly Asp Val Val Ser Ala Ala Arg Lys Gly Arg
65                  70                  75                  80 cct gtc cgc gtc aag gac agc gac gag atc cgc tca aag att gac aaa        288
Pro Val Arg Val Lys Asp Ser Asp Glu Ile Arg Ser Lys Ile Asp Lys
                85                  90                  95 tcg gtc gag ttc ttg cgc tcg caa ctc tcc atg agc gtc tac ggc gtc        336
Ser Val Glu Phe Leu Arg Ser Gln Leu Ser Met Ser Val Tyr Gly Val
            100                 105                 110 acg act gga ttt ggc gga tcc gca gac acc cgc acc gag gac gcc atc        384
Thr Thr Gly Phe Gly Gly Ser Ala Asp Thr Arg Thr Glu Asp Ala Ile
        115                 120                 125 tcg ctc cag aag gct ctc ctc gag cac cag ctc tgc ggt gtt ctc cct        432
Ser Leu Gln Lys Ala Leu Leu Glu His Gln Leu Cys Gly Val Leu Pro
    130                 135                 140 tcg tcg ttc gac tcg ttc cgc ctc ggc cgc ggt ctc gag aac tcg ctt        480
Ser Ser Phe Asp Ser Phe Arg Leu Gly Arg Gly Leu Glu Asn Ser Leu
145                 150                 155                 160 ccc ctc gag gtt gtt cgc ggc gcc atg aca atc cgc gtc aac agc ttg        528
Pro Leu Glu Val Val Arg Gly Ala Met Thr Ile Arg Val Asn Ser Leu
                165                 170                 175 acc cgc ggc cac tcg gct gtc cgc ctc gtc gtc ctc gag gcg ctc acc        576
Thr Arg Gly His Ser Ala Val Arg Leu Val Val Leu Glu Ala Leu Thr
            180                 185                 190
```

```
aac ttc ctc aac cac ggc atc acc ccc atc gtc ccc ctc cgc ggc acc     624
Asn Phe Leu Asn His Gly Ile Thr Pro Ile Val Pro Leu Arg Gly Thr
            195                 200                 205 atc tct gcg tcg ggc gac ctg tct cct ctc tcc tac att gca gcg gcc     672
Ile Ser Ala Ser Gly Asp Leu Ser Pro Leu Ser Tyr Ile Ala Ala Ala
    210                 215                 220 atc agc ggt cac ccg gac agc aag gtg cac gtc gtc cac gag ggc aag     720
Ile Ser Gly His Pro Asp Ser Lys Val His Val Val His Glu Gly Lys
225                 230                 235                 240 gag aag atc ctg tac gcc cgc gag gcg atg gcg ctc ttc aac ctc gag     768
Glu Lys Ile Leu Tyr Ala Arg Glu Ala Met Ala Leu Phe Asn Leu Glu
                245                 250                 255 ccc gtc gtc ctc ggc ccg aag gaa ggt ctc ggt ctc gtc aac ggc acc     816
Pro Val Val Leu Gly Pro Lys Glu Gly Leu Gly Leu Val Asn Gly Thr
            260                 265                 270 gcc gtc tca gca tcg atg gcc acc ctc gct ctg cac gac gct cac atg     864
Ala Val Ser Ala Ser Met Ala Thr Leu Ala Leu His Asp Ala His Met
    275                 280                 285 ctc tcg ctc ctc tcg cag tcg ctc acg gcc atg acg gtc gaa gcg atg     912
Leu Ser Leu Leu Ser Gln Ser Leu Thr Ala Met Thr Val Glu Ala Met
290                 295                 300 gtc ggc cac gcc ggc tcg ttc cac ccc ttc ctt cac gac gtc acg cgc     960
Val Gly His Ala Gly Ser Phe His Pro Phe Leu His Asp Val Thr Arg
305                 310                 315                 320 cct cac ccg acg cag atc gaa gtc gcg gga aac atc cgc aag ctc ctc    1008
Pro His Pro Thr Gln Ile Glu Val Ala Gly Asn Ile Arg Lys Leu Leu
                325                 330                 335 gag gga agc cgc ttt gct gtc cac cat gag gag gag gtc aag gtc aag    1056
Glu Gly Ser Arg Phe Ala Val His His Glu Glu Glu Val Lys Val Lys
            340                 345                 350 gac gac gag ggc att ctc cgc cag gac cgc tac ccc ttg cgc acg tct    1104
Asp Asp Glu Gly Ile Leu Arg Gln Asp Arg Tyr Pro Leu Arg Thr Ser
    355                 360                 365 cct cag tgg ctc ggc ccg ctc gtc agc gac ctc att cac gcc cac gcc    1152
Pro Gln Trp Leu Gly Pro Leu Val Ser Asp Leu Ile His Ala His Ala
370                 375                 380 gtc ctc acc atc gag gcc ggc cag tcg acg acc gac aac cct ctc atc    1200
Val Leu Thr Ile Glu Ala Gly Gln Ser Thr Thr Asp Asn Pro Leu Ile
385                 390                 395                 400 gac gtc gag aac aag act tcg cac cac ggc ggc aat ttc cag gct gcc    1248
Asp Val Glu Asn Lys Thr Ser His His Gly Gly Asn Phe Gln Ala Ala
                405                 410                 415 gct gtg gcc aac acc atg gag aag act cgc ctc ggg ctc gcc cag atc    1296
Ala Val Ala Asn Thr Met Glu Lys Thr Arg Leu Gly Leu Ala Gln Ile
            420                 425                 430 ggc aag ctc aac ttc acg cag ctc acc gag atg ctc aac gcc ggc atg    1344
Gly Lys Leu Asn Phe Thr Gln Leu Thr Glu Met Leu Asn Ala Gly Met
    435                 440                 445 aac cgc ggc ctc ccc tcc tgc ctc gcg gcc gaa gac ccc tcg ctc tcc    1392
Asn Arg Gly Leu Pro Ser Cys Leu Ala Ala Glu Asp Pro Ser Leu Ser
450                 455                 460 tac cac tgc aag ggc ctc gac atc gcc gct gcg gcg tac acc tcg gag    1440
Tyr His Cys Lys Gly Leu Asp Ile Ala Ala Ala Ala Tyr Thr Ser Glu
465                 470                 475                 480 ttg gga cac ctc gcc aac cct gtg acg acg cat gtc cag ccg gct gag    1488
Leu Gly His Leu Ala Asn Pro Val Thr Thr His Val Gln Pro Ala Glu
                485                 490                 495 atg gcg aac cag gcg gtc aac tcg ctt gcg ctc atc tcg gct cgt cgc    1536
Met Ala Asn Gln Ala Val Asn Ser Leu Ala Leu Ile Ser Ala Arg Arg
            500                 505                 510
```

-continued

| | | |
|---|---|---|
| acg acc gag tcc aac gac gtc ctt tct ctc ctc ctc gcc acc cac ctc<br>Thr Thr Glu Ser Asn Asp Val Leu Ser Leu Leu Leu Ala Thr His Leu<br>515 520 525 | | 1584 |
| tac tgc gtt ctc caa gcc atc gac ttg cgc gcg atc gag ttc gag ttc<br>Tyr Cys Val Leu Gln Ala Ile Asp Leu Arg Ala Ile Glu Phe Glu Phe<br>530 535 540 | | 1632 |
| aag aag cag ttc ggc cca gcc atc gtc tcg ctc atc gac cag cac ttt<br>Lys Lys Gln Phe Gly Pro Ala Ile Val Ser Leu Ile Asp Gln His Phe<br>545 550 555 560 | | 1680 |
| ggc tcc gcc atg acc ggc tcg aac ctg cgc gac gag ctc gtc gag aag<br>Gly Ser Ala Met Thr Gly Ser Asn Leu Arg Asp Glu Leu Val Glu Lys<br>565 570 575 | | 1728 |
| gtg aac aag acg ctc gcc aag cgc ctc gag cag acc aac tcg tac gac<br>Val Asn Lys Thr Leu Ala Lys Arg Leu Glu Gln Thr Asn Ser Tyr Asp<br>580 585 590 | | 1776 |
| ctc gtc ccg cgc tgg cac gac gcc ttc tcc ttc gcc gcc ggc acc gtc<br>Leu Val Pro Arg Trp His Asp Ala Phe Ser Phe Ala Ala Gly Thr Val<br>595 600 605 | | 1824 |
| gtc gag gtc ctc tcg tcg acg tcg ctc tcg ctc gcc gcc gtc aac gcc<br>Val Glu Val Leu Ser Ser Thr Ser Leu Ser Leu Ala Ala Val Asn Ala<br>610 615 620 | | 1872 |
| tgg aag gtc gcc gcc gcc gag tcg gcc atc tcg ctc acc cgc caa gtc<br>Trp Lys Val Ala Ala Ala Glu Ser Ala Ile Ser Leu Thr Arg Gln Val<br>625 630 635 640 | | 1920 |
| cgc gag acc ttc tgg tcc gcc gcg tcg acc tcg tcg ccc gcg ctc tcg<br>Arg Glu Thr Phe Trp Ser Ala Ala Ser Thr Ser Ser Pro Ala Leu Ser<br>645 650 655 | | 1968 |
| tac ctc tcg ccg cgc act cag atc ctc tac gcc ttc gtc cgc gag gag<br>Tyr Leu Ser Pro Arg Thr Gln Ile Leu Tyr Ala Phe Val Arg Glu Glu<br>660 665 670 | | 2016 |
| ctt ggc gtc aag gcc cgc cgc gga gac gtc ttc ctc ggc aag caa gag<br>Leu Gly Val Lys Ala Arg Arg Gly Asp Val Phe Leu Gly Lys Gln Glu<br>675 680 685 | | 2064 |
| gtg acg atc ggc tcg aac gtc tcc aag atc tac gag gcc atc aag tcg<br>Val Thr Ile Gly Ser Asn Val Ser Lys Ile Tyr Glu Ala Ile Lys Ser<br>690 695 700 | | 2112 |
| ggc agg atc aac aac gtc ctc ctc aag atg ctc gct tag<br>Gly Arg Ile Asn Asn Val Leu Leu Lys Met Leu Ala<br>705 710 715 | | 2151 |

<210> SEQ ID NO 2
<211> LENGTH: 716
<212> TYPE: PRT
<213> ORGANISM: Rhodotorula glutinis

<400> SEQUENCE: 2

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
                20                  25                  30

Ala Gly Ser His Leu Pro Thr Thr Gln Val Thr Gln Val Asp Ile Val
            35                  40                  45

Glu Lys Met Leu Ala Ala Pro Thr Asp Ser Thr Leu Glu Leu Asp Gly
        50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

```
Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
            115                 120                 125

Ser Leu Gln Lys Ala Leu Leu Glu His Gln Leu Cys Gly Val Leu Pro
        130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
```

```
                515                 520                 525
Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 3
<211> LENGTH: 2151
<212> TYPE: DNA
<213> ORGANISM: artificial sequence
<220> FEATURE:
<223> OTHER INFORMATION: Synthetic gene

<400> SEQUENCE: 3
atggctccct ctctggactc catctctcac tccttcgcca acggtgttgc ctctgctaag      60
caggcagtga acggagcttc gaccaacctt gccgtcgctg ctctcacttg cccaccact     120 caggtgacac aggttgacat tgtcgagaag atgctcgctc tcctaccga ctccactctg     180 gagctcgatg ctactcgct gaacctcgga gacgtcgtct ctgctgcccg aaagggtaga     240
cccgttcgag tgaaggactc cgatgagatt cgatcgaaga tcgacaagtc cgtcgagttc     300
ctgcgatctc aactctcgat gtccgtgtac ggtgtcacca ctggatttgg tggctctgcc     360
gacacacgaa ctgaagatgc catctccctt cagaaggctc tgctggagca ccagctctgc     420
ggtgtgcttc cctcgtcctt tgactccttc cgtctgggac gaggactgga gaactctctt     480
cctctggagg tcgtccgagg agccatgacc atccgagtga actctctgac tcgaggccac     540
tccgctgttc gactcgtcgt ccttgaggca ttgaccaact tcctgaatca tggcatcaca     600
cccattgttc ccccttcgagg caccatctcc gcctctggtg atctgtctcc tctctcctac     660
attgctgcag ccatctctgg acatcccgac tcgaaagtgc acgtcgtcca cgaaggcaag     720
gagaagattc tgtacgcacg agaggctatg gccctcttca acctggagcc tgtcgtcctt     780
ggacccaagg aaggtctcgg actggtcaac ggcactgccg tgtccgcatc tatggctacc     840
ctcgctctgc acgacgctca catgctccg ctgctctctc agtccctgac tgccatgacc     900
gtcgaagcta tggttggaca cgctggctcc tttcatccct ttctccacga tgtgactcga     960
```

-continued

```
cctcatccca cacagatcga agtcgctggc aacatccgaa agcttctgga gggttctcga      1020
tttgccgtcc accacgagga ggaagtcaaa gtcaaggacg acgaaggcat tctcagacag      1080
gatcgttatc ccttgcgaac ctctcctcag tggctcggac ccctggtctc tgacctcatc      1140
cacgctcatg ccgtgctcac cattgaggct ggtcagtcca ctaccgacaa ccctctgatt      1200
gatgtcgaga acaagacctc gcatcacgga ggcaacttcc aggctgccgc tgtggccaac      1260
actatggaga agactcgact tggactcgct cagattggca agctcaactt cacccagctg      1320
actgagatgc tcaatgcagg catgaaccga ggtctgccct cctgtcttgc tgccgaagat      1380
ccctctctgt cctaccactg caagggactc gacatcgctg ccgctgccta cacctctgag      1440
ctgggtcatc tcgccaaccc tgtcaccact acgtgcagc ctgctgagat ggcgaaccag       1500
gcagtcaact cccttgccct catctctgct cgacgaacca ccgagtccaa cgacgttctc      1560
tctctgctcc ttgccactca cctctactgt gtcctgcaag ccattgacct gcagctatc       1620 gagttcgagt tcaagaagca gtttggtcct gccatcgtgt ctctcattga tcagcacttt      1680
ggctctgcca tgactggatc gaacctgcga gacgagcttg ttgagaaggt caacaagaca      1740
ctggccaaac gactcgagca gaccaactcc tacgacctgg ttcccagatg gcacgatgcc      1800
ttctcctttg ctgccggaac tgtcgtcgaa gtgctctctt ccacctcgct gtctcttgct      1860
gccgtcaatg cctggaaggt tgccgctgcc gagtctgcca tctctctgac tcgacaagtc      1920
cgagagacct tctggtctgc tgcctctacc tcctctcctg ccctctccta cctctctccc      1980
agaactcaga ttctgtacgc cttcgtccga gaggaacttg gtgtgaaggc tcgacgagga      2040
gacgtctttc tcggcaagca agaggtgacc attggctcca acgtctccaa aatctacgaa      2100
gccatcaagt ctggcagaat caacaatgtg ctgctcaaga tgctcgctta a              2151
```

<210> SEQ ID NO 4
<211> LENGTH: 1569
<212> TYPE: DNA
<213> ORGANISM: Streptomyces coelicolor

<400> SEQUENCE: 4

```
gtgttccgca gcgagtacgc agacgtcccg cccgtcgacc tgcccatcca cgacgccgtg       60
ctcggcgggg ccgccgcctt cgggagcacc ccggcgctga tcgacggcac cgacggcacc      120
accctcacct acgagcaggt ggaccggttc accggcgcg tcgccgccgc cctcgccgag       180
accggcgtgc gcaagggcga cgtcctcgcc ctgcacagcc caacaccgt cgccttcccc        240 ctggccttct acgccgccac ccgcgcgggc gcctccgtca ccacggtgca tccgctcgcg      300
acggcggagg agttcgccaa gcagctgaag gacagcgcgg cccgctggat cgtcaccgtc      360
tcaccgctcc tgtccaccgc ccgccgggcc gcgaactcg cgggcggcgt ccaggagatc       420
ctggtctgcg acagcgcgcc cggtcaccgc tcccctcgtcg acatgctggc ctcgaccgcg      480
cccgaaccgt ccgtcgccat cgacccggcc gaggacgtcg ccgccctgcc gtactcctcg      540
ggcaccaccg gcaccccaa gggcgtcatg ctcacacacc ggcagatcgc caccaacctc       600
gcccagctcg aaccgtcgat gccgtccgcg cccggcgacc gcgtcctcgc cgtgctgccg      660
ttcttccaca tctacggcct gaccgccctg atgaacgccc cgctccggct cggcgccacc      720
gtcgtggtcc tgccccgctt cgacctggag cagttcctcg ccgccatcca gaaccaccgc     780
atcaccagcc tgtacgtcgc cccgccgatc gtcctggccc tcgccaaaca ccccctggtc     840
gccgactacg acctctcctc gctgaggtac atcgtcagcg ccgccgcccc gctcgacgcg     900
```

-continued

```
cgtctcgccg ccgcctgctc gcagcggctc ggcctgccgc ccgtcggcca ggcctacggc    960
atgaccgaac tgtccccggg cacccacgtc gtccccctgg acgcgatggc cgacgcgccc   1020
cccggcaccg tcggcaggct catcgcgggc accgagatgc gcatcgtctc cctcaccgac   1080
ccgggcacgg acctccccgc cggagagtcc ggggagatcc tcatccgcgg ccccagatc    1140
atgaagggct acctgggccg ccccgacgcc accgccgcca tgatcgacga ggagggctgg   1200
ctgcacaccg ggacgtcgg acacgtcgac gccgacggct ggctgttcgt cgtcgaccgc   1260
gtcaaggaac tgatcaagta caagggcttc caggtggccc ccgccgaact ggaggcccac   1320
ctgctcaccc accccggcgt cgccgacgcg ccgtcgtcg cgcctacga cgacgacggc   1380
aacgaggtac cgcacgcctt cgtcgtccgc cagccggccg cacccggcct cgcggagagc   1440
gagatcatga tgtacgtcgc cgaacgcgtc gccccctaca aacgcgtccg ccgggtcacc   1500
ttcgtcgacg ccgtccccg cgccgcctcc ggcaagatcc tccgccgaca gctcagggag   1560
ccgcgatga                                                          1569
```

<210> SEQ ID NO 5
<211> LENGTH: 522
<212> TYPE: PRT
<213> ORGANISM: Streptomyces coelicolor

<400> SEQUENCE: 5

```
Val Phe Arg Ser Glu Tyr Ala Asp Val Pro Val Asp Leu Pro Ile
1               5                   10                  15

His Asp Ala Val Leu Gly Gly Ala Ala Ala Phe Gly Ser Thr Pro Ala
            20                  25                  30

Leu Ile Asp Gly Thr Asp Gly Thr Thr Leu Thr Tyr Glu Gln Val Asp
        35                  40                  45

Arg Phe His Arg Val Ala Ala Leu Ala Glu Thr Gly Val Arg
    50                  55                  60

Lys Gly Asp Val Leu Ala Leu His Ser Pro Asn Thr Val Ala Phe Pro
65                  70                  75                  80

Leu Ala Phe Tyr Ala Ala Thr Arg Ala Gly Ala Ser Val Thr Thr Val
                85                  90                  95

His Pro Leu Ala Thr Ala Glu Glu Phe Ala Lys Gln Leu Lys Asp Ser
            100                 105                 110

Ala Ala Arg Trp Ile Val Thr Val Ser Pro Leu Leu Ser Thr Ala Arg
        115                 120                 125

Arg Ala Ala Glu Leu Ala Gly Gly Val Gln Glu Ile Leu Val Cys Asp
    130                 135                 140

Ser Ala Pro Gly His Arg Ser Leu Val Asp Met Leu Ala Ser Thr Ala
145                 150                 155                 160

Pro Glu Pro Ser Val Ala Ile Asp Pro Ala Glu Asp Val Ala Ala Leu
                165                 170                 175

Pro Tyr Ser Ser Gly Thr Thr Gly Thr Pro Lys Gly Val Met Leu Thr
            180                 185                 190

His Arg Gln Ile Ala Thr Asn Leu Ala Gln Leu Glu Pro Ser Met Pro
        195                 200                 205

Ser Ala Pro Gly Asp Arg Val Leu Ala Val Leu Pro Phe Phe His Ile
    210                 215                 220

Tyr Gly Leu Thr Ala Leu Met Asn Ala Pro Leu Arg Leu Gly Ala Thr
225                 230                 235                 240

Val Val Val Leu Pro Arg Phe Asp Leu Glu Gln Phe Leu Ala Ala Ile
                245                 250                 255
```

Gln Asn His Arg Ile Thr Ser Leu Tyr Val Ala Pro Pro Ile Val Leu
            260                 265                 270

Ala Leu Ala Lys His Pro Leu Val Ala Asp Tyr Asp Leu Ser Ser Leu
        275                 280                 285

Arg Tyr Ile Val Ser Ala Ala Pro Leu Asp Ala Arg Leu Ala Ala
    290                 295                 300

Ala Cys Ser Gln Arg Leu Gly Leu Pro Val Gly Gln Ala Tyr Gly
305                 310                 315                 320

Met Thr Glu Leu Ser Pro Gly Thr His Val Val Pro Leu Asp Ala Met
                325                 330                 335

Ala Asp Ala Pro Pro Gly Thr Val Gly Arg Leu Ile Ala Gly Thr Glu
        340                 345                 350

Met Arg Ile Val Ser Leu Thr Asp Pro Gly Thr Asp Leu Pro Ala Gly
            355                 360                 365

Glu Ser Gly Glu Ile Leu Ile Arg Gly Pro Gln Ile Met Lys Gly Tyr
    370                 375                 380

Leu Gly Arg Pro Asp Ala Thr Ala Ala Met Ile Asp Glu Glu Gly Trp
385                 390                 395                 400

Leu His Thr Gly Asp Val Gly His Val Asp Ala Asp Gly Trp Leu Phe
                405                 410                 415

Val Val Asp Arg Val Lys Glu Leu Ile Lys Tyr Lys Gly Phe Gln Val
        420                 425                 430

Ala Pro Ala Glu Leu Glu Ala His Leu Leu Thr His Pro Gly Val Ala
            435                 440                 445

Asp Ala Ala Val Val Gly Ala Tyr Asp Asp Asp Gly Asn Glu Val Pro
    450                 455                 460

His Ala Phe Val Val Arg Gln Pro Ala Ala Pro Gly Leu Ala Glu Ser
465                 470                 475                 480

Glu Ile Met Met Tyr Val Ala Glu Arg Val Ala Pro Tyr Lys Arg Val
                485                 490                 495

Arg Arg Val Thr Phe Val Asp Ala Val Pro Arg Ala Ala Ser Gly Lys
        500                 505                 510

Ile Leu Arg Arg Gln Leu Arg Glu Pro Arg
            515                 520

```
<210> SEQ ID NO 6
<211> LENGTH: 1569
<212> TYPE: DNA
<213> ORGANISM: artificial sequence
<220> FEATURE:
<223> OTHER INFORMATION: Synthetic gene

<400> SEQUENCE: 6
atgtttcgat ccgagtacgc cgacgttcct cccgtcgacc tgcccattca cgatgctgtg      60
ctcggaggtg ctgccgcttt cggctctact cctgccctga tcgacggaac cgacggcacc     120
actctcacct acgagcaggt ggaccgattt cacagacgag tcgctgcagc ccttgccgag     180
acaggcgttc gaaagggaga cgtcttggct ctgcactctc ccaacactgt tgccttccca     240
cttgccttct acgctgccac cagagctggt gcctccgtca ccactgtgca tcctcttgct     300
acagcagaag agtttgccaa gcagctgaag gactctgctg cccgatggat tgtcaccgtt     360
tcccctctcc tgtccactgc cgacgagct gccgagcttg ctggaggcgt ccaggagatt     420
ctggtttgcg acagcgcacc cggtcaccga tccttgtcg atatgctggc tctacagct      480 cccgaacctt ccgtcgccat cgaccctgca gaggacgttg ctgccttgcc ctactcttcc     540
```

-continued

```
ggaactaccg gtactcccaa gggtgtcatg ctcacccatc gacagattgc caccaacctg    600
gctcaactcg aaccttccat gccctctgct cctggagatc gagttcttgc agtgcttccc    660
ttctttcaca tctatggtct gactgccctc atgaacgctc tctgcgact cggagccacc     720 gtcgtggttc ttccacgatt cgacctggag cagtttctcg ctgccattca gaaccaccga    780
atcacttcgc tgtacgtcgc tcctcccatt gtgctggcac ttgccaaaca tcccttggtt    840
gccgactacg atctctcctc gctgagatac atcgtgtcgg ctgccgcacc tctcgatgct    900
cgacttgccg ctgcctgttc ccagcgactc ggactgcctc ccgtcggtca ggcttacggc    960
atgaccgagc tgtctcctgg aacacacgtg gttcccttgg acgcaatggc cgatgctcct   1020
cctggcactg tcggtcgact cattgccgga accgagatgc gaatcgtctc cctcaccgat   1080
ccaggtacag accttcctgc tggagagtct ggcgagattc tcattcgagg tccccagatc   1140
atgaagggct acttgggaag acccgatgcc actgctgcca tgatcgacga agaaggctgg   1200
ctgcacacag gtgatgtcgg acacgtggat gccgatggct ggctgtttgt tgtcgaccga   1260
gtcaaggagc ttatcaagta caagggattc caggttgctc ctgccgagct ggaagcccac   1320
ctgctcactc atccaggtgt cgcagacgct gccgtggttg agcctacga cgatgacggc    1380 aacgaggttc cccatgcctt cgtcgtgcga caacctgccg ctcccggtct tgccgagtcc   1440
gagatcatga tgtacgttgc cgaacgagtc gctccctaca agcgagtgcg acgagttacc   1500
ttcgtcgatg ccgttcccag agctgcctcc ggcaagattc tccgaagaca gctgcgagag   1560
cctcgataa                                                          1569

<210> SEQ ID NO 7
<211> LENGTH: 1179
<212> TYPE: DNA
<213> ORGANISM: Vitis sp.
<220> FEATURE:
<221> NAME/KEY: CDS
<222> LOCATION: (1)..(1179)

<400> SEQUENCE: 7 atg gct tca gtt gag gaa ttt aga aac gct caa cgt gcc aag ggt ccg     48
Met Ala Ser Val Glu Glu Phe Arg Asn Ala Gln Arg Ala Lys Gly Pro
1               5                   10                  15 gcc act atc cta gcc att ggc aca gct act cct gac cac tgt gtc tac     96
Ala Thr Ile Leu Ala Ile Gly Thr Ala Thr Pro Asp His Cys Val Tyr
            20                  25                  30 cag tct gat tat gct gat tac tat ttc agg gtc act aag agc gag cac    144
Gln Ser Asp Tyr Ala Asp Tyr Tyr Phe Arg Val Thr Lys Ser Glu His
        35                  40                  45 atg act gag ttg aag aag aag ttc aat cgc ata tgt gac aaa tca atg    192
Met Thr Glu Leu Lys Lys Lys Phe Asn Arg Ile Cys Asp Lys Ser Met
    50                  55                  60 atc aag aag cgt tac att cac ttg acc gaa gaa atg ctt gag gag cac    240
Ile Lys Lys Arg Tyr Ile His Leu Thr Glu Glu Met Leu Glu Glu His
65                  70                  75                  80 cca aac att ggt gct tat atg gct cca tct ctt aac ata cgc caa gag    288
Pro Asn Ile Gly Ala Tyr Met Ala Pro Ser Leu Asn Ile Arg Gln Glu
                85                  90                  95 att atc act gct gag gta cct aga ctt ggt agg gat gca gca ttg aag    336
Ile Ile Thr Ala Glu Val Pro Arg Leu Gly Arg Asp Ala Ala Leu Lys
            100                 105                 110 gct ctt aaa gag tgg ggc caa cca aag tcc aag atc acc cat ctt gta    384
Ala Leu Lys Glu Trp Gly Gln Pro Lys Ser Lys Ile Thr His Leu Val
        115                 120                 125
```

| | | | | | | | | | | | | | | | |
|---|---|---|---|---|---|---|---|---|---|---|---|---|---|---|---|
| ttt | tgt | aca | acc | tcc | ggt | gta | gaa | atg | ccc | ggt | gcg | gat | tac | aaa | ctc | 432
| Phe | Cys | Thr | Thr | Ser | Gly | Val | Glu | Met | Pro | Gly | Ala | Asp | Tyr | Lys | Leu |
| | 130 | | | | 135 | | | | 140 | | | | | |

| | | | | | | | | | | | | | | | |
|---|---|---|---|---|---|---|---|---|---|---|---|---|---|---|---|
| gct | aat | ctc | tta | ggt | ctt | gaa | aca | tcg | gtt | aga | agg | gtg | atg | ttg | tac | 480
| Ala | Asn | Leu | Leu | Gly | Leu | Glu | Thr | Ser | Val | Arg | Arg | Val | Met | Leu | Tyr |
| 145 | | | | | 150 | | | | | 155 | | | | | 160 |

| | | | | | | | | | | | | | | | |
|---|---|---|---|---|---|---|---|---|---|---|---|---|---|---|---|
| cat | caa | ggg | tgc | tat | gca | ggt | gga | act | gtc | ctt | cga | act | gct | aag | gat | 528
| His | Gln | Gly | Cys | Tyr | Ala | Gly | Gly | Thr | Val | Leu | Arg | Thr | Ala | Lys | Asp |
| | | | | 165 | | | | | 170 | | | | | 175 |

| | | | | | | | | | | | | | | | |
|---|---|---|---|---|---|---|---|---|---|---|---|---|---|---|---|
| ctt | gca | gaa | aat | aat | gca | gga | gca | cga | gtt | ctt | gtg | gtg | tgc | tct | gag | 576
| Leu | Ala | Glu | Asn | Asn | Ala | Gly | Ala | Arg | Val | Leu | Val | Val | Cys | Ser | Glu |
| | | | 180 | | | | | 185 | | | | | 190 |

| | | | | | | | | | | | | | | | |
|---|---|---|---|---|---|---|---|---|---|---|---|---|---|---|---|
| atc | act | gtt | gtt | aca | ttc | cgt | ggc | cct | tcc | gaa | gat | gct | ttg | gac | tct | 624
| Ile | Thr | Val | Val | Thr | Phe | Arg | Gly | Pro | Ser | Glu | Asp | Ala | Leu | Asp | Ser |
| | 195 | | | | 200 | | | | 205 |

| | | | | | | | | | | | | | | | |
|---|---|---|---|---|---|---|---|---|---|---|---|---|---|---|---|
| tta | gtt | ggc | caa | gcc | ctt | ttt | ggt | gat | ggg | tct | tca | gct | gtg | att | gtt | 672
| Leu | Val | Gly | Gln | Ala | Leu | Phe | Gly | Asp | Gly | Ser | Ser | Ala | Val | Ile | Val |
| 210 | | | | | 215 | | | | | 220 |

| | | | | | | | | | | | | | | | |
|---|---|---|---|---|---|---|---|---|---|---|---|---|---|---|---|
| gga | tca | gat | cca | gat | gtc | tcg | att | gaa | cga | cca | ctc | ttc | caa | ctt | gtt | 720
| Gly | Ser | Asp | Pro | Asp | Val | Ser | Ile | Glu | Arg | Pro | Leu | Phe | Gln | Leu | Val |
| 225 | | | | 230 | | | | | 235 | | | | | 240 |

| | | | | | | | | | | | | | | | |
|---|---|---|---|---|---|---|---|---|---|---|---|---|---|---|---|
| tca | gca | gcc | caa | aca | ttt | att | cct | aat | tca | gca | gga | gcc | att | gcc | gga | 768
| Ser | Ala | Ala | Gln | Thr | Phe | Ile | Pro | Asn | Ser | Ala | Gly | Ala | Ile | Ala | Gly |
| | | | | 245 | | | | | 250 | | | | | 255 |

| | | | | | | | | | | | | | | | |
|---|---|---|---|---|---|---|---|---|---|---|---|---|---|---|---|
| aac | tta | cgt | gag | gtg | ggg | ctc | acc | ttt | cat | ttg | tgg | ccc | aat | gtg | cct | 816
| Asn | Leu | Arg | Glu | Val | Gly | Leu | Thr | Phe | His | Leu | Trp | Pro | Asn | Val | Pro |
| | | 260 | | | | | 265 | | | | | 270 |

| | | | | | | | | | | | | | | | |
|---|---|---|---|---|---|---|---|---|---|---|---|---|---|---|---|
| act | ttg | att | tct | gag | aac | ata | gag | aaa | tgc | ttg | acc | cag | gct | ttt | gac | 864
| Thr | Leu | Ile | Ser | Glu | Asn | Ile | Glu | Lys | Cys | Leu | Thr | Gln | Ala | Phe | Asp |
| | | | 275 | | | | | 280 | | | | | 285 |

| | | | | | | | | | | | | | | | |
|---|---|---|---|---|---|---|---|---|---|---|---|---|---|---|---|
| cca | ctt | ggt | att | agc | gat | tgg | aac | tcg | tta | ttt | tgg | att | gct | cac | cca | 912
| Pro | Leu | Gly | Ile | Ser | Asp | Trp | Asn | Ser | Leu | Phe | Trp | Ile | Ala | His | Pro |
| | 290 | | | | | 295 | | | | | 300 |

| | | | | | | | | | | | | | | | |
|---|---|---|---|---|---|---|---|---|---|---|---|---|---|---|---|
| ggt | ggc | cct | gca | att | ctc | gat | gca | gtt | gaa | gca | aaa | ctc | aat | tta | gag | 960
| Gly | Gly | Pro | Ala | Ile | Leu | Asp | Ala | Val | Glu | Ala | Lys | Leu | Asn | Leu | Glu |
| 305 | | | | | 310 | | | | | 315 | | | | | 320 |

| | | | | | | | | | | | | | | | |
|---|---|---|---|---|---|---|---|---|---|---|---|---|---|---|---|
| aaa | aag | aaa | ctc | gaa | gca | act | agg | cat | gtg | tta | agt | gag | tac | ggt | aac | 1008
| Lys | Lys | Lys | Leu | Glu | Ala | Thr | Arg | His | Val | Leu | Ser | Glu | Tyr | Gly | Asn |
| | | | | 325 | | | | | 330 | | | | | 335 |

| | | | | | | | | | | | | | | | |
|---|---|---|---|---|---|---|---|---|---|---|---|---|---|---|---|
| atg | tca | agt | gca | tgt | gtg | ttg | ttt | att | ctg | gat | gag | atg | aga | aag | aaa | 1056
| Met | Ser | Ser | Ala | Cys | Val | Leu | Phe | Ile | Leu | Asp | Glu | Met | Arg | Lys | Lys |
| | | | 340 | | | | | 345 | | | | | 350 |

| | | | | | | | | | | | | | | | |
|---|---|---|---|---|---|---|---|---|---|---|---|---|---|---|---|
| tcc | ttg | aag | ggg | gaa | aag | gct | acc | aca | ggt | gaa | gga | ttg | gat | tgg | gga | 1104
| Ser | Leu | Lys | Gly | Glu | Lys | Ala | Thr | Thr | Gly | Glu | Gly | Leu | Asp | Trp | Gly |
| | | 355 | | | | | 360 | | | | | 365 |

| | | | | | | | | | | | | | | | |
|---|---|---|---|---|---|---|---|---|---|---|---|---|---|---|---|
| gta | tta | ttt | ggt | ttt | ggg | ccg | ggc | ttg | acc | atc | gaa | act | gtt | gtg | ctg | 1152
| Val | Leu | Phe | Gly | Phe | Gly | Pro | Gly | Leu | Thr | Ile | Glu | Thr | Val | Val | Leu |
| 370 | | | | | 375 | | | | | 380 |

| | | | | | | |
|---|---|---|---|---|---|---|
| cat | agc | gtt | cct | aca | gtt | aca | aat taa | 1179
| His | Ser | Val | Pro | Thr | Val | Thr | Asn |
| 385 | | | | | 390 |

<210> SEQ ID NO 8
<211> LENGTH: 392
<212> TYPE: PRT
<213> ORGANISM: Vitis sp.

<400> SEQUENCE: 8

Met Ala Ser Val Glu Glu Phe Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Tyr Tyr Phe Arg Val Thr Lys Ser Glu His
        35                  40                  45

Met Thr Glu Leu Lys Lys Lys Phe Asn Arg Ile Cys Asp Lys Ser Met
    50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Arg Leu Gly Arg Asp Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
    130                 135                 140

Ala Asn Leu Leu Gly Leu Glu Thr Ser Val Arg Arg Val Met Leu Tyr
145                 150                 155                 160

His Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ile Thr Val Val Thr Phe Arg Gly Pro Ser Glu Asp Ala Leu Asp Ser
        195                 200                 205

Leu Val Gly Gln Ala Leu Phe Gly Asp Gly Ser Ser Ala Val Ile Val
    210                 215                 220

Gly Ser Asp Pro Asp Val Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Lys Cys Leu Thr Gln Ala Phe Asp
        275                 280                 285

Pro Leu Gly Ile Ser Asp Trp Asn Ser Leu Phe Trp Ile Ala His Pro
    290                 295                 300

Gly Gly Pro Ala Ile Leu Asp Ala Val Glu Ala Lys Leu Asn Leu Glu
305                 310                 315                 320

Lys Lys Lys Leu Glu Ala Thr Arg His Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Leu Lys Gly Glu Lys Ala Thr Thr Gly Gly Leu Asp Trp Gly
        355                 360                 365

Val Leu Phe Gly Phe Gly Pro Gly Leu Thr Ile Glu Thr Val Val Leu
    370                 375                 380

His Ser Val Pro Thr Val Thr Asn
385                 390

<210> SEQ ID NO 9
<211> LENGTH: 1179
<212> TYPE: DNA
<213> ORGANISM: artificial sequence
<220> FEATURE:

<223> OTHER INFORMATION: Synthetic gene

<400> SEQUENCE: 9

| | | | | | |
|---|---|---|---|---|---|
| atggcctccg | ttgaggaatt | ccgaaacgct | cagcgagcca | agggtcccgc | taccatcctg | 60 |
| gccattggca | ctgctacccc | tgaccactgt | gtctaccagt | ctgactatgc | cgattactac | 120 |
| ttccgagtga | ccaagtccga | gcacatgacc | gagctcaaga | agaagttcaa | ccggatctgt | 180 |
| gacaaatcca | tgattaagaa | gcgatacatc | cacctgactg | aagagatgct | cgaagagcat | 240 |
| cccaacattg | cgcttacat | ggctccttct | ctgaacatcc | gacaggagat | tataccgct | 300 |
| gaggttcccc | gactcggtcg | ggatgctgcc | ctgaaggctc | tcaaagagtg | gggacagccc | 360 |
| aagtccaaga | tcacccatct | ggtcttctgt | actacctctg | gtgtggaaat | gcctggagcc | 420 |
| gactacaagc | tcgctaacct | gctcggcctt | gaaacctccg | tccgacgagt | catgctgtac | 480 |
| caccaaggct | gctacgctgg | tggcaccgtg | ctccgaactg | ccaaggacct | ggccgagaac | 540 |
| aacgctggag | cacgagtcct | cgttgtgtgc | tccgaaatca | ctgtcgtgac | cttccgaggt | 600 |
| ccctctgaag | atgccctgga | ctccctcgtc | ggccaggctc | tgtttggtga | tggctcctct | 660 |
| gccgtgattg | ttggatccga | tcccgatgtc | tctatcgagc | gaccccctctt | ccagcttgtc | 720 |
| tccgctgccc | aaacctttat | ccccaactct | gctggtgcca | ttgccggaaa | cctgcgagag | 780 |
| gttggcctca | ccttccacct | gtggcctaat | gtgcccactc | tcatctccga | gaacattgag | 840 |
| aagtgcctga | cccaggcttt | cgaccctctc | ggtatctccg | actggaactc | tctgttctgg | 900 |
| attgctcatc | ccgaggtcc | tgccatcctc | gacgcagttg | aggctaagct | caacctggag | 960 |
| aagaagaagc | tcgaagccac | tcgacacgtg | ctgagcgagt | acggcaacat | gtcctctgct | 1020 |
| tgtgtgctct | tcattctgga | cgagatgcga | aagaaatccc | tcaagggaga | gaaggccacc | 1080 |
| actggtgaag | gcctggactg | gggagtcctc | ttcggctttg | gtcctggact | gaccatcgaa | 1140 |
| actgtcgtgc | tccactctgt | tcccaccgtc | actaactaa | | | 1179 |

<210> SEQ ID NO 10
<211> LENGTH: 995
<212> TYPE: DNA
<213> ORGANISM: Yarrowia lipolytica

<400> SEQUENCE: 10

| | | | | | |
|---|---|---|---|---|---|
| agtgtacgca | gtactataga | ggaacaattg | ccccggagaa | gacggccagg | ccgcctagat | 60 |
| gacaaattca | acaactcaca | gctgactttc | tgccattgcc | actagggggg | ggccttttta | 120 |
| tatggccaag | ccaagctctc | cacgtcggtt | gggctgcacc | caacaataaa | tgggtagggt | 180 |
| tgcaccaaca | aagggatggg | atgggggta | gaagatacga | ggataacggg | gctcaatggc | 240 |
| acaaataaga | acgaatactg | ccattaagac | tcgtgatcca | gcgactgaca | ccattgcatc | 300 |
| atctaagggc | ctcaaaacta | cctcggaact | gctgcgctga | tctggacacc | acagaggttc | 360 |
| cgagcacttt | aggttgcacc | aaatgtccca | ccaggtgcag | gcagaaaacg | ctggaacagc | 420 |
| gtgtacagtt | tgtcttaaca | aaaagtgagg | gcgctgaggt | cgagcagggt | ggtgtgactt | 480 |
| gttatagcct | ttagagctgc | gaaagcgcgt | atggatttgg | ctcatcaggc | cagattgagg | 540 |
| gtctgtggac | acatgtcatg | ttagtgtact | tcaatcgccc | cctggatata | gccccgacaa | 600 |
| taggccgtgg | cctcattttt | ttgccttccg | cacatttcca | ttgctcggta | cccacacctt | 660 |
| gcttctcctg | cacttgccaa | ccttaatact | ggtttacatt | gaccaacatc | ttacaagcgg | 720 |
| ggggcttgtc | tagggtatat | ataaacagtg | gctctcccaa | tcggttgcca | gtctcttttt | 780 |
| tcctttcttt | ccccacagat | tcgaaatcta | aactacacat | cacacaatgc | ctgttactga | 840 |

```
cgtccttaag cgaaagtccg gtgtcatcgt cggcgacgat gtccgagccg tgagtatcca      900
cgacaagatc agtgtcgaga cgacgcgttt tgtgtaatga cacaatccga aagtcgctag      960
caacacacac tctctacaca aactaaccca gctct                                 995

<210> SEQ ID NO 11
<211> LENGTH: 31
<212> TYPE: DNA
<213> ORGANISM: artificial sequence
<220> FEATURE:
<223> OTHER INFORMATION: Promoter

<400> SEQUENCE: 11
acggaattcc tgcaggccca tcgatgcaga a                                      31

<210> SEQ ID NO 12
<211> LENGTH: 31
<212> TYPE: DNA
<213> ORGANISM: artificial sequence
<220> FEATURE:
<223> OTHER INFORMATION: Promoter

<400> SEQUENCE: 12
ttctgcatcg atgggcctgc aggaattccg t                                      31

<210> SEQ ID NO 13
<211> LENGTH: 19
<212> TYPE: DNA
<213> ORGANISM: artificial sequence
<220> FEATURE:
<223> OTHER INFORMATION: Promoter

<400> SEQUENCE: 13
agagaccggg ttggcggcg                                                    19

<210> SEQ ID NO 14
<211> LENGTH: 30
<212> TYPE: DNA
<213> ORGANISM: artificial sequence
<220> FEATURE:
<223> OTHER INFORMATION: Promoter

<400> SEQUENCE: 14
ttggatcctt tgaatgattc ttatactcag                                        30

<210> SEQ ID NO 15
<211> LENGTH: 173
<212> TYPE: DNA
<213> ORGANISM: artificial sequence
<220> FEATURE:
<223> OTHER INFORMATION: XPR2 terminator

<400> SEQUENCE: 15
ccgcggcccg agattccggc ctcttcggcc gccaagcgac ccgggtggac gtctagaggt       60
acctagcaat taacagatag tttgccggtg ataattctct taacctccca cactcctttg     120
acataacgat ttatgtaacg aaactgaaat ttgaccagat attgtgtccg cgg             173

<210> SEQ ID NO 16
<211> LENGTH: 29
<212> TYPE: DNA
<213> ORGANISM: artificial sequence
<220> FEATURE:
<223> OTHER INFORMATION: Promoter
```

```
<400> SEQUENCE: 16
tttccgcggc ccgagattcc ggcctcttc                                           29

<210> SEQ ID NO 17
<211> LENGTH: 31
<212> TYPE: DNA
<213> ORGANISM: artificial sequence
<220> FEATURE:
<223> OTHER INFORMATION: Promoter

<400> SEQUENCE: 17
tttccgcgga cacaatatct ggtcaaattt c                                        31

<210> SEQ ID NO 18
<211> LENGTH: 788
<212> TYPE: DNA
<213> ORGANISM: artificial sequence
<220> FEATURE:
<223> OTHER INFORMATION: 5' end of codon optimized coumaroyl CoA ligase

<400> SEQUENCE: 18
atgtttcgat ccgagtacgc cgacgttcct cccgtcgacc tgcccattca cgatgctgtg         60
ctcggaggtg ctgccgcttt cggctctact cctgccctga tcgacggaac cgacggcacc        120
actctcacct acgagcaggt ggaccgattt cacagacgag tcgctgcagc ccttgccgag        180
acaggcgttc gaaagggaga cgtcttggct ctgcactctc ccaacactgt tgccttccca        240
cttgccttct acgctgccac cagagctggt gcctccgtca ccactgtgca tcctcttgct        300
acagcagaag agtttgccaa gcagctgaag gactctgctg cccgatggat tgtcaccgtt        360
tcccctctcc tgtccactgc ccgacgagct gccgagcttg ctggaggcgt ccaggagatt        420
ctggtttgcg acagcgcacc cggtcaccga tcccttgtcg atatgctggc ctctacagct        480
cccgaacctt ccgtcgccat cgaccctgca gaggacgttg ctgccttgcc ctactcttcc        540
ggaactaccg gtactcccaa gggtgtcatg ctcacccatc gacagattgc caccaacctg        600
gctcaactcg aaccttccat gcccctctgct cctggagatc gagttcttgc agtgcttccc        660
ttctttcaca tctatggtct gactgccctc atgaacgctc ctctgcgact cggagccacc        720
gtcgtggttc ttccacgatt cgacctggag cagtttctcg ctgccattca gaaccaccga        780
atcacttc                                                                788

<210> SEQ ID NO 19
<211> LENGTH: 33
<212> TYPE: DNA
<213> ORGANISM: artificial sequence
<220> FEATURE:
<223> OTHER INFORMATION: Promoter

<400> SEQUENCE: 19
tttccatggt tcgatccgag tacgccgacg ttc                                      33

<210> SEQ ID NO 20
<211> LENGTH: 29
<212> TYPE: DNA
<213> ORGANISM: artificial sequence
<220> FEATURE:
<223> OTHER INFORMATION: Promoter

<400> SEQUENCE: 20
cagcgaagtg attcggtggt tctgaatgg                                           29
```

<210> SEQ ID NO 21
<211> LENGTH: 2860
<212> TYPE: DNA
<213> ORGANISM: artificial sequence
<220> FEATURE:
<223> OTHER INFORMATION: Chimeric gene

<400> SEQUENCE: 21

| | | | | | |
|---|---|---|---|---|---|
| caattgcccc | ggagaagacg | gccaggccgc | ctagatgaca | aattcaacaa | ctcacagctg | 60 |
| actttctgcc | attgccacta | ggggggggcc | tttttatatg | gccaagccaa | gctctccacg | 120 |
| tcggttgggc | tgcacccaac | aataaatggg | tagggttgca | ccaacaaagg | gatgggatgg | 180 |
| ggggtagaag | atacgaggat | aacggggctc | aatggcacaa | ataagaacga | atactgccat | 240 |
| taagactcgt | gatccagcga | ctgacaccat | tgcatcatct | aagggcctca | aaactacctc | 300 |
| ggaactgctg | cgctgatctg | gacaccacag | aggttccgag | cactttaggt | tgcaccaaat | 360 |
| gtcccaccag | gtgcaggcag | aaaacgctgg | aacagcgtgt | acagtttgtc | ttaacaaaaa | 420 |
| gtgagggcgc | tgaggtcgag | cagggtggtg | tgacttgtta | tagcctttag | agctgcgaaa | 480 |
| gcgcgtatgg | atttggctca | tcaggccaga | ttgagggtct | gtggacacat | gtcatgttag | 540 |
| tgtacttcaa | tcgcccctg | gatatagccc | cgacaatagg | ccgtggcctc | attttttgc | 600 |
| cttccgcaca | tttccattgc | tcggtaccca | caccttgctt | ctcctgcact | tgccaacctt | 660 |
| aatactggtt | tacattgacc | aacatcttac | aagcgggggg | cttgtctagg | gtatatataa | 720 |
| acagtggctc | tcccaatcgg | ttgccagtct | ctttttcct | ttctttcccc | acagattcga | 780 |
| aatctaaact | acacatcaca | caatgcctgt | tactgacgtc | cttaagcgaa | agtccggtgt | 840 |
| catcgtcggc | gacgatgtcc | gagccgtgag | tatccacgac | aagatcagtg | tcgagacgac | 900 |
| gcgttttgtg | taatgacaca | atccgaaagt | cgctagcaac | acacactctc | tacacaaact | 960 |
| aacccagctc | tccatggttc | gatccgagta | cgccgacgtt | cctcccgtcg | acctgcccat | 1020 |
| tcacgatgct | gtgctcggag | gtgctgccgc | tttcggctct | actcctgccc | tgatcgacgg | 1080 |
| aaccgacggc | accactctca | cctacgagca | ggtggaccga | tttcacagac | gagtcgctgc | 1140 |
| agcccttgcc | gagacaggcg | ttcgaaaggg | agacgtcttg | gctctgcact | ctcccaacac | 1200 |
| tgttgccttc | ccacttgcct | tctacgctgc | caccagagct | ggtgcctccg | tcaccactgt | 1260 |
| gcatcctctt | gctacagcag | aagagtttgc | caagcagctg | aaggactctg | ctgcccgatg | 1320 |
| gattgtcacc | gtttccctc | tcctgtccac | tgcccgacga | gctgccgagc | ttgctggagg | 1380 |
| cgtccaggag | attctggttt | gcgacagcgc | acccggtcac | cgatcccttg | tcgatatgct | 1440 |
| ggcctctaca | gctcccgaac | cttccgtcgc | catcgaccct | gcagaggacg | ttgctgcctt | 1500 |
| gccctactct | tccggaacta | ccggtactcc | caagggtgtc | atgctcaccc | atcgacagat | 1560 |
| tgccaccaac | ctggctcaac | tcgaaccttc | catgccctct | gctcctggag | atcgagttct | 1620 |
| tgcagtgctt | cccttctttc | acatctatgg | tctgactgcc | tcatgaacg | ctcctctgcg | 1680 |
| actcggagcc | accgtcgtgg | ttcttccacg | attcgacctg | gagcagtttc | tcgctgccat | 1740 |
| tcagaaccac | cgaatcactt | cgctgtacgt | cgctcctccc | attgtgctgg | cacttgccaa | 1800 |
| acatcccttg | gttgccgact | acgatctctc | ctcgctgaga | tacatcgtgt | cggctgccgc | 1860 |
| acctctcgat | gctcgacttg | ccgctgcctg | ttcccagcga | tcggactgc | ctcccgtcgg | 1920 |
| tcaggcttac | ggcatgaccg | agctgtctcc | tggaacacac | gtggttccct | ggacgcaat | 1980 |
| ggccgatgct | cctcctggca | ctgtcggtcg | actcattgcc | ggaaccgaga | tgcgaatcgt | 2040 |
| ctccctcacc | gatccaggta | cagaccttcc | tgctggagag | tctggcgaga | ttctcattcg | 2100 |

-continued

```
aggtccccag atcatgaagg gctacttggg aagacccgat gccactgctg ccatgatcga   2160
cgaagaaggc tggctgcaca caggtgatgt cggacacgtg gatgccgatg gctggctgtt   2220
tgttgtcgac cgagtcaagg agcttatcaa gtacaaggga ttccaggttg ctcctgccga   2280
gctggaagcc cacctgctca ctcatccagg tgtcgcagac gctgccgtgg ttggagccta   2340
cgacgatgac ggcaacgagg ttccccatgc cttcgtcgtg cgacaacctg ccgctcccgg   2400
tcttgccgag tccgagatca tgatgtacgt tgccgaacga gtcgctccct acaagcgagt   2460
gcgacgagtt accttcgtcg atgccgttcc cagagctgcc tccggcaaga ttctccgaag   2520
acagctgcga gagcctcgat aagcggccgc aagtgtggat ggggaagtga gtgcccggtt   2580
ctgtgtgcac aattggcaat ccaagatgga tggattcaac acagggatat agcgagctac   2640
gtggtggtgc gaggatatag caacggatat ttatgtttga cacttgagaa tgtacgatac   2700
aagcactgtc caagtacaat actaaacata ctgtacatac tcatactcgt acccgggcaa   2760
cggtttcact tgagtgcagt ggctagtgct cttactcgta cagtgtgcaa tactgcgtat   2820
catagtcttt gatgtatatc gtattcattc atgttagttg                         2860

<210> SEQ ID NO 22
<211> LENGTH: 24
<212> TYPE: DNA
<213> ORGANISM: artificial sequence
<220> FEATURE:
<223> OTHER INFORMATION: Promoter
<400> SEQUENCE: 22
ggaaaaggtc gacgagtatc tgtc                                            24

<210> SEQ ID NO 23
<211> LENGTH: 33
<212> TYPE: DNA
<213> ORGANISM: artificial sequence
<220> FEATURE:
<223> OTHER INFORMATION: Promoter
<400> SEQUENCE: 23
cccttaatta agtcatacac aagtcagctt tct                                  33

<210> SEQ ID NO 24
<211> LENGTH: 33
<212> TYPE: DNA
<213> ORGANISM: artificial sequence
<220> FEATURE:
<223> OTHER INFORMATION: Promoter
<400> SEQUENCE: 24
acaattccac acaacgtacg agccggaagc ata                                  33

<210> SEQ ID NO 25
<211> LENGTH: 33
<212> TYPE: DNA
<213> ORGANISM: artificial sequence
<220> FEATURE:
<223> OTHER INFORMATION: Promoter
<400> SEQUENCE: 25
tatgcttccg gctcgtacgt tgtgtggaat tgt                                  33

<210> SEQ ID NO 26
<211> LENGTH: 1341
<212> TYPE: DNA
<213> ORGANISM: Mortierella alpina
```

<400> SEQUENCE: 26

```
atgggaacgg accaaggaaa aaccttcacc tgggaagagc tggcggccca taacaccaag      60
gacgacctac tcttggccat ccgcggcagg gtgtacgatg tcacaaagtt cttgagccgc     120
catcctggtg gagtggacac tctcctgctc ggagctggcc gagatgttac tccggtcttt     180
gagatgtatc acgcgtttgg ggctgcagat gccattatga agaagtacta tgtcggtaca     240
ctggtctcga atgagctgcc catcttcccg gagccaacgg tgttccacaa aaccatcaag     300
acgagagtcg agggctactt tacgatcgg aacattgatc ccaagaatag accagagatc     360
tggggacgat acgctcttat ctttggatcc ttgatcgctt cctactacgc gcagctcttt     420
gtgccttttcg ttgtcgaacg cacatggctt caggtggtgt ttgcaatcat catgggattt     480
gcgtgcgcac aagtcggact caaccctctt catgatgcgt ctcactttc agtgacccac     540
aaccccactg tctggaagat tctgggagcc acgcacgact ttttcaacgg agcatcgtac     600
ctggtgtgga tgtaccaaca tatgctcggc catcacccct acaccaacat tgctggagca     660
gatcccgacg tgtcgacgtc tgagcccgat gttcgtcgta tcaagcccaa ccaaaagtgg     720
tttgtcaacc acatcaacca gcacatgttt gttccttttcc tgtacggact gctggcgttc     780
aaggtgcgca ttcaggacat caacattttg tactttgtca agaccaatga cgctattcgt     840
gtcaatccca tctcgacatg gcacactgtg atgttctggg gcggcaaggc tttctttgtc     900
tggtatcgcc tgattgttcc cctgcagtat ctgcccctgg gcaaggtgct gctcttgttc     960
acggtcgcgg acatggtgtc gtcttactgg ctggcgctga ccttccaggc gaaccacgtt    1020
gttgaggaag ttcagtggcc gttgcctgac gagaacggga tcatccaaaa ggactgggca    1080
gctatgcagg tcgagactac gcaggattac gcacacgatt cgcacctctg gaccagcatc    1140
actggcagct tgaactacca ggctgtgcac catctgttcc ccaacgtgtc gcagcaccat    1200
tatcccgata ttctggccat catcaagaac acctgcagcg agtacaaggt tccataacctt    1260
gtcaaggata cgttttggca agcatttgct tcacatttgg agcacttgcg tgttcttgga    1320
ctccgtccca aggaagagta g                                              1341
```

<210> SEQ ID NO 27
<211> LENGTH: 30
<212> TYPE: DNA
<213> ORGANISM: artificial sequence
<220> FEATURE:
<223> OTHER INFORMATION: Promoter

<400> SEQUENCE: 27

```
ttttccatgg gaacggacca aggaaaaacc                                       30
```

<210> SEQ ID NO 28
<211> LENGTH: 30
<212> TYPE: DNA
<213> ORGANISM: artificial sequence
<220> FEATURE:
<223> OTHER INFORMATION: Promoter

<400> SEQUENCE: 28

```
tttgcggccg cctactcttc cttgggacgg                                       30
```

<210> SEQ ID NO 29
<211> LENGTH: 32
<212> TYPE: DNA
<213> ORGANISM: artificial sequence
<220> FEATURE:

<223> OTHER INFORMATION: Promoter

<400> SEQUENCE: 29
tgacataacg atttaaatgt aacgaaactg aa                          32

<210> SEQ ID NO 30
<211> LENGTH: 32
<212> TYPE: DNA
<213> ORGANISM: artificial sequence
<220> FEATURE:
<223> OTHER INFORMATION: Promoter

<400> SEQUENCE: 30
ttcagtttcg ttacatttaa atcgttatgt ca                          32

<210> SEQ ID NO 31
<211> LENGTH: 31
<212> TYPE: DNA
<213> ORGANISM: artificial sequence
<220> FEATURE:
<223> OTHER INFORMATION: Promoter

<400> SEQUENCE: 31
tcaacggatg ctcaatcgat ttcgacagta a                           31

<210> SEQ ID NO 32
<211> LENGTH: 31
<212> TYPE: DNA
<213> ORGANISM: artificial sequence
<220> FEATURE:
<223> OTHER INFORMATION: Promoter

<400> SEQUENCE: 32
ttactgtcga aatcgattga gcatccgttg a                           31

<210> SEQ ID NO 33
<211> LENGTH: 31
<212> TYPE: DNA
<213> ORGANISM: artificial sequence
<220> FEATURE:
<223> OTHER INFORMATION: Promoter

<400> SEQUENCE: 33
gagcttggcg taatcgatgg tcatagctgt t                           31

<210> SEQ ID NO 34
<211> LENGTH: 31
<212> TYPE: DNA
<213> ORGANISM: artificial sequence
<220> FEATURE:
<223> OTHER INFORMATION: Promoter

<400> SEQUENCE: 34
aacagctatg accatcgatt acgccaagct c                           31

<210> SEQ ID NO 35
<211> LENGTH: 33
<212> TYPE: DNA
<213> ORGANISM: artificial sequence
<220> FEATURE:
<223> OTHER INFORMATION: Promoter

<400> SEQUENCE: 35
aaaccatggt tgtaatatgt gtgtttgttt gga                         33

<210> SEQ ID NO 36
<211> LENGTH: 33
<212> TYPE: DNA
<213> ORGANISM: artificial sequence
<220> FEATURE:
<223> OTHER INFORMATION: Promoter

<400> SEQUENCE: 36
ggcgtttaaa ccattaattc tcacgtgaca cag     33

<210> SEQ ID NO 37
<211> LENGTH: 31
<212> TYPE: DNA
<213> ORGANISM: artificial sequence
<220> FEATURE:
<223> OTHER INFORMATION: Promoter

<400> SEQUENCE: 37
tttgcggccg ctatttatca ctctttacaa c     31

<210> SEQ ID NO 38
<211> LENGTH: 30
<212> TYPE: DNA
<213> ORGANISM: artificial sequence
<220> FEATURE:
<223> OTHER INFORMATION: Promoter

<400> SEQUENCE: 38
tttatcgata ggaagaggac aagcggctgc     30

<210> SEQ ID NO 39
<211> LENGTH: 31
<212> TYPE: DNA
<213> ORGANISM: artificial sequence
<220> FEATURE:
<223> OTHER INFORMATION: Promoter

<400> SEQUENCE: 39
atcgaaacca gcatgtgatc gaatggcata c     31

<210> SEQ ID NO 40
<211> LENGTH: 31
<212> TYPE: DNA
<213> ORGANISM: artificial sequence
<220> FEATURE:
<223> OTHER INFORMATION: Promoter

<400> SEQUENCE: 40
gtatgccatt cgatcacatg ctggtttcga t     31

<210> SEQ ID NO 41
<211> LENGTH: 32
<212> TYPE: DNA
<213> ORGANISM: artificial sequence
<220> FEATURE:
<223> OTHER INFORMATION: Promoter

<400> SEQUENCE: 41
tttgcggccg caagtgtgga tggggaagtg ag     32

<210> SEQ ID NO 42
<211> LENGTH: 30
<212> TYPE: DNA
<213> ORGANISM: artificial sequence
<220> FEATURE:
<223> OTHER INFORMATION: Promoter

```
<400> SEQUENCE: 42
tttcgtacga ttgacgcaac taacatgaat                                    30

<210> SEQ ID NO 43
<211> LENGTH: 1035
<212> TYPE: DNA
<213> ORGANISM: Yarrowia lipolytica

<400> SEQUENCE: 43
gtagctaacg gtagcaggcg aactactggt acatacctcc cccggaatat gtacaggcat    60
aatgcgtatc tgtgggacat gtggtcgttg cgccattatg taagcagcgt gtactcctct   120
gactgtccat atggtttgct ccatctcacc ctcatcgttt tcattgttca caggcggcca   180
caaaaaaact gtcttctctc cttctctctt cgccttagtc tactcggacc agttttagtt   240
tagcttggcg ccactggata aatgagacct caggccttgt gatgaggagg tcacttatga   300
agcatgttag gaggtgcttg tatggataga aagcaccca aaataataag aataataata    360
aaacaggggg cgttgtcatt tcatatcgtg ttttcaccat caatacacct ccaaacaatg   420
cccttcatgt ggccagcccc aatattgtcc tgtagttcaa ctctatgcag ctcgtatctt   480
attgagcaag taaaactctg tcagccgata ttgcccgacc cgcgacaagg gtcaacaagg   540
tggtgtaagg ccttcgcaga agtcaaaact gtgccaaaca aacatctaga gtctctttgg   600
tgtttctcgc atatatttwa tcggctgtct tacgtatttg cgcctcggta ccggactaat   660
ttcggatcat ccccaatacg ctttttcttc gcagctgtca acagtgtcca tgatctatcc   720
acctaaatgg gtcatatgag gcgtataatt tcgtggtgct gataataatt cccatatatt   780
tgacacaaaa cttcccccc tagcataca tctcacaatc tcacttcttg tgcttctgtc    840
acacatctcc tccagctgac ttcaactcac acctctgccc cagttggtct acagcggtat   900
aaggtttctc cgcatagagg tgcaccactc ctcccgatac ttgtttgtgt gacttgtggg   960
tcacgacata tatatctaca cacattgcgc cacccctttgg ttcttccagc acaacaaaaa  1020
cacgacacgc taacc                                                   1035

<210> SEQ ID NO 44
<211> LENGTH: 39
<212> TYPE: DNA
<213> ORGANISM: artificial sequence
<220> FEATURE:
<223> OTHER INFORMATION: Promoter

<400> SEQUENCE: 44
gccatttaaa tgtagctaac ggtagcaggc gaactactg                          39

<210> SEQ ID NO 45
<211> LENGTH: 34
<212> TYPE: DNA
<213> ORGANISM: artificial sequence
<220> FEATURE:
<223> OTHER INFORMATION: Promoter

<400> SEQUENCE: 45
tttccatggt tagcgtgtcg tgttttttgtt gtgc                              34

<210> SEQ ID NO 46
<211> LENGTH: 36
<212> TYPE: DNA
<213> ORGANISM: artificial sequence
<220> FEATURE:
<223> OTHER INFORMATION: Promoter
```

<400> SEQUENCE: 46
atgatgactc aggcgtttaa acgacggaat tcctgc                                    36

<210> SEQ ID NO 47
<211> LENGTH: 36
<212> TYPE: DNA
<213> ORGANISM: artificial sequence
<220> FEATURE:
<223> OTHER INFORMATION: Promoter

<400> SEQUENCE: 47
gcaggaattc cgtcgtttaa acgcctgagt catcat                                    36

<210> SEQ ID NO 48
<211> LENGTH: 8560
<212> TYPE: DNA
<213> ORGANISM: artificial sequence
<220> FEATURE:
<223> OTHER INFORMATION: Plasmid
<220> FEATURE:
<221> NAME/KEY: misc_feature
<222> LOCATION: (692)..(695)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t

<400> SEQUENCE: 48
catggcgtcc acttcggctc tgcccaagca gaaccctgcg cttagacgca ccgtcacctc         60
aactactgtg acggattctg agtctgccgc cgtctctcct tcagactctc cccgccactc        120
ggcctcttcc acatcgctct cgtccatgtc cgaggttgat atcgccaagc ccaagtccga        180
gtatggtgtc atgctcgaca cctacggcaa ccagttcgag gttcccgact ttaccatcaa        240
ggacatctac aatgccatcc ctaagcactg cttcaagcgc tccgctctca agggatacgg        300
ttatatcctc cgcgacattg tcctcctgac taccactttc agcatctggt acaactttgt        360 gaccccgaa tatatcccct ccaccccgc ccgcgctggt ctgtgggccg tgtacaccgt         420
tcttcagggt cttttcggta ctggtctctg ggttattgcc catgagtgcg gtcacggtgc        480
tttctccgat tctcgcatca tcaacgacat tactggctgg gttcttcact cttccctcct        540
tgtcccctac ttcagctggc aaatctccca ccgaaagcac acaaggcca ctggcaacat         600 ggagcgtgac atggtcttcg ttccccgaac ccgcgagcag caggctactc gtctcggaaa        660 gatgaccac gagctcgctc atcttactga gnnnntcgtn ggctggccca actacctcat         720
caccaatgtt accggccaca actaccacga gcgccagcgt gagggtcgcg gcaagggcaa        780
gcataacggc ctcggcggtg gtgttaacca cttcgatccc cgcagccctc tgtacgagaa        840
cagtgacgct aagctcatcg tcctcagcga tattggtatc ggtctgatgg ccactgctct        900
gtacttcctc gttcagaagt tcggtttcta caacatggcc atctggtact tgttccccta        960
cctctgggtt aaccactggc tcgttgccat caccttcctc cagcacaccg accctaccct       1020
tccccactac accaacgacg agtggaactt cgtccgtggt gccgctgcta ccattgaccg       1080
tgagatgggc ttcatcggcc gccaccttct ccacggcatc atcgagactc atgtcctcca       1140
ccactacgtc agcagcatcc ccttctacaa cgcggacgag gccaccgagg ccattaagcc       1200
catcatgggc aagcactacc gggctgatgt ccaggatggt cctcgtgcct catccgcgc       1260 catgtaccgc agtgcgcgta tgtgccagtg ggttgagccc agcgctggtg ccgagggtgc       1320

```
tggtaagggt gttctgttct tccgcaaccg caacaacgtg ggcacccccc ccgctgttat   1380
caagcccgtt gcttaagtag gcgcggccgc aagtgtggat ggggaagtga gtgcccggtt   1440
ctgtgtgcac aattggcaat ccaagatgga tggattcaac acagggatat agcgagctac   1500
gtggtggtgc gaggatatag caacggatat ttatgtttga cacttgagaa tgtacgatac   1560
aagcactgtc caagtacaat actaaacata ctgtacatac tcatactcgt acccgggcaa   1620
cggtttcact tgagtgcagt ggctagtgct cttactcgta cagtgtgcaa tactgcgtat   1680
catagtcttt gatgtatatc gtattcattc atgttagttg cgtacgggtg aagcttccac   1740
tggtcggcgt ggtagtgggg cagagtgggg tcggtgtgct gcaggtaggt gatggccacg   1800
agccagtggt tgacccacag gtaggggatc aggtagtaga gggtgacgga agccaggccc   1860
catcggttga tggagtatgc gatgacggac atggtgatac caataccgac gttagagatc   1920
cagatgttga accagtcctt cttctcaaac agcggggcgt tggggttgaa gtggttgaca   1980
gcccatttgt tgagcttggg gtacttctgt ccggtaacgt aagacagcag atacagaggc   2040
catccaaaca cctgctgggt gatgaggccg tagagggtca tgaggggagc gtcctcagca   2100
agctcagacc agtcatgggc gcctcggttc tccataaact cctttcggtc cttgggcaca   2160
aacaccatat cacgggtgag gtgaccagtg gacttgtggt gcatggagtg ggtcagcttc   2220
caggcgtagt aagggaccag catggaggag tgcagaaccc atccggtgac gttgttgacg   2280
gtgttagagt cggagaaagc agagtggcca cactcgtggg caagaaccca cagaccggtg   2340
ccaaacagac cctggacaat ggagtacatg gcccaggcca cagctcggcc ggaagccgag   2400
ggaataagag gcaggtacgc gtaggccatg taggcaaaaa cggcgataaa gaagcaggcg   2460
cgccagctgc attaatgaat cggccaacgc gcggggagag gcggtttgcg tattgggcgc   2520
tcttccgctt cctcgctcac tgactcgctg cgctcggtcg ttcggctgcg gcgagcggta   2580
tcagctcact caaaggcggt aatacggtta tccacagaat caggggataa cgcaggaaag   2640
aacatgtgag caaaaggcca gcaaaaggcc aggaaccgta aaaaggccgc gttgctggcg   2700
tttttccata ggctccgccc ccctgacgag catcacaaaa atcgacgctc aagtcagagg   2760
tggcgaaacc cgacaggact ataaagatac caggcgtttc cccctggaag ctccctcgtg   2820
cgctctcctg ttccgaccct gccgcttacc ggatacctgt ccgcctttct cccttcggga   2880
agcgtggcgc tttctcatag ctcacgctgt aggtatctca gttcggtgta ggtcgttcgc   2940
tccaagctgg gctgtgtgca cgaaccccccc gttcagcccg accgctgcgc cttatccggt   3000
aactatcgtc ttgagtccaa cccggtaaga cacgacttat cgccactggc agcagccact   3060
ggtaacagga ttagcagagc gaggtatgta ggcggtgcta cagagttctt gaagtggtgg   3120
cctaactacg gctacactag aagaacagta tttggtatct gcgctctgct gaagccagtt   3180
accttcggaa aaagagttgg tagctcttga tccggcaaac aaaccaccgc tggtagcggt   3240
ggtttttttg tttgcaagca gcagattacg cgcagaaaaa aaggatctca agaagatcct   3300
ttgatctttt ctacggggtc tgacgctcag tggaacgaaa actcacgtta agggattttg   3360
gtcatgagat tatcaaaaag gatcttcacc tagatccttt taaattaaaa atgaagtttt   3420
aaatcaatct aaagtatata tgagtaaact tggtctgaca gttaccaatg cttaatcagt   3480
gaggcaccta tctcagcgat ctgtctattt cgttcatcca tagttgcctg actccccgtc   3540
gtgtagataa ctacgatacg ggagggctta ccatctggcc ccagtgctgc aatgataccg   3600
cgagacccac gctcaccggc tccagattta tcagcaataa accagccagc cggaagggcc   3660
gagcgcagaa gtggtcctgc aactttatcc gcctccatcc agtctattaa ttgttgccgg   3720
```

```
gaagctagag taagtagttc gccagttaat agtttgcgca acgttgttgc cattgctaca    3780
ggcatcgtgg tgtcacgctc gtcgtttggt atggcttcat tcagctccgg ttcccaacga    3840
tcaaggcgag ttacatgatc ccccatgttg tgcaaaaaag cggttagctc cttcggtcct    3900
ccgatcgttg tcagaagtaa gttggccgca gtgttatcac tcatggttat ggcagcactg    3960
cataattctc ttactgtcat gccatccgta agatgctttt ctgtgactgg tgagtactca    4020
accaagtcat tctgagaata gtgtatgcgg cgaccgagtt gctcttgccc ggcgtcaata    4080
cgggataata ccgcgccaca tagcagaact ttaaaagtgc tcatcattgg aaaacgttct    4140
tcggggcgaa aactctcaag gatcttaccg ctgttgagat ccagttcgat gtaacccact    4200
cgtgcaccca actgatcttc agcatctttt actttcacca gcgtttctgg gtgagcaaaa    4260
acaggaaggc aaaatgccgc aaaaaaggga ataagggcga cacggaaatg ttgaatactc    4320
atactcttcc tttttcaata ttattgaagc atttatcagg gttattgtct catgagcgga    4380
tacatatttg aatgtattta gaaaaataaa caaatagggg ttccgcgcac atttccccga    4440
aaagtgccac ctgatgcggt gtgaaatacc gcacagatgc gtaaggagaa ataccgcat    4500
caggaaattg taagcgttaa tattttgtta aaattcgcgt taaattttg ttaaatcagc    4560
tcatttttta accataggc cgaaatcggc aaaatccctt ataaatcaaa agaatagacc    4620
gagatagggt tgagtgttgt tccagtttgg aacaagagtc cactattaaa gaacgtggac    4680
tccaacgtca aagggcgaaa aaccgtctat cagggcgatg gcccactacg tgaaccatca    4740
ccctaatcaa gttttttggg gtcgaggtgc cgtaaagcac taaatcggaa ccctaaaggg    4800
agcccccgat ttagagcttg acggggaaag ccggcgaacg tggcgagaaa ggaagggaag    4860
aaaagcgaaa gagcgggcgc tagggcgctg gcaagtgtag cggtcacgct gcgcgtaacc    4920
accacacccg ccgcgcttaa tgcgccgcta cagggcgcgt ccattcgcca ttcaggctgc    4980
gcaactgttg ggaagggcga tcggtgcggg cctcttcgct attacgccag ctggcgaaag    5040
ggggatgtgc tgcaaggcga ttaagttggg taacgccagg gttttcccag tcacgacgtt    5100
gtaaaacgac ggccagtgaa ttgtaatacg actcactata gggcgaattg ggcccgacgt    5160
cgcatgcttg aatctacaag taggagggtt ggagtgatta agtgaaactt ctttaacggc    5220
tctatgccaa ttctattgat atccgaaaca tcagtatgaa ggtctgataa gggtgacttc    5280
ttcccacaga ttcgtatcag tacgagtacg agaccggtac ttgtaacagt attgatacta    5340
aagggaaact acaacggttg tcagcgtaat gtgacttcgc ccatgaacgc agacacgcag    5400
tgccgagtgc ggtgatatcg cctactcgtt acgtccatgg actacacaac ccctcggctt    5460
cgcttggctt agcctcgggc tcggtgctgt tcagttaaaa cacaatcaaa taacatttct    5520
acttttaga aggcaggccg tcaggagcaa ctccgactcc attgacgttt ctaaacatct    5580
gaatgccttc cttaccttca acaaactgga aggttcgggc gacagtgtaa agagacttga    5640
tgaagttggt gtcgtcgtgt cggtagtgct tgcccatgac cttcttgatc ttctcagtgg    5700
cgattcgggc gttgtagaag ggaattccgt cgtcgcctga gtcgacgagt atctgtctga    5760
ctcgtcattg ccgcctttgg agtacgactc caactatgag tgtgcttgga tcactttgac    5820
gatacattct tcgttggagg ctgtgggtct gacagctgcg ttttcggcgc ggttggccga    5880
caacaatatc agctgcaacg tcattgctgg ctttcatcat gatcacattt ttgtcggcaa    5940
aggcgacgcc cagagagcca ttgacgttct ttctaatttg gaccgatagc cgtatagtcc    6000
agtctatcta taagttcaac taactcgtaa ctattaccat aacatatact tcactgcccc    6060
```

```
agataaggtt ccgataaaaa gttctgcaga ctaaatttat ttcagtctcc tcttcaccac   6120
caaaatgccc tcctacgaag ctcgagctaa cgtccacaag tccgcctttg ccgctcgagt   6180
gctcaagctc gtggcagcca agaaaaccaa cctgtgtgct tctctggatg ttaccaccac   6240
caaggagctc attgagcttg ccgataaggt cggaccttat gtgtgcatga tcaaaaccca   6300
tatcgacatc attgacgact tcacctacgc cggcactgtg ctccccctca aggaacttgc   6360
tcttaagcac ggtttcttcc tgttcgagga cagaaagttc gcagatattg caacactgt   6420 caagcaccag taccggtgtc accgaatcgc cgagtggtcc gatatcacca acgcccacgg   6480
tgtacccgga accggaatca ttgctggcct gcgagctggt gccgaggaaa ctgtctctga   6540
acagaagaag gaggacgtct ctgactacga gaactcccag tacaaggagt tcctagtccc   6600
ctctcccaac gagaagctgg ccagaggtct gctcatgctg gccgagctgt cttgcaaggg   6660
ctctctggcc actggcgagt actccaagca gaccattgag cttgcccgat ccgaccccga   6720
gtttgtggtt ggcttcattg cccagaaccg acctaagggc gactctgagg actggcttat   6780
tctgaccccc ggggtgggtc ttgacgacaa gggagacgct ctcggacagc agtaccgaac   6840
tgttgaggat gtcatgtcta ccggaacgga tatcataatt gtcggccgag gtctgtacgg   6900
ccagaaccga gatcctattg aggaggccaa gcgataccag aaggctggct gggaggctta   6960
ccagaagatt aactgttaga ggttagacta tggatatgta atttaactgt gtatatagag   7020
agcgtgcaag tatggagcgc ttgttcagct tgtatgatgg tcagacgacc tgtctgatcg   7080
agtatgtatg atactgcaca acctgtgtat ccgcatgatc tgtccaatgg ggcatgttgt   7140
tgtgtttctc gatacggaga tgctgggtac agtgctaata cgttgaacta cttatactta   7200
tatgaggctc gaagaaagct gacttgtgta tgacttaatt aatttgaatc gaatcgatga   7260
gcctaaaatg aacccgagta tatctcataa aattctcggt gagaggtctg tgactgtcag   7320
tacaaggtgc cttcattatg ccctcaacct taccataccct cactgaatgt agtgtacctc   7380
taaaaatgaa atacagtgcc aaaagccaag gcactgagct cgtctaacgg acttgatata   7440
caaccaatta aaacaaatga aaagaaatac agttctttgt atcatttgta acaattaccc   7500
tgtacaaact aaggtattga aatcccacaa tattcccaaa gtccaccct ttccaaattg   7560 tcatgcctac aactcatata ccaagcacta acctaccgtt taaacagtgt acgcagatct   7620
actatagagg aacatttaaa ttgccccgga gaagacggcc aggccgccta gatgacaaat   7680
tcaacaactc acagctgact ttctgccatt gccactaggg gggggccttt ttatatggcc   7740
aagccaagct ctccacgtcg gttgggctgc acccaacaat aaatgggtag ggttgcacca   7800
acaaagggat gggatggggg gtagaagata cgaggataac ggggctcaat ggcacaaata   7860
agaacgaata ctgccattaa gactcgtgat ccagcgactg acaccattgc atcatctaag   7920
ggcctcaaaa ctacctcgga actgctgcgc tgatctggac accacagagg ttccgagcac   7980
tttaggttgc accaaatgtc ccaccaggtg caggcagaaa acgctggaac agcgtgtaca   8040
gtttgtctta acaaaaagtg agggcgctga ggtcgagcag ggtggtgtga cttgttatag   8100
cctttagagc tgcgaaagcg cgtatggatt tggctcatca ggccagattg agggtctgtg   8160
gacacatgtc atgttagtgt acttcaatcg ccccctggat atagccccga caataggccg   8220
tggcctcatt tttttgcctt ccgcacattt ccattgctcg atacccacac cttgcttctc   8280
ctgcacttgc caaccttaat actggtttac attgaccaac atcttacaag cgggggggctt   8340 gtctaggta tatataaaca gtggctctcc caatcggttg ccagtctctt tttccttc   8400 tttcccaca gattcgaaat ctaaaactaca catcacagaa ttccgagccg tgagtatcca   8460
```

```
cgacaagatc agtgtcgaga cgacgcgttt tgtgtaatga cacaatccga aagtcgctag      8520
caacacacac tctctacaca aactaaccca gctctggtac                           8560

<210> SEQ ID NO 49
<211> LENGTH: 730
<212> TYPE: DNA
<213> ORGANISM: Yarrowia lipolytica

<400> SEQUENCE: 49
tgcttcttta tcgccgtttt tgcctacatg gcctacgcgt acctgcctct tattccctcg       60
gcttccggcc gagctgtggc ctgggccatg tactccattg tccagggtct gtttggcacc      120
ggtctgtggg ttcttgccca cgagtgtggc cactctgctt tctccgactc taacaccgtc      180
aacaacgtca ccggatgggt tctgcactcc tccatgctgg tcccttacta cgcctggaag      240 ctgaccccact ccatgcacca caagtccact ggtcacctca cccgtgatat ggtgtttgtg     300
cccaaggacc gaaaggagtt tatggagaac cgaggcgccc atgactggtc tgagcttgct      360
gaggacgctc ccctcatgac cctctacggc ctcatcaccc agcaggtgtt tggatggcct      420
ctgtatctgc tgtcttacgt taccggacag aagtacccca agctcaacaa atgggctgtc      480
aaccacttca cccccaacgc cccgctgttt gagaagaagg actggttcaa catctggatc      540
tctaacgtcg gtattggtat caccatgtcc gtcatcgcat actccatcaa ccgatggggc      600
ctggcttccg tcaccctcta ctacctgatc ccctacctgt gggtcaacca ctggctcgtg      660
gccatcacct acctgcagca caccgacccc actctgcccc actaccacgc cgaccagtgg      720
aagcttcacc                                                            730

<210> SEQ ID NO 50
<211> LENGTH: 573
<212> TYPE: DNA
<213> ORGANISM: Yarrowia lipolytica

<400> SEQUENCE: 50
ttgaatctac aagtaggagg gttggagtga ttaagtgaaa cttctttaac ggctctatgc       60
cagttctatt gatatccgaa acatcagtat gaaggtctga taagggtgac ttcttcccac      120
agattcgtat cagtacgagt acgagaccgg tacttgtaac agtattgata ctaaagggaa      180
actacaacgg ttgtcagcgt aatgtgactt cgcccatgaa cgcagacacg cagtgccgag      240
tgcggtgata tcgcctactc gttacgtcca tggactacac aaccccctcgg cttcgcttgg      300 cttagcctcg ggctcggtgc tgttcagtta aaacacaatc aaataacatt tctactttttt     360 agaaggcagg ccgtcaggag caactccgac tccattgacg tttctaaaca tctgaatgcc      420
ttccttacct tcaacaaact ggcaggttcg ggcgacagtg taaagagact tgatgaagtt      480
ggtgtcgtcg tgtcggtagt gcttgcccat gaccttcttg atcttctcag tggcgattcg      540
ggcgttgtag aagggaattc cgtcgtcgcc tga                                  573

<210> SEQ ID NO 51
<211> LENGTH: 920
<212> TYPE: DNA
<213> ORGANISM: artificial sequence
<220> FEATURE:
<223> OTHER INFORMATION: Promoter

<400> SEQUENCE: 51
tgccccggag aagacggcca ggccgcctag atgacaaatt caacaactca cagctgactt       60
```

```
tctgccattg ccactagggg ggggcctttt tatatggcca agccaagctc tccacgtcgg    120
ttgggctgca cccaacaata aatgggtagg gttgcaccaa caaagggatg ggatgggggg    180
tagaagatac gaggataacg gggctcaatg gcacaaataa gaacgaatac tgccattaag    240
actcgtgatc cagcgactga caccattgca tcatctaagg gcctcaaaac tacctcggaa    300
ctgctgcgct gatctggaca ccacagaggt tccgagcact ttaggttgca ccaaatgtcc    360
caccaggtgc aggcagaaaa cgctggaaca gcgtgtacag tttgtcttaa caaaaagtga    420
gggcgctgag gtcgagcagg gtggtgtgac ttgttatagc ctttagagct gcgaaagcgc    480
gtatggattt ggctcatcag gccagattga gggtctgtgg acacatgtca tgttagtgta    540
cttcaatcgc cccctggata tagccccgac aataggccgt ggcctcattt ttttgccttc    600
cgcacatttc cattgctcga tacccacacc ttgcttctcc tgcacttgcc aaccttaata    660
ctggtttaca ttgaccaaca tcttacaagc gggggcttg tctagggtat atataaacag    720
tggctctccc aatcggttgc cagtctcttt tttcctttct ttcccacag attcgaaatc    780 taaactacac atcacagaat tccgagccgt gagtatccac gacaagatca gtgtcgagac    840
gacgcgtttt gtgtaatgac acaatccgaa agtcgctagc aacacacact ctctacacaa    900
actaacccag ctctggtacc                                                920
```

<210> SEQ ID NO 52
<211> LENGTH: 1399
<212> TYPE: DNA
<213> ORGANISM: Fusarium moniliforme
<220> FEATURE:
<221> NAME/KEY: misc_feature
<222> LOCATION: (691)..(694)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t

<400> SEQUENCE: 52

```
atggcgtcca cttcggctct gcccaagcag aaccctgcgc ttagacgcac cgtcacctca     60
actactgtga cggattctga gtctgccgcc gtctctcctt cagactctcc ccgccactcg    120
gcctcttcca catcgctctc gtccatgtcc gaggttgata tcgccaagcc caagtccgag    180
tatggtgtca tgctcgacac ctacggcaac cagttcgagg ttcccgactt taccatcaag    240
gacatctaca atgccatccc taagcactgc ttcaagcgct ccgctctcaa gggatacggt    300
tatatcctcc gcgacattgt cctcctgact accactttca gcatctggta caactttgtg    360
acccccgaat atatcccctc caccccgcc cgcgctggtc tgtgggccgt gtacaccgtt    420
cttcagggtc ttttcggtac tggtctctgg ttattgccc atgagtgcgg tcacggtgct    480
ttctccgatt ctcgcatcat caacgacatt actggctggg ttcttcactc ttccctcctt    540
gtcccctact tcagctggca aatctcccac cgaaagcacc acaaggccac tggcaacatg    600
gagcgtgaca tggtcttcgt tccccgaacc cgcgagcagc aggctactcg tctcggaaag    660
atgacccacg agctcgctca tcttactgag nnnntcgtng gctggcccaa ctacctcatc    720
accaatgtta ccggccacaa ctaccacgag cgccagcgtg agggtcgcgg caagggcaag    780
cataacggcc tcggcggtgg tgttaaccac ttcgatcccc gcagccctct gtacgagaac    840
agtgacgcta agctcatcgt cctcagcgat attggtatcg gtctgatggc cactgctctg    900
tacttcctcg ttcagaagtt cggtttctac aacatggcca tctggtactt tgttccctac    960
ctctgggtta ccactggct cgttgccatc accttcctcc agcacaccga ccctaccctt   1020
```

```
ccccactaca ccaacgacga gtggaacttc gtccgtggtg ccgctgctac cattgaccgt    1080
gagatgggct tcatcggccg ccaccttctc cacggcatca tcgagactca tgtcctccac    1140
cactacgtca gcagcatccc cttctacaac gcggacgagg ccaccgaggc cattaagccc    1200
atcatgggca agcactaccg ggctgatgtc caggatggtc ctcgtggctt catccgcgcc    1260
atgtaccgca gtgcgcgtat gtgccagtgg gttgagccca cgctggtgc cgagggtgct    1320 ggtaagggtg ttctgttctt ccgcaaccgc aacaacgtgg gcacccccc cgctgttatc    1380 aagcccgttg cttaagtag                                                 1399

<210> SEQ ID NO 53
<211> LENGTH: 310
<212> TYPE: DNA
<213> ORGANISM: Yarrowia lipolytica

<400> SEQUENCE: 53
aagtgtggat ggggaagtga gtgcccggtt ctgtgtgcac aattggcaat ccaagatgga    60
tggattcaac acagggatat agcgagctac gtggtggtgc gaggatatag caacggatat   120
ttatgtttga cacttgagaa tgtacgatac aagcactgtc caagtacaat actaaacata   180
ctgtacatac tcatactcgt acccgggcaa cggtttcact tgagtgcagt ggctagtgct   240
cttactcgta cagtgtgcaa tactgcgtat catagtcttt gatgtatatc gtattcattc   300
atgttagttg                                                          310

<210> SEQ ID NO 54
<211> LENGTH: 855
<212> TYPE: DNA
<213> ORGANISM: Yarrowia lipolytica

<400> SEQUENCE: 54
atgccctcct acgaagctcg agctaacgtc cacaagtccg cctttgccgc tcgagtgctc    60
aagctcgtgg cagccaagaa aaccaacctg tgtgcttctc tggatgttac caccaccaag   120
gagctcattg agcttgccga taaggtcgga ccttatgtgt gcatgatcaa acccatatc    180 gacatcattg acgacttcac ctacgccggc actgtgctcc ccctcaagga acttgctctt   240
aagcacggtt tcttcctgtt cgaggacaga aagttcgcag atattggcaa cactgtcaag   300
caccagtacc ggtgtcaccg aatcgccgag tggtccgata tcaccaacgc cacggtgta   360 cccggaaccg gaatcattgc tggcctgcga gctggtgccg aggaaactgt ctctgaacag   420
aagaaggagg acgtctctga ctacgagaac tcccagtaca aggagttcct agtcccctct   480
cccaacgaga gctggccag aggtctgctc atgctgcccg agctgtcttg caagggctct   540
ctggccactg gcgagtactc caagcagacc attgagcttg cccgatccga ccccgagttt   600
gtggttggct tcattgccca gaaccgacct aagggcgact ctgaggactg gcttattctg   660
acccccgggg tgggtcttga cgacaaggga gacgctctcg acagcagta ccgaactgtt   720 gaggatgtca tgtctaccgg aacggatatc ataattgtcg gccgaggtct gtacggccag   780
aaccgagatc ctattgagga ggccaagcga taccagaagg ctggctggga ggcttaccag   840
aagattaact gttag                                                    855

<210> SEQ ID NO 55
<211> LENGTH: 13797
<212> TYPE: DNA
<213> ORGANISM: Artificial sequence
<220> FEATURE:
```

<223> OTHER INFORMATION: Plasmid

<400> SEQUENCE: 55

```
taaccctcac taaagggaac aaaagctgga gctccaccgc ggacacaata tctggtcaaa      60
tttcagtttc gttacataaa tcgttatgtc aaaggagtgt gggaggttaa gagaattatc     120
accggcaaac tatctgttaa ttgctaggta cctctagacg tccacccggg tcgcttggcg     180
gccgaagagg ccggaatctc gggccgcggt ggcggccgct tagttagtga cggtgggaac     240
agagtggagc acgacagttt cgatggtcag tccaggacca aagccgaaga ggactcccca     300
gtccaggcct tcaccagtgg tggccttctc tcccttgagg gatttctttc gcatctcgtc     360
cagaatgaag agcacacaag cagaggacat gttgccgtac tcgctcagca cgtgtcgagt     420
ggcttcgagc ttcttcttct ccaggttgag cttagcctca actgcgtcga ggatggcagg     480
acctccggga tgagcaatcc agaacagaga gttccagtcg agataccga gagggtcgaa      540
agcctgggtc aggcacttct caatgttctc ggagatgaga gtgggcacat taggccacag     600
gtggaaggtg aggccaacct ctcgcaggtt ccggcaatg gcaccagcag agttggggat      660
aaaggtttgg gcagcggaga caagctgaa gaggggtcgc tcgatagaga catcgggatc      720
ggatccaaca atcacggcag aggagccatc accaaacaga gcctggccga cgagggagtc     780
cagggcatct tcagagggac ctcggaaggt cacgacagtg atttcggagc acacaacgag     840
gactcgtgct ccagcgttgt tctcggccag gtccttggca gttcggagca cggtgccacc     900
agcgtagcag ccttggtggt acagcatgac tcgtcggacg gaggtttcaa ggccgagcag     960
gttagcgagc ttgtagtcgg ctccaggcat ttccacacca gaggtagtac agaagaccag    1020
atgggtgatc ttggacttgg gctgtcccca ctctttgaga gccttcaggg cagcatcccg    1080
accgagtcgg ggaacctcag cggtgataat ctcctgtcgg atgttcagag aaggagccat    1140
gtaagcgcca atgttgggat gctcttcgag catctcttca gtcaggtgga tgtatcgctt    1200
cttaatcatg gatttgtcac agatccggtt gaacttcttc ttgagctcgg tcatgtgctc    1260
ggacttggtc actcggaagt agtaatcggc atagtcagac tggtagacac agtggtcagg    1320
ggtagcagtg ccaatggcca ggatggtagc gggacccttg gctcgctgag cgtttcggaa    1380
ttcctcaacg gaggccatgg tgaatgattc ttatactcag aaggaaatgc ttaacgattt    1440
cgggtgtgag ttgacaagga gagagagaaa agaagaggaa aggtaattcg gggacggtgg    1500
tcttttatac ccttggctaa agtcccaacc acaaagcaaa aaaattttca gtagtctatt    1560
ttgcgtccgg catgggttac ccggatggcc agacaaagaa actagtacaa agtctgaaca    1620
agcgtagatt ccagactgca gtaccctacg cccttaacgg caagtgtggg aaccggggga    1680
ggtttgatat gtggggtgaa ggggggctctc gccggggttg ggcccgctac tgggtcaatt    1740
tggggtcaat tggggcaatt ggggctgttt tttgggacac aaatacgccg ccaacccggt    1800
ctctcctgaa ttctgcatcg atcgaggaag aggacaagcg gctgcttctt aagtttgtga    1860
catcagtatc caaggcacca ttgcaaggat tcaaggcttt gaacccgtca tttgccattc    1920
gtaacgctgg tagacaggtt gatcggttcc ctacggcctc cacctgtgtc aatcttctca    1980
agctgcctga ctatcaggac attgatcaac ttcggaagaa acttttgtat gccattcgat    2040
cacatgctgt tttcgatttg tcttagagga acgcatatac agtaatcata gagaataaac    2100
gatattcatt tattaaagta gatagttgag gtagaagttg taaagagtga taaatagcgg    2160
ccgcttaagc gagcatcttg agcagcacat tgttgattct gccagacttg atggcttcgt    2220
agattttgga gacgttggag ccaatggtca cctcttgctt gccgagaaag acgtctcctc    2280
```

```
gtcgagcctt cacaccaagt tcctctcgga cgaaggcgta cagaatctga gttctgggag    2340
agaggtagga gagggcagga gaggaggtag aggcagcaga ccagaaggtc tctcggactt    2400
gtcgagtcag agagatggca gactcggcag cggcaacctt ccaggcattg acggcagcaa    2460
gagacagcga ggtggaagag agcacttcga cgacagttcc ggcagcaaag agaaggcat     2520 cgtgccatct gggaaccagg tcgtaggagt tggtctgctc gagtcgtttg ccagtgtct     2580 tgttgacctt ctcaacaagc tcgtctcgca ggttcgatcc agtcatggca gagccaaagt    2640
gctgatcaat gagagacacg atggcaggac caaactgctt cttgaactcg aactcgatag    2700
ctcgcaggtc aatggcttgc aggacacagt agaggtgagt ggcaaggagc agagagagaa    2760
cgtcgttgga ctcggtggtt cgtcgagcag agatgagggc aagggagttg actgcctggt    2820
tcgccatctc agcaggctgc acgtgagtgg tgacagggtt ggcgagatga cccagctcag    2880
aggtgtaggc agcggcagcg atgtcgagtc ccttgcagtg gtaggacaga gagggatctt    2940
cggcagcaag acaggagggc agacctcggt tcatgcctgc attgagcatc tcagtcagct    3000
gggtgaagtt gagcttgcca atctgagcga gtccaagtcg agtcttctcc atagtgttgg    3060
ccacagcggc agcctggaag ttgcctccgt gatgcgaggt cttgttctcg acatcaatca    3120
gagggttgtc ggtagtggac tgaccagcct caatggtgag cacggcatga gcgtggatga    3180
ggtcagagac caggggtccg agccactgag gagaggttcg caaggataa cgatcctgtc     3240 tgagaatgcc ttcgtcgtcc ttgactttga cttcctcctc gtggtggacg gcaaatcgag    3300
aaccctccag aagctttcgg atgttgccag cgacttcgat ctgtgtggga tgaggtcgag    3360
tcacatcgtg gagaaaggga tgaaaggagc cagcgtgtcc aaccatagct tcgacggtca    3420
tggcagtcag ggactgagag agcagcgaga gcatgtgagc gtcgtgcaga gcgagggtag    3480
ccatagatgc ggacacggca gtgccgttga ccagtccgag accttccttg ggtccaagga    3540
cgacaggctc caggttgaag agggccatag cctctcgtgc gtacagaatc ttctccttgc    3600
cttcgtggac gacgtgcact ttcgagtcgg gatgtccaga gatggctgca gcaatgtagg    3660
agagaggaga cagatcacca gaggcggaga tggtgcctcg aagggaaaca atgggtgtga    3720
tgccatgatt caggaagttg gtcaatgcct caaggacgac gagtcgaaca gcggagtggc    3780
ctcgagtcag agagttcact cggatggtca tggctcctcg gacgacctcc agaggaagag    3840
agttctccag tcctcgtccc agacggaagg agtcaaagga cgagggaagc acaccgcaga    3900
gctggtgctc cagcagagcc ttctgaaggg agatggcatc ttcagttcgt gtgtcggcag    3960
agccaccaaa tccagtggtg acaccgtaca cggacatcga gagttgagat cgcaggaact    4020
cgacggactt gtcgatcttc gatcgaatct catcggagtc cttcactcga acgggtctac    4080
cctttcgggc agcagagacg acgtctccga ggttcagcga gtagccatcg agctccagag    4140
tggagtcggt aggagcagcg agcatcttct cgacaatgtc aacctgtgtc acctgagtgg    4200
tgggcaagtg agagccagcg acggcaaggt tggtcgaagc tccgttcact gcctgcttag    4260
cagaggcaac accgttggcg aaggagtgag agatggagtc cagagaggga gccatggaga    4320
gctgggttag tttgtgtaga gagtgtgtgt tgctagcgac tttcggattg tgtcattaca    4380
caaaacgcgt cgtctcgaca ctgatcttgt cgtggatact cacggctcgg acatcgtcgc    4440
cgacgatgac accggacttt cgcttaagga cgtcagtaac aggcattgtg tgatgtgtag    4500
tttagatttc gaatctgtgg ggaaagaaag gaaaaagag actggcaacc gattgggaga     4560
gccactgttt atatataccc tagacaagcc ccccgcttgt aagatgttgg tcaatgtaaa    4620
```

```
ccagtattaa ggttggcaag tgcaggagaa gcaaggtgtg ggtaccgagc aatggaaatg    4680
tgcggaaggc aaaaaaatga ggccacggcc tattgtcggg gctatatcca gggggcgatt    4740
gaagtacact aacatgacat gtgtccacag accctcaatc tggcctgatg agccaaatcc    4800
atacgcgctt tcgcagctct aaaggctata acaagtcaca ccaccctgct cgacctcagc    4860
gccctcactt tttgttaaga caaactgtac acgctgttcc agcgttttct gcctgcacct    4920
ggtgggacat ttggtgcaac ctaaagtgct cggaacctct gtggtgtcca gatcagcgca    4980
gcagttccga ggtagttttg aggcccttag atgatgcaat ggtgtcagtc gctggatcac    5040
gagtcttaat ggcagtattc gttcttattt gtgccattga gccccgttat cctcgtatct    5100 tctaccccc atcccatccc tttgttggtg caaccctacc catttattgt tgggtgcagc    5160
ccaaccgacg tggagagctt ggcttggcca tataaaaagg cccccccta gtggcaatgg     5220 cagaaagtca gctgtgagtt gttgaatttg tcatctaggc ggcctggccg tcttctccgg    5280
ggcaattgtt cctctatagt actgcgtaca ctgtttaaac agtgtacgca gatctactat    5340
agaggaacat ttaaatgtag ctaacggtag caggcgaact actggtacat acctcccccg    5400
gaatatgtac aggcataatg cgtatctgtg ggacatgtgg tcgttgcgcc attatgtaag    5460
cagcgtgtac tcctctgact gtccatatgg tttgctccat ctcaccctca tcgttttcat    5520
tgttcacagg cggccacaaa aaaactgtct tctctccttc tctcttcgcc ttagtctact    5580
cggaccagtt ttagtttagc ttggcgccac tggataaatg agacctcagg ccttgtgatg    5640
aggaggtcac ttatgaagca tgttaggagg tgcttgtatg gatagagaag cacccaaaat    5700
aataagaata ataataaaac aggggggcgtt gtcatttcat atcgtgtttt caccatcaat   5760
acacctccaa acaatgccct tcatgtggcc agccccaata ttgtcctgta gttcaactct    5820
atgcagctcg tatcttattg agcaagtaaa actctgtcag ccgatattgc ccgacccgcg    5880
acaagggtca acaaggtggt gtaaggcctt cgcagaagtc aaaactgtgc caaacaaaca    5940
tctagagtct ctttggtgtt tctcgcatat atttwatcgg ctgtcttacg tatttgcgcc    6000
tcggtaccgg actaatttcg gatcatcccc aatacgcttt tcttcgcag ctgtcaacag    6060 tgtccatgat ctatccacct aaatgggtca tatgaggcgt ataatttcgt ggtgctgata    6120
ataattccca tatatttgac acaaaacttc cccccctaga catacatctc acaatctcac    6180
ttcttgtgct tctgtcacac atctcctcca gctgacttca actcacacct ctgccccagt    6240
tggtctacag cggtataagg tttctccgca tagaggtgca ccactcctcc cgatacttgt    6300
ttgtgtgact tgtgggtcac gacatatata tctacacaca ttgcgccacc ctttggttct    6360
tccagcacaa caaaaacacg acacgctaac catggttcga tccgagtacg ccgacgttcc    6420
tcccgtcgac ctgcccattc acgatgctgt gctcggaggt gctgccgctt tcggctctac    6480
tcctgccctg atcgacggaa ccgacggcac cactctcacc tacgagcagg tggaccgatt    6540
tcacagacga gtcgctgcag cccttgccga gacaggcgtt cgaaagggag acgtcttggc    6600
tctgcactct cccaacactg ttgccttccc acttgccttc tacgctgcca ccagagctgg    6660
tgcctccgtc accactgtgc atcctcttgc tacagcagaa gagtttgcca agcagctgaa    6720
ggactctgct gcccgatgga ttgtcaccgt ttcccctctc ctgtccactg cccgacgagc    6780
tgccgagctt gctggaggcg tccaggagat tctggtttgc gacagcgcac ccggtcaccg    6840
atcccttgtc gatatgctgg cctctacagc tcccgaacct tccgtcgcca tcgaccctgc    6900
agaggacgtt gctgccttgc cctactcttc cggaactacc ggtactccca agggtgtcat    6960
gctcacccat cgacagattg ccaccaacct ggctcaactc gaaccttcca tgccctctgc    7020
```

```
tcctggagat cgagttcttg cagtgcttcc cttctttcac atctatggtc tgactgccct    7080
catgaacgct cctctgcgac tcggagccac cgtcgtggtt cttccacgat tcgacctgga    7140
gcagtttctc gctgccattc agaaccaccg aatcacttcg ctgtacgtcg ctcctcccat    7200
tgtgctggca cttgccaaac atcccttggt tgccgactac gatctctcct cgctgagata    7260
catcgtgtcg gctgccgcac ctctcgatgc tcgacttgcc gctgcctgtt cccagcgact    7320
cggactgcct cccgtcggtc aggcttacgg catgaccgag ctgtctcctg aacacacgt    7380 ggttcccttg gacgcaatgg ccgatgctcc tcctggcact gtcggtcgac tcattgccgg    7440
aaccgagatg cgaatcgtct ccctcaccga tccaggtaca gaccttcctg ctggagagtc    7500
tggcgagatt ctcattcgag gtccccagat catgaagggc tacttgggaa gacccgatgc    7560
cactgctgcc atgatcgacg aagaaggctg gctgcacaca ggtgatgtcg gacacgtgga    7620
tgccgatggc tggctgtttg ttgtcgaccg agtcaaggag cttatcaagt acaagggatt    7680
ccaggttgct cctgccgagc tggaagccca cctgctcact catccaggtg tcgcagacgc    7740
tgccgtggtt ggagcctacg acgatgacgg caacgaggtt ccccatgcct tcgtcgtgcg    7800
acaacctgcc gctcccggtc ttgccgagtc cgagatcatg atgtacgttg ccgaacgagt    7860
cgctccctac aagcgagtgc gacgagttac cttcgtcgat gccgttccca gagctgcctc    7920
cggcaagatt ctccgaagac agctgcgaga gcctcgataa gcggccgcaa gtgtggatgg    7980
ggaagtgagt gcccggttct gtgtgcacaa ttgcaatcc aagatggatg gattcaacac    8040
agggatatag cgagctacgt ggtggtgcga ggatatagca acgatatt atgtttgaca    8100 cttgagaatg tacgatacaa gcactgtcca agtacaatac taaacatact gtacatactc    8160
atactcgtac ccgggcaacg gtttcacttg agtgcagtgg ctagtgctct tactcgtaca    8220
gtgtgcaata ctgcgtatca tagtctttga tgtatatcgt attcattcat gttagttgcg    8280
tacgggtgaa gcttccactg gtcggcgtgg tagtggggca gagtggggtc ggtgtgctgc    8340
aggtaggtga tggccacgag ccagtggttg acccacaggt aggggatcag gtagtagagg    8400
gtgacggaag ccaggcccca tcggttgatg gagtatgcga tgacggacat ggtgatacca    8460
ataccgacgt tagagatcca gatgttgaac cagtccttct tctcaaacag cggggcgttg    8520
gggttgaagt ggttgacagc ccatttgttg agcttgggt acttctgtcc ggtaacgtaa    8580
gacagcagat acagaggcca tccaaacacc tgctgggtga tgaggccgta gagggtcatg    8640
aggggagcgt cctcagcaag ctcagaccag tcatgggcgc ctcggttctc cataaactcc    8700
tttcggtcct tgggcacaaa caccatatca cgggtgaggt gaccagtgga cttgtggtgc    8760
atggagtggg tcagcttcca ggcgtagtaa gggaccagca tggaggagtg cagaacccat    8820
ccggtgacgt tgttgacggt gttagagtcg gagaaagcag agtggccaca ctcgtgggca    8880
agaacccaca gaccggtgcc aaacagaccc tggacaatgg agtacatggc ccaggccaca    8940
gctcggccgg aagccgaggg aataagaggc aggtacgcgt aggccatgta ggcaaaaacg    9000
gcgataaaga agcaggcgcg ccagctgcat taatgaatcg ccaacgcgc ggggagaggc    9060 ggtttgcgta ttgggcgctc ttccgcttcc tcgctcactg actcgctgcg ctcggtcgtt    9120
cggctgcggc gagcggtatc agctcactca aaggcggtaa tacggttatc cacagaatca    9180
ggggataacg caggaaagaa catgtgagca aaaggccagc aaaaggccag gaaccgtaaa    9240
aaggccgcgt tgctggcgtt tttccatagg ctccgccccc ctgacgagca tcacaaaaat    9300
cgacgctcaa gtcagaggtg gcgaaacccg acaggactat aaagatacca ggcgtttccc    9360
```

```
cctggaagct ccctcgtgcg ctctcctgtt ccgaccctgc cgcttaccgg atacctgtcc    9420
gcctttctcc cttcgggaag cgtggcgctt tctcatagct cacgctgtag gtatctcagt    9480
tcggtgtagg tcgttcgctc caagctgggc tgtgtgcacg aaccccccgt tcagcccgac    9540
cgctgcgcct tatccggtaa ctatcgtctt gagtccaacc cggtaagaca cgacttatcg    9600
ccactggcag cagccactgg taacaggatt agcagagcga ggtatgtagg cggtgctaca    9660
gagttcttga agtggtggcc taactacggc tacactagaa gaacagtatt tggtatctgc    9720
gctctgctga agccagttac cttcggaaaa agagttggta gctcttgatc cggcaaacaa    9780
accaccgctg gtagcggtgg ttttttttgtt tgcaagcagc agattacgcg cagaaaaaaa    9840
ggatctcaag aagatccttt gatcttttct acggggtctg acgctcagtg gaacgaaaac    9900
tcacgttaag ggattttggt catgagatta tcaaaaagga tcttcaccta gatccttta    9960 aattaaaaat gaagttttaa atcaatctaa agtatatatg agtaaacttg gtctgacagt    10020
taccaatgct taatcagtga ggcacctatc tcagcgatct gtctatttcg ttcatccata    10080
gttgcctgac tccccgtcgt gtagataact acgatacggg agggcttacc atctggcccc    10140
agtgctgcaa tgataccgcg agacccacgc tcaccggctc cagatttatc agcaataaac    10200
cagccagccg gaagggccga gcgcagaagt ggtcctgcaa ctttatccgc ctccatccag    10260
tctattaatt gttgccggga agctagagta agtagttcgc cagttaatag tttgcgcaac    10320
gttgttgcca ttgctacagg catcgtggtg tcacgctcgt cgtttggtat ggcttcattc    10380
agctccggtt cccaacgatc aaggcgagtt acatgatccc ccatgttgtg caaaaaagcg    10440
gttagctcct tcggtcctcc gatcgttgtc agaagtaagt tggccgcagt gttatcactc    10500
atggttatgg cagcactgca taattctctt actgtcatgc catccgtaag atgcttttct    10560
gtgactggtg agtactcaac caagtcattc tgagaatagt gtatgcggcg accgagttgc    10620
tcttgcccgg cgtcaatacg ggataatacc gcgccacata gcagaacttt aaaagtgctc    10680
atcattggaa aacgttcttc ggggcgaaaa ctctcaagga tcttaccgct gttgagatcc    10740
agttcgatgt aacccactcg tgcacccaac tgatcttcag catctttac tttcaccagc    10800 gtttctgggt gagcaaaaac aggaaggcaa aatgccgcaa aaaagggaat aagggcgaca    10860
cggaaatgtt gaatactcat actcttcctt tttcaatatt attgaagcat ttatcagggt    10920
tattgtctca tgagcggata catatttgaa tgtatttaga aaaataaaca ataggggtt    10980 ccgcgcacat ttccccgaaa agtgccacct gatgcggtgt gaaataccgc acagatgcgt    11040
aaggagaaaa taccgcatca ggaaattgta agcgttaata ttttgttaaa attcgcgtta    11100
aatttttgtt aaatcagctc attttttaac caataggccg aaatcggcaa aatcccttat    11160
aaatcaaaag aatagaccga gatagggttg agtgttgttc cagtttggaa caagagtcca    11220
ctattaaaga acgtggactc caacgtcaaa gggcgaaaaa ccgtctatca gggcgatggc    11280
ccactacgtg aaccatcacc ctaatcaagt tttttggggt cgaggtgccg taaagcacta    11340
aatcggaacc ctaaagggag cccccgattt agagcttgac ggggaaagcc ggcgaacgtg    11400
gcgagaaagg aagggaagaa agcgaaagga gcgggcgcta gggcgctggc aagtgtagcg    11460
gtcacgctgc gcgtaaccac cacacccgcc gcgcttaatg cgccgctaca gggcgcgtcc    11520
attcgccatt caggctgcgc aactgttggg aagggcgatc ggtgcgggcc tcttcgctat    11580
tacgccagct ggcgaaaggg ggatgtgctg caaggcgatt aagttgggta acgccagggt    11640
tttcccagtc acgacgttgt aaaacgacgg ccagtgaatt gtaatacgac tcactatagg    11700
gcgaattggg cccgacgtcg catgcttgaa tctacaagta ggagggttgg agtgattaag    11760
```

| | | | | |
|---|---|---|---|---|
| tgaaacttct | ttaacggctc | tatgccagtt | ctattgatat | ccgaaacatc agtatgaagg | 11820 |
| tctgataagg | gtgacttctt | cccacagatt | cgtatcagta | cgagtacgag accggtactt | 11880 |
| gtaacagtat | tgatactaaa | gggaaactac | aacggttgtc | agcgtaatgt gacttcgccc | 11940 |
| atgaacgcag | acacgcagtg | ccgagtgcgg | tgatatcgcc | tactcgttac gtccatggac | 12000 |
| tacacaaccc | ctcggcttcg | cttggcttag | cctcgggctc | ggtgctgttc agttaaaaca | 12060 |
| caatcaaata | acatttctac | ttttagaag | gcaggccgtc | aggagcaact ccgactccat | 12120 |
| tgacgtttct | aaacatctga | atgccttcct | taccttcaac | aaactggcag gttcgggcga | 12180 |
| cagtgtaaag | agacttgatg | aagttggtgt | cgtcgtgtcg | gtagtgcttg cccatgacct | 12240 |
| tcttgatctt | ctcagtggcg | attcgggcgt | tgtagaaggg | aattccgtcg tcgcctgagt | 12300 |
| cgacgagtat | ctgtctgact | cgtcattgcc | gcctttggag | tacgactcca actatgagtg | 12360 |
| tgcttggatc | actttgacga | tacattcttc | gttggaggct | gtgggtctga cagctgcgtt | 12420 |
| ttcggcgcgg | ttggccgaca | acaatatcag | ctgcaacgtc | attgctggct ttcatcatga | 12480 |
| tcacattttt | gtcggcaaag | gcgacgccca | gagagccatt | gacgttcttt ctaatttgga | 12540 |
| ccgatagccg | tatagtccag | tctatctata | agttcaacta | actcgtaact attaccataa | 12600 |
| catatacttc | actgccccag | ataaggttcc | gataaaaagt | tctgcagact aaatttattt | 12660 |
| cagtctcctc | ttcaccacca | aaatgccctc | ctacgaagct | cgagctaacg tccacaagtc | 12720 |
| cgcctttgcc | gctcgagtgc | tcaagctcgt | ggcagccaag | aaaaccaacc tgtgtgcttc | 12780 |
| tctggatgtt | accaccacca | aggagctcat | tgagcttgcc | gataaggtcg gaccttatgt | 12840 |
| gtgcatgatc | aaaacccata | tcgacatcat | tgacgacttc | acctacgccg gcactgtgct | 12900 |
| cccccctcaag | gaacttgctc | ttaagcacgg | tttcttcctg | ttcgaggaca gaaagttcgc | 12960 |
| agatattggc | aacactgtca | agcaccagta | ccggtgtcac | cgaatcgccg agtggtccga | 13020 |
| tatcaccaac | gcccacggtg | tacccggaac | cggaatcatt | gctggcctgc gagctggtgc | 13080 |
| cgaggaaact | gtctctgaac | agaagaagga | ggacgtctct | gactacgaga actcccagta | 13140 |
| caaggagttc | ctagtccccct | ctcccaacga | gaagctggcc | agaggtctgc tcatgctggc | 13200 |
| cgagctgtct | tgcaagggct | ctctggccac | tggcgagtac | tccaagcaga ccattgagct | 13260 |
| tgcccgatcc | gaccccgagt | ttgtggttgg | cttcattgcc | cagaaccgac ctaagggcga | 13320 |
| ctctgaggac | tggcttattc | tgaccccgg | ggtgggtctt | gacgacaagg gagacgctct | 13380 |
| cggacagcag | taccgaactg | ttgaggatgt | catgtctacc | ggaacggata tcataattgt | 13440 |
| cggccgaggt | ctgtacggcc | agaaccgaga | tcctattgag | gaggccaagc gataccagaa | 13500 |
| ggctggctgg | gaggcttacc | agaagattaa | ctgttagagg | ttagactatg gatatgtaat | 13560 |
| ttaactgtgt | atatagagag | cgtgcaagta | tggagcgctt | gttcagcttg tatgatggtc | 13620 |
| agacgacctg | tctgatcgag | tatgtatgat | actgcacaac | ctgtgtatcc gcatgatctg | 13680 |
| tccaatgggg | catgttgttg | tgtttctcga | tacggagatg | ctgggtacag tgctaatacg | 13740 |
| ttgaactact | tatacttata | tgaggctcga | agaaagctga | cttgtgtatg acttaat | 13797 |

<210> SEQ ID NO 56
<211> LENGTH: 13203
<212> TYPE: DNA
<213> ORGANISM: artificial sequence
<220> FEATURE:
<223> OTHER INFORMATION: Plasmid

<400> SEQUENCE: 56

```
taaccctcac taaagggaac aaaagctgga gctccaccgc ggacacaata tctggtcaaa    60
tttcagtttc gttacataaa tcgttatgtc aaaggagtgt gggaggttaa gagaattatc   120
accggcaaac tatctgttaa ttgctaggta cctctagacg tccacccggg tcgcttggcg   180
gccgaagagg ccggaatctc gggccgcggt ggcggccgct tagttagtga cggtgggaac   240
agagtggagc acgacagttt cgatggtcag tccaggacca aagccgaaga ggactcccca   300
gtccaggcct tcaccagtgg tggccttctc tcccttgagg gatttctttc gcatctcgtc   360
cagaatgaag agcacacaag cagaggacat gttgccgtac tcgctcagca cgtgtcgagt   420
ggcttcgagc ttcttcttct ccaggttgag cttagcctca actgcgtcga ggatggcagg   480
acctccggga tgagcaatcc agaacagaga gttccagtcg agataccga gagggtcgaa    540
agcctgggtc aggcacttct caatgttctc ggagatgaga gtgggcacat taggccacag   600
gtggaaggtg aggccaacct ctcgcaggtt tccggcaatg gcaccagcag agttggggat   660
aaaggtttgg gcagcggaga caagctggaa gaggggtcgc tcgatagaga catcgggatc   720
ggatccaaca atcacggcag aggagccatc accaaacaga gcctggccga cgagggagtc   780
cagggcatct tcagagggac ctcggaaggt cacgacagtg atttcggagc acacaacgag   840
gactcgtgct ccagcgttgt tctcggccag gtccttggca gttcggagca cggtgccacc   900
agcgtagcag ccttggtggt acagcatgac tcgtcggacg gaggtttcaa ggccgagcag   960
gttagcgagc ttgtagtcgg ctccaggcat ttccacacca gaggtagtac agaagaccag  1020
atgggtgatc ttggacttgg gctgtcccca ctctttgaga gccttcaggg cagcatcccg  1080
accgagtcgg ggaacctcag cggtgataat ctcctgtcgg atgttcagag aaggagccat  1140
gtaagcgcca atgttgggat gctcttcgag catctcttca gtcaggtgga tgtatcgctt  1200
cttaatcatg gatttgtcac agatccggtt gaacttcttc ttgagctcgg tcatgtgctc  1260
ggacttggtc actcggaagt agtaatcggc atagtcagac tggtagacac agtggtcagg  1320
ggtagcagtg ccaatggcca ggatggtagc gggacccttg gctcgctgag cgtttcggaa  1380
ttcctcaacg gaggccatgg tgaatgattc ttatactcag aaggaaatgc ttaacgattt  1440
cgggtgtgag ttgacaagga gagagagaaa agaagaggaa aggtaattcg gggacggtgg  1500
tcttttatac ccttggctaa agtcccaacc acaaagcaaa aaaattttca gtagtctatt  1560
ttgcgtccgg catgggttac ccggatggcc agacaaagaa actagtacaa agtctgaaca  1620
agcgtagatt ccagactgca gtaccctacg cccttaacgg caagtgtggg aaccggggga  1680
ggtttgatat gtgggtgaa gggggctctc gccggggttg ggcccgctac tgggtcaatt   1740
tggggtcaat tggggcaatt ggggctgttt tttgggacac aaatacgccg ccaacccggt  1800
ctctcctgaa ttctgcatcg atcgaggaag aggacaagcg gctgcttctt aagtttgtga  1860
catcagtatc caaggcacca ttgcaaggat tcaaggcttt gaacccgtca tttgccattc  1920
gtaacgctgg tagacaggtt gatcggttcc ctacggcctc cacctgtgtc aatcttctca  1980
agctgcctga ctatcaggac attgatcaac ttcggaagaa acttttgtat gccattcgat  2040
cacatgctgg tttcgatttg tcttagagga acgcatatac agtaatcata gagaataaac  2100
gatattcatt tattaaagta gatagttgag gtagaagttg taaagagtga taaatagcgg  2160
ccgcttaagc gagcatcttg agcagcacat tgttgattct gccagacttg atggcttcgt  2220
agattttgga gacgttggag ccaatggtca cctcttgctt gccgagaaag acgtctcctc  2280
gtcgagcctt cacaccaagt tcctctcgga cgaaggcgta cagaatctga gttctggag   2340
agaggtagga gagggcagga gaggaggtag aggcagcaga ccagaaggtc tctcggactt  2400
```

```
gtcgagtcag agagatggca gactcggcag cggcaacctt ccaggcattg acggcagcaa    2460
gagacagcga ggtggaagag agcacttcga cgacagttcc ggcagcaaag gagaaggcat    2520
cgtgccatct gggaaccagg tcgtaggagt tggtctgctc gagtcgtttg ccagtgtct     2580
tgttgacctt ctcaacaagc tcgtctcgca ggttcgatcc agtcatggca gagccaaagt    2640
gctgatcaat gagagacacg atggcaggac caaactgctt cttgaactcg aactcgatag    2700
ctcgcaggtc aatggcttgc aggacacagt agaggtgagt ggcaaggagc agagagagaa    2760
cgtcgttgga ctcggtggtt cgtcgagcag agatgagggc aagggagttg actgcctggt    2820
tcgccatctc agcaggctgc acgtgagtgg tgacagggtt ggcgagatga cccagctcag    2880
aggtgtaggc agcggcagcg atgtcgagtc ccttgcagtg gtaggacaga gagggatctt    2940
cggcagcaag acaggagggc agacctcggt tcatgcctgc attgagcatc tcagtcagct    3000
gggtgaagtt gagcttgcca atctgagcga gtccaagtcg agtcttctcc atagtgttgg    3060
ccacagcggc agcctggaag ttgcctccgt gatgcgaggt cttgttctcg acatcaatca    3120
gagggttgtc ggtagtggac tgaccagcct caatggtgag cacggcatga gcgtggatga    3180
ggtcagagac caggggtccg agccactgag gagaggttcg caagggataa cgatcctgtc    3240
tgagaatgcc ttcgtcgtcc ttgactttga cttcctcctc gtggtggacg gcaaatcgag    3300
aaccctccag aagctttcgg atgttgccag cgacttcgat ctgtgtggga tgaggtcgag    3360
tcacatcgtg gagaaaggga tgaaaggagc cagcgtgtcc aaccatagct tcgacggtca    3420
tggcagtcag ggactgagag agcagcgaga gcatgtgagc gtcgtgcaga gcgagggtag    3480
ccatagatgc ggacacggca gtgccgttga ccagtccgag accttccttg ggtccaagga    3540
cgacaggctc caggttgaag agggccatag cctctcgtgc gtacagaatc ttctccttgc    3600
cttcgtggac gacgtgcact ttcgagtcgg gatgtccaga gatggctgca gcaatgtagg    3660
agagaggaga cagatcacca gaggcggaga tggtgcctcg aagggggaaca atgggtgtga    3720
tgccatgatt caggaagttg gtcaatgcct caaggacgac gagtcgaaca gcggagtggc    3780
ctcgagtcag agagttcact cggatggtca tggctcctcg gacgacctcc agaggaagag    3840
agttctccag tcctcgtccc agacggaagg agtcaaagga cgagggaagc acaccgcaga    3900
gctggtgctc cagcagagcc ttctgaaggg agatggcatc ttcagttcgt gtgtcggcag    3960
agccaccaaa tccagtggtg acaccgtaca cggacatcga gagttgagat cgcaggaact    4020
cgacggactt gtcgatcttc gatcgaatct catcggagtc cttcactcga acgggtctac    4080
cctttcgggc agcagagacg acgtctccga ggttcagcga gtagccatcg agctccagag    4140
tggagtcggt aggagcagcg agcatcttct cgacaatgtc aacctgtgtc acctgagtgg    4200
tgggcaagtg agagccagcg acggcaaggt tggtcgaagc tccgttcact gcctgcttag    4260
cagaggcaac accgttggcg aaggagtgag agatggagtc cagagaggga gccatggaga    4320
gctgggttag tttgtgtaga gagtgtgtgt tgctagcgac tttcggattg tgtcattaca    4380
caaaacgcgt cgtctcgaca ctgatcttgt cgtggatact cacggctcgg acatcgtcgc    4440
cgacgatgac accggacttt cgcttaagga cgtcagtaac aggcattgtg tgatgtgtag    4500
tttagatttc gaatctgtgg ggaaagaaag gaaaaaagag actggcaacc gattgggaga    4560
gccactgttt atatatacc tagacaagcc ccccgcttgt aagatgttgg tcaatgtaaa    4620
ccagtattaa ggttggcaag tgcaggagaa gcaggtgtg ggtaccgagc aatggaaatg    4680
tgcggaaggc aaaaaaatga ggccacggcc tattgtcggg gctatatcca gggggcgatt    4740
```

```
gaagtacact aacatgacat gtgtccacag accctcaatc tggcctgatg agccaaatcc   4800
atacgcgctt tcgcagctct aaaggctata acaagtcaca ccaccctgct cgacctcagc   4860
gccctcactt tttgttaaga caaactgtac acgctgttcc agcgttttct gcctgcacct   4920
ggtgggacat ttggtgcaac ctaaagtgct cggaacctct gtggtgtcca gatcagcgca   4980
gcagttccga ggtagttttg aggccctag atgatgcaat ggtgtcagtc gctggatcac    5040
gagtcttaat ggcagtattc gttcttattt gtgccattga gccccgttat cctcgtatct   5100
tctaccccc atcccatccc tttgttggtg caaccctacc catttattgt tgggtgcagc    5160
ccaaccgacg tggagagctt ggcttggcca tataaaaagg cccccccta gtggcaatgg    5220
cagaaagtca gctgtgagtt gttgaatttg tcatctaggc ggcctggccg tcttctccgg   5280
ggcaattgtt cctctatagt actgcgtaca ctgtttaaac agtgtacgca gatctactat   5340
agaggaacat ttaaacgacg gaattcctgc agcccatctg cagaattcag gagagaccgg   5400
gttggcggcg tatttgtgtc ccaaaaaaca gccccaattg ccccaattga ccccaaattg   5460
acccagtagc gggcccaacc ccggcgagag cccccttcac cccacatatc aaacctcccc   5520
cggttcccac acttgccgtt aagggcgtag ggtactgcag tctggaatct acgcttgttc   5580
agactttgta ctagtttctt tgtctggcca tccgggtaac ccatgccgga cgcaaaatag   5640
actactgaaa atttttttgc tttgtggttg ggacttagc caagggtata aaagaccacc    5700
gtccccgaat tacctttcct cttcttttct ctctctcctt gtcaactcac acccgaaatc   5760
gttaagcatt tccttctgag tataagaatc attcaccatg gttcgatccg agtacgccga   5820
cgttcctccc gtcgacctgc ccattcacga tgctgtgctc ggaggtgctg ccgctttcgg   5880
ctctactcct gccctgatcg acggaaccga cggcaccact ctcacctacg agcaggtgga   5940
ccgatttcac agacgagtcg ctgcagccct tgccgagaca ggcgttcgaa agggagacgt   6000
cttggctctg cactctccca acactgttgc cttcccactt gccttctacg ctgccaccag   6060
agctggtgcc tccgtcacca ctgtgcatcc tcttgctaca gcagaagagt ttgccaagca   6120
gctgaaggac tctgctgccc gatggattgt caccgttttcc cctctcctgt ccactgcccg   6180
acgagctgcc gagcttgctg gaggcgtcca ggagattctg gtttgcgaca gcgcacccgg   6240
tcaccgatcc cttgtcgata tgctggcctc tacagctccc gaaccttccg tcgccatcga   6300
ccctgcagag gacgttgctg ccttgcccta ctcttccgga actaccggta ctcccaaggg   6360
tgtcatgctc acccatcgac agattgccac caacctggct caactcgaac cttccatgcc   6420
ctctgctcct ggagatcgag ttcttgcagt gcttccctc tttcacatct atggtctgac    6480
tgccctcatg aacgctcctc tgcgactcgg agccaccgtc gtggttcttc cacgattcga   6540
cctggagcag tttctcgctg ccattcagaa ccaccgaatc acttcgctgt acgtcgctcc   6600
tcccattgtg ctggcacttg ccaaacatcc cttggttgcc gactacgatc tctcctcgct   6660
gagatacatc gtgtcggctg ccgcacctct cgatgctcga cttgccgctg cctgttccca   6720
gcgactcgga ctgcctcccg tcggtcaggc ttacggcatg accgagctgt ctcctggaac   6780
acacgtggtt cccttggacg caatggccga tgctcctcct ggcactgtcg gtcgactcat   6840
tgccggaacc gagatgcgaa tcgtctccct caccgatcca ggtacagacc ttcctgctgg   6900
agagtctggc gagattctca ttcgaggtcc ccagatcatg aagggctact gggaagacc    6960
cgatgccact gctgccatga tcgacgaaga aggctggctg cacacaggtg atgtcggaca   7020
cgtggatgcc gatggctggc tgtttgttgt cgaccgagtc aaggagctta tcaagtacaa   7080
gggattccag gttgctcctg ccgagctgga agcccacctg ctcactcatc caggtgtcgc   7140
```

```
agacgctgcc gtggttggag cctacgacga tgacggcaac gaggttcccc atgccttcgt     7200
cgtgcgacaa cctgccgctc ccggtcttgc cgagtccgag atcatgatgt acgttgccga     7260
acgagtcgct ccctacaagc gagtgcgacg agttaccttc gtcgatgccg ttcccagagc     7320
tgcctccggc aagattctcc gaagacagct gcgagagcct cgataagcgg ccgcaagtgt     7380
ggatggggaa gtgagtgccc ggttctgtgt gcacaattgg caatccaaga tggatggatt     7440
caacacaggg atatagcgag ctacgtggtg gtgcgaggat atagcaacgg atatttatgt     7500
ttgacacttg agaatgtacg atacaagcac tgtccaagta caatactaaa catactgtac     7560
atactcatac tcgtacccgg gcaacggttt cacttgagtg cagtggctag tgctcttact     7620
cgtacagtgt gcaatactgc gtatcatagt ctttgatgta tatcgtattc attcatgtta     7680
gttgcgtacg ggtgaagctt ccactggtcg gcgtggtagt ggggcagagt ggggtcggtg     7740
tgctgcaggt aggtgatggc cacgagccag tggttgaccc acaggtaggg gatcaggtag     7800
tagagggtga cggaagccag gccccatcgg ttgatggagt atgcgatgac ggacatggtg     7860
ataccaatac cgacgttaga gatccagatg ttgaaccagt ccttcttctc aaacagcggg     7920
gcgttggggt tgaagtggtt gacagcccat ttgttgagct tggggtactt ctgtccggta     7980
acgtaagaca gcagatacag aggccatcca aacacctgct gggtgatgag gccgtagagg     8040
gtcatgaggg gagcgtcctc agcaagctca gaccagtcat gggcgcctcg gttctccata     8100
aactcctttc ggtccttggg cacaaacacc atatcacggg tgaggtgacc agtggacttg     8160
tggtgcatgg agtgggtcag cttccaggcg tagtaaggga ccagcatgga ggagtgcaga     8220
acccatccgg tgacgttgtt gacggtgtta gagtcggaga aagcagagtg gccacactcg     8280
tgggcaagaa cccacagacc ggtgccaaac agacccggga caatgagta catggcccag     8340 gccacagctc ggccggaagc cgagggaata agaggcaggt acgcgtaggc catgtaggca     8400
aaaacggcga taagaagca ggcgcgccag ctgcattaat gaatcggcca acgcgcgggg     8460
agaggcggtt tgcgtattgg gcgctcttcc gcttcctcgc tcactgactc gctgcgctcg     8520
gtcgttcggc tgcggcgagc ggtatcagct cactcaaagg cggtaatacg gttatccaca     8580
gaatcagggg ataacgcagg aaagaacatg tgagcaaaag gccagcaaaa ggccaggaac     8640
cgtaaaaagg ccgcgttgct ggcgtttttc cataggctcc gcccccctga cgagcatcac     8700
aaaaatcgac gctcaagtca gaggtggcga aacccgacag gactataaag ataccaggcg     8760
tttccccctg gaagctccct cgtgcgctct cctgttccga ccctgccgct taccggatac     8820
ctgtccgcct ttctcccttc gggaagcgtg gcgctttctc atagctcacg ctgtaggtat     8880
ctcagttcgg tgtaggtcgt tcgctccaag ctgggctgtg tgcacgaacc ccccgttcag     8940
cccgaccgct gcgccttatc cggtaactat cgtcttgagt ccaacccggt aagacacgac     9000
ttatcgccac tggcagcagc cactggtaac aggattagca gagcgaggta tgtaggcggt     9060
gctacagagt tcttgaagtg gtggcctaac tacggctaca ctagaagaac agtatttggt     9120
atctgcgctc tgctgaagcc agttaccttc ggaaaaagag ttggtagctc ttgatccggc     9180
aaacaaacca ccgctggtag cggtggtttt tttgtttgca agcagcagat tacgcgcaga     9240
aaaaaaggat ctcaagaaga tcctttgatc ttttctacgg ggtctgacgc tcagtggaac     9300
gaaaactcac gttaagggat tttggtcatg agattatcaa aaaggatctt cacctagatc     9360
cttttaaatt aaaaatgaag ttttaaatca atctaaagta tatatgagta aacttggtct     9420
gacagttacc aatgcttaat cagtgaggca cctatctcag cgatctgtct atttcgttca     9480
```

```
tccatagttg cctgactccc cgtcgtgtag ataactacga tacgggaggg cttaccatct    9540
ggccccagtg ctgcaatgat accgcgagac ccacgctcac cggctccaga tttatcagca    9600
ataaaccagc cagccggaag ggccgagcgc agaagtggtc ctgcaacttt atccgcctcc    9660
atccagtcta ttaattgttg ccgggaagct agagtaagta gttcgccagt taatagtttg    9720
cgcaacgttg ttgccattgc tacaggcatc gtggtgtcac gctcgtcgtt tggtatggct    9780
tcattcagct ccggttccca acgatcaagg cgagttacat gatcccccat gttgtgcaaa    9840
aaagcggtta gctccttcgg tcctccgatc gttgtcagaa gtaagttggc cgcagtgtta    9900
tcactcatgg ttatggcagc actgcataat tctcttactg tcatgccatc cgtaagatgc    9960
ttttctgtga ctggtgagta ctcaaccaag tcattctgag aatagtgtat gcggcgaccg   10020
agttgctctt gcccggcgtc aatacgggat aataccgcgc cacatagcag aactttaaaa   10080
gtgctcatca ttggaaaacg ttcttcgggg cgaaaactct caaggatctt accgctgttg   10140
agatccagtt cgatgtaacc cactcgtgca cccaactgat cttcagcatc ttttactttc   10200
accagcgttt ctgggtgagc aaaaacagga aggcaaaatg ccgcaaaaaa gggaataagg   10260
gcgacacgga aatgttgaat actcatactc ttcctttttc aatattattg aagcatttat   10320
cagggttatt gtctcatgag cggatacata tttgaatgta tttagaaaaa taaacaaata   10380
ggggttccgc gcacatttcc ccgaaaagtg ccacctgatg cggtgtgaaa taccgcacag   10440
atgcgtaagg agaaaatacc gcatcaggaa attgtaagcg ttaatatttt gttaaaattc   10500
gcgttaaatt tttgttaaat cagctcattt tttaaccaat aggccgaaat cggcaaaatc   10560
ccttataaat caaaagaata gaccgagata gggttgagtg ttgttccagt ttggaacaag   10620
agtccactat taaagaacgt ggactccaac gtcaaagggc gaaaaaccgt ctatcagggc   10680
gatggcccac tacgtgaacc atcaccctaa tcaagttttt tggggtcgag gtgccgtaaa   10740
gcactaaatc ggaaccctaa agggagcccc cgatttagag cttgacgggg aaagccggcg   10800
aacgtggcga gaaaggaagg gaagaaagcg aaaggagcgg gcgctagggc gctggcaagt   10860
gtagcggtca cgctgcgcgt aaccaccaca cccgccgcgc ttaatgcgcc gctacagggc   10920
gcgtccattc gccattcagg ctgcgcaact gttgggaagg gcgatcggtg cgggcctctt   10980
cgctattacg ccagctggcg aaagggggat gtgctgcaag gcgattaagt tgggtaacgc   11040
cagggttttc ccagtcacga cgttgtaaaa cgacggccag tgaattgtaa tacgactcac   11100
tatagggcga attgggcccg acgtcgcatg cttgaatcta caagtaggag ggttggagtg   11160
attaagtgaa acttctttaa cggctctatg ccagttctat tgatatccga aacatcagta   11220
tgaaggtctg ataagggtga cttcttccca cagattcgta tcagtacgag tacgagaccg   11280
gtacttgtaa cagtattgat actaaaggga actacaacg gttgtcagcg taatgtgact   11340
tcgcccatga acgcagacac gcagtgccga gtgcggtgat atcgcctact cgttacgtcc   11400
atggactaca caaccctcg gcttcgcttg cttagcctc gggctcggtg ctgttcagtt   11460
aaaacacaat caaataacat ttctactttt tagaaggcag gccgtcagga gcaactccga   11520
ctccattgac gtttctaaac atctgaatgc cttccttacc ttcaacaaac tggcaggttc   11580
gggcgacagt gtaaagagac ttgatgaagt tggtgtcgtc gtgtcggtag tgcttgccca   11640
tgaccttctt gatcttctca gtggcgattc gggcgttgta gaagggaatt ccgtcgtcgc   11700
ctgagtcgac gagtatctgt ctgactcgtc attgccgcct ttggagtacg actccaacta   11760
tgagtgtgct tggatcactt tgacgataca ttcttcgttg gaggctgtgg gtctgacagc   11820
tgcgttttcg gcgcggttgg ccgacaacaa tatcagctgc aacgtcattg ctggctttca   11880
```

```
tcatgatcac attttgtcg gcaaaggcga cgcccagaga gccattgacg ttctttctaa    11940
tttggaccga tagccgtata gtccagtcta tctataagtt caactaactc gtaactatta    12000
ccataacata tacttcactg ccccagataa ggttccgata aaaagttctg cagactaaat    12060
ttatttcagt ctcctcttca ccaccaaaat gccctcctac gaagctcgag ctaacgtcca    12120
caagtccgcc tttgccgctc gagtgctcaa gctcgtggca gccaagaaaa ccaacctgtg    12180
tgcttctctg gatgttacca ccaccaagga gctcattgag cttgccgata aggtcggacc    12240
ttatgtgtgc atgatcaaaa cccatatcga catcattgac gacttcacct acgccggcac    12300
tgtgctcccc ctcaaggaac ttgctcttaa gcacggtttc ttcctgttcg aggacagaaa    12360
gttcgcagat attggcaaca ctgtcaagca ccagtaccgg tgtcaccgaa tcgccgagtg    12420
gtccgatatc accaacgccc acggtgtacc cggaaccgga atcattgctg gcctgcgagc    12480
tggtgccgag gaaactgtct ctgaacagaa gaaggaggac gtctctgact acgagaactc    12540
ccagtacaag gagttcctag tcccctctcc caacgagaag ctggccagag gtctgctcat    12600
gctggccgag ctgtcttgca agggctctct ggccactggc gagtactcca agcagaccat    12660
tgagcttgcc cgatccgacc ccgagtttgt ggttggcttc attgcccaga accgacctaa    12720
gggcgactct gaggactggc ttattctgac ccccggggtg ggtcttgacg caagggaga     12780 cgctctcgga cagcagtacc gaactgttga ggatgtcatg tctaccggaa cggatatcat    12840
aattgtcggc cgaggtctgt acggccagaa ccgagatcct attgaggagg ccaagcgata    12900
ccagaaggct ggctgggagg cttaccagaa gattaactgt tagaggttag actatggata    12960
tgtaatttaa ctgtgtatat agagagcgtg caagtatgga gcgcttgttc agcttgtatg    13020
atggtcagac gacctgtctg atcgagtatg tatgatactg cacaacctgt gtatccgcat    13080
gatctgtcca atggggcatg ttgttgtgtt tctcgatacg gagatgctgg gtacagtgct    13140
aatacgttga actacttata cttatatgag gctcgaagaa agctgacttg tgtatgactt    13200
aat                                                                   13203
```

<210> SEQ ID NO 57
<211> LENGTH: 7323
<212> TYPE: DNA
<213> ORGANISM: artificial sequence
<220> FEATURE:
<223> OTHER INFORMATION: Plasmid

<400> SEQUENCE: 57

```
gtacgagccg gaagcataaa gtgtaaagcc tggggtgcct aatgagtgag ctaactcaca     60
ttaattgcgt tgcgctcact gcccgctttc cagtcgggaa acctgtcgtg ccagctgcat    120
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
```

```
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg ttttttttgtt   900 tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatccttttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg aagggccga gcgcagaagt    1320 ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
```

```
actccatcta ccgcctccaa atgatgttct caaaatatat tgtatgaact tattttattt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatccttt gtttattaca tgggctggat acataaaggt attttgattt    3720
aattttttgc ttaaattcaa tcccccctcg ttcagtgtca actgtaatgg taggaaatta   3780
ccatactttt gaagaagcaa aaaaatgaa agaaaaaaaa aatcgtattt ccaggttaga    3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttacttt agcttatgca    4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg ccagagagc ccttgcaaga    4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gaggggagc acagtgccgg cgtaggtgaa gtcgtcaatg atgtcgatat gggttttgat    5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtgacgt tagctcgagc ttcgtaggag ggcatttgg tggtgaagag     5340
gagactgaaa taaatttagt ctgcagaact ttttatcgga accttatctg gggcagtgaa   5400
```

```
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
gggttggcgg cgtatttgtg tcccaaaaaa cagccccaat tgccccggag aagacggcca    5820
ggccgcctag atgacaaatt caacaactca cagctgactt tctgccattg ccactagggg    5880
ggggcctttt tatatggcca agccaagctc tccacgtcgg ttgggctgca cccaacaata    5940
aatgggtagg gttgcaccaa caaagggatg ggatggggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc cccctggata    6360
tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc ggggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggatccagg    6780
cctgttaacg gccattacgg cctgcaggat ccgaaaaaac ctcccacacc tcccctgaa     6840 cctgaaacat aaaatgaatg caattgttgt tgttaacttg tttattgcag cttataatgg    6900
ttacaaataa agcaatagca tcacaaattt cacaaataaa gcatttttt cactgcattc     6960 tagttgtggt ttgtccaaac tcatcaatgt atcttatcat gtctgcggcc gcaagtgtgg    7020
atggggaagt gagtgcccgg ttctgtgtgc acaattggca atccaagatg gatggattca    7080
acacagggat atagcgagct acgtggtggt gcgaggatat agcaacggat atttatgttt    7140
gacacttgag aatgtacgat acaagcactg tccaagtaca atactaaaca tactgtacat    7200
actcatactc gtacccgggc aacggtttca cttgagtgca gtggctagtg ctcttactcg    7260
tacagtgtgc aatactgcgt atcatagtct ttgatgtata tcgtattcat tcatgttagt    7320
tgc                                                                  7323
```

<210> SEQ ID NO 58
<211> LENGTH: 28
<212> TYPE: DNA
<213> ORGANISM: artificial sequence
<220> FEATURE:
<223> OTHER INFORMATION: Promoter

<400> SEQUENCE: 58
gatcccatgg atccaggcct gttaacgg                                         28

<210> SEQ ID NO 59
<211> LENGTH: 32
<212> TYPE: DNA
<213> ORGANISM: artificial sequence
<220> FEATURE:
<223> OTHER INFORMATION: Promoter

<400> SEQUENCE: 59
gatcgcggcc gcagacatga taagatacat tg                32

<210> SEQ ID NO 60
<211> LENGTH: 253
<212> TYPE: DNA
<213> ORGANISM: artificial sequence
<220> FEATURE:
<223> OTHER INFORMATION: Multiple Cloning Site

<400> SEQUENCE: 60
gatcccatgg atccaggcct gttaacggcc attacggcct gcaggatccg aaaaaacctc    60
ccacacctcc ccctgaacct gaaacataaa atgaatgcaa ttgttgttgt taacttgttt   120
attgcagctt ataatggtta caaataaagc aatagcatca caaatttcac aaataaagca   180 ttttttttcac tgcattctag ttgtggtttg tccaaactca tcaatgtatc ttatcatgtc   240
tgcggccgcg atc                                                      253

<210> SEQ ID NO 61
<211> LENGTH: 1003
<212> TYPE: DNA
<213> ORGANISM: Yarrowia lipolytica

<400> SEQUENCE: 61
ggagtttggc gcccgttttt tcgagcccca cacgtttcgg tgagtatgag cggcggcaga    60
ttcgagcgtt tccggtttcc gcggctggac gagagcccat gatggggggct cccaccacca   120 gcaatcaggg ccctgattac acacccacct gtaatgtcat gctgttcatc gtggttaatg   180
ctgctgtgtg ctgtgtgtgt gtgttgtttg gcgctcattg ttgcgttatg cagcgtacac   240
cacaatattg gaagcttatt agcctttcta ttttttcgtt tgcaaggctt aacaacattg   300
ctgtggagag ggatggggat atggaggccg ctggagggag tcggagaggc gttttggagc   360
ggcttggcct ggcgcccagc tcgcgaaacg cacctaggac cctttggcac gccgaaatgt   420 gccactttc agtctagtaa cgccttacct acgtcattcc atgcatgcat gtttgcgcct   480
tttttccctt gccttgatc gccacacagt acagtgcact gtacagtgga ggttttgggg   540
gggtcttaga tgggagctaa agcggccta gcggtacact agtgggattg tatggagtgg   600
catggagcct aggtggagcc tgacaggacg cacgaccggc tagcccgtga cagacgatgg   660
gtggctcctg ttgtccaccg cgtacaaatg tttgggccaa agtcttgtca gccttgcttg   720
cgaacctaat tcccaatttt gtcacttcgc accccattg atcgagccct aaccctgcc   780 catcaggcaa tccaattaag ctcgcattgt ctgccttgtt tagtttggct cctgcccgtt   840
tcggcgtcca cttgcacaaa cacaaacaag cattatatat aaggctcgtc tctccctccc   900
aaccacactc acttttttgc ccgtcttccc ttgctaacac aaaagtcaag aacacaaaca   960
accaccccaa ccccctaca cacaagacat atctacagca atg                    1003

<210> SEQ ID NO 62
<211> LENGTH: 32
<212> TYPE: DNA
<213> ORGANISM: artificial sequence
<220> FEATURE:

<223> OTHER INFORMATION: Promoter

<400> SEQUENCE: 62
gatcctcgag ggagtttggc gcccgttttt tc                                      32

<210> SEQ ID NO 63
<211> LENGTH: 34
<212> TYPE: DNA
<213> ORGANISM: artificial sequence
<220> FEATURE:
<223> OTHER INFORMATION: Promoter

<400> SEQUENCE: 63
gatcccatgg ttgtagatat gtcttgtgtg taag                                    34

<210> SEQ ID NO 64
<211> LENGTH: 7277
<212> TYPE: DNA
<213> ORGANISM: artificial sequence
<220> FEATURE:
<223> OTHER INFORMATION: Plasmid

<400> SEQUENCE: 64
catggatcca ggcctgttaa cggccattac ggcctgcagg atccgaaaaa acctcccaca        60 cctcccctg aacctgaaac ataaaatgaa tgcaattgtt gttgttaact tgtttattgc       120
agcttataat ggttacaaat aaagcaatag catcacaaat ttcacaaata aagcattttt       180
ttcactgcat tctagttgtg gtttgtccaa actcatcaat gtatcttatc atgtctgcgg       240
ccgcaagtgt ggatggggaa gtgagtgccc ggttctgtgt gcacaattgg caatccaaga       300
tggatggatt caacacaggg atatagcgag ctacgtggtg gtgcgaggat atagcaacgg       360
atatttatgt ttgacacttg agaatgtacg atacaagcac tgtccaagta caatactaaa       420
catactgtac atactcatac tcgtacccgg caacggtttt cacttgagtg cagtggctag       480
tgctcttact cgtacagtgt gcaatactgc gtatcatagt ctttgatgta tatcgtattc       540
attcatgtta gttgcgtacg agccggaagc ataaagtgta aagcctgggg tgcctaatga       600
gtgagctaac tcacattaat tgcgttgcgc tcactgcccg ctttccagtc gggaaacctg       660
tcgtgccagc tgcattaatg aatcggccaa cgcgcgggga gaggcggttt gcgtattggg       720
cgctcttccg cttcctcgct cactgactcg ctgcgctcgg tcgttcggct gcggcgagcg       780
gtatcagctc actcaaaggc ggtaatacgg ttatccacag aatcagggga taacgcagga       840
aagaacatgt gagcaaaagg ccagcaaaag gccaggaacc gtaaaaaggc cgcgttgctg       900
gcgtttttcc ataggctccg ccccctgac gagcatcaca aaaatcgacg ctcaagtcag       960
aggtggcgaa acccgacagg actataaaga taccaggcgt ttccccctgg aagctccctc      1020
gtgcgctctc ctgttccgac cctgccgctt accggatacc tgtccgcctt tctcccttcg      1080
ggaagcgtgg cgctttctca tagctcacgc tgtaggtatc tcagttcggt gtaggtcgtt      1140
cgctccaagc tgggctgtgt gcacgaaccc cccgttcagc ccgaccgctg cgccttatcc      1200
ggtaactatc gtcttgagtc aacccggta agacacgact tatcgccact ggcagcagcc      1260
actggtaaca ggattagcag agcgaggtat gtaggcggtg ctacagagtt cttgaagtgg      1320
tggcctaact acggctacac tagaaggaca gtatttggta tctgcgctct gctgaagcca      1380
gttaccttcg gaaaaagagt tggtagctct tgatccggca acaaaccac cgctggtagc       1440 ggtggttttt tgtttgcaa gcagcagatt acgcgcagaa aaaaaggatc tcaagaagat      1500
cctttgatct tttctacggg gtctgacgct cagtggaacg aaaactcacg ttaagggatt      1560

| | |
|---|---|
| ttggtcatga gattatcaaa aaggatcttc acctagatcc tttaaatta aaaatgaagt | 1620 |
| tttaaatcaa tctaaagtat atatgagtaa acttggtctg acagttacca atgcttaatc | 1680 |
| agtgaggcac ctatctcagc gatctgtcta tttcgttcat ccatagttgc ctgactcccc | 1740 |
| gtcgtgtaga taactacgat acgggagggc ttaccatctg gccccagtgc tgcaatgata | 1800 |
| ccgcgagacc cacgctcacc ggctccagat ttatcagcaa taaaccagcc agccggaagg | 1860 |
| gccgagcgca gaagtggtcc tgcaacttta tccgcctcca tccagtctat taattgttgc | 1920 |
| cgggaagcta gagtaagtag ttcgccagtt aatagtttgc gcaacgttgt tgccattgct | 1980 |
| acaggcatcg tggtgtcacg ctcgtcgttt ggtatggctt cattcagctc cggttcccaa | 2040 |
| cgatcaaggc gagttacatg atcccccatg ttgtgcaaaa aagcggttag ctccttcggt | 2100 |
| cctccgatcg ttgtcagaag taagttggcc gcagtgttat cactcatggt tatggcagca | 2160 |
| ctgcataatt ctcttactgt catgccatcc gtaagatgct tttctgtgac tggtgagtac | 2220 |
| tcaaccaagt cattctgaga atagtgtatg cggcgaccga gttgctcttg cccggcgtca | 2280 |
| atacgggata taccgcgcc acatagcaga actttaaaag tgctcatcat tggaaaacgt | 2340 |
| tcttcggggc gaaaactctc aaggatctta ccgctgttga tccagttc gatgtaaccc | 2400 |
| actcgtgcac ccaactgatc ttcagcatct tttactttca ccagcgtttc tgggtgagca | 2460 |
| aaaacaggaa ggcaaaatgc cgcaaaaaag gaataaggg cgacacggaa atgttgaata | 2520 |
| ctcatactct tcctttttca atattattga agcatttatc agggttattg tctcatgagc | 2580 |
| ggatacatat ttgaatgtat ttagaaaaat aaacaaatag gggttccgcg cacatttccc | 2640 |
| cgaaaagtgc cacctgacgc gccctgtagc ggcgcattaa gcgcggcggg tgtggtggtt | 2700 |
| acgcgcagcg tgaccgctac acttgccagc gccctagcgc ccgctccttt cgctttcttc | 2760 |
| ccttcctttc tcgccacgtt cgccggcttt ccccgtcaag ctctaaatcg ggggctccct | 2820 |
| ttagggttcc gatttagtgc tttacggcac ctcgacccca aaaaacttga ttagggtgat | 2880 |
| ggttcacgta gtgggccatc gccctgatag acggtttttc gccctttgac gttggagtcc | 2940 |
| acgttcttta atagtggact cttgttccaa actggaacaa cactcaaccc tatctcggtc | 3000 |
| tattcttttg atttataagg gattttgccg atttcggcct attggttaaa aaatgagctg | 3060 |
| atttaacaaa aatttaacgc gaattttaac aaaatattaa cgcttacaat ttccattcgc | 3120 |
| cattcaggct gcgcaactgt tgggaagggc gatcggtgcg ggcctcttcg ctattacgcc | 3180 |
| agctggcgaa agggggatgt gctgcaaggc gattaagttg ggtaacgcca gggttttccc | 3240 |
| agtcacgacg ttgtaaaacg acggccagtg aattgtaata cgactcacta tagggcgaat | 3300 |
| tgggtaccgg gccccccctc gaggtcgatg gtgtcgataa gcttgatatc gaattcatgt | 3360 |
| cacacaaacc gatcttcgcc tcaaggaaac ctaattctac atccgagaga ctgccgagat | 3420 |
| ccagtctaca ctgattaatt ttcgggccaa taatttaaaa aaatcgtgtt atataatatt | 3480 |
| atatgtatta tatatataca tcatgatgat actgacagtc atgtcccatt gctaaataga | 3540 |
| cagactccat ctgccgcctc caactgatgt tctcaatatt taaggggtca tctcgcattg | 3600 |
| tttaataata aacagactcc atctaccgcc tccaaatgat gttctcaaaa tatattgtat | 3660 |
| gaacttattt ttattactta gtattattag acaactact tgctttatga aaaacacttc | 3720 |
| ctatttagga aacaatttat aatggcagtt cgttcattta acaatttatg tagaataaat | 3780 |
| gttataaatg cgtatgggaa atcttaaata tggatagcat aaatgatatc tgcattgcct | 3840 |
| aattcgaaat caacagcaac gaaaaaaatc ccttgtacaa cataaatagt catcgagaaa | 3900 |

```
tatcaactat caaagaacag ctattcacac gttactattg agattattat tggacgagaa   3960
tcacacactc aactgtcttt ctctcttcta gaaatacagg tacaagtatg tactattctc   4020
attgttcata cttctagtca tttcatccca catattcctt ggatttctct ccaatgaatg   4080
acattctatc ttgcaaattc aacaattata ataagatata ccaaagtagc ggtatagtgg   4140
caatcaaaaa gcttctctgg tgtgcttctc gtatttattt ttattctaat gatccattaa   4200
aggtatatat ttatttcttg ttatataatc cttttgttta ttacatgggc tggatacata   4260
aaggtatttt gatttaattt tttgcttaaa ttcaatcccc cctcgttcag tgtcaactgt   4320
aatggtagga aattaccata cttttgaaga agcaaaaaaa atgaaagaaa aaaaaaatcg   4380
tatttccagg ttagacgttc cgcagaatct agaatgcggt atgcggtaca ttgttcttcg   4440
aacgtaaaag ttgcgctccc tgagatattg tacattttg ctttacaag tacaagtaca   4500 tcgtacaact atgtactact gttgatgcat ccacaacagt ttgttttgtt ttttttttgtt   4560 tttttttttt ctaatgattc attaccgcta tgtataccta cttgtacttg tagtaagccg   4620
ggttattggc gttcaattaa tcatagactt atgaatctgc acggtgtgcg ctgcgagtta   4680
cttttagctt atgcatgcta cttgggtgta atattgggat ctgttcggaa atcaacggat   4740
gctcaatcga tttcgacagt aattaattaa gtcatacaca agtcagcttt cttcgagcct   4800
catataagta taagtagttc aacgtattag cactgtaccc agcatctccg tatcgagaaa   4860
cacaacaaca tgccccattg gacagatcat gcggatacac aggttgtgca gtatcataca   4920
tactcgatca gacaggtcgt ctgaccatca tacaagctga acaagcgctc catacttgca   4980
cgctctctat atacacagtt aaattacata tccatagtct aacctctaac agttaatctt   5040
ctggtaagcc tcccagccag ccttctggta tcgcttggcc tcctcaatag gatctcggtt   5100
ctggccgtac agacctcggc cgacaattat gatatccgtt ccggtagaca tgacatcctc   5160
aacagttcgg tactgctgtc cgagagcgtc tcccttgtcg tcaagaccca ccccggggggt   5220 cagaataagc cagtcctcag agtcgcccctt aggtcggttc tgggcaatga agccaaccac   5280
aaactcgggg tcggatcggg caagctcaat ggtctgcttg gagtactcgc cagtggccag   5340
agagcccttg caagacagct cggccagcat gagcagacct ctggccagct tctcgttggg   5400 agagggact aggaactcct tgtactggga gttctcgtag tcagacgt cctccttctt   5460 ctgttcagag acagtttcct cggcaccagc tcgcaggcca gcaatgattc cggttccggg   5520
tacaccgtgg gcgttggtga tatcggacca ctcggcgatt cggtgacacc ggtactggtg   5580
cttgacagtg ttgccaatat ctgcgaactt tctgtcctcg aacaggaaga aaccgtgctt   5640
aagagcaagt tccttgaggg ggagcacagt gccggcgtag gtgaagtcgt caatgatgtc   5700
gatatgggtt ttgatcatgc acacataagg tccgaccta tcggcaagct caatgagctc   5760
cttggtggtg gtaacatcca gagaagcaca caggttggtt ttcttggctg ccacgagctt   5820
gagcactcga gcggcaaagg cggacttgtg gacgttagct cgagcttcgt aggagggcat   5880
tttggtggtg aagaggagac tgaaataaat ttagtctgca gaactttta tcggaaccctt   5940 atctggggca gtgaagtata tgttatggta atagttacga gttagttgaa cttatagata   6000
gactggacta tacggctatc ggtccaaatt agaaagaacg tcaatggctc tctgggcgtc   6060
gcctttgccg acaaaaatgt gatcatgatg aaagccagca atgacgttgc agctgatatt   6120
gttgtcggcc aaccgcgccg aaaacgcagc tgtcagaccc acagcctcca acgaagaatg   6180
tatcgtcaaa gtgatccaag cacactcata gttggagtcg tactccaaag gcggcaatga   6240
cgagtcagac agatactcgt cgaccgtacg gggagtttgg cgcccgtttt ttcgagcccc   6300
```

-continued

| | |
|---|---|
| acacgtttcg gtgagtatga gcggcggcag attcgagcgt ttccggtttc cgcggctgga | 6360 |
| cgagagccca tgatggggc tcccaccacc agcaatcagg ccctgatta cacacccacc | 6420 |
| tgtaatgtca tgctgttcat cgatggttaa tgctgctgtg tgctgtgtgt gtgtgttgtt | 6480 |
| tggcgctcat tgttgcgtta tgcagcgtac accacaatat tggaagctta ttagcctttc | 6540 |
| tatttttcg tttgcaaggc ttaacaacat tgctgtggag agggatgggg atatggaggc | 6600 |
| cgctggaggg agtcggagag gcgttttgga gcggcttggc ctggcgccca gctcgcgaaa | 6660 |
| cgcacctagg acccttggc acgccgaaat gtgccacttt tcagtctagt aacgccttac | 6720 |
| ctacgtcatt ccatgcgtgc atgtttgcgc cttttttccc ttgcccttga tcgccacaca | 6780 |
| gtacagtgca ctgtacagtg gaggttttgg ggggtctta gatgggagct aaaagcggcc | 6840 |
| tagcggtaca ctagtgggat tgtatggagt ggcatggagc ctaggtggag cctgacagga | 6900 |
| cgcacgaccg gctagcccgt gacagacgat gggtggctcc tgttgtccac cgcgtacaaa | 6960 |
| tgtttgggcc aaagtcttgt cagccttgct tgcgaaccta attcccaatt ttgtcacttc | 7020 |
| gcaccccat tgatcgagcc ctaacccctg cccatcaggc aatccaatta agctcgcatt | 7080 |
| gtctgccttg tttagtttgg ctcctgcccg tttcggcgtc cacttgcaca aacacaaaca | 7140 |
| agcattatat ataaggctcg tctctccctc ccaaccacac tcactttttt gcccgtcttc | 7200 |
| ccttgctaac acaaaagtca agaacacaaa caaccacccc aacccccta cacacaagac | 7260 |
| atatctacag caatggc | 7277 |

<210> SEQ ID NO 65
<211> LENGTH: 14213
<212> TYPE: DNA
<213> ORGANISM: artificial sequence
<220> FEATURE:
<223> OTHER INFORMATION: Plasmid

<400> SEQUENCE: 65

| | |
|---|---|
| cgatcgagga agaggacaag cggctgcttc ttaagtttgt gacatcagta tccaaggcac | 60 |
| cattgcaagg attcaaggct ttgaacccgt catttgccat tcgtaacgct ggtagacagg | 120 |
| ttgatcggtt ccctacggcc tccacctgtg tcaatcttct caagctgcct gactatcagg | 180 |
| acattgatca acttcggaag aaacttttgt atgccattcg atcacatgct ggtttcgatt | 240 |
| tgtcttagag gaacgcatat acagtaatca tagagaataa acgatattca tttattaaag | 300 |
| tagatagttg aggtagaagt tgtaaagagt gataaatagc ggccgcttaa gcgagcatct | 360 |
| tgagcagcac attgttgatt ctgccagact tgatggcttc gtagattttg gagacgttgg | 420 |
| agccaatggt cacctcttgc ttgccgagaa agacgtctcc tcgtcgagcc ttcacaccaa | 480 |
| gttcctctcg gacgaaggcg tacagaatct gagttctggg agagaggtag gagagggcag | 540 |
| gagaggaggt agaggcagca gaccagaagg tctctcggac ttgtcgagtc agagagatgg | 600 |
| cagactcggc agcggcaacc ttccaggcat tgacggcagc aagagacagc gaggtggaag | 660 |
| agagcacttc gacgacagtt ccggcagcaa aggagaaggc atcgtgccat ctgggaacca | 720 |
| ggtcgtagga gttggtctgc tcgagtcgtt tggccagtgt cttgttgacc ttctcaacaa | 780 |
| gctcgtctcg caggttcgat ccagtcatgg cagagccaaa gtgctgatca atgagagaca | 840 |
| cgatggcagg accaaactgc ttcttgaact cgaactcgat agctcgcagg tcaatggctt | 900 |
| gcaggacaca gtagaggtga gtggcaagga gcagagagag aacgtcgttg gactcggtgg | 960 |
| ttcgtcgagc agagatgagg gcaagggagt tgactgcctg gttcgccatc tcagcaggct | 1020 |

```
gcacgtgagt ggtgacaggg ttggcgagat gacccagctc agaggtgtag gcagcggcag    1080
cgatgtcgag tcccttgcag tggtaggaca gagagggatc ttcggcagca agacaggagg    1140
gcagacctcg gttcatgcct gcattgagca tctcagtcag ctgggtgaag ttgagcttgc    1200
caatctgagc gagtccaagt cgagtcttct ccatagtgtt ggccacagcg gcagcctgga    1260
agttgcctcc gtgatgcgag gtcttgttct cgacatcaat cagagggttg tcggtagtgg    1320
actgaccagc ctcaatggtg agcacggcat gagcgtggat gaggtcagag accagggtc     1380 cgagccactg aggagaggtt cgcaagggat aacgatcctg tctgagaatg ccttcgtcgt    1440
ccttgacttt gacttcctcc tcgtggtgga cggcaaatcg agaaccctcc agaagctttc    1500
ggatgttgcc agcgacttcg atctgtgtgg gatgaggtcg agtcacatcg tggagaaagg    1560
gatgaaagga gccagcgtgt ccaaccatag cttcgacggt catggcagtc agggactgag    1620
agagcagcga gagcatgtga gcgtcgtgca gagcgagggt agccatagat gcggacacgg    1680
cagtgccgtt gaccagtccg agaccttcct tgggtccaag gacgacaggc tccaggttga    1740
agagggccat agcctctcgt gcgtacagaa tcttctcctt gccttcgtgg acgacgtgca    1800 cttcgagtc gggatgtcca gagatggctg cagcaatgta ggagagagga gacagatcac     1860
cagaggcgga gatggtgcct cgaaggggaa caatgggtgt gatgccatga ttcaggaagt    1920
tggtcaatgc ctcaaggacg acgagtcgaa cagcggagtg gcctcgagtc agagagttca    1980
ctcggatggt catggctcct cggacgacct ccagaggaag agagttctcc agtcctcgtc    2040
ccagacggaa ggagtcaaag gacgagggaa gcacaccgca gagctggtgc tccagcagag    2100
ccttctgaag ggagatggca tcttcagttc gtgtgtcggc agagccacca aatccagtgg    2160
tgacaccgta cacggacatc gagagttgag atcgcaggaa ctcgacggac ttgtcgatct    2220
tcgatcgaat ctcatcggag tccttcactc gaacgggtct acccttcgg gcagcagaga    2280 cgacgtctcc gaggttcagc gagtagccat cgagctccag agtggagtcg gtaggagcag    2340
cgagcatctt ctcgacaatg tcaacctgtg tcacctgagt ggtgggcaag tgagagccag    2400
cgacggcaag gttggtcgaa gctccgttca ctgcctgctt agcagaggca acaccgttgg    2460
cgaaggagtg agagatggag tccagagagg gagccatgga gagctgggtt agtttgtgta    2520
gagagtgtgt gttgctagcg actttcggat tgtgtcatta cacaaaacgc gtcgtctcga    2580
cactgatctt gtcgtggata ctcacggctc ggacatcgtc gccgacgatg acaccggact    2640
ttcgcttaag gacgtcagta acaggcattg tgtgatgtgt agtttagatt tcgaatctgt    2700
ggggaaagaa aggaaaaaag agactggcaa ccgattggga gagccactgt ttatatatac    2760
cctagacaag cccccgctt gtaagatgtt ggtcaatgta aaccagtatt aaggttggca     2820
agtgcaggag aagcaaggtg tgggtaccga gcaatgaaaa tgtgcggaag gcaaaaaaat    2880
gaggccacgg cctattgtcg gggctatatc caggggcga ttgaagtaca ctaacatgac     2940
atgtgtccac agaccctcaa tctggcctga tgagccaaat ccatacgcgc tttcgcagct    3000
ctaaaggcta taacaagtca caccaccctg ctcgacctca gcgccctcac tttttgttaa    3060
gacaaactgt acacgctgtt ccagcgtttt ctgcctgcac ctggtgggac atttggtgca    3120
acctaaagtg ctcggaacct ctgtggtgtc cagatcagcg cagcagttcc gaggtagttt    3180
tgaggccctt agatgatgca atggtgtcag tcgctggatc acgagtctta atggcagtat    3240
tcgttcttat ttgtgccatt gagccccgtt atcctcgtat cttctacccc ccatcccatc    3300
cctttgttgg tgcaaccta cccatttatt gttgggtgca gcccaaccga cgtgagagc     3360 ttggcttggc catataaaaa ggcccccccc tagtggcaat ggcagaaagt cagctgtgag    3420
```

```
ttgttgaatt tgtcatctag gcggcctggc cgtcttctcc ggggcaattg ttcctctata   3480
gtactgcgta cactgtttaa acagtgtacg cagatctact atagaggaac atttaaatgt   3540
agctaacggt agcaggcgaa ctactggtac atacctcccc cggaatatgt acaggcataa   3600
tgcgtatctg tgggacatgt ggtcgttgcg ccattatgta agcagcgtgt actcctctga   3660
ctgtccatat ggtttgctcc atctcaccct catcgttttc attgttcaca ggcggccaca   3720
aaaaaactgt cttctctcct tctctcttcg ccttagtcta ctcggaccag ttttagttta   3780
gcttggcgcc actggataaa tgagacctca ggccttgtga tgaggaggtc acttatgaag   3840
catgttagga ggtgcttgta tggatagaga agcacccaaa ataataagaa taataataaa   3900
acaggggcg ttgtcatttc atatcgtgtt tcaccatca atacacctcc aaacaatgcc   3960
cttcatgtgg ccagccccaa tattgtcctg tagttcaact ctatgcagct cgtatcttat   4020
tgagcaagta aaactctgtc agccgatatt gcccgacccg cgacaagggt caacaaggtg   4080
gtgtaaggcc ttcgcagaag tcaaaactgt gccaaacaaa catctagagt ctctttggtg   4140
tttctcgcat atatttwatc ggctgtctta cgtatttgcg cctcggtacc ggactaattt   4200
cggatcatcc ccaatacgct tttcttcgc agctgtcaac agtgtccatg atctatccac   4260
ctaaatgggt catatgaggc gtataatttc gtggtgctga taataattcc catatatttg   4320
acacaaaact tcccccccta gacatacatc tcacaatctc acttcttgtg cttctgtcac   4380
acatctcctc cagctgactt caactcacac ctctgcccca gttggtctac agcggtataa   4440
ggtttctccg catagaggtg caccactcct cccgatactt gtttgtgtga cttgtgggtc   4500
acgacatata tatctacaca cattgcgcca ccctttggtt cttccagcac aacaaaaaca   4560
cgacacgcta accatggttc gatccgagta cgccgacgtt cctcccgtcg acctgcccat   4620
tcacgatgct gtgctcggag gtgctgccgc tttcggctct actcctgccc tgatcgacgg   4680
aaccgacggc accactctca cctacgagca ggtggaccga tttcacagac gagtcgctgc   4740
agcccttgcc gagacaggcg ttcgaaaggg agacgtcttg gctctgcact ctcccaacac   4800
tgttgccttc ccacttgcct tctacgctgc caccagagct ggtgcctccg tcaccactgt   4860
gcatcctctt gctacagcag aagagtttgc caagcagctg aaggactctg ctgcccgatg   4920
gattgtcacc gtttcccctc tcctgtccac tgcccgacga gctgccgagc ttgctggagg   4980
cgtccaggag attctggttt gcgacagcgc accggtcac cgatcccttg tcgatatgct   5040
ggcctctaca gctcccgaac cttcgtcgc catcgaccct gcagaggacg ttgctgcctt   5100
gccctactct tccggaacta ccggtactcc caagggtgtc atgctcaccc atcgacagat   5160
tgccaccaac ctggctcaac tcgaaccttc catgccctct gctcctggag atcgagttct   5220
tgcagtgctt cccttctttc acatctatgg tctgactgcc ctcatgaacg ctcctctgcg   5280
actcggagcc accgtcgtgg ttcttccacg attcgacctg gagcagtttc tcgctgccat   5340
tcagaaccac cgaatcactt cgctgtacgt cgctcctccc attgtgctgg cacttgccaa   5400
acatcccttg gttgccgact acgatctctc ctcgctgaga tacatcgtgt cggctgccgc   5460
acctctcgat gctcgacttg ccgctgcctg ttcccagcga ctcggactgc ctcccgtcgg   5520
tcaggcttac ggcatgaccg agctgtctcc tggaacacac gtggttccct tggacgcaat   5580
ggccgatgct cctcctggca ctgtcggtcg actcattgcc ggaaccgaga tgcgaatcgt   5640
ctccctcacc gatccaggta cagaccttcc tgctggagag tctggcgaga ttctcattcg   5700
aggtccccag atcatgaagg gctacttggg aagacccgat gccactgctg ccatgatcga   5760
```

```
cgaagaaggc tggctgcaca caggtgatgt cggacacgtg gatgccgatg gctggctgtt    5820
tgttgtcgac cgagtcaagg agcttatcaa gtacaaggga ttccaggttg ctcctgccga    5880
gctggaagcc cacctgctca ctcatccagg tgtcgcagac gctgccgtgg ttggagccta    5940
cgacgatgac ggcaacgagg ttccccatgc cttcgtcgtg cgacaacctg ccgctcccgg    6000
tcttgccgag tccgagatca tgatgtacgt tgccgaacga gtcgctccct acaagcgagt    6060
gcgacgagtt accttcgtcg atgccgttcc cagagctgcc tccggcaaga ttctccgaag    6120
acagctgcga gagcctcgat aagcggccgc aagtgtggat ggggaagtga gtgcccggtt    6180
ctgtgtgcac aattggcaat ccaagatgga tggattcaac acaggatat agcgagctac     6240 gtggtggtgc gaggatatag caacggatat ttatgtttga cacttgagaa tgtacgatac    6300
aagcactgtc caagtacaat actaaacata ctgtacatac tcatactcgt acccgggcaa    6360
cggtttcact tgagtgcagt ggctagtgct cttactcgta cagtgtgcaa tactgcgtat    6420
catagtcttt gatgtatatc gtattcattc atgttagttg cgtacgggtg aagcttccac    6480
tggtcggcgt ggtagtgggg cagagtgggg tcggtgtgct gcaggtaggt gatggccacg    6540
agccagtggt tgacccacag gtaggggatc aggtagtaga gggtgacgga agccaggccc    6600
catcggttga tggagtatgc gatgacggac atggtgatac caataccgac gttagagatc    6660
cagatgttga accagtcctt cttctcaaac agcggggcgt tggggttgaa gtggttgaca    6720
gcccatttgt tgagcttggg gtacttctgt ccggtaacgt aagacagcag atacagaggc    6780
catccaaaca cctgctgggt gatgaggccg tagagggtca tgagggggagc gtcctcagca    6840 agctcagacc agtcatgggc gcctcggttc tccataaact cctttcggtc cttgggcaca    6900
aacaccatat cacgggtgag gtgaccagtg gacttgtggt gcatggagtg ggtcagcttc    6960
caggcgtagt aagggaccag catggaggag tgcagaaccc atccggtgac gttgttgacg    7020
gtgttagagt cggagaaagc agagtggcca cactcgtggg caagaaccca cagaccggtg    7080
ccaaacagac cctggacaat ggagtacatg gcccaggcca cagctcggcc ggaagccgag    7140
ggaataagag gcaggtacgc gtaggccatg taggcaaaaa cggcgataaa gaagcaggcg    7200
cgccagctgc attaatgaat cggccaacgc gcggggagag gcggtttgcg tattgggcgc    7260
tcttccgctt cctcgctcac tgactcgctg cgctcggtcg ttcggctgcg gcgagcggta    7320
tcagctcact caaaggcggt aatacggtta tccacagaat caggggataa cgcaggaaag    7380
aacatgtgag caaaaggcca gcaaaaggcc aggaaccgta aaaaggccgc gttgctggcg    7440
tttttccata ggctccgccc ccctgacgag catcacaaaa atcgacgctc aagtcagagg    7500
tggcgaaacc cgacaggact ataaagatac caggcgtttc ccctggaag ctccctcgtg     7560 cgctctcctg ttccgaccct gccgcttacc ggatacctgt ccgcctttct cccttcggga    7620
agcgtggcgc tttctcatag ctcacgctgt aggtatctca gttcggtgta ggtcgttcgc    7680
tccaagctgg gctgtgtgca cgaaccccc gttcagcccg accgctgcgc cttatccggt      7740
aactatcgtc ttgagtccaa cccggtaaga cacgacttat cgccactggc agcagccact    7800
ggtaacagga ttagcagagc gaggtatgta ggcggtgcta cagagttctt gaagtggtgg    7860
cctaactacg gctacactag aagaacagta tttggtatct gcgctctgct gaagccagtt    7920
accttcggaa aaagagttgg tagctcttga tccggcaaac aaaccaccgc tggtagcggt    7980
ggtttttttg tttgcaagca gcagattacg cgcagaaaaa aaggatctca agaagatcct    8040
ttgatctttt ctacggggtc tgacgctcag tggaacgaaa actcacgtta agggattttg    8100
gtcatgagat tatcaaaaag gatcttcacc tagatccttt taaattaaaa atgaagtttt    8160
```

```
aaatcaatct aaagtatata tgagtaaact tggtctgaca gttaccaatg cttaatcagt      8220
gaggcaccta tctcagcgat ctgtctattt cgttcatcca tagttgcctg actccccgtc      8280
gtgtagataa ctacgatacg ggagggctta ccatctggcc ccagtgctgc aatgataccg      8340
cgagacccac gctcaccggc tccagattta tcagcaataa accagccagc cggaagggcc      8400
gagcgcagaa gtggtcctgc aactttatcc gcctccatcc agtctattaa ttgttgccgg      8460
gaagctagag taagtagttc gccagttaat agtttgcgca acgttgttgc cattgctaca      8520
ggcatcgtgg tgtcacgctc gtcgtttggt atggcttcat tcagctccgg ttcccaacga      8580
tcaaggcgag ttacatgatc ccccatgttg tgcaaaaaag cggttagctc cttcggtcct      8640
ccgatcgttg tcagaagtaa gttggccgca gtgttatcac tcatggttat ggcagcactg      8700
cataattctc ttactgtcat gccatccgta agatgctttt ctgtgactgg tgagtactca      8760
accaagtcat tctgagaata gtgtatgcgg cgaccgagtt gctcttgccc ggcgtcaata      8820
cgggataata ccgcgccaca tagcagaact ttaaaagtgc tcatcattgg aaaacgttct      8880
tcggggcgaa aactctcaag gatcttaccg ctgttgagat ccagttcgat gtaacccact      8940
cgtgcaccca actgatcttc agcatctttt actttcacca gcgtttctgg gtgagcaaaa      9000
acaggaaggc aaaatgccgc aaaaaaggga ataaggcga cacgaaatg ttgaatactc       9060 atactcttcc ttttcaata ttattgaagc atttatcagg gttattgtct catgagcgga      9120
tacatatttg aatgtattta gaaaaataaa caaatagggg ttccgcgcac atttccccga      9180
aaagtgccac ctgatgcggt gtgaaatacc gcacagatgc gtaaggagaa aataccgcat      9240
caggaaattg taagcgttaa tattttgtta aaattcgcgt taaatttttg ttaaatcagc      9300
tcatttttta accataggc cgaaatcggc aaaatccctt ataaatcaaa agaatagacc        9360
gagatagggt tgagtgttgt tccagtttgg aacaagagtc cactattaaa gaacgtggac      9420
tccaacgtca aagggcgaaa aaccgtctat cagggcgatg gcccactacg tgaaccatca      9480
ccctaatcaa gttttttggg gtcgaggtgc cgtaaagcac taaatcggaa ccctaaaggg      9540
agcccccgat ttagagcttg acggggaaag ccggcgaacg tggcgagaaa ggaagggaag      9600
aaagcgaaag gagcgggcgc tagggcgctg gcaagtgtag cggtcacgct gcgcgtaacc      9660
accacacccg ccgcgcttaa tgcgccgcta caggcgcgt ccattcgcca ttcaggctgc       9720
gcaactgttg ggaagggcga tcggtgcggg cctcttcgct attacgccag ctggcgaaag      9780
ggggatgtgc tgcaaggcga ttaagttggg taacgccagg gttttcccag tcacgacgtt      9840
gtaaaacgac ggccagtgaa ttgtaatacg actcactata gggcgaattg gcccgacgt       9900 cgcatgcttg aatctacaag taggagggtt ggagtgatta agtgaaactt ctttaacggc      9960
tctatgccag ttctattgat atccgaaaca tcagtatgaa ggtctgataa gggtgacttc      10020
ttcccacaga ttcgtatcag tacgagtacg agaccggtac ttgtaacagt attgatacta     10080
aagggaaact acaacggttg tcagcgtaat gtgacttcgc ccatgaacgc agacacgcag     10140
tgccgagtgc ggtgatatcg cctactcgtt acgtccatgg actacacaac ccctcggctt     10200
cgcttggctt agcctcgggc tcggtgctgt tcagttaaaa cacaatcaaa taacatttct     10260 acttttaga aggcaggccg tcaggagcaa ctccgactcc attgacgttt ctaaacatct      10320
gaatgccttc cttaccttca acaaactggc aggttcgggc gacagtgtaa agagacttga     10380
tgaagttggt gtcgtcgtgt cggtagtgct tgcccatgac cttcttgatc ttctcagtgg     10440
cgattcgggc gttgtagaag ggaattccgt cgtcgcctga gtcgacgagt atctgtctga    10500
```

```
ctcgtcattg ccgcctttgg agtacgactc caactatgag tgtgcttgga tcactttgac    10560
gatacattct tcgttggagg ctgtgggtct gacagctgcg ttttcggcgc ggttggccga    10620
caacaatatc agctgcaacg tcattgctgg ctttcatcat gatcacattt ttgtcggcaa    10680
aggcgacgcc cagagagcca ttgacgttct ttctaatttg daccgatagc cgtatagtcc    10740
agtctatcta taagttcaac taactcgtaa ctattaccat aacatatact tcactgcccc    10800
agataaggtt ccgataaaaa gttctgcaga ctaaatttat ttcagtctcc tcttcaccac    10860
caaaatgccc tcctacgaag ctcgagctaa cgtccacaag tccgcctttg ccgctcgagt    10920
gctcaagctc gtggcagcca agaaaaccaa cctgtgtgct tctctggatg ttaccaccac    10980
caaggagctc attgagcttg ccgataaggt cggaccttat gtgtgcatga tcaaaaccca    11040
tatcgacatc attgacgact tcacctacgc cggcactgtg ctcccccctca aggaacttgc    11100
tcttaagcac ggtttcttcc tgttcgagga cagaaagttc gcagatattg caacactgt    11160
caagcaccag taccggtgtc accgaatcgc cgagtggtcc gatatcacca acgcccacgg    11220
tgtacccgga accggaatca ttgctggcct gcgagctggt gccgaggaaa ctgtctctga    11280
acagaagaag gaggacgtct ctgactacga gaactcccag tacaaggagt tcctagtccc    11340
ctctcccaac gagaagctgg ccagaggtct gctcatgctg gccgagctgt cttgcaaggg    11400
ctctctggcc actggcgagt actccaagca gaccattgag cttgcccgat ccgaccccga    11460
gtttgtggtt ggcttcattg cccagaaccg acctaagggc gactctgagg actggcttat    11520
tctgaccccc ggggtgggtc ttgacgacaa gggagacgct ctcggacagc agtaccgaac    11580
tgttgaggat gtcatgtcta ccggaacgga tatcataatt gtcggccgag gtctgtacgg    11640
ccagaaccga gatcctattg aggaggccaa gcgataccag aaggctggct gggaggctta    11700
ccagaagatt aactgttaga ggttagacta tggatatgta atttaactgt gtatatagag    11760
agcgtgcaag tatggagcgc ttgttcagct tgtatgatgg tcagacgacc tgtctgatcg    11820
agtatgtatg atactgcaca acctgtgtat ccgcatgatc tgtccaatgg ggcatgttgt    11880
tgtgtttctc gatacggaga tgctgggtac agtgctaata cgttgaacta cttatactta    11940
tatgaggctc gaagaaagct gacttgtgta tgacttaatt aaccctcact aaagggaaca    12000
aaagctggag ctccaccgcg gacacaatat ctggtcaaat ttcagtttcg ttacataaat    12060
cgttatgtca aaggagtgtg ggaggttaag agaattatca ccggcaaact atctgttaat    12120
tgctaggtac ctctagacgt ccacccgggt cgcttggcgg ccgaagaggc cggaatctcg    12180
ggccgcggtg gcggccgctt agttagtgac ggtgggaaca gagtggagca cgacagtttc    12240
gatggtcagt ccaggaccaa agccgaagag gactccccag tccaggcctt caccagtggt    12300
ggccttctct cccttgaggg atttctttcg catctcgtcc agaatgaaga gcacacaagc    12360
agaggacatg ttgccgtact cgctcagcac gtgtcgagtg gcttcgagct tcttcttctc    12420
caggttgagc ttagcctcaa ctgcgtcgag gatggcagga cctccgggat gagcaatcca    12480
gaacagagag ttccagtcgg agataccgag agggtcgaaa gcctgggtca ggcacttctc    12540
aatgttctcg gagatgagag tgggcacatt aggccacagg tggaaggtga ggccaaccte    12600
tcgcaggttt ccggcaatgg caccagcaga gttggggata aggtttggg cagcggagac    12660
aagctggaag aggggtcgct cgatagagac atcgggatcg gatccaacaa tcacggcaga    12720
ggagccatca ccaaacagag cctggccgac gagggagtcc agggcatctt cagagggacc    12780
tcggaaggtc acgacagtga tttcggagca cacaacgagg actcgtgctc cagcgttgtt    12840
ctcggccagg tccttggcag ttcggagcac ggtgccacca gcgtagcagc cttggtggta    12900
```

```
cagcatgact cgtcggacgg aggtttcaag gccgagcagg ttagcgagct tgtagtcggc    12960
tccaggcatt tccacaccag aggtagtaca gaagaccaga tgggtgatct tggacttggg    13020
ctgtccccac tctttgagag ccttcagggc agcatcccga ccgagtcggg gaacctcagc    13080
ggtgataatc tcctgtcgga tgttcagaga aggagccatg taagcgccaa tgttgggatg    13140
ctcttcgagc atctcttcag tcaggtggat gtatcgcttc ttaatcatgg atttgtcaca    13200
gatccggttg aacttcttct tgagctcggt catgtgctcg gacttggtca ctcggaagta    13260
gtaatcggca tagtcagact ggtagacaca gtggtcaggg gtagcagtgc caatggccag    13320
gatggtagcg ggacccttgg ctcgctgagc gtttcggaat tcctcaacgg aggccatggc    13380
cattgctgta gatatgtctt gtgtgtaagg gggttgtggt ggttgtttgt gttcttgact    13440
tttgtgttag caagggaaga cgggcaaaaa agtgagtgtg gttgggaggg agagacgagc    13500
cttatatata atgcttgttt gtgtttgtgc aagtggacgc cgaaacgggc aggagccaaa    13560
ctaaacaagg cagacaatgc gagcttaatt ggattgcctg atgggcaggg gttagggctc    13620
gatcaatggg ggtgcgaagt gacaaaattg ggaattaggt tcgcaagcaa ggctgacaag    13680
actttggccc aaacatttgt acgcggtgga caacaggagc cacccatcgt ctgtcacggg    13740
ctagccggtc gtgcgtcctg tcaggctcca cctaggctcc atgccactcc atacaatccc    13800
actagtgtac cgctaggccg cttttagctc ccatctaaga cccccccaaa acctccactg    13860
tacagtgcac tgtactgtgt ggcgatcaag ggcaagggaa aaaaggcgca acatgcacg    13920 catggaatga cgtaggtaag gcgttactag actgaaaagt ggcacatttc ggcgtgccaa    13980
agggtcctag gtgcgtttcg cgagctgggc gccaggccaa gccgctccaa aacgcctctc    14040
cgactccctc cagcggcctc catatcccca tccctctcca cagcaatgtt gttaagcctt    14100
gcaaacgaaa aaatagaaag gctaataagc ttccaatatt gtggtgtacg ctgcataacg    14160
caacaatgag cgccaaacaa cacacacaca cagcacacag cagcattaac cat           14213

<210> SEQ ID NO 66
<211> LENGTH: 2142
<212> TYPE: DNA
<213> ORGANISM: Rhodotorula mucilaginosa

<400> SEQUENCE: 66
atggccccct ccgtcgactc gatcgcgact tcggttgcca actccctctc gaacgggttg     60
cacgccgccg ccgccgccaa cggtggcgac gtccacaaga agacggccgg tgctggctcc    120
ctcctcccga ccaccgagac gacccagctc gacatcgttg agcgcatctt ggccgacgcc    180
ggcgcgacgg accagatcaa actcgatggg tacacccctca cgctcggcga cgtcgtcggc    240
gctgctcgcc gtggccgctc cgtcaaggtc gcagacagcc cgcacatccg cgagaagatc    300
gatgccagtg tcgagttcct ccgtactcag ctcgacaaca gtgtctacgg tgtcacgact    360
ggtttcggcg gctcggccga caccggact gaggatgcga tctcgctcca aaaggccctg    420
ctcgagcacc agtctgcgg tgtcctcccc acctcgatgg atggctttgc gctcggtcgc    480
ggcctcgaga actcgcttcc gctcgaagtc gtccgaggcg cgatgaccat ccgtgtcaac    540
tcgctcactc gcggtcactc ggcggtccga atcgtcgtcc tcgaagccct caccaacttc    600
ctcaaccacg gcatcacccc gatcgtcccg cttgaggcca ccatctcggc gtcgggcgac    660 ctttccccccc tctcttacat cgccgcctcg atcaccggcc accgactc gaaggtccac    720 gtcgacggca agatcatgtc cgcccaggag gcgatcgcgc tcaagggtct tcagcccgtc    780
```

```
gtcctcggtc cgaaggaggg tctcggtctc gtcaacggca cggccgtctc cgcctcgatg      840
gcgacgctgg ccctcaccga cgcacacgtc ctctcgctcc tcgcacaggc gctcactgct      900
cttactgtcg aggccatggt cggacacgcc ggctcgttcc acccattcct ccacgacgtc      960
acgcgccctc acccgaccca gatcgaggtg gcgcgcaaca tccggactct tctcgagggc     1020
agcaagtacg ccgtccacca cgagactgaa gtcaaggtca aggacgacga gggcatcctc     1080
aggcaggacc ggtacccgct ccgctgctcg ccgcagtggc tcggtcccct tgtcagcgac     1140
atgattcacg ctcacgctgt cctctcgctc gaggctggtc agtcgaccac cgacaacccg     1200
ctgatcgacc tcgagaacaa gatgacccac catggcggag ccttcatggc gagcagcgtc     1260
ggaaacacga tggagaagac tcgcctcgcc gtcgcgctga tgggcaaggt cagctttact     1320
cagctcaccg agatgctcaa cgccggcatg aaccgggccc ttccgtcctg cctcgctgcc     1380
gaggacccct ccctctctta tcactgcaag ggtctcgaca ttgctgcggc cgcctacact     1440
tccgagctcg gtcaccttgc caacccggtt cgacccacg tccagccggc cgagatgggc     1500
aaccaggcca tcaactcgct cgccctcatc tcggcccgcc gcaccgccga ggcgaacgac     1560
gttctctccc tcctcctcgc cacccacctc tactgcgtcc tccaggccgt cgacctccgc     1620
gcgatggagt ttgagcacac caaggcgttc gagccgatgg tcactgagct gttgaagcag     1680
cactttggcg cgctcgcgac ggccgaagtc gaggacaagg tccgcaagtc gatctacaag     1740
cggttgcagc agaacaactc gtacgacctc gagcagcggt ggcacgacac gttctcggtc     1800
gcgaccggtg ccgtcgtcga ggcgctcgcc ggccaggagg tctcgctcgc gagcctcaac     1860
gcctggaagg tcgcctgcgc cgagaaggct atcgcgctca cgcgctccgt ccgcgactcg     1920
ttctgggcgg ctccgtcgtc gtcgtcgccc gcgctcaagt acctctcccc gcggacgcgc     1980
gtcctgtatt cgttcgtccg ggaggaggtc ggcgtcaagg cccgccgcgg cgatgtctac     2040
ctcggcaagc aggaggtcac gatcggcacc aacgtcagcc gcatctacga ggcgatcaag     2100
agcggttgca tcgcccccgt cctcgtcaag atgatggcat ag                        2142

<210> SEQ ID NO 67
<211> LENGTH: 2311
<212> TYPE: DNA
<213> ORGANISM: Amanita muscaria

<400> SEQUENCE: 67
gtcgctcgca aatctaaatg ggtctcgata actccaagaa cactgccaaa ttttttgacc       60
taccaaaagc cgtccatggt atgaatggta caaccccgt caatggtttt aaagcgacag      120
cgctttccaa ggcctcccga acaatgacca agactagcgc actctcgcaa ttcttagaag      180
cgtaccgtga actcgagggc tacaagaatg gtagagccat caaggttgac ggtcaaacgt      240
tatctattgc agccgtcgct gcagctgctc gctacaatgc ggccgttgag ttggacgaat      300
ccccacttgt taaggagcgc gtgaggaaaa gtcagcttgc tatcgcaaac aaagtatcga      360
ccggtgccag cgtatacgga ctgtcaactg gtttcggtgg cagtgctgat acacggacgg      420
acaaaccgat gttgttgggg tttgcccttt tgcaacacca acatgtaggg atactgccca      480
cctcgactga gcctttggac gtcctacctc tccaagatgc aaataacaca agcatgccag      540
aggcgtggat tcgcggggcc attttgatcc gtatgaattc gctaattcgt ggccactctg      600
gaatcagatg ggagttgatc gaaaagatga gagaactact cgcggccaat gtgatacctg      660 tcgttccccct gagaggcagc atctcctcat ccggagatct gtctcccta tcctatatcg      720 caggcacgat tattggcaac ccatcaatca aggtatatca cggtccatca aagtccggaa      780
```

-continued

```
ttcgccaaat tggatcctcg aaggatgtct tggctctgca taatatcgaa cctttcccac      840
tggaatcgaa agaacctctt ggtattttga atgggaccgc attctcggca tctgtggcag      900
ctttagccct aaacgaagct atccatcttg tcttgttggc tcaagtgtgc acggctatgg      960
ggaccgaggc attgataggc actcgcgctt ctcatgcacc gttcattcat gccaccgcac     1020
gaccacatcc cggtcaagta aatgtgctg agaacatttg gaatttgctc gatgggagta      1080
aattggctca gttagaagag cacgaagttc gcctagaaga cgataaatac acccttcggc     1140
aggaccgtta tccactccga acttcgcctc aattccttgg gcctcagatt gaagacataa     1200
tctccgcttt ccagactgta acgcaggagt gtaattactt accagctact gacaatccac     1260
tgattgatgg ggagactggc gaatctcacc acggtggcaa tttccaagcg atggctgtaa     1320
ctaatgcaat ggagaagacg cgacttgctt tacatcacgt tggcaaatta ctatttttccc    1380
agagcactga attagtcaat cctgcgatga accgcgtct gccgccttca gtagctgcca     1440
cagatccatc tctcaactac cacgccaaag gactagacat agcaactgcg gcctacgtag     1500
ccgaagcgac tcctggcccc actcacattc agtcggcaga aatgcacaac caagctgtta     1560
actccctggc gttgatttct gctcgggcta ccatcacatc gttggaagtg ctaacatctc     1620
tgatcgcgtc ttacttgtat attctatgcc aagctctcga cctccgtgcc cttcagcgcg     1680
agttcttgcc cggtctagac atcatcattc gtgaggagtt aagatcgtca tttggatctt     1740
tcctgtcatc agaacagatg gagaaattgc aacaaaatct aactagtgca tttgaagatc     1800
atcttgacaa gaccacgaca atggataata ctgatcgaat gactacgatg gctgctacat     1860
catcatcagt tctacttcaa ttcttttactg attctggcgc gtctgttcct ccctcgtctt     1920
gcgatcttct ctccagtgtc tcgtccttcc aatcttctgt ggcgacacgg tcttcagttc     1980
tcatggatga cctacggaaa gaatatattt ttggagaccg tggccccacg cccgcaagcc     2040
aatacatcgg aaagacacgg ccagtatacc aattcattag aacaactata ggcgttcgta     2100
agcatggttc tgagaactac aacaagtttt ataatgggct gggtgtcgaa gacgttacca     2160
tcggtcaaaa tatatcacgc atatacgagt caatccggga cggcaaaatg caatccatta     2220
ttgtctcgtt gtttgattag gtcttgaaag cttgtatctt attaataacc atacacttcc     2280
tcgaggtcta aaaaaaaaaa aaaaaaaaa a                                     2311
```

<210> SEQ ID NO 68
<211> LENGTH: 3047
<212> TYPE: DNA
<213> ORGANISM: Ustilago maydis

<400> SEQUENCE: 68

```
ggtgctcccc aacaaatggc gcgctttttt cggtagcatg caggataatc tgttcatcac       60
tgtgagggtt cacgttcgtg attaaacaac gcgcacattc cctgtttggc tgtcatcgga      120
tattccgcga caactcggta tattattagt gtagtttgac agagggagtg gacgcggctg      180
agatgggacc gttccgtgtc aggagagtgg acaacgcatt gcgcggaatg aagtcagaat      240
cgatgcatca atgattcacg attgttgctc tgacgatcgg ctcgcccgtt ccgttcgcgg      300
tgcgcatcct gattgccaga tagccagaga cgtggagcct gaaggtgact atagtatggg      360
acagcaatcc tagccgactt tctcacctcc tatccgccca tatctgcgtg ccgtgcctct      420
tcgatcgtct ctacacgacc ataacagctg tcctctcgcg tccataccgt tcctcttccc      480
accgcatctg gcatcatggc tccaaccgca gacgtgctcc ctcccgtcga ggcatccacg      540
```

```
cgtccaggct tgctcgtcca gccttcggat accaaacttc gcaaagcatc gtccttccga   600
accgagcagg tcgttatcga cggctacaat ctcaagatcc agggtctcgt cgcttccgct   660
cgatacggtc acgttacccg tcctcgaccc tccgctgaga cgcgaaagcg tattgatgac   720
tcggtccagt ccttaatcgc caagctcgac ggtggcgagt caatctacgg catcaacacg   780
gggttcggtg gtccgccga ctcgaggacc gccaacacac gtgcgcttca gctggccttg    840
ctccagatgc agcagtgtgg cgtgctcccc gtgccatcca cattcccac gggcgaaccc    900 agctcggcac cctttgcact cccttttgacg gacacagagt cttcactgat catgccggag   960
gcatgggtaa ggggtgccat cgtggttagg ctcagctctc tgatgcgcgg tcattcgggt  1020
gtgcgttggg aggtgctcga caagatgcag aagcttttcc tccagaacaa cgtcactcca  1080
gtcgtaccag tcaggtcgag tatctccggcc agtggtgatc ttagcccact tagctacgta  1140
gccggtgcgc ttgccggtca gcgtggcatc tactgctttg tcaccgacgg ccgtggtcag  1200
cgtgtcaagg tgactgcgga tgaggcttgt cgcatgcaca agatcacccc cgtccagtat  1260
gagcccaagg aggcgcttgg tctgctcaac ggcaccgctt tttcagcctc tgttgcgggt  1320
ctcgctacct acgaggccga aaatctagcc tctctgacgc agctcaccac cgctatggcc  1380
gtcgaagccc tcaagggtac cgatgccagc tttgctcctt tcattcacga aatcgcccgc  1440
ccgcatcctg gtcagatcaa gagcgccaag tttatccgcg cgcatctttc cggctctagg  1500
ctagcagagc atctcgaaaa cgaaaagcac gtcctcttct ccgaagacaa cggaacgctg  1560
cgtcaggacc gttacacgct gcaaaccgcc tcccagtggg tcggcccggg tctcgaggac  1620
atcgaaaacg caaagcgatc cgtcgacttt gagattaaca gcaccacaga taaccccatg  1680
atcgacccgt acgacggcga cggtcgcatc caccacggag gcaacttcca ggccatggcc  1740
atgacgaatg ccgtcgagaa gatccgcctc gccttgtgtg ctatgggcaa aatgacgttc  1800
cagcagatga cagagctcgt caacccggca atgaaccgag gattgcccgc caacttggct  1860
tccacgcctg atctgtcgct caacttccac gccaagggaa tcaatattgc gcttgccagt  1920
gtcacttcgg aactcatgtt cctcggcaac cccgtttcaa cgcatgtaca aagtgcagag  1980
atggccaacc aggccttcaa ctcgctggcg ctcatcagcg gccgccagac gctgcaggcg  2040
atcgagtgcc tctcgatgat tcaggcttgg tcgctctacc tcttgtgcca agcactcgat  2100
attcgcgctt tgcagtataa ggttgctgag cagctgccca cgctcatctt ggcatcgctg  2160
cacagtcact tggcgagtg gatgatgag accaagcagc aagagattgc agcacaggtg    2220
ctcaagagca tgagcaagcg tctcgacgaa acctcgtcca aggaccttcg cgatcgactg  2280
gtcgagacgt accaagacgc gtcgtctgtg cttgtgaggt acttttccga gctgcctagc  2340
ggtggtggtg cggatccgct gaggaacatt gtcaagtggc gcgccaccgg tgtagctgac  2400
acggaaaaga tttacaggca ggtaacgatc gaatttcttg acaacccata cgcttgccat  2460
gccagccacc tgttgggcaa gaccaagcgc gcctacgagt ttgtcaggaa gacgctgggt  2520
gtgcccatgc atggtaagga gaacctcaac gaattcaagg gcgaatttga gcaatggaac  2580
acgacgggcg gttacgtctc ggtcatctat gctagtattc gagatggcga gttgtataac  2640
atgctgagcg agctcgaaag ggatttgtaa aggggtgcaa gcagcgtatt aatagttagt  2700
ataaattggc catctacggt gacaaattgc gtgtgagtgc caaaagggcc atcgaaatga  2760
tcatggacag cgacagactg tgtgttgatt tgtcaaagtg atttggcact accgaatatg  2820
accgtgtgta ccggcaccaa ggcgaggtga tgcgaatgca tgttttttgcg tggcgtcaaa  2880 gggggatgca ggacatggtc gactgcttgt cggagctgat gaggtcgtag cggattcgga  2940
```

| | |
|---|---:|
| atttgggttc gagggctgtg aagggatgtt gaggtgtatc aaagggactt ggcttgtgct | 3000 |
| gcgcttggga gtgggaggga catttcaggt gcatctgctt tcgggat | 3047 |

<210> SEQ ID NO 69
<211> LENGTH: 2209
<212> TYPE: DNA
<213> ORGANISM: Arabidopsis thaliana

<400> SEQUENCE: 69

| | |
|---|---:|
| atggagatta acggggcaca caagagcaac ggaggaggag tggacgctat gttatgcggc | 60 |
| ggagacatca agacaaagaa catggtgatc aacgcggagg atcctctcaa ctggggagct | 120 |
| gcagcggagc aaatgaaagg tagccatttg gatgaagtga agagaatggt tgctgagttt | 180 |
| aggaagccag ttgtgaatct tggtggtgag actctgacca ttggacaagt ggctgcgatc | 240 |
| tcaactattg gtaacagtgt gaaggtggag ctatcggaga cagctagagc cggtgtgaat | 300 |
| gctagtagtg attgggttat ggagagtatg aacaaaggca ctgatagtta tggtgttact | 360 |
| actggttttg gtgctacttc tcatcggaga accaaaaacg tgtcgcact tcagaaggaa | 420 |
| cttattagat tccttaacgc cggaatattc ggaagcacga agaaacaag ccacacattg | 480 |
| ccacactccg ccacaagagc cgccatgctt gtacgaatca acactctcct ccaaggattt | 540 |
| tccggtatcc gatttgagat tctcgaagca attaccagtt tcctcaacaa caacatcact | 600 |
| ccatctctcc ccctccgtgg tacaatcacc gcctccggag atctcgttcc tctctcctac | 660 |
| atcgccggac ttctccaccgg tcgtcccaat tccaaagcta ctggtcccaa cggtgaagct | 720 |
| ttaacagcag aggaagcttt caaattagca ggaatcagct ccggattctt tgatctccag | 780 |
| cctaaggaag gtctcgcgct agtcaatggc acggcggttg gatctggaat ggcgtcaatg | 840 |
| gtgttattcg aaacgaatgt tctctctgtt ttggctgaga ttttgtcggc ggttttcgca | 900 |
| gaggtgatga gtggtaagcc tgagttcacc gatcatctca ctcacagact taaacatcat | 960 |
| cccggtcaaa tcgaagcggc ggcgataatg gagcatatcc tcgacggaag ctcgtacatg | 1020 |
| aaattagctc agaagcttca cgagatggat ccgttacaga aacctaaaca agatcgttac | 1080 |
| gctcttcgta cttctcctca atggttaggt cctcaaatcg aagtgatccg ttacgcaacg | 1140 |
| aaatcgatcg agcgtgagat taactccgtc aacgataatc cgttgatcga tgtttcgagg | 1200 |
| aacaaggcga ttcacggtgg taacttccaa ggaacaccaa tcggagtttc aatggataac | 1260 |
| acgagattgg cgatagcagc gattggtaaa ctcatgtttg ctcaattctc agagcttgtg | 1320 |
| aatgatttct acaacaatgg tttaccctcg aatctaaccg cttcgaggaa tccaagtttg | 1380 |
| gattatggat tcaagggagc tgagattgca atggcttctt attgttcaga gcttcaatac | 1440 |
| ttagctaatc ctgtgactag ccatgttcaa tcagcagagc aacataacca agatgtcaac | 1500 |
| tctttgggac taatctcgtc tcgcaaaact tctgaagctg ttgatattct caagcttatg | 1560 |
| tcaacaacgt tcctcgttgc gatttgtcaa gctgtggatt tgagacattt ggaggagaat | 1620 |
| ttgagacaga ctgtgaagaa cactgtctct caagtggcga agaaagttct tactactgga | 1680 |
| gtcaatggtg agcttcatcc ttctcgcttc tgcgaaaagg atttactcaa agttgtagac | 1740 |
| cgtgaacaag tctacacata cgcggatgat ccttgtagcg caacgtaccc gttgattcag | 1800 |
| aagctgagac aagttattgt tgaccatgct ttgatcaatg gtgagagtga aagaatgca | 1860 |
| gtgacttcaa tcttccataa gattggagct ttcgaggagg agcttaaggc agtgctaccg | 1920 |
| aaagaagtgg aagcagcaag agcagcctac gataacggaa catcggctat cccgaacagg | 1980 |

-continued

```
atcaaggaat gtaggtcgta tccattgtat agattcgtga gggaagagct tggaacagag    2040
cttttgaccg gagagaaagt gacgtcgcct ggagaagagt cgacaaggt tttcacggcg     2100 atttgtgaag gtaaaatcat tgatccgatg atggaatgtc tcaacgagtg gaacggagct    2160
cccattccaa tatgttaaga gtatagtcct ctgttttttt cttaccata               2209
```

<210> SEQ ID NO 70
<211> LENGTH: 2439
<212> TYPE: DNA
<213> ORGANISM: Rubus idaeus

<400> SEQUENCE: 70

```
aaacactcca taactccata actccatttc tgaaattcat ttctgggtta ttttctcaca     60
ctacaatgga gagcataacc cagaatggac accaccacca gaatgggatc caaaacggtt    120
cgttggacga cggtctctgc atcaaaacag agtccatcaa acgggctac tctgtttcgg     180 acccgcttaa ctggggagca gccgccgagt caatgacagg cagccacctc gacgaagtta    240
ggcgcatggt ggccgagtac aggaaaccgg tggtgaagct cggtggagaa accttgacta    300
tttcccaggt ggcggccata gccaaccatg actctggtgt caaggttgaa ctcgctgagt    360
ccgccagggc gggtgtgaag gccagtagtg attgggtcat ggattccatg aacaaaggga    420
ctgatagcta tggtgtcacc actgggttcg gtgcgacctc ccacagacga accaaacaag    480
gcgctgcact tcaaaaggag ttaattagat tcttgaatgc tggagtattg cgcaatggaa    540
cagagtcagc tcacactctg cctcactctg caacaagagc agccatgctc gtcagaatca    600
acacactcct ccaaggctac tccggcataa gattcgaaat cttagaagcc atctccaaat    660
ttctcaacca aacataact ccatgcttgc ctcttcgtgg cacgatcacc gcctccggag    720
accttgttcc gctgtcctac atcgccggac tactaacggg ccggcccaat tccaaggcgg    780
tcgggccaaa aggcgagacc ctcaatgccg ctgaggcttt tgcacaagtc ggtatcagct    840
cagggttttt cgagctgcag cctaaagaag gacttgctct tgttaacggc actgctgttg    900
gctctggctt ggcctccacg gttctttttcg agaccaacat tttggccttg ctgtccgaaa    960
tcttgtctgc gattttcgct gaagtgatgc aggggaagcc cgaattcaca gaccacttga   1020
cacataaatt gaagcaccac ccgggtcaaa ttgaggctgc tgcaattatg gaacacattt   1080
tggatggtag ctcttacgtc aaagctgccg agaaacttca tgagcaggac cctcttcaga   1140
agcctaaaca agaccgctac gctctccgaa catcaccaca atggctcggt ccacaaatcg   1200
aagtgatcag attttcgact aaatctattg agagggagat taattctgtc aatgacaacc   1260
ctttgattga tgtttcgagg aacaaggcat tgcatggtgg caacttccag ggtaccccaa   1320
ttggagtgtc catggacaac acccgtttgg ctattgcatc cattgggaag ctcatgtttg   1380
ctcagttttc tgaacttgtc aatgacttt acaacaacgg tttgccatcg aatttatcgg   1440
gtgggaggga cccagtttg gattatggct tcaagggagc tgagattgcc atggcatctt   1500
attgttccga gcttcagttt ctagccaatc cggtgactaa ccatgtccag agcgccgagc   1560
agcacaacca ggatgtgaac tctttgggc tgatttcgtc gcgaaaaacc gcagaagctg   1620
ttgacatatt gaagctcatg tcttccacat tcttagttgc gctttgccaa gccattgact   1680
tgaggcattt ggaggagaac ttgaagagca cggttaaaaa cactgtgagt caattggcta   1740
agagggtttt gactactggg gttaatgggg agcttcaccc gtcgaggttc tgcgagaagg   1800
atttgcttat ggttgttgaa agggagtacc ttttcgccta cattgacgat ccttgcagcg   1860
ccacatatcc attgatgcaa aggctaaggc aagtgcttgt tgaacacgct ttgacaaacg   1920
```

```
gtgagaatga gaaaaatgca agcacttcta ttttccaaaa gattacggct tttgaggagg    1980
agctgaagac cattttgcct aaggaggttg agagcgctag ggctgcgtac gagagcggga    2040
atgctgctat tccaaacagg attgtggagt gcaggtcata tcctttgtac aaatttgtga    2100
gggaggagtt ggggggagag ttcctgacgg gtgaaaaggt cagatccccc ggggaggagt    2160
gtgacaaagt gttcacagct atgtgccagg caacattat tgatcccatt ctcgactgcc     2220
tcagcggttg aacggtgaa cctcttccga tctgctagcc ttaatttcgg tacccgtttt     2280
gagtgatgtg tgtcattcca ttccacttcg atcttctggc tccatagttt taagtttgat    2340
gaggattgct agctttaatt gtgtgactat atataaaacc taataaaatg taaaaccatc    2400
tgtttatttg aaactgtagt tcttcttttc ttacttacc                            2439

<210> SEQ ID NO 71
<211> LENGTH: 2409
<212> TYPE: DNA
<213> ORGANISM: Medicago savita

<400> SEQUENCE: 71
cttctttctt tcataatcat tagaatttcc attctatcaa aattctaggt accaccacac      60
aacatattaa ggaacattaa tcaatactat taagatatgg aaacaatatc agcagctatc    120
acaaaaaaca atgccaatga atcattctgc ttgattcatg caaagaataa taataacatg    180
aaagtgaatg aagctgatcc tttgaattgg ggggtggcag ctgaggcaat gaaaggcagt    240
caccttgatg aaggtgaagcg tatggtgca gagtaccgga accggtggt ccgtcttggt     300 ggcgagacac tgacgatttc tcaggtggct gccattgctg cacatgacca tggtgtgcag    360
gtggacctgt ctgaatctgc tagggatgga gttaaggcca gcagtgaatg ggtgatggag    420
agtatgaaca aaggcacgga cagttacggt gtcaccaccg ggttcggcgc cacctcgcac    480
agccgtacca aacaaggtgg tgctttgcag aaagaactca tcaggttttt gaatgcagga    540
atattcggaa atggaacaga gtcaaatcac acactaccaa aaacagcaac aagagcagcc    600
atgctagtga ggatcaacac actcctccaa ggttattcag gaatagattt tgaaatcttg    660
gaagccatca ctaagcccct taacaaaacc gtcactccat gtttaccgct tcgtggtaca    720
atcacagctt caggtgattt agttcctctt tcatacattg ctggtttact caccggaaga    780
ccaaattcaa aagctcatgg accatctgga gaagtactta atgcaaaaga agcttttaat    840
ttggctggaa tcaatgctga gttctttgaa ttacaaccaa agaaggtct tgcccttgtt      900 aacggaacag ctgttggttc cggtttagct tctattgttc tctttgaggc taacattttg    960
gctgtgttgt ctgaagttct atcagctatt tttgctgaag ttatgcaagg gaaacctgaa   1020
tttaccgatc atttgacaca caagttgaaa caccaccctg gtcaaattga ggctgctgcg   1080
attatggaac acattttgga cggcagctct tatgtcaaag cagctaagaa gttgcatgag   1140
atagatcctt tgcagaagcc aaaacaagat agatatgcac ttagaacttc accacaatgg   1200
cttggtcctt tggttgaagt gattagattc tctaccaagt caattgagag agagatcaac   1260
tctgtcaatg acaaccctt gattgatgtt tcaagaaaca aagctttgca cggcggaaac   1320
tttcaaggaa cacctattgg agtatccatg gataatacac gtttggctct cgcatcaatt   1380
ggcaaactta tgtttgctca attctctgag cttgttaatg acttttacaa caatggattg   1440
ccttcaaatc tttctgctag tagaaatcct agcttggatt atggtttcaa gggagctgaa   1500
attgccatgg cttcctattg ttctgagttg caatatcttg caaatccggt tacaacccac   1560
```

```
gtccaaagtg ctgagcagca caaccaagat gtgaactctt tgggtttgat ttctgctaga   1620
aaaacaaatg aagccattga gatccttcag ctcatgtctt ccaccttctt gattgcacta   1680
tgccaagcaa ttgatttaag acatttggag gagaacttga aaaactcagt caagaacacc   1740
gtaagtcaag ttgccaaaaa gactcttacc atgggtgtca atggagaact tcacccttca   1800
agattctgcg aaaagacttt gttgaaagtg gttgacaggg agcatgtatt tgcttatatt   1860
gatgatcctt gtagcgctac atacccgttg agtcaaaaac taaggcaagt gttggtagat   1920
catgcactag taaatggaga gagtgagaag aattttaaca cttcaatctt tcaaaagatt   1980
gctacttttg aggaagagtt gaagaccctc ttgccaaaag ggttgaaaag tgcaaggacc   2040
gcatatgaga gtggaaaccc aacaatccca acaagatca atggatgcag atcttatcca    2100
ctttacaagt ttgtgagaga ggagctagga actggtttac taaccggaga aaatgtcatt   2160
tcaccaggag aagagtgtga caaactattt tcagctatgt gtcagggaaa aatcatcgat   2220
cctcttcttg aatgtttggg agagtggaac ggtgctcccc ttcctatttg ttaactttgt   2280
tggttacttt tgaaaatgct ttatttgtat tttatacaag tgtatcaaaa atcatatagg   2340
tttttcatgc tttaacaaat taatatggaa agctaaaaag ctccagttca gtttcctcca   2400
aaaaaaaaa                                                           2409

<210> SEQ ID NO 72
<211> LENGTH: 2444
<212> TYPE: DNA
<213> ORGANISM: Rehmannia glutinosa

<400> SEQUENCE: 72
acacaaaaac acacacacaa gagcaaaaaa ataataacac ctatcgtgtg tgtgttctgt     60
gtgaaaaaaa aaaaaaaaca acccaaagtc gtgatatcta aaagcgcgta tcaatggaga    120
atgggcacca ccactcgaac gggttgtgcg tggagactac gcgtgatccg ttgaactggg    180
tggcggcggc ggagtcgctg aagggagcc acctggacga ggtgaagagg atggtggagg    240
agttcaggaa gccggcggtg aagctcggcg gtgagagcct gactatagcg caggtggcgg    300
cgatcgcggc gagggataat gcggtggcgg tggagctggc ggagacggcg cgtgcggggg    360
ttaaggcgag tagcgattgg gttatggaga gtatgaataa agggactgac agttatggag    420
ttacaacggg ttttggtgcc acgtcacata ggaggactaa acaaggtggt gctcttcaga    480
aggagctcat taggttcttg aatgccggaa tattcggcaa cggcacggaa tctaaccacg    540
cgctgccaca ctccgccacg agagccgcca tgctcgtccg aatcaacacg ctcctccaag    600
gatattccgg catccgattt gaaatcctag aagccctaac aaaattcctc aaccacaaca    660
tcaccccctg tttgcccctc cgcggcacga tcaccgcctc cggcgacctc gtcccgctat    720
cctacattgc cgggctttta acgggccggc ccaactccaa ggccgtcggc ccaaacggcg    780
aagccctcaa cgccggcgag ctttcagcc tcgccgcgt tagcggcttc ttcgagctgc    840
agcccaaaga aggcctcgcg ctagtcaacg ggacagctgt cgggtccgga ttggcctcga    900
tcgccctgta cgacgcgaac atcctcgccg tcctgtcgga agtgacgtca gtgatttccg    960
ctgaggtcat gaatgggaaa cctgaattta cggatcattt gacacataag ctgaaacatc   1020
accctggcca aattgaggcc gctgctataa tggaacacat tttagatggt agcgcgtacg   1080
ttaaggctgc tcagaaattg cacgaaaccg atccgttgca aaaaccgaaa caggatcgt    1140 acgcgcttag aacgtcgcct caatggctcg gcccccaaat cgaagttatc cgaaccgcga   1200
cgaaaatgat cgagcgggaa attaattcgg ttaacgacac acctctaatc gatgtctcga   1260
```

```
gaaataaagc gttacatggc ggtaacttcc agggcacgcc aatcgggta tcgatggaca    1320 acaccagatt ggcgatagca gctatcggaa aattgatgtt cgctcaattt tccgagctgg   1380
ttaatgattt ctacaacaat ggattgccgt ctaatctctc tggcggtagg aatccgagct   1440
tggattacgg tttcaaaggg tccgaaatcg cgatggcttc gtattgttcg gagcttcaat   1500
ttttagctaa tcctgttacc aatcatgtcc aaagtgcaga gcaacataac caagatgtga   1560
attcacttgg attgatttct tctagaaaga ccgtcgaggc tctggatatt ctaaagctga   1620
tgtcatccac atatttaatc gcgctatgcc aggccgtcga tttgaggcac ttggaggaga   1680
atttgaggct ttcagttaaa acaccgttta gccaagtggc gaagaggact ctgacaatgg   1740
gtattaatgg cgaacttcat ccgtcaagat tctgcgagaa ggatcttctc cgtgtggtgg   1800
accgcgagta cgtgtttgca tacatcgacg atccgtgcag cgggacctac cccttgatgc   1860
agaagttgag gcaagttctc gtggaccacg cgttgaacaa cggtgagagt gagaaaaacg   1920
tgagcacgtc tattttttcaa aagatcgagg cgtttgaggt agagttgaag gcgatcttgc   1980
ctaaagaggt cgagagtgca cggatcgcgt tggagagtgg aaatccggcg attggtaaca   2040
ggattacgga atgcagatcg tatccgttgt acaagtttat cagagaggaa cttgggacga   2100
actacttgac gggcgaaaag gtcgtttctc cggggagga atgtgataag gtgttcacag   2160 cttttgagcaa gggtttgatt gttgatcctt tgttgaagtg tcttgagggt tggaatggtg   2220
cacctccccc tatctgctag ttcaattaaa atttgttttg tggttaagga cttttgtgtt   2280
tgttaatgtt ttcctctcaa tgttggttta attataatgt gattctgtct agggtgaaat   2340
aaattgtaaa aaaattatg agttcttatg tttttttaaa aaaaaaaaa aaaaaaaaa    2400 aaaaaaaaa aaaaaaaaaa aaaaaaaaa aaaaaaaaaa aaaa                     2444

<210> SEQ ID NO 73
<211> LENGTH: 2442
<212> TYPE: DNA
<213> ORGANISM: Lactuca sativa

<400> SEQUENCE: 73
gagcaatctg atcaataccc attcacgcac aaagagtgtg agtctagtgt gtgaagaagt    60
acacaattag attgttcttg tttctttgat ctatagtcta caatctgtat aaataataat   120
ggagaacggt aatcacgtta atggagtcgt taatgagttg tgcatcaagg atccattgaa   180
ctggggagtt gcagcggagg cgttgaccgg aagtcacctt gatgaggtga agaagatggt   240
tgcggagttc agaaagccgg tggtgaagct cggaggagag acgcttacag tttctcaggt   300 ggcgggatc gcagctgcta atgacagtga caccgtgaag gtggagctgt cggaagccgc   360
gagggctgga gttaaggcga gtagtgattg ggttatggag agcatgaata aaggaactga   420
tagttatggt gtcaccaccg gcttcggcgc cacctctcac cggagaacta agcaaggcgg   480
tgctttacag aaggagctca ttagattttt gaacgccgga atattcggca atggaacgga   540
aacaagccac acacttccac attcagccac cagagccgcc atgatcgtca gaatcaacac   600
cctcctccag ggttactccg gcatccgatt cgagatcttg gaagccatca ccaagttcct   660
taacaacaac atcaccccct tgtttaccct ccgtggaacc atcaccgcct ccggtgacct   720
tgtcccatta tcatacatcg ccggcctctt aaccggccgc cccaactcca agccgttgg   780 ccccaccgga gaagtcctca atgccgaaaa ggccttcgct gcagccggag ttgaaggtgg   840
gttcttcgag ttacagccga aagaagggct agcacttgtt aacggcaccg ccgtgggggtc   900
```

-continued

```
cgggatggct tccatggttc tatttgatgc taatgtactt gcgttgttgt cggaagtgtt      960
atcggcgatc ttcgctgagg ttatgcaagg gaagccggag tttaccgatc acttgacaca     1020
caaattgaag catcaccctg gtcaaatcga ggcggcggcg atcatggagt atattttgga     1080
cggaagcgat tacgtcaagg cggcgcaaaa ggtccacgaa atggacccgt tacagaaacc     1140
aaaacaagat cgttatgctc tccgtacatc tccccaatgg ctcggacctc aaatcgaagt     1200
aatccgatca tcaaccaaaa tgatcgagag ggaaatcaat tccgtcaacg acaacccatt     1260
gatcgacgtt tccagaaaca aagctttaca cggtggtaac ttccaaggaa ccccaatcgg     1320
agtttccatg gacaacaccc gtctcgccat tgctgcaatc ggaaaactca tgttcgctca     1380
attttctgag ctggttaacg atttctacaa caatggatta ccatcgaatc tctccggtgg     1440
acgtaaccct agtttggact acgggttcaa aggtggagaa atcgccatgg cttcttactg     1500
ttctgagctt cagtttctcg caaatccagt caccaaccat gttcaaagcg ccgaacaaca     1560
caatcaagac gttaattctc tcggattaat ttcagcgagg aaaaccgcag aagcagtcga     1620
catcttaaaa ctcatgtcgt cgacatactt agtcgctcta tgccaatcca tcgatttacg     1680
ccatttggaa gagaacatga aatcgacagt gaagaacacc gtaagccaag tcgcgaaaaa     1740
ggtcctcacc atgggcgtca acggcgagct ccaccgtcg agattctgcg agaaagatct     1800
cctccgtgtt gttgatcgtg aatacgtctt cgcttacatc gacgacgttt gcagcggcac     1860
atacccatta atgcagaagc tccgacaggt tctggtcgac cacgctctaa caacggcga     1920
aacggagaag aacactaaca cctccatctt ccaaaagatc gctaccttcg aagaagaatt     1980
gaaagtcctg ttaccgaaag aagttgaagg tgttagaatc gcttatgaga atgatacatt     2040
gtcgattcca aacaggatta aagcttgcag atcgtacccg ttgtataggt ttgtaaggga     2100
ggagctcggc agagggtttt tgaccggaga aaaggtgacg tcgccgggag aggagttcga     2160
cagggtgttc acggcgatgt gcaaaggtca aattattgat ccgttgttgg agtgtcttgg     2220
agggtggaat ggggaacctc ttccaatatg ttaggaaagt gagtgtgaaa ccgtttgaat     2280
tgtatttgta atattctgtt tttttttttt tttttaaat tttatttgca tttaatatct     2340
catcaaagac ttccactttc aagtgtggtg tatgtggttg taaatcatat atattaactt     2400
attattttg ctaaaaaaaa aaaaaaaaaa aaaaaaaaa aa                         2442
```

<210> SEQ ID NO 74
<211> LENGTH: 2403
<212> TYPE: DNA
<213> ORGANISM: Petroselinium crispum

<400> SEQUENCE: 74

```
tttgctacat tgttcttcat tcattataag taagttacat ataaaatttg taacgtaaat      60
agagtttatt taatttattc taaagatcat ggcatatgta aatggtacca ccaacgggca     120
tgcaaacggg aacggattag atttgtgcat gaagaaggaa gatcctttga actggggagt     180
ggctgcggag gcattgacag ggagtcattt ggacgaagtt aagaggatgg tggctgagta     240
caggaagccg gtggtgaagc tggaaggaga aacactgaca atttctcagg tggctgctat     300
ttcggctagg gatgatagtg gtgttaaggt ggagctttcc gaggaggcga gagctggcgt     360
taaggctagt agtgactggg tgatggatag tatgaataaa gggacggata gttatggtgt     420
tactactggc tttggtgcta cttctcatag gaggactaaa caaggtggtg ctcttcaaaa     480
ggagcttatt aggttcttga atgctggaat atttggaagt ggagctgaag ctggtaacaa     540
cacattacca cactccgcaa caagagcagc aatgcttgtg agaatcaaca cactcctcca     600
```

```
aggctattca ggaatccgat tcgagatcct tgaagccatc accaagtttc ttaaccacaa      660
cattactcct tgtttgccac tccgtggtac aatcactgct tctggtgatc ttgtgccatt      720
gtcctacatt gctggacttc tcactggtcg tcccaactcc aaggctgttg daccgactgg      780
agtaacactc agccccgaag aagcatttaa gcttgctggt gtggaaggtg dattttttga      840
gttacagcca aaggaaggcc tagcacttgt taatggaaca gctgttggtt ctggaatggc      900
ctctatggta cttttttgagg ctaatatatt agcagtttta gctgaagtta tgtcagcaat      960
tttcgctgaa gtgatgcaag ggaagcctga atttaccgac catttgacac ataagttgaa     1020
gcaccatccc ggccaaattg aggctgcagc tataatggaa cacattttgg atggaagcgc     1080
atacgttaag gctgctcaaa agctacatga aatggatcca ttacaaaaac caaacaaga      1140 cagatatgct cttagaacat ctcctcaatg gcttggtcct caaattgaag ttatcagatc     1200
atcaactaaa atgatcgaaa gagagattaa ctctgtcaat gataacccat tgattgatgt     1260
ttccaggaac aaggctattc acggtggaaa tttccagggc agcccaattg gtgtttcaat     1320
ggacaataca cgtctggcta ttgcagccat aggaaagctt atgtttgctc aattttcaga     1380
acttgtcaac gacttttaca caatggggtt gccatcaaat ttgtctggag ggcgtaaccc     1440
gagcttggat tatggattca agggtgctga aattgccatg gcatcatact gctccgaact     1500
ccagttttta gccaatccag tgactaacca tgtccaaagt gctgaacagc acaaccaaga     1560
tgtgaactct ttgggtttaa tatcttcaag gaaaacatca gaagctgttg aaatcttgaa     1620
actcatgtct actacgtttt tggtgggtct atgccaagct atagacttaa ggcatttgga     1680
ggaaaatttg aagagcactg ttaaaaacac agtgagccaa gtagctaagc gagtactaac     1740
catgggtgtc aacggtgagc tccatccctc aagattctgc gagaaagatt tgcttagagt     1800
tgtagaccgc gaatacatat ttgcatacat tgatgatccc tgcagcgcaa cctacccatt     1860
gatgcaaaaa ctaagggaaa ctctagttga gcatgcattg aacaatggtg ataaagagag     1920
gaacttgagc acttccatct tccaaaagat tgcagcattc gaggatgaac taaaggctct     1980
tctgcctaaa gaagtcgaaa ctgctagagc cgcacttgaa agtggaaatc cggcaatccc     2040
caacaggatt aaggagtgca ggtcttaccc tctgtacaag tttgtgaggg aagaattggg     2100
aactgagtat cttacaggag aaaaagtgcg gtcacctggg gaagaattcg aaaaggtatt     2160
cacagcaatg tcgaaaggag agataattga tccattgttg gagtgtctcg agtcatggaa     2220
tggtgctcct cttccaatct gctaaattgg catgcagtcc agcaatgtat taggaactgt     2280
ttatctctct gtcaagattt atcttcttgt ttgttgatgt ctctccctag tgaatgtctg     2340
taaaattctt ttaaaacgct gtaaaatctt ttgtaatact aatgtacaag tctacgcggc     2400
cgc                                                                   2403
```

<210> SEQ ID NO 75
<211> LENGTH: 2448
<212> TYPE: DNA
<213> ORGANISM: Prunus avium

<400> SEQUENCE: 75

```
ggggagatgg tcaggctctt tcgtgctccc aaacactttg ctctcatcag tttttgtatt       60
ttcccatctg ggttttttggt aattaacatg gcaaccaact ccatcaagca aaatggtcac      120
aaaaacggat cggtagagtt acctgagctc tgcataaaga aggacccttt gaactggggt      180
gtggcagcag agacactaaa agggagccac ttggatgagg tgaagcgcat ggtggctgag      240
```

```
tacaggaagc cggtggtgaa gctcggtgga gagagcctga ccatttccca agtggcggcc    300
atagccactc atgactctgg ggtcaaggtt gagctctctg agtcagcccg ggccggggtc    360
aaggccagca gcgactgggt catggacagc atgagcaaag ggactgacag ctatggtgtc    420
accaccgggt ttggtgctac ctcccacaga agaacaaagc aagggctgcc ccttcagaag    480
gagctcatta gattcttgaa cgctggagtg tttgggagca cgaaagagtc gggccacact    540
ttgcctcacc aggcaacaag agcagccatg ttggttagga tcaacacact cctccagggc    600
tactctggca taagatttga gatcttggaa gtcatcacca agttcctcaa caacaatgtc    660
actccatgct tgcccctacg cggcacgatc acagcctccg gtgaccttgt cccgctgtcc    720
tacatcgccg ggatgctaac tggcaggcct aattccaagg ctgttggacc agatggccag    780
accctcagtg ctgcagaggc ctttgagttt gttggtatca attccgggtt ctttgagttg    840
cagcctaaag aaggcctggc tcttgttaat ggcactgctg ttggttctgg cttggcttcc    900
acggttcttt tcgacactaa cattttggca ttgctgtcag aaattctatc agcaattttt    960
gctgaagtta tgcaggggaa gcctgaattt actgaccact tgacgcataa gttgaagcac   1020
caccctggcc aaattgaagc tgcagcaatt atggaacata ttttgatgg tagctcttat   1080
gttaaagctg ctaagaagtt gcacgagcag gaccctctgc agaagccaaa acaggatcga   1140
tatgctctcc gaacttcacc tcaatggctc ggtccacaga tcgaagtgat ccggtactcc   1200
accaaatcca ttgagaggga gatcgactca gtcaatgaca ccctttgat tgatgtgtca   1260
aggaacaagg ccttgcatgg tggcaacttc caggggaccc caattggtgt ctctatggac   1320
aatactcgtt tggctattgc atccattggg aagctcatgt ttgctcaatt ttctgagctt   1380
gtcaatgact tttacaacaa cggattgcca tcaaatctgt ctggaggcag gaacccaagt   1440
ttggattatg gcttcaaggg ggctgagatt gccatggcat cttattgttc tgagcttcag   1500
tttctcgcga acccggtcac taaccatgtc cagagtgcag agcagcacaa ccaagacgtg   1560
aactctttgg ggttgatctc ttcaagaaag acagctgaag ctgttgatat cttgaagctc   1620
atgtcttcca cattttttggt ggcactttgc caagcaattg atttgaggca tttggaggag   1680
aacttgagga acacagttaa gaacacagtg agccaagtgg ctaagagaac tttgacaact   1740
ggggttaatg gagagctcca cccatcaaga ttctgtgaga aggatttgct taaagtggtc   1800
gatagggaat atgttttcgc ctacatcgac gacccctgca gtgccactta cccattgatg   1860
caaaaactaa ggcaagtgct ggttgagcat gctttgacaa atggtgagaa tgagaagaat   1920
gcaagcactt caatcttcca aaagattgtt gcttttgagg aagagctgaa ggtgcttttg   1980
cctaaagagg tggatagtgc aagggctgca ttggacagtg gaagtgctgg agttccaaac   2040
aggattacgg aatgcaggtc ttaccccttg tacaaatttg tgagggagga gttgggtgca   2100
gagtacctaa caggggaaaa ggtcaggtca ccgggcgaag aatgcgacaa ggtgttcaca   2160
gctatctgcg agggaaagat tatcgacccg attctggatt gcctcgaggg ctggaacggt   2220
gcaccacttc cgatctgtta gcatttcgtt acgctttgag tgctgcattc cattccacta   2280
cttctgtgtc cataagtttg attgcattgc tggtagactg tgtgactata cctatttttac   2340
ctaataaatg taaaaccatc tacttatgct ttttgattct ttctaagttc tttaccactt   2400
ctttgttatt tagtgagaat agtattcaaa tagtcaggaa aaaaaaa             2448
```

<210> SEQ ID NO 76
<211> LENGTH: 2441
<212> TYPE: DNA
<213> ORGANISM: Lithospermum erythrorhizon

```
<400> SEQUENCE: 76
tccacacgca tattcctctc tacattctct acatacattt taatttgtct ctctttgtgt      60
ttgtcacatt tcttcaacta ccctatagtt agttcccatt tattttcttt ggatcaagaa     120
aacattacta cattattagt acacacatat atattacaaa atggaaacca tagtggaaaa     180
tggaaatgga aaaactatgg agttttgcat gaaagatcca ttgaactggg aaatggcatc     240
tgagtcaatg aaggggagcc accttgatga agtgaaaaac atggtggctg agttcaggaa     300
accggtggtg caacttgccg gtaagacttt gactatcggt caggtggcgg cgattgctgc     360
ccgtgacgac ggagtcacgg tggagctagc ggaagctgcc cgggaaggtg ttaaggctag     420
tagtgattgg gttatggata gtatgaataa gggcacggat agttatggtg taaccactgg     480
cttcggtgcc acttcacata ggaggactaa acaagggggt gcccttcaaa aggaacttat     540
tagattcttg aatgctggaa tatttggcaa tggaacagaa actagccaca cattaccaca     600
ctcagcaaca agagcagcca tgcttgttag gatcaatact ttgcttcaag gttattcagg     660
catcaggttt gagatcctgg aagctatcac caagttcctc aacaccaaca tcactccatg     720
cctacccctt cgtggcacga tcaccgcctc tggtgacctc gtcccccctct catacattgc     780
cggactactt actggccgtc ccaattccaa ggccgttgga cctaccgggg agaagatcaa     840
tgcggaggaa gcttttcgtc tagctgggat cagtaccggg ttcttcgagt tgcagcctaa     900
ggaaggactt gcccttgtta atggaacagc tgttggttct ggaatggctt caatggttct     960
ttatgaagcc aacattttgg ctgtcttgtc tgaagtgatc tcggctattt tcgctgaggt    1020
gatgaatgga aagcctgaat tcaccgacca tttgacacac aaactgaaac accatccagg    1080
acagattgag gctgctgcta tcatggagca cattttggat ggtagtggat atgttaaggc    1140
tgctcagaag ttacatgaga tggatcctct gcagaagcct aagcaagatc gttatgccct    1200
ccgtacatcg cctcaatggc ttggtcctca gatcgaagtg atccgttctg ctaccaagat    1260
gattgagagg gaaatcaact ctgttaacga caacccattg atcgatgttt cgaggaacaa    1320
ggccttacat ggaggaaact tccagggcac acctattggt gtggccatgg acaacactcg    1380
ccttgccatc gcctcaattg gaaagcttct atttgctcaa ttttctgaat tggttaatga    1440
ttactacaac aatgggttgc catcaaattt gacaggcagc agaaatccaa gcttggatta    1500
tggttttaag ggagctgaaa tcgccatggc ttcgtactgc tcagaactcc agttcttggc    1560
taatccagtc accaaccatg tccagagtgc tgaacaacac aaccaagatg tcaactcttt    1620
gggcttaatc tcttcaagaa agacatccga ggctgtcgaa atcctgaagc tcatgtcttc    1680
atcattttg gttgcactct tccaagctgt tgatttgagg catattgagg agaatgtgag    1740
actcgcagtc aagaacacgg ttagtcaggt tgccaagcgg acattaacca caggcgttaa    1800
tggcgagctc cacccatcaa gattcagcga aaaggacttg cttcgcgtgg ttgatcgcga    1860
gtatgtcttt gcctacgcag acgacccttg cctcaccacc tacccettga tgcagaagct    1920
aagagaaact ctcgttggac acgccttaga caatggcgag aatgagaagg atgtgaacac    1980
ttcaatcttc cataaaatag ccattttcga agaagaattg aaggccattc tccctaaaga    2040
ggtggagaat gcacgcgcct cggtcgaaaa tggcattcca gcaatctcca acaggattga    2100
ggaatgtagg tcatatccat tgtacaagtt tgtgagggaa gaattgggga ctgaattgtt    2160
gactggtgag aaggttagat caccaggtga ggaattggac aaagtattca ctgcaatgtg    2220
tgaaggcaag cttgttgatc cacttctggc ttgtttggag gcttggaatg gtgctcctct    2280
```

-continued

| | |
|---|---|
| tccaatctgt taaataaaca gttttgtgga ctatttcatg tacttaacta cttctttttg | 2340 |
| ttctttttctt tttctatgtt catattaatt cttctgttga tttgtttgta aggtgttgtc | 2400 |
| ttatcaatat tatctaatgg aacaactaat agattcctat t | 2441 |

<210> SEQ ID NO 77
<211> LENGTH: 2607
<212> TYPE: DNA
<213> ORGANISM: Citrus limon

<400> SEQUENCE: 77

| | |
|---|---|
| ccacgcgtcc gcttggcttg aaaatttccc tttcatcatc gtcacagatt cacgtttaca | 60 |
| tgcaataaat atataattgc ccccacaaaa gatttcccca cccatttttct ctcccaccca | 120 |
| tcagtacatt tacttctttt aactaaaaaa caacaaggaa aaaaaaaatg gagttgtcac | 180 |
| atgaaacttg caatggcatc aagaatgata ggaatggtgg tacttcgtca ttggggttgt | 240 |
| gcacaggtac tgacccttttg aactggaccg tggcagcgga ctcattgaaa gggagtcacc | 300 |
| ttgatgaagt gaaacggatg attgacgagt acaggaggcc ggtggtgaag ctcggcggcg | 360 |
| agtccttgac cattggccaa gtgactgcta tcgcggccca cgactctgga gtcaaggtgg | 420 |
| agctagcgga ggccgcccgc gccggcgtca aggccagcag cgattgggtg atggacagca | 480 |
| tgatgaaagg gactgatagc tatggtgtca ccactggctt tggtgcaact tctcaccggc | 540 |
| gaaccaagca aggtggtgct ttgcaaaagg agctcattag attcttgaat tctggaattt | 600 |
| ttggcaatgg cactgaatca agccacacat gcctcactc ggcaacaagg gcagcaatgc | 660 |
| tggtgagagt caacaccttg ttacaaggat actcaggcat caggtttgag atcctggaaa | 720 |
| ccattaccaa gttccttaac cataacatca ccccttgctt gccgctacgt ggcacgatca | 780 |
| ccgcgtcggg cgacctggtc ccactctcgt acattgctgg gcttttgaca ggcaggccca | 840 |
| actcgaaggc tgttgggtcc aacggccaag ttctcaaccc caccgaggcc ttcaacctag | 900 |
| ctggggtcac tagtggattt tttgaattgc agcctaagga aggtcttgcc ctggtgaatg | 960 |
| gcacagcggt tggctctggt ttagctgcca cggtactctt tgaggctaac atattagcca | 1020 |
| ttatgtctga agttttatct gcaattttg cggaagtgat gaatgggaaa cctgaattta | 1080 |
| cagaccactt gacacataag ttgaagcacc atccgggaca aattgaagct gcagctatta | 1140 |
| tggaacacat tttggatggc agctcttatg ttaaagcagc acaaaagtta catgaaaccg | 1200 |
| atcctcttca aaagccaaag caagacagat atgctcttcg aacatcgcct caatggctag | 1260 |
| gtcctcagat tgaagtgatc agggcagcta ccaaaatgat tgaaagagag attaactccg | 1320 |
| tgaatgacaa tccattgata gatgtatcaa ggaacaaggc gcttcatgga ggcaattttc | 1380 |
| agggggacccc aattggtgtt tccatggaca cacccgtct agccattgct tcaattggca | 1440 |
| agctcatgtt tgcacaattc tctgagcttg tcaatgattt ctacaacaac gggttgcctt | 1500 |
| caaatcttac tgggggacgt aatccaagct tggattacgg attcaagggt gccgaaattg | 1560 |
| caatggcatc atactgttct gaactccaat tcctcgccaa tcctgtcacc aatcatgtcc | 1620 |
| aaagtgctga gcaacacaac caagatgtga actccttagg cctcaattct tctaggaaaa | 1680 |
| ctgctgaagc agtagacata ttgaagctta tgtcgtcaac tttccttagtt gctctatgcc | 1740 |
| aagcgattga cttgaggcat ctggaagaga acctcaagaa cacagtgaag aacaccgtga | 1800 |
| gtcaagttgc caagagagtc ttgaccatgg gagtgaatgg agagcttcac ccttcaagat | 1860 |
| tctgcgaaaa agacttgatc aaagttgtgg acagagaata tgtctttgca tacattgatg | 1920 |
| atccttgcag tgcaagttca ccattgatgc agaagctgag gcaagtgctt gttgatcatg | 1980 |

| | |
|---|---|
| cgttggacaa tggagacaga gagaagaatt caaccacttc aatcttccaa aagattggag | 2040 |
| cctttgagga tgaactaaag acccttttgc ctaaagaggt cgaaatcgcc agaactgaac | 2100 |
| ttgagagtgg aaatgcagcc attccaaaca ggatcaagga atgcaggtcc tatccgttat | 2160 |
| acaaaattgt gagagaagat attggaacaa gtttgttgac tggcgaaaag gttcgatccc | 2220 |
| caggtgaaga attcgacaaa gttttcacag caatgtgtga agggaagttg attgatccta | 2280 |
| tgcttgaatg cttgaaggag tggaatggtg ctcctcttcc catttgccag aattaatggt | 2340 |
| ttgattaagt acagttttat gactgtcttt ttttattctt cttgttctta tgcttttact | 2400 |
| tgccatgttg tgtagtcaac ttgaaacagt caattcaatt gcttttttgg ttttttctgta | 2460 |
| tttggaaaag ttgggacaat aacaaatgta atgttgataa caagaacaga caggtgttca | 2520 |
| gcatgttctt cttcactgtt gctaaagata agagcatcgt caatatagat aaggctttgt | 2580 |
| taaaaaaaaa aaaaaaaaaa aaaaagg | 2607 |

<210> SEQ ID NO 78
<211> LENGTH: 2151
<212> TYPE: DNA
<213> ORGANISM: Rhodotorula glutinis

<400> SEQUENCE: 78

| | |
|---|---|
| atggcaccct cgctcgactc gatctcgcac tcgttcgcaa acggcgtcgc atccgcaaag | 60 |
| caggctgtca atggcgcctc gaccaacctc gcagtcgcag gctcgcacct gcccacaacc | 120 |
| caggtcacgc aggtcgacat cgtcgagaag atgctgccg cgccgaccga ctcgacgctc | 180 |
| gaactcgacg gctactcgct caacctcgga gacgtcgtct cggccgcgag gaagggcagg | 240 |
| cctgtccgcg tcaaggacag cgactgagatc cgctcaaaga ttgacaaatc ggtcgagttc | 300 |
| ttgcgctcgc aactctccat gagcgtctac ggcgtcacga ctggatttgg cggatccgca | 360 |
| gacacccgca ccgaggacgc catctcgctc cagaaggctc tcctcgagca ccagctctgc | 420 |
| ggtgttctcc cttcgtcgtt cgactcgttc cgcctcggcc gcggtctcga gaactcgctt | 480 |
| cccctcgagg ttgttcgcgg cgccatgaca atcgcgtca acagcttgac ccgcggccac | 540 |
| tcggctgtcc gcctcgtcgt cctcgaggcg ctcaccaact tcctcaacca cggcatcacc | 600 |
| cccatcgtcc cctccgcgg caccatctct gcgtcgggcg acctctctcc tctctcctac | 660 |
| attgcagcgg ccatcagcgg tcacccggac agcaaggtgc acgtcgtcca cgagggcaag | 720 |
| gagaagatcc tgtacgcccg cgaggcgatg gcgctcttca acctcgagcc cgtcgtcctc | 780 |
| ggcccgaagg agggtctcgg tctcgtcaac ggcaccgccg tctcagcatc gatggccacc | 840 |
| ctcgctctgc acgacgcaca catgctctcg ctcctctcgc agtcgctcac ggccatgacg | 900 |
| gtcgaagcga tggtcggcca cgccggctcg ttccacccct tccttcacga cgtcacgcgc | 960 |
| cctcacccga cgcagatcga agtcgcggga acatccgca agctcctcga gggaagccgc | 1020 |
| tttgctgtcc accatgagga ggaggtcaag gtcaaggacg acgagggcat tctccgccag | 1080 |
| gaccgctacc ccttgcgcac gtctcctcag tggctcggcc cgctcgtcag cgacctcatt | 1140 |
| cacgcccacg ccgtcctcac catcgaggcc ggccagtcga cgaccgacaa ccctctcatc | 1200 |
| gacgtcgaga acaagacttc gcaccacggc ggcaatttcc aggctgccgc tgtggccaac | 1260 |
| accatggaga agactcgcct cgggctcgcc cagatcggca agctcaactt cacgcagctc | 1320 |
| accgagatgc tcaacgccgg catgaaccgc ggctctcccct cctgcctcgc ggccgaagac | 1380 |
| ccctcgctct cctaccactg caagggcctc gacatcgccg ctgcggcgta cacctcggag | 1440 |

```
ttgggacacc tcgccaaccc tgtgacgacg catgtccagc cggctgagat ggcgaaccag    1500
gcggtcaact cgcttgcgct catctcggct cgtcgcacga ccgagtccaa cgacgtcctt    1560
tctctcctcc tcgccaccca cctctactgc gttctccaag ccatcgactt gcgcgcgacc    1620
gagttcgagt tcaagaagca gttcggccca gccatcgtct cgctcatcga ccagcacttt    1680
ggctccgcca tgaccggctc gaacctgcgc gacgagctcg tcgagaaggt gaacaagacg    1740
ctcgccaagc gcctcgagca gaccaactcg tacgacctcc cccgcgctg gcacgacgcc    1800 ttctccttcg ccgccggcac cgtcgtcgag gtcctctcgt cgacgtcgct ctcgctcgcc    1860
gccgtcaacg cctggaaggt cgccgccgcc gagtcggcca tctcgctcac ccgccaagtc    1920
cgcgagacct tctggtccgc cgcgtcgacc tcgtcgcccg cgctctcgta cctctcgccg    1980
cgcactcaga tcctctacgc cttcgtccgc gaggagcttg gcgtcaaggc ccgccgcgga    2040
gacgtcttcc tcggcaagca agaggtgacg atcggctcga acgtctccaa gatctacgag    2100
gccatcaagt cgggcaggat caacaacgtc ctcctcaaga tgctcgctta g            2151

<210> SEQ ID NO 79
<211> LENGTH: 1572
<212> TYPE: DNA
<213> ORGANISM: Rhodobacter sphaeroides

<400> SEQUENCE: 79
atgctcgcca tgagcccccc gaagccggcc gtcgagctgg atcgccacat cgatctggac      60
caggcccatg ccgtggcgag cggcggcgcg cggattgtcc ttgcccctcc ggcgcgcgac     120
cggtgccgtg cgtccgaagc gcggctcggc gctgtcatcc gcgaggcgcg ccatgtctac     180
ggactgacaa ccggcttcgg tccccttgcg aaccgcctga tctcaggtga aatgtccga     240 acgctgcagg ccaatcttgt ccatcatctg gccagcggcg tgggaccggt gcttgactgg     300
acgacggcgc gcgccatggt tctggcgcgt ctggtgtcga tcgctcaggg agcctccggt     360
gccagcgagg ggaccatcgc tcgcctgatc gacctgctca attccgagct cgctccggcc     420
gttcccagcc gcggcacggt gggcgcgtcg ggtgacctga caccgcttgc gcatatggtg     480
ctctgcctcc agggccgggg agacttcctg gaccgggacg ggacgcggct tgacggcgca     540
gaagggctcc ggcgcggacg gctgcaaccg ctcgatctct cccatcgcga tgcactggcg     600
ctggtcaacg ggacctccgc catgaccggg atcgcgctgt gaatgctca cgcctgccgc     660 catctcggca actgggcggt ggcgttgacg gccctgcttg cggaatgtct gagaggccgg     720
accgaggcat gggccgcggc actgtccgac ctgcggccga tcccggaca gaaggacgcc     780 gcagcgaggc tgcgcgcccg cgtggacggc agcgcgcggg tggtccggca cgtcattgcc     840
gagcggaggc tcgacgccgg cgatatcggg acggagccgg aggcggggca ggatgcctac     900
agcctgcgct cgctccgca ggttctcggg gcgggcttcg acacgctcgc atggcatgac     960
cgggtgctga cgatcgagct gaacgcggtg accgacaatc cggtgtttcc gcccgatggc    1020
agcgtgcccg ccctgcacgg gggcaatttc atgggccagc atgtggcgct gacgtccgat    1080
gcgctcgcca cggccgtcac cgttctggcg ggccttgcgg agcgccagat tgcacgtctg    1140
acagatgaaa ggctgaaccg tgggctgccc cccttcctcc accggggccc cgccgggttg    1200
aattccggct tcatgggcgc acaggtgacg gcgaccgcgc tcctggccga gatgcgagcc    1260
acgggacctg cctcgatcca ttcgatctcc acgaacgccg ccaatcagga tgtggtctcg    1320
cttgggacca tcgccgcgcg cctctgccgc gagaagatcg accgttgggc ggagatcctt    1380
gcgatcctcg ctctctgtct tgcacaagct gcggagctgc gctgcggcag cggcctagac    1440
```

```
ggggtgtctc ccgcggggaa gaagctggtg caggccctgc gcgagcagtt cccgccgctt    1500
gagacggacc ggcccctggg acaggaaatt gccgcgcttg ctacgcacct cttgcagcaa    1560
tctcccgtct ga                                                        1572

<210> SEQ ID NO 80
<211> LENGTH: 2465
<212> TYPE: DNA
<213> ORGANISM: Trichosporon  cutaneum
<220> FEATURE:
<221> NAME/KEY: misc_feature
<222> LOCATION: (1607)..(1607)
<223> OTHER INFORMATION: n is a, c, g, or t

<400> SEQUENCE: 80
tggaatgcat gctccggcga cagcccggca taccacactg taacacactc gtctccccccc     60 tcccaccctc tcttatcgcg tcacatggct aactctctga ctgctcgcac ctaacacgaa    120
cacggcgccg agcgaggcga tgaacgctat ataacaatcc gtggtgttgc cacctcctcc    180
ccaccgatca cactcagctc agctcgctcc tcgccagccc ctctcgctct aactcgctct    240
acgctatcgc ggtaccgcac cccatacaac aaacccctcc cgagtggcaa tgtttattga    300
gaccaatgtc gccaagcccg cttccaccaa ggcgatgaac gccggttcgg ccaaggccgc    360
tcctgtgtga gtacccacca ctaactgggg agtcaccgct gacatgcagt gagccgttcg    420
ctacctatgc ccactcccag gctaccaaga ccgtcagcat cgacggccac accatgaagg    480
tcggtgacgt cgtcgccgtc gcccgccacg gcgccaaggt cgagctcgcg gcctcggtcg    540
ccggccccgt ccgggcctcg gtcgacttca aggagtccaa gaagcacacg tcgatctacg    600
gcgtcaccac cggctttggc ggctcggccg acacgcgcac cagcgacacc gaggcgctcc    660
agatctcgct cctcgagcac cagctctgcg gcttcctccc caccgacgcc acctacgagg    720
gcatgctcct cgccgcgatg ccgatcccca tcgtccgcgg cgccatggcc gtccgcgtca    780
acagctgcgt ccgcggccac tcgggcgtcc gcctcgaggt cctccagtcg tttgccgact    840
ttatcaacag aggcctcgtc ccctgcgtgc ccctccgcgg caccatctcg gcctcgggcg    900
acctctcgcc cctctcgtac attgccggtg cgatctgcgg ccaccccgac gtcaaggtgt    960
tcgacaccgc ggcgtcgccc ccacggttc tcacctcccc cgaggcgatc gccaagtacg   1020
gcctcaagac cgtcaagctc gcctccaagg agggcctcgg cctcgtcaac ggcacggccg   1080
tctcggcggc cgcggggcgcg ctcgcgctct acgacgccga gtgcctcgcc atcatgagcc   1140
agaccaacac tgtgctcacg gtcgaggcgc tcgacggcca cgtcggctcg tttgccccct   1200
tcatccagga gatccgccct cacgccggcc agatcgaggc cgctagaaac attagacaca   1260
tgctcggtgg ctccaagctc gccgtgcacg aggagtccga gctcctcgcc gaccaggacg   1320
ccggcatcct ccgccaggac cgctacgcgc tccgcacctc ggcgcagtgg atcggcccgc   1380
agctcgaggc gctcggcctc gcccgccagc agatcgagac cgagctcaac tcgaccaccg   1440
acaacccgct catcgatgtc gagggcggca tgttccacca cggcggcaac ttccaggcca   1500
tggccgtcac ctcggccatg gactcggccc gcatcgtcct ccagaacctc ggcaagctca   1560
gctttgccca ggtcaccgag ctcatcaact gcgagatgaa ccacggnctc ccctccaacc   1620
tcgccggctc cgagcctagc accaactacc actgcaaggg tctcgacatc cactgcgggcg   1680 cctactgcgc cgagctcggc ttcctcgcca accccatgag caaccacgtc cagagcaccg   1740
agatgcacaa ccagagcgtg aactcgatgg cgttcgcgtc cgcccgcagg acgatggagg   1800
```

```
ccaacgaggt cctctcgctc ctcctcggct cgcagatgta ctgcgcgacc caggccctcg    1860
acctccgcgt catggaggtc aagttcaaga tggccatcgt caagctcctc aacgagaccc    1920
tcaccaagca ctttgcggcc ttcctcacgc ccgagcagct cgccaagctc aacacccacg    1980
ccgccatcac gctgtacaag cgcctcaacc agacgcccag ctgggactcg gccccgcgct    2040
tcgaggacgc cgccaagcac ctcgtcggcg tcatcatgga cgccctcatg gtcaacgacg    2100
acatcaccga cctcaccaac ctccccaagt ggaagaagga gttcgccaag gaggccggca    2160
acctctaccg ctcgatcctc gtcgcgacca ccgccgacgg ccgcaacgac ctcgagcccg    2220
ccgagtacct cggccagacg cgcgccgtct acgaggccgt ccgctccgag ctcggcgtca    2280
aggtccgccg cggcgacgtc gccgagggca agagcggcaa gagcatcggc tcgagcgtcg    2340
ccaagatcgt cgaggcgatg cgcgacgccg cctcatggg cgctgttggc aagatgttct    2400
aagccaccag acatttctct atagggtagc aactgtttca gtagcacatg catcattgta    2460
ctatt                                                                2465

<210> SEQ ID NO 81
<211> LENGTH: 1569
<212> TYPE: DNA
<213> ORGANISM: Streptomyces coelicolor

<400> SEQUENCE: 81
gtgttccgca gcgagtacgc agacgtcccg cccgtcgacc tgcccatcca cgacgccgtg      60
ctcggcgggg ccgccgcctt cgggagcacc ccggcgctga tcgacggcac cgacggcacc     120
accctcacct acgagcaggt ggaccggttc caccggcgcg tcgccgccgc cctcgccgag     180
accggcgtgc gcaagggcga cgtcctcgcc ctgcacagcc caacaccgt cgccttcccc     240 ctggccttct acgccgccac ccgcgcgggc gcctccgtca ccacggtgca tccgctcgcg     300
acggcggagg agttcgccaa gcagctgaag gacagcgcgg cccgctggat cgtcaccgtc     360
tcaccgctcc tgtccaccgc ccgccgggcc gccgaactcg cgggcggcgt ccaggagatc     420
ctggtctgcg acagcgcgcc cggtcaccgc tccctcgtcg acatgctggc ctcgaccgcg     480
cccgaaccgt ccgtcgccat cgaccggcc gaggacgtcg ccgccctgcc gtactcctcg     540
ggcaccaccg gcaccccaa gggcgtcatg ctcacacacc ggcagatcgc caccaacctc     600
gcccagctcg aaccgtcgat gccgtccgcg cccggcgacc gcgtcctcgc cgtgctgccg     660
ttcttccaca tctacggcct gaccgccctg atgaacgccc cgctccggct cggcgccacc     720
gtcgtggtcc tgccccgctt cgacctggag cagttcctcg ccgccatcca gaaccaccgc     780
atcaccagcc tgtacgtcgc cccgccgatc gtcctggccc tcgccaaaca cccctggtc     840 gccgactacg acctctcctc gctgaggtac atcgtcagcg ccgccgcccc gctcgacgcg     900
cgtctcgccg ccgcctgctc gcagcggctc ggcctgccgc cgtcggcca ggcctacggc     960 atgaccgaac tgtccccggg cacccacgtc gtccccctgg acgcgatggc cgacgcgccc    1020
cccggcaccg tcggcaggct catcgcgggc accgagatgc gcatcgtctc cctcaccgac    1080
ccgggcacgg acctccccgc cggagagtcc ggggagatcc tcatccgcgg ccccccagatc  1140 atgaagggct acctgggccg ccccgacgcc accgccgcca tgatcgacga ggagggctgg    1200
ctgcacaccg gggacgtcgg acacgtcgac gccgacggct ggctgttcgt cgtcgaccgc    1260
gtcaaggaac tgatcaagta caagggcttc caggtggccc ccgccgaact ggaggcccac    1320
ctgctcaccc accccggcgt cgccgacgcg ccgtcgtcg cgcctacga cgacgacggc    1380 aacgaggtac cgcacgcctt cgtcgtccgc cagccggccg cacccggcct cgcggagagc    1440
```

```
gagatcatga tgtacgtcgc cgaacgcgtc gcccctaca aacgcgtccg ccgggtcacc    1500
ttcgtcgacg ccgtccccg cgccgcctcc ggcaagatcc tccgccgaca gctcagggag    1560
ccgcgatga                                                           1569

<210> SEQ ID NO 82
<211> LENGTH: 1626
<212> TYPE: DNA
<213> ORGANISM: Allium cepa

<400> SEQUENCE: 82
atgggttcaa tatcaatgga tcaagaaacg atattcaggt cgaaacttcc ggatatttac     60
atccccgacc atctacctct ccactcctac tgcttccagc acattcaaga gttctccgac    120
aaaccctgca tcatagatgg cataactgaa aaggtgtata cttacgcaga cgtcgagcta    180
acatcaaaac gtgtggcagt cggtctgcgc gacttgggca tcagaaaagg ccatgtcatc    240
atgatcctcc tacccaactc tccggagttc gccttctcct tcctcggagc ttcctacctc    300
ggcgccatgt ccacaacagc gaatccttac tacaccccag ctgagatcaa aaagcaggca    360
atgggatccg gcgttagggt cataataaca gaatcctgct acgtgcccaa gatcaaagac    420
ttagaacaca acgtaaagat cgtagtcatc gatgagttgg tcgatgaaca cagtacatgc    480
atcccctttt cacaactgtc ttccgctgat gaaaggaagc tcccggaggt ggaaatcagt    540
cctgacgatg tggtggcact tccttattca tcgggaacta cagggctacc gaaaggagtt    600
atgctgacac atgaaggctt gattacaagc gtggctcagc aggtggatgg agagaatccg    660
aatttgtatt tcagaagcga cgatgtgctt ttgtgtgtat accgcttttt tcacatatat    720
tcgctgaact cggttttgtt gtgtggactg agggcgggt cgacgatttt gttgatgagg    780
aagtttgatt tgactaaagt ggtggagttg gttggaaaat acagggtgac gatagcgcca    840
tttgtgcctc ctatttgtat tgaaattgct aagaatgaca tggttggaat gtgtaatttg    900
ttgaacatta ggatggttat gtcggggcg gcacccatgg ggaaggagtt ggaggataag    960
ttgaaggaga gatgcctaa tgccgtactt ggccagggtt acggaatgac tgaagcaggt   1020
cctgtaatat caatgtgtcc tggctttgca aaacatccaa ctcaagccaa atccggatca   1080
tgtgaaacta tcgttagaaa tgcagaacta aaagtgatgg atccagaaac aggcttttct   1140
cttggccgca accttcctgg agaaatttgc atccgtggtc cccagataat gaaaggttat   1200
cttaatgacc ctgaggcaac ttcttcaact atagacttag aaggttggct acatactgga   1260
gatattggtt atgttgatga tgatgatgaa gtattcattg ttgacagagt taaggaactg   1320
atcaaattta aagggtttca ggtaccgccg gctgagctcg agtctctgct tgttagtcac   1380
ccttgtattg cagatgcagc tgtgattcct caaaagatg aagttgccgg tgaggttcct   1440
gttgcatttg ttgttaaagc gagtggttca gacattactg aagacgctgt gaaggaattc   1500
atttcaaagc aggtggtgtt ttacaagaga ttgcagacgg tttatttgt tcacgcaatt   1560 ccaaaatctc cttcaggaaa gatattaagg aaggatctga gagctcgact ttcttcgttt   1620
acatag                                                             1626

<210> SEQ ID NO 83
<211> LENGTH: 1575
<212> TYPE: DNA
<213> ORGANISM: Streptomyces avermitilis

<400> SEQUENCE: 83
```

```
gtgttccgca gcgagtacgc agacgtcccg cccgtcgaac tccccatcca cgaggcggtg      60
ctgggccggg ccgcggagtt cggggaggca cccgccctcg tcgacgcagt ggacggcacc     120
accctcacgt acgaacaact ggaccggttc caccggcgga tcgccgcggc gctggccgag     180
gcgggcgtcc gcaagggcga cgtcctcgcc ctgcacagcc cgaacaccat cgccttcccg     240
acggcgttct acgccgccac gcgcgcgggc gcgtcggtca ccaccgtgca cccgctcgcc     300
acggcggagg agttcgccaa gcagctgagc gactgctccg cccgctggat cgtcaccgtg     360
tcgccgctcc tggacaccgc ccgcagggcg gccgaactcg cgggcggcgt ccgggagatc     420
ttcgtctgcg acagcgcgcc cgggcaccgc tcactgatcg acatgctggc caccgccgcc     480
cccgagccgc gggtcgacat cgaccccgcg gaggacgtcg cggccctccc gtactcctcg     540
ggcacgaccg gcacacccaa gggcgtgatg ctcacccacc ggtccatcgc caccaacctc     600
gcccagctcg aaccggccgt gccgacgggg ccgggcgagc gcatcctcgc cgtcctgccc     660
ttcttccaca tctacggcct gaccgccctc atgaacgcgc cctcaggct cggcgccacg     720 gtcgtcgtac tgccccgctt cgacctcgac acgttcctcg cggccatcga gaaacaccgg     780
atcacccacc tgtacgtcgc cccgccgatc gtcctcgcgc tggccaagca cccggccgtc     840
gcgcagtacg acctgtcgtc cctgaagtac gtcatcagcg ccgccgcgcc cctggacgcc     900
gacaccgccg cggcctgctc gcgacgcctg ggggtgcccc cggtcggaca ggcgtacggc     960
atgacggagc tgtcacccgg cacccacgtg gtcccgctga acgccgtgaa cccgccccg    1020 gggaccgtcg gcaagctcgt cgcgggcacg gagatgcgca tcctctccct cgacgacccg    1080
gaccaggacc tgcccgtcgg cgaggccggt gagatcgcca tccgcggccc ccaggtcatg    1140
aagggctacc tggggcgccc ggaagccacc gccgcgatga tcgacgagga cggctggctg    1200
cacaccgggg acgtcgggcg cgtggacgcc gacggctggc tgttcgtcgt cgaccgcgtc    1260
aaggaactca tcaagtacaa gggcttccag gtcgcccccg ccgagctgga ggcgctcctg    1320
ctgacccacc cgaagatcgc ggacgccgcc gtcatcggcg tctacaacga cgacaacaac    1380
gaggtccccg cacgccacgt ggtgcgccag ccgtccgcgg ccgacctctc gcgggcgag    1440 gtgatgatgt acgtcgccga acgcgtcgcc ccctacaaac ggatccggca cgtcaccttc    1500
ctcgacgagg tgccccgggc cgcctccggg aagatcctcc gacgacagct gcgagacctg    1560
cgggagcact catga                                                   1575

<210> SEQ ID NO 84
<211> LENGTH: 1915
<212> TYPE: DNA
<213> ORGANISM: Populus tremuloides

<400> SEQUENCE: 84
ccctcgcgaa actccgaaaa cagagagcac ctaaaactca ccatctctcc ctctgcatct      60
ttagcccgca atggacgcca caatgaatcc acaagaattc atctttcgct caaaattacc     120
agacatctac atcccgaaaa accttcccct gcattcatac gttcttgaga acttgtctaa     180
acattcatca aaaccttgcc tgataaatgg cgcgaatgga gatgtctaca cctatgctga     240
tgttgagctc acagcaagaa gagttgcttc tggtctgaac aagattggta ttcaacaagg     300
tgacgtgatc atgctcttcc taccaagttc acctgaattc gtgcttgctt tcctaggcgc     360
ttcacacaga ggtgccatga tcactgctgc caatcctttc tccacccctg cagagctagc     420
aaaacatgcc aaggcctcga gagcaaagct tctgataaca caggcttgtt actacgagaa     480
ggttaaagat tttgcccgag aaagtgatgt taaggtcatg tgcgtggact ctgccccgga     540
```

```
cggtgcttca cttttcagag ctcacacaca ggcagacgaa aatgaagtgc ctcaggtcga      600
cattagtcct gatgatgtcg tagcattgcc ttattcatca gggactacag ggttgccaaa      660
agggtcatg ttaacgcaca aagggctaat aaccagtgtg ctcaacagg tagatggaga       720
caatcctaac ctgtattttc acagtgaaga tgtgattctg tgtgtgcttc ctatgttcca     780
tatctatgct ctgaattcaa tgatgctctg tggtctgaga gttggtgcct cgattttgat     840
aatgccaaag tttgagattg gttctttgct gggattgatt gagaagtaca aggtatctat     900
agcaccagtt gttccacctg tgatgatggc aattgctaag tcacctgatc ttgacaagca     960
tgacctgtct tctttgagga tgataaaatc tggaggggct ccattgggca aggaacttga    1020
agatactgtc agagctaagt ttcctcaggc tagacttggt cagggatatg aatgaccga     1080
ggcaggacct gttctagcaa tgtgcttggc atttgccaag gaaccattcg acataaaacc    1140
aggtgcatgt ggaactgtag tcaggaatgc agagatgaag attgttgacc agaaacagg    1200
ggtctctcta ccgaggaacc agcctggtga gatctgcatc cggggtgatc agatcatgaa    1260
aggatatctt aatgaccccg aggcaacctc aagaacaata gacaaagaag gatggctgca   1320
cacaggcgat atcggctaca ttgatgatga tgatgagctt ttcatcgttg acagattgaa   1380
ggaattgatc aagtataaag ggtttcaggt tgctcctact gaactcgaag ctttgttaat   1440
agcccatcca gagatatccg atgctgctgt agtaggatta aagatgagg atgcgggaga    1500
agttcctgtt gcatttgtag tgaaatcaga aaagtctcag gccaccgaag atgaaattaa   1560
gcagtatatt tcaaaacagg tgatcttcta caagagaata aaacgagttt tcttcattga   1620
agcaattccc aaggcaccat caggcaagat cctgaggaag aatctgaaag agaagttgcc   1680
aggcatataa ctgaagatgt tactgaacat ttaaccctct gtcttatttc tttaatactt   1740
gcgaatcatt gtagtgttga accaagcatg cttggaaaag acacgtaccc aacgtaagac   1800
agttactgtt cctagtatac aagctcttta atgttcgttt tgaacttggg aaaacataag   1860
ttctcctgtc gccatatgga gtaattcaat tgaatatttt ggtttcttta atgat        1915

<210> SEQ ID NO 85
<211> LENGTH: 1979
<212> TYPE: DNA
<213> ORGANISM: Oryza sativa (japonica cultivar-group)

<400> SEQUENCE: 85
caggaatcgg tagttgtcat cacgcgcact tccattccgc tcacctaccc accggagaag      60
aggtagtcgc cgccgccgcc gctgtcgccg tcgccggaga agaagaatgg gttcgttgcc    120
ggagcagttc gtcttccgct cgaggctccc cgacatcgcc atcccggacc acctcccgct    180
gcacgactac gtgttcgagc gcctcgccga ccgccgcgac cgggcatgcc ttatcgatgg    240
cgccacgggg gagacgctct cgttcggcga cgtcgacgcg ctgtcgcgcc gcgtggcggc    300
tgggttgagc tcgattggtg tttgccatgg tagtaccgtg atgctgctgc tgccgaactc    360
cgtcgagttc gcggtggcgt tcctcgcgtc gtcacggctc ggggcggtca ccaccacggc    420
caacccgctg cacaccccgc cggagatcgc caagcaggtg gcggcgtccg gcgcgacggt    480
ggtggtcacc gagccggcgt tcgtcgccaa ggtgagcggc ctcgcggggcg tgaccgtcgt   540
cgccaccggg ggcggcgccg agaggtgcgc gtcgttcgcg ggcctcgccg ccgccgacgg   600
ctcggcgctg ccggaggtcg ccatcgacgt cgccaacgac gccgtggcgc tgccctactc    660
gtcgggcacg acgggctcc ccaaggggt gatgctgtcg caccgcgggc tggtgaccag    720
```

```
cgtggcgcag ctcgtcgacg gcgagaaccc gaacctccac ctccgggagg acgacgtggt      780
gctctgcgtg ctccccatgt tccacgtcta ctccctccac tccatcctcc tctgcgggat      840
gcgcgccggc gccgccatcg tggtcatgaa gcggttcgac accgtcaaga tgctgcagct      900
ggtggagcgc cacggcgtca ccatcgcgcc gctcgtccct cccatcgtcg tcgagatggc      960
caagagcgac gccctcgacc gccacgacct ctcctccatc cgcatggtca tctccggcgc     1020
cgcccccatg ggcaaggagc ttcaggacat cgtccacgcc aagctcccca cgccgtcct      1080 cggacagggg tacgggatga cggaggcagg gccggtgcta tcaatgtgca tggcgttcgc     1140
gaaggagccg acgccggtga agtccggcgc gtgcggcacg gtggtgcgga cgccgagct      1200 gaagatcgtc gacccggaca ccggcttgtc actcccgcgc aaccagccgg gggagatttg     1260
catcagggga aaacaaatca tgaaaggata cctgaacaac ccggaggcga ccgagaagac     1320
gatcgacaag gacgggtggc tgcacactgg cgacatcggc ttcgtcgacg acgacgacga     1380
gatcttcatc gtggaccggc tcaaggagct catcaagtac aagggcttcc aggtcgcccc     1440
cgccgagctc gaggccatgc tcatcgccca cgccgccgtc gccgacgccg ccgtcgtccc     1500
aatgaaggac gattcctgcg gcgagatccc agtggcgttc gtcgtcgcac gcgacggctc     1560
ggggatcacc gacgacgaga tcaagcagta cgtcgcaaag caggtggtgt tctacaagag     1620
gctgcacaag atcttcttcg tggacgcaat cccgaaggcg ccgtcgggaa agattttgag     1680
gaaggatctg agagcaaagt tggctgctgg aattccggcg tgctgatgaa actggcatga     1740
gctagcttgc ctgagatatc cagctattgt ttggttttg ttttgatcat acttaaaaag     1800
atatagtgaa atgtaaacat gatgtagtca gcaatgtaaa aggaacacgc cctctggata     1860
tacatgaaag tttgagaggt gatctcatcg gtcatcagta acacaaattt gtcgcaaaga     1920 ttttattt ttgttgttgc acccgtgtaa aagtgaattg atgccatttt atttgttgg        1979

<210> SEQ ID NO 86
<211> LENGTH: 1911
<212> TYPE: DNA
<213> ORGANISM: Amorpha fruticosa

<400> SEQUENCE: 86
tcacaaacac aaaataccat tcccgcaatg gcatttgaga cagaagaacc aaaggaattc       60
atcttcaggt caaaattacc agaaatccca atctccaaac accttcccct tcactcttac      120
tgctttgaga acctctcaga attcgggtca cgtccatgct tgatcagtgc cccaacaggg      180
gacgtgtaca cctactatga cgtggaactc accgctagaa gagttgcctc tggactcaac      240
aaattgggtg tccaacaagg tgatgtcatc atgctccttc ttcctaattc accagaattt      300
gtgttctcct tcttgggtgc ctcttaccgt ggtgccatga tcactgctgc caacccattc      360
ttcacatccg ctgagattgc aaaacaggcc aaagcctcca acaccaagtt gcttataaca      420
caagcttctt actacgacaa ggttaaggat ttggatgtga agttggtgtt cgtggactct      480 cccccctgatg ggcacatgca ctattcagag ctgcgtgagg ctgatgagag tgacatgcct      540
gaggtgaaga ccaaccctga tgatgtggtg cacttccct attcgtcagg acaacaggg      600 ttgcccaaag gggtgatgtt atctcacaaa gggttggcga ccagcatagc acaacaagtt      660 gatgggaaa accccaacct ctactttcac aatgaggatg tcatattgtg tgtgcttcca      720
ctctttcata tatattctct caattctgtt ctgttgtgtg ggttgagagc caaggctgct      780
attttgctga tgccaaagtt tgagatcaat gccttgttgg gtctcattca gaaacaccga      840
gtaacaattg cccctattgt cccacccatt gttttggcca ttgccaagtc accggatctt      900
```

-continued

```
gaaaagtatg atctctcttc cattagggtg ttgaaatctg gaggggcttc tctgggcaaa      960
gaactcgaag acactgtgag ggctaaattc cccaaggcca aacttggaca gggatacgga     1020
atgactgagg cagggccagt gctaacaatg tgcttagcat ttgctaagga accgatagat     1080
gtaaaaccag gtgcatgtgg aaccgttgta agaaatgcag agatgaagat tgtggatcct     1140
gaaactggta attcgttgcc acgaaaccag tccggtgaaa tttgcataag aggcgaccag     1200
atcatgaaag gttatctaaa tgatcaagag gctacgcaga gaaccataga caaagaaggg     1260
tggttgcata caggtgacat cggctacatc gacgatgacg atgagttatt catcgttgac     1320
aggcttaagg aattgatcaa atacaaagga tttcaggtgg ctcctgctga actcgaagcc     1380
cttcttctct ctcatcccaa gatcaccgat gctgctgtgg ttccaatgaa ggatgaagca     1440
gctggagagg tacctgttgc atttgtggtg agatcaaatg gtcacacaga cacaaccgag     1500
gatgaaatta agcagtttat ctccaaacag gtggtgtttt ataaaagaat aagcagagta     1560
ttcttcattg atgcaattcc caagtcaccg tcaggtaaaa tcttacgaaa ggatctaaga     1620
gcaaagcttg cagcaggtgt tccaaattga aaattctaat tccaagatat atgatattac     1680
cattatcata cgatgcccgc acaaagctcc ataaaccttg aaggccagag tgcggacgcg     1740
tgcttggagc ttgaccgcat tacttatatt cacacgaggg cagacatgat tacccttaaaa    1800
ggggggggttg ctaattatat tttaaaacta tattgggtaa aatttgattc gatcaaggac    1860
tttcatatta tataatatcg aagtataatt tttcaaaaaa aaaaaaaaaa a             1911
```

<210> SEQ ID NO 87
<211> LENGTH: 1740
<212> TYPE: DNA
<213> ORGANISM: Populus tomentosa

<400> SEQUENCE: 87

```
cgcaatggac gccacaatga atccacaaga agaattcatc tttcgctcaa aattaccaga       60
catctacatc ccgaaaaacc ttcccctgca ttcatacgtt cttgaaaact tgtctaacca      120
ttcatcaaaa ccttgcctga taaatggcgc gaatggagat gtctacacct atgctgacgt      180
tgagctcaca gcaagaagag ttgcttctgg tctgaacaag attggtattc aacaaggtga      240
cgtgatcatg ctcttcctac caagttcacc tgaattcgtg cttgctttcc taggcgcttc      300
acacagaggt gccattatca ctgctgccaa tcctttctcc accccctgcag agctagcaaa      360
acatgccaag gcctcgagag caaagcttct gataacacag gcttgttact acgagaaggt      420
taaagatttt gcccgagaaa gtgatgttaa ggtcatgtgc gtggactctg ccccggatgg      480
atgcttgcac ttttcagagc taacacaggc agacgaaaat gaagcgcctc aggtcgacat      540
tagtcccgat gatgtcgtag cattgcctta ttcatcaggg actacagggt tgccaaaagg      600
ggtcatgtta acgcacaaag ggctaataac cagtgttgct caacaggtag atggagacaa      660
tcctaacctg tattttcaca gtgaagatgt gattctgtgt gtgctgccta tgttccatat      720
ctatgctctg aattcaataa tgctctgcgg gctgagagtc ggtgccccga ttttgataat      780
gccaaagttt gagattggtt ctttactggg attgattgag aagtacaagg tatctatagc      840
accggttgtt ccacctgtga tgatgtcaat tgctaagtca cctgatcttg acaagcatga      900
cttgtcttct ttgaggatga taaatctggg aggggctcca ttgggcaagg aacttgaaga      960
tactgtcaga gctaagtttc ctcaggctag acttggtcag ggatatggaa tgaccgaggc     1020
aggacctgtt ctagcaatgt gcttggcatt tgccaaggaa ccattcgaca taaaaccagg     1080
```

```
tgcatgtggg actgtagtca ggaatgcaga gatgaagatt gttgacccag aaacaggggc    1140
ctctctaccg aggaaccagc ctggtgagat ctgcatccgg ggtgatcaga tcatgaaagg    1200
atatcttaat gaccctgagg caacctcaag aacaatagac aaagaaggat ggctgcacac    1260
aggcgatatc ggctacattg atgatgatga tgagcttttc atcgttgaca gattgaagga    1320
attgatcaag tataaagggt ttcaggttgc tcctgctgaa ctcgaagctt tgttaatagc    1380
ccatccagag atatccgatg ctgctgtagt aggattgaaa gatgaggatg cgggagaagt    1440
tcctgttgca tttgtagtga aatcagaaaa gtctcaggcc accgaagatg aaattaagca    1500
gtatatttca aaacaggtga tattctacaa gagaataaaa cgagttttct tcattgaagc    1560
tattcccaag gcaccatctg gcaagatcct gaggaagaat ctgaaagaaa gttggcagg    1620 catataactg aagatgttac tgaacattta atcctctgtc ttatttcttt aatacttgag    1680
aatcattgta gtgttgaacc aagcatgctt ggaaaagaca cgtacccaac gtaagacagt    1740
```

<210> SEQ ID NO 88
<211> LENGTH: 1888
<212> TYPE: DNA
<213> ORGANISM: Nicotiana tabacum

<400> SEQUENCE: 88

```
agcgtgtcca ttttttcaaa ctacttttac cgatggagaa agatacaaaa catggcgata      60
taattttcag atcaaaactc cctgatattt acatccctaa tcatcttcct ttacactctt     120
actgctttga aaacatttca gagttcagtt ctcgaccttg tttaatcaat ggagccaaca     180
aacaaattta tacgtatgct gatgttgaac tcagttcaag aaaagttgct gctggtcttc     240
acaaacaagg gatccaacaa aaggatacaa tcatgatcct attgcctaac tccccagaat     300
ttgtgtttgc tttcattggt gcatcgtacc ttggagctat ttctacaatg gccaatcctt     360
tgtttacggc cgctgaggtt gtgaagcaag tcaaggcttc tggtgctaag atcattgtca     420
cacaagcgtg tcatgttaac aaagtgaaag attatgcttt ggagaataat gttaagatca     480
tatgcatcga ctcggcaccg gagggttgtc tccacttctc cgtgctaact caggccgatg     540
agcacgatat tcctgaggta gaaatccaac ccgatgatgt ggtggcgttg ccctactcct     600
ctgggacgac tggattacct aaaggagtga tgttgacaca caaggacttg tcacaagcg     660 tggcacaaca agtcgatggt gaaaatcgga atttgtatat ccatagcgag gacgtgttgc     720
tttgtgtctt gccccttgttt catatctatt ccctcaactc cgttttgctt tgtggattaa     780
gggttggagc agcgattttg attatgcaga aatttgtat tgttccattc ttggagttga     840
tacaaaatta caaggtgaca atagggccgt ttgtaccgcc tattgtcttg gccattgcta     900
agagtcctat ggttgatgat tatgatcttt catcagtaag aactgtcatg tctgggctg     960 caccattagg aaaggagctt gaagacactg ttcgagccaa atttcctaat gctaaacttg    1020
gtcagggtta tggtatgaca gaagctggac cagtgttggc aatgtgcttg catttgcaa    1080 aagaacccctt tgaaataaaa tcaggggcat gtgggacagt tgtgagaaat gctgagatga    1140
aaattgtgga tcctgaaact ggtaattctc ttcccaggaa tcagtctgga gaaatttgca    1200
taagaggaga ccaaatcatg aaaggctacc tgaatgatcc agaggccaca gcaagaacaa    1260
tagacaaaga aggatggtta tatacaggtg acattggcta tattgatgat gacgacgagc    1320 ttttttattgt ggatcgattg aaggagctga ttaaatacaa aggatttcaa gttgcacctg    1380
ctgagctcga agctctcctt ctcaaccatc caacattttc tgatgctgct gttgtccccca    1440 tgaaagacga acaagcggaa gaagttccag tggcttttgt tgttagatcc agtggatcca    1500
```

-continued

| | |
|---|---|
| ccattactga agatgaagtc aaggatttca tctcaaagca ggtgatattt tataagagga | 1560 |
| taaagcgggt attttcgtg gatgctgttc ctaaatctcc atctggcaaa atccttcgaa | 1620 |
| aagatttgag agctaaactg gctgctgggc ttccaaatta atactttcag tttagcttta | 1680 |
| atagtggcaa taactataac cagttcgcca ttgaagacaa tttatttttt attaaaatgt | 1740 |
| tacataatat gttcttttga ttgtaccttc aactacgtgc ctcttcggtc agaattaatt | 1800 |
| taccgaattg gcaaaaggag gaaaatgtat gtaaatttga ctgtaagaac ttcaattttt | 1860 |
| taaatgtctt tttggtatta ttttattc | 1888 |

<210> SEQ ID NO 89
<211> LENGTH: 1972
<212> TYPE: DNA
<213> ORGANISM: Pinus taeda PT4CL2

<400> SEQUENCE: 89

| | |
|---|---|
| ctcattcaat tcttcccact gcaggctaca tttgtcagac acgttttccg ccattttcg | 60 |
| cctgttctg cggagaattt gatcaggttc ggattgggat tgaatcaatt gaaaggtttt | 120 |
| tattttcagt atttcgatcg ccatggccaa cggaatcaag aaggtcgagc atctgtacag | 180 |
| atcgaagctt cccgatatcg agatctccga ccatctgcct cttcattcgt attgctttga | 240 |
| gagagtagcg gaattcgcag acagaccctg tctgatcgat ggggcgacag acagaactta | 300 |
| ttgctttca gaggtggaac tgatttctcg caaggtcgct gccggtctgg cgaagctcgg | 360 |
| gttgcagcag gggcaggttg tcatgcttct ccttccgaat tgcatcgaat ttgcgtttgt | 420 |
| gttcatgggg gcctctgtcc ggggcgccat tgtgaccacg gccaatcctt tctacaagcc | 480 |
| gggcgagatc gccaaacagg ccaaggccgc gggcgcgcgc atcatagtta ccctggcagc | 540 |
| ttatgttgag aaactggccg atctgcagag ccacgatgtg ctcgtcatca aatcgatga | 600 |
| tgctcccaag gaaggttgcc aacatatttc cgttctgacc gaagccgacg aaacccaatg | 660 |
| cccggccgtg aaaatccacc cggacgatgt cgtggcgttg ccctattctt ccggaaccac | 720 |
| ggggctcccc aagggcgtga tgttaacgca caaaggcctg tgtccagcg ttgcccagca | 780 |
| ggtcgatggt gaaaatccca atctgtattt ccattccgat gacgtgatac tctgtgtctt | 840 |
| gcctctttc cacatctatt ctctcaattc ggttctcctc tgcgcgctca gagccggggc | 900 |
| tgcgacctg attatgcaga aattcaacct cacgacctgt ctggagctga ttcagaaata | 960 |
| caaggttacc gttgccccaa ttgtgcctcc aattgtcctg acatcacaa agagcccat | 1020 |
| cgtttcccag tacgatgtct cgtccgtccg gataatcatg tccggcgctg cgcctctcgg | 1080 |
| gaaggaactc gaagatgccc tcagagagcg ttttcccaag gccatcttcg ggcagggcta | 1140 |
| cggcatgaca gaagcaggcc cggtgctggc aatgaaccta gccttcgcaa agaatccttt | 1200 |
| cccgtcaaa tctggctcct gcggaacagt cgtccggaac gctcaaataa agatcctcga | 1260 |
| tacagaaact ggcgaatctc tcccgcacaa tcaagccggc gaaatctgca tccgcggacc | 1320 |
| cgaaataatg aaaggatata ttaacgaccc ggaatccacg gccgctacaa tcgatgaaga | 1380 |
| aggctggctt cacacaggcg acgtcgggta cattgacgat gacgaagaaa tcttcatagt | 1440 |
| cgacagagta aaggagatta tcaaatataa gggcttccag gtggctcctg ctgagctgga | 1500 |
| agctttactt gtggctcatc cgtcaattgc tgacgcagca gtcgttcctc aaaagcacga | 1560 |
| ggaggcgggc gaggttccgg tggcgttcgt ggtgaagtcg tcggaaatca gcagcaggga | 1620 |
| aatcaaggag ttcgtggcaa agcaggtgat tttctacaag aaaatacaca gagtttactt | 1680 |

-continued

| | |
|---|---|
| tgtggatgcg attcctaagt cgccgtccgg caagattctg agaaaggatt tgagaagcag | 1740 |
| actggcagca aaatgaaaat gaatttccat atgattctaa gattcctttg ccgataatta | 1800 |
| taggattcct ttctgttcac ttctatttat ataataaagt ggtgcagagt aagcgcccta | 1860 |
| taaggagaga gagagagctt atcaattgta tcatatggat tgtcaacgcc ctacactctt | 1920 |
| gcgatcgctt tcaatatgca tattactata aacgatatat gttttttttt tt | 1972 |

<210> SEQ ID NO 90
<211> LENGTH: 1825
<212> TYPE: DNA
<213> ORGANISM: Glycine max

<400> SEQUENCE: 90

| | |
|---|---|
| aaagtcgcaa aaattctcct cctacaccaa caaaaatggc accttctcca caagaaatca | 60 |
| tcttccgatc cccactcccc gatattccga tccccacaca tctcccattg tactcttact | 120 |
| gcttccaaaa cttgtcacag ttccatgacc gtccatgcct catcgacggc gacaccggcg | 180 |
| agaccctcac ctacgccgac gtcgacctcg ctgctcgccg catcgcctcc ggcctccaca | 240 |
| aaatcggcat ccgccagggt gacgtcatca tgctcgtcct acgcaactgc cgcagttcg | 300 |
| ccctcgcctt cctcggcgcc acccaccgtg gcgccgtcgt caccacagcc aaccccttct | 360 |
| acacgccggc ggagcttgcg aagcaagcga cggccacgaa aaccaggctc gtcataacgc | 420 |
| aatccgcgta cgtagagaaa atcaagagtt tcgcggacag cagcagcgat gtcatggtga | 480 |
| tgtgcattga tgatgatttt tcttatgaaa acgacgcgct tttgcatttc tcaacgctca | 540 |
| gtaacgccga cgaaacggaa gcccctgccg ttaagattaa ccctgacgag ctcgttgcgc | 600 |
| ttccgttttc ttctggcacg tctgggctcc ccaagggcgt tatgttatcg cataaaaact | 660 |
| tggtcaccac gatagcgcag ttagttgacg gcgaaaaccc gcaccaatac actcacagcg | 720 |
| aggatgtgct actctgtgtg ttgcctatgt ttcatatcta tgcgctcaat tccatttgc | 780 |
| tctgcgggat tcgttccggt gcggccgtgc ttattttgca gaagtttgag atcactactc | 840 |
| tgttggagct catcgagaag tacaaggtga cggttgcgtc gtttgtgccg cccatcgttt | 900 |
| tggcgttggt taagagcgga gagactcatc gctacgacct gtcgtctatt cgcgctgtgg | 960 |
| tcaccggcgc ggcacccta ggaggggaac ttcaagaagc cgttaaggct aggctaccac | 1020 |
| acgctacttt tggacaggga tatgggatga cagaagcagg accacttgcc attagcatgg | 1080 |
| catttgcaaa agtaccctct aagattaaac caggtgcatg cggaaccgtt gtgagaaacg | 1140 |
| ccgagatgaa aatcgtggat acagaaacgg gtgattcact tccaagaaac aaacacggtg | 1200 |
| aaatttgcat aataggcaca aaggtcatga aggatatct aaatgaccca gaggctacag | 1260 |
| agagaactgt agacaaagaa ggatggttac acacaggaga tattggtttc attgatgatg | 1320 |
| atgatgaact cttcattgtt gatcggttaa aggaattgat caaatacaaa ggattccaag | 1380 |
| tggctcctgc tgagcttgaa gcattgttga ttgcccaccc aaacatttct gatgctgccg | 1440 |
| ttgtaggcat gaaagatgaa gctgcagggg aaattccagt tgcatttgtt gtaaggtcaa | 1500 |
| atggttctga gatagccgag gatgaaatca agaaatacat ttcacaacag gtggtttttt | 1560 |
| acaagagaat atgtagagtt ttcttcacgg actctattcc taaagcaccc tcaggcaaaa | 1620 |
| ttctgcgaaa ggtattaact gcaagactta acgaaggttt ggtggtggcc aattaggtcc | 1680 |
| ataattgtga cagaggaaaa tcgtggctgt tttacttacc gtaccacagg cccttcctgt | 1740 |
| tgtggttttt gttccaattt tatatctcgt tatcaatata tatatataat atgcaagtat | 1800 |
| tgcatgaaaa aaaaaaaaaa aaaaa | 1825 |

<210> SEQ ID NO 91
<211> LENGTH: 1957
<212> TYPE: DNA
<213> ORGANISM: Arabidopsis thaliana

<400> SEQUENCE: 91

| | | | | | |
|---|---|---|---|---|---|
| caaacgttac | tttccaaaac | aatcttttca | gttttagata | aaaatttgat | attaacttct | 60 |
| gattcatgac | gacacaagat | gtgatagtca | atgatcagaa | tgatcagaaa | cagtgtagta | 120 |
| atgacgtcat | tttccgatcg | agattgcctg | atatatacat | ccctaaccac | ctcccactcc | 180 |
| acgactacat | cttcgaaaat | atctcagagt | tcgccgctaa | gccatgcttg | atcaacggtc | 240 |
| ccaccggcga | agtatacacc | tacgccgatg | tccacgtaac | atctcggaaa | ctcgccgccg | 300 |
| gtcttcataa | cctcggcgtg | aagcaacacg | acgttgtaat | gatcctcctc | ccgaactctc | 360 |
| ctgaagtagt | cctcactttc | cttgccgcct | ccttcatcgg | cgcaatcacc | acctccgcga | 420 |
| acccgttctt | cactccggcg | gagatttcta | acaagccaa | agcctccgcg | gcgaaactca | 480 |
| tcgtcactca | atcccgttac | gtcgataaaa | tcaagaacct | ccaaaacgac | ggcgttttga | 540 |
| tcgtcaccac | cgactccgac | gccatccccg | aaaactgcct | ccgtttctcc | gagttaactc | 600 |
| agtccgaaga | accacgagtg | gactcaatac | cggagaagat | ttcgccagaa | gacgtcgtgg | 660 |
| cgcttccttt | ctcatccggc | acgacgggtc | tccccaaagg | agtgatgcta | acacacaaag | 720 |
| gtctagtcac | gagcgtggcg | cagcaagtcg | acggcgagaa | tccgaatctt | tacttcaaca | 780 |
| gagacgacgt | gatcctctgt | gtcttgccta | tgttccatat | atacgctctc | aactccatca | 840 |
| tgctctgtag | tctcagagtt | ggtgccacga | tcttgataat | gcctaagttc | gaaatcactc | 900 |
| tcttgttaga | gcagatacaa | aggtgtaaag | tcacggtggc | tatggtcgtg | ccaccgatcg | 960 |
| ttttagctat | cgcgaagtcg | ccggagacgg | agaagtatga | tctgagctcg | gttaggatgg | 1020 |
| ttaagtctgg | agcagctcct | cttggtaagg | agcttgaaga | tgctattagt | gctaagtttc | 1080 |
| ctaacgccaa | gcttggtcag | ggctatggga | tgacagaagc | aggtccggtg | ctagcaatgt | 1140 |
| cgttagggtt | tgctaaagag | ccgtttccag | tgaagtcagg | agcatgtggt | acggtggtga | 1200 |
| ggaacgccga | gatgaagata | cttgatccag | acacaggaga | ttctttgcct | aggaacaaac | 1260 |
| ccggcgaaat | atgcatccgt | ggcaaccaaa | tcatgaaagg | ctatctcaat | gacccttgg | 1320 |
| ccacggcatc | gacgatcgat | aaagatggtt | ggcttcacac | tggagacgtc | ggatttatcg | 1380 |
| atgatgacga | cgagcttttc | attgtggata | gattgaaaga | actcatcaag | tacaaaggat | 1440 |
| ttcaagtggc | tccagctgag | ctagagtctc | tcctcatagg | tcatccagaa | atcaatgatg | 1500 |
| ttgctgtcgt | cgccatgaag | gaagaagatg | ctggtgaggt | tcctgttgcg | tttgtggtga | 1560 |
| gatcgaaaga | ttcaaatata | tccgaagatg | aaatcaagca | attcgtgtca | aaacaggttg | 1620 |
| tgttttataa | gagaatcaac | aaagtgttct | tcactgactc | tattcctaaa | gctccatcag | 1680 |
| ggaagatatt | gaggaaggat | ctaagagcaa | gactagcaaa | tggattaatg | aactaggttt | 1740 |
| tatatgatcc | acgtatatga | atgcaatctt | atcagaaaaa | tgaaacaaaa | tttcgttttg | 1800 |
| tgaacaaagg | aattaaactt | acacgtaaaa | gaataatatt | tgtgcttttt | cctttatgtg | 1860 |
| tatgtaatgg | ataaatagtt | gtatcttttg | tttggtggga | atgatgtaac | ctttccatat | 1920 |
| tgtggcatat | tgctcgaata | taatcaataa | ttgcctt | | | 1957 |

<210> SEQ ID NO 92
<211> LENGTH: 1689
<212> TYPE: DNA

<213> ORGANISM: Arabidopsis thaliana

<400> SEQUENCE: 92

| | | | | | |
|---|---|---|---|---|---|
| atgctgacga | aaaccaacga | cagccgtttg | attgaccgga | gctccggctt | cgatcaacgg | 60 |
| acaggaatct | atcacagtct | tcgtccctct | ctttctctac | ctcctataga | tcaacctctc | 120 |
| tccgccgccg | aattcgcgct | ttctctccta | ctcaaatcct | caccacctgc | caccgccggg | 180 |
| aaaaacattg | aagccttaac | ctacctagtt | aactcgagct | ctggtgataa | cctcacttat | 240 |
| ggagagcttc | ttcgtagagt | tcgttctctt | gctgtatctc | tccgggagcg | atttccttct | 300 |
| cttgcctcca | gaaatgtcgc | ttttatcctc | tctccttctt | cgttggacat | accagtgctt | 360 |
| tacttagctt | tgatgtcgat | cggtgttgtt | gtttcaccgg | cgaacccaat | cggatctgaa | 420 |
| tcggaggtga | gtcatcaagt | cgaagtcagt | gaaccagtaa | ttgcgttcgc | gacatcgcag | 480 |
| acggttaaga | agcttcaatc | ctcttctttg | cctctcggaa | ctgttctgat | ggactcgact | 540 |
| gagtttctct | cctggttaaa | tcgatcggat | tcttcatcgg | ttaatccatt | tcaggttcag | 600 |
| gtcaaccaat | cggaccctgc | cgctatcctc | ttttcctctg | aacaaccgg | gcgggtcaaa | 660 |
| ggcgttttgc | tcactcaccg | taacctaatc | gcctcgaccg | ccgtatctca | ccaacggact | 720 |
| ctccaagatc | cggttaatta | cgatcgcgtt | ggactgttct | cgcttccgct | cttccacgtg | 780 |
| tttggtttca | tgatgatgat | tcgagccatc | tcgcttggag | agacattggt | gcttttaggg | 840 |
| agatttgaac | tcgaggcgat | gtttaaggcg | gtggagaaat | ataaggttac | tggtatgcct | 900 |
| gtatctcctc | cgttgattgt | agcgttggtc | aaatcggagc | tcacgaagaa | gtacgatctc | 960 |
| cggtcgttgc | gttcccttgg | ctgcggagga | gctccactcg | gcaaagacat | cgcagagagg | 1020 |
| tttaagcaga | aattcccaga | tgtagatatt | gtacagggct | atggcttgac | agagagctcg | 1080 |
| ggaccagctg | cctcaacgtt | tggacctgaa | gagatggtaa | aatatggctc | agttggtcgt | 1140 |
| atctctgaga | atatggaagc | caaaattgtt | gatccatcca | ccggagaatc | cttgccaccg | 1200 |
| ggaaaaactg | gtgaactctg | gctccgagga | ccagtcatca | tgaaaggtta | tgtgggaaac | 1260 |
| gagaaagcga | gtgcggagac | agtagacaaa | gaagggtggt | taaagactgg | tgatctctgt | 1320 |
| tattttgatt | cggaagattt | tctatatatt | gttgatcggc | taaaggagct | aatcaaatac | 1380 |
| aaggcttatc | aggttccacc | ggtagagttg | gagcagattc | ttcactcgaa | tccagatgtg | 1440 |
| attgatgctg | cagttgttcc | gttccctgac | gaggatgcag | gagagattcc | aatggctttc | 1500 |
| atagtgagaa | aaccaggaag | caatctcaac | gaagcgcaaa | tcattgattt | cgtagctaaa | 1560 |
| caagttactc | cgtacaagaa | ggtaagacga | gttgctttta | taaatgcaat | cccaaaaaat | 1620 |
| cctgctggca | agattctgcg | tcgggagctt | actaaaatcg | ctgtggatgg | caatgcatca | 1680 |
| aaactttga | | | | | | 1689 |

<210> SEQ ID NO 93
<211> LENGTH: 1849
<212> TYPE: DNA
<213> ORGANISM: Rubus idaeus

<400> SEQUENCE: 93

| | | | | | |
|---|---|---|---|---|---|
| tcttcgaaat | cccatttcgc | aatggcggtc | caaacacctc | aacacaacat | cgtctaccgc | 60 |
| tccaagctcc | cggacatcca | tatcccaaac | cacctccctc | tccattccta | catattccaa | 120 |
| aacaaatccc | acctcacctc | aaagccctgc | atcatcaatg | gcactactgg | cgacatccac | 180 |
| acctacgcca | aattcaaact | caccgcccgg | aaagtcgcct | ccggcctcaa | caagctcggc | 240 |
| atcgagaaag | gcgacgtctt | catgcttttg | ctccccaaca | cttccgaatt | cgtctttgcc | 300 |

```
ttcttgggag cctcgttctg cggagccatg atgacagccg ccaacccttt cttcactccg    360
gcggaaatcg cgaaacaggc caaggcgtcg aaggcgaagc tgatcatcac tttcgcttgc    420
tattacgaca aagtaaaaga cttatcatgc gacgaagtga agttgatgtg cattgactcg    480
ccgccacctg actcgtcttg tcttcatttc tccgaactga ctcagtcaga cgagaacgac    540
gtgccggatg tggacatcag cccggacgac gtcgtggcgt taccttattc ctccgggacg    600
acgggactgc cgaaagggt gatgttgacg cacaaagggc tggtgacgag cgtgtctcag    660
caggtggacg gagagaatcc gaatttgtac tacagcagcg acgacgtcgt tctgtgcgtg    720
ctgccgctgt ttcatattta ctcgctgaac tcggtcttgc tatgcgggtt aagagccgga    780
gctgccattc tgctgatgca gaagtttgag attgtgtcgc ttttggagct gatgcagaag    840
cataggtta gtgttgcgcc gattgtgcct ccgactgttt tggcgatcgc caagtttcca    900
gatcttgaca gtatgatttt gggatccata agggtgctga agagtggagg agcaccattg    960
gggaaggagc ttgaagatac agtcagagct aaatttccca atgtcacact cggtcaggga   1020
tatggaatga cagaggcagg tccggtgttg acaatgtcgt tggcatttgc aaaggaaccc   1080
ttcgaggtga accaggtgg gtgtgggact gtcgtcagaa acgcagagtt gaagatcgtt   1140
gatcctgaaa ctggtgcctc tttgccgcgc aaccaccctg gtgagatttg catcagaggc   1200
caccagatca tgaaaggtta tcttaatgat ccggaggcca agaacaac catagacaag    1260
caaggttggc tacacacagg tgacataggc ttcattgatg acgatgaaga gctcttcatt   1320
gttgatcgat taaaggagct catcaaatac aaaggctttc aggttgcccc tgctgagctt   1380
gaagccttgc tcgtcaccca tcctaacatc tctgatgctg ccgttgtccc aatgaaggat   1440
gacgcagctg gcgaggttcc ggttgcattt gtcgtgagtc caaagggctc tcaaatcact   1500
gaggatgaaa tcaagcaatt tatttcaaaa caggttgtat tctacaaaag aataaaacga   1560
gtattttca ttgaagccat tcccaagtcc ccatcgggca agatcttgcg gaaggagttg   1620
agagcaaagc ttgctgctgg ctttgcaaat tgaggaatgt tgccctcca tttatccta    1680
tcatgaaagg gctatgtata cttattaaaa ggttttttt ttcctttttt ttttctggac   1740
ttaaaagttt gattaatgtg attcatcctt aattaatttg aatccggaat ttctacaaac   1800
ttaatttatg taaaaatcaa ttgaaactat atattgcttc gaaaaaaaac              1849

<210> SEQ ID NO 94
<211> LENGTH: 2213
<212> TYPE: DNA
<213> ORGANISM: Lithospermum erythrorhizon

<400> SEQUENCE: 94
cttgaacttt cctgcattct tgcacatttc ttgttctaat ttatttattt ataaatcatt     60
tcaagaaaag aagtaaggtg cttttggtata cccaagccaa ggagagttgg ttagaagaga    120
aagagtgaga tagagaacca aatttaaaag aaagctcatc acagaagtga ggtgggaata    180
aatcccagaa aaacacaaaa acaaggcaat attattacca cctatagtat tatcaccaaa    240
ccaaccgaac aacaacaaat aacaatgttg tctgtagctt cccctgaaac ccaaaagcca    300
gagctttcct ccattgctgc cccccttct tccaccccc aaaaccaatc ctccattct     360
ggagataaca actccaatga aaccatcatc ttcagatcca aactacctga tatacccatc    420
tccaataacc tccctctcca cacatactgc ttccagaatg cttctgaata ccccaacaga    480
acatgcatca ttgatagcaa aactggaaaa caatacactt tttctgaaac agattcaatc    540
```

```
tgcagaaaag ttgcagctgg attatcaaat cttggcatcc aaaaaggaga tgtgatcatg    600
gtcctcctcc aaaactgtgc tgaattcgtt ttcaccttca tgggtgcttc cataataggt    660
gcagtcatca ccacaggaaa ccccttctac acaactgcag aaatcttcaa acaagtcaac    720
gtctccaaca caaaactcat cattactcaa tccaactacg ttgacaagct ccgtaacacc    780
accataaacg aatccgacaa caaatatcca aaacttggag aggattttaa ggtgatcaca    840
attgataccc cccagaaaa ctgcctaccc ttttcactcc tcattgaaaa cacccaagaa     900
aaccaagtta catcagtttc catcgactca aacgacccaa tagcattacc attttcctca    960
ggcaccacag ggttaccaaa aggagtgatc ctaacacaca aaagcctcat tacaagcgtt   1020
gcacaacaag tagatggaga cacccaaac ttgtacctaa acatgatga tgtagtacta    1080
tgtgtacttc ctttgttcca tatatactcc ctaaattcag tacttttgtg ttcattaaga   1140
gctggagcag cagtgttgat catgcagaaa tttgagatag gggcattgtt ggaacttata   1200
caaagccacc gtgtatcggt ggcggcggtg gtgcctccgc tagtattggc gttggcaaag   1260
aatccaatgg tggataaata tgatctgagt tcgataaggg tggtgttgtc gggggcggcg   1320
ccgctgggga gggagttgga actagcgtta cttaatagag tcccacatgc cattttgggg   1380
cagggttatg gcatgactga agctggacca gtactatcaa tgtcccttc atttgcaaag   1440
cacccatacc cagcaaaatc cgggtcatgt ggaactgtag ttagaaatgc agacctcaag   1500
gtgattgacc ccgaaaccgg ttcctccctc ggccgaaacc aacctggaga aatttgcatt   1560
cgtggcgaac agatcatgaa aggctatctc aacgaccccg aggcaactgc caggaccgtt   1620
gacatcgagg ggtggctcca taccggtgac attggctatg tggacgacga tgatgaagtg   1680
ttcattgttg atagggtgaa ggaactcatc aaattcaagg ggttccaagt tccaccagct   1740
gagcttgagg ctctcctcat ttcccaccc aacattgctg atgctgctgt tgtaccgcaa   1800
aaagatgctg ctgctggaga agtccctgtt gcttttgtgg ttccttctaa tgatggcttt   1860
gaattaacag aagaagctgt caaagaattc atttctaaac aggttgtgtt ctacaaaagg   1920
ttgcacaagg tgtactttgt ccactctatt ccaaagtcgc cgtccggcaa gattttgagg   1980
aaagatctca gagccaaact ggccgccgcc gcctcctctt gaattcttat tgttcgatag   2040
ttgcataaaa gttattattg ccatgtatta tggctaatta ataaataata ggaattattt   2100
ttcaaatgta gtcattattg tttatctatg tgaatgtttg catgagactg agtaattgaa   2160
ctcattgatg agttcttttg ttatgtgtga gaatggaatc caaccatttt act         2213
```

<210> SEQ ID NO 95
<211> LENGTH: 1668
<212> TYPE: DNA
<213> ORGANISM: Zea mays
<220> FEATURE:
<221> NAME/KEY: misc_feature
<222> LOCATION: (603)..(603)
<223> OTHER INFORMATION: n is a, c, g, or t

<400> SEQUENCE: 95

```
atgggttccg tagacgcggc gatcgcggtg ccggtgccgg cggcggagga gaaggcggtg     60
gaggagaagg cgatggtgtt ccggtccaag cttcccgaca tcgagatcga cagcagcatg    120
gcgctgcaca cctactgctt cgggaagatg gcgaggtgg cggagcgggc gtgcctgatc    180
gacgggctga cggcgcgtc gtacacgtac gcggaggtgg agtccctgtc ccggcgcgcc    240
gcgtcggggc tgcgcgccat gggggtgggc aaggcgacg tggtgatgag cctgctccgc    300
aactgccccg agttcgcctt caccttcctg ggcgccgccc gcctgggcgc cgccaccacc    360
```

```
acggccaacc cgttctacac cccgcacgag gtgcaccgcc aggcggaggc ggccggcgcc    420
cggctcatcg tgaccgaggc ctgcgccgtg gagaaggtgc gggagttcgc ggcggagcgg    480 ggcatcccg tggtcaccgt cgacgggcgc ttcgacggct gcgtggagtt cgccgagctg    540
atcgcggccg aggagctgga ggctgacgcc gacatccacc ccgacgacgt cgtcgcgctg    600
ccntactcct ccggcaccac cgggctgccc aagggcgtca tgctcaccca ccgcagcctc    660
atcaccagcg tcgcgcagca ggttgatggc gagaacccga acctgtactt ccgcaaggac    720
gacgtggtgc tgtgcctgct gccgctgttc cacatctact cgctgaactc ggtgctgctg    780
gccggcctgc gcgcgggctc caccatcgtg atcatgcgca agttcgacct gggcgcgctg    840
gttgacctgg tgcgcaggta cgtgatcacc atcgcgccct tcgtgccgcc catcgtggtg    900
gagatcgcca agagcccccg cgtgaccgcc ggcgacctcg cgtccatccg catggtcatg    960
tccggcgccg cgcccatggg caaggagctc caggacgcct tcatggccaa gatccccaat   1020
gccgtgctcg gcaggggta cgggatgacg gaggcaggcc ccgtgctggc gatgtgcctg   1080
gccttcgcca aggagccgta cccggtcaag tccgggtcgt gcggcaccgt ggtgcggaac   1140
gcggagctga agatcgtcga ccccgacacc ggcgccgccc tcggccggaa ccagcccggc   1200
gagatctgca tccgcgggga gcagatcatg aaaggttacc tgaacgaccc cgagtcgacg   1260
aagaacacca tcgaccagga cggctggctg cacaccggcg acatcggcta cgtggacgac   1320
gacgacgaga tcttcatcgt cgacaggctc aaggagatca tcaagtacaa gggcttccag   1380
gtgccgccgg cggagctgga ggcgctcctc atcacgcacc cggagatcaa ggacgccgcc   1440
gtcgtctcaa tgaacgacga ccttgctggt gaaatcccgg tcgccttcat cgtgcggacc   1500
gaaggttctc aagtcaccga ggatgagatc aagcaattcg tcgccaagga ggtggttttc   1560
tacaagaaga tccacaaggt cttcttcacc gaatccatcc ccaagaaccc gtcgggcaag   1620
atcctgagga aggacttgag agccaggctc gccgccggtg ttcactga              1668

<210> SEQ ID NO 96
<211> LENGTH: 1300
<212> TYPE: DNA
<213> ORGANISM: Vitis sp. cv. Optima

<400> SEQUENCE: 96
cttaatctta agcttcaatt tcattacgta tctagcatcc atggcttcag ttgaggaatt     60
tagaaacgct caacgtgcca agggtccggc cactatccta gccattggca cagctactcc    120
tgaccactgt gtctaccagt ctgattatgc tgattactat ttcagggtca ctaagagcga    180
gcacatgact gagttgaaga agaagttcaa tcgcatatgt gacaaatcaa tgatcaagaa    240
gcgttacatt cacttgaccg aagaaatgct tgaggagcac ccaaacattg gtgcttatat    300
ggctccatct cttaacatac gccaagagat tatcactgct gaggtaccta gcttggtag    360 ggatgcagca ttgaaggctc ttaaagagtg ggcccaacca aagtccaaga tcacccatct    420 tgtatttgt acaacctccg gtgtagaaat gcccggtgcg gattacaaac tcgctaatct    480
cttaggtctt gaaacatcgg ttagaagggt gatgttgtac catcaagggt gctatgcagg    540
tggaactgtc cttcgaactg ctaaggatct tgcagaaaat aatgcaggag cacgagttct    600
tgtggtgtgc tctgagatca ctgttgttac attccgtggc ccttccgaag atgctttgga    660
ctctttagtt ggccaagccc tttttggtga tgggtcttca gctgtgattg ttggatcaga    720
tccagatgtc tcgattgaac gaccactctt ccaacttgtt tcagcagccc aaacatttat    780
```

```
tcctaattca gcaggagcca ttgccggaaa cttacgtgag gtggggctca cctttcattt      840
gtggcccaat gtgcctactt tgatttctga aacatagag aaatgcttga cccaggcttt       900
tgacccactt ggtattagcg attggaactc gttattttgg attgctcacc caggtggccc      960
tgcaattctc gatgcagttg aagcaaaact caatttagag aaaagaaac tcgaagcaac       1020 taggcatgtg ttaagtgagt acggtaacat gtcaagtgca tgtgtgttgt ttattctgga      1080
tgagatgaga agaaatcct tgaaggggga aaaggctacc acaggtgaag gattggattg       1140
gggagtatta tttggttttg gccgggcttt gaccatcgaa actgttgtgc tgcatagcgt      1200
tcctacagtt acaaattaag agaaataaaa gagaatggtt gacccttcaa tggcgtaatg      1260
tatcaaatag gagttagcaa aggtatttat ctccgaaatt                            1300

<210> SEQ ID NO 97
<211> LENGTH: 1185
<212> TYPE: DNA
<213> ORGANISM: Vitis vinifera

<400> SEQUENCE: 97
atggcttcag tcgaggaatt tagaaacgct caacgtgcca agggtccggc caccatccta       60
gccattggca cagctacccc cgaccactgt gtctaccagt ctgattatgc tgattactat      120
ttcagggtca ctaagagcga gcacatgact gagttgaaga agaagttcaa tcgcatatgt      180
gacaaatcaa tgatcaagaa gcgttacatt cacttgaccg aagaaatgct tgaggagcac      240
ccaaacattg gtgcttatat ggctccatct cttaacatac gccaagagat tatcactgct      300
gaggtaccta gacttggtag agatgcagca ttgaaggctc ttaaagagtg gggccaacca      360
aagtccaaga tcacccatct tgcattttgt acaacctccg gtgtagaaat gcccggtgcg      420
gattacaaac tcgctaatct cttaggtctt gaaacatcgg ttagaagggt gatgttgtac      480
catcaagggt gctatgcagg tggaactgtc cggcgaactg ctaaggatct tgcagaaaat      540
aatgcaggag cacgagttct tgtggtgtgc tctgagatca ctgttgttac attccgtggg      600
ccttccgaag atgctttgga cccctttagtt ggccaagccc ttttggtga tgggtcttca      660 gctgtgattg ttggatcaga tccagatgtc tcgattgaac gaccactctt ccaacttgtt      720
tcagcagccc aaacattttat tcctaattca gcaggagcca ttgccggaaa cttacgtgag      780
gtggggctca cctttcattt gtggcccaat gtgcctactt tgatttctga aacatagag       840 aaatgcttga ctcaggcttt tgacccactt ggtattagcg attggaactc gttattttgg      900
attgctcacc caggtggccc tgcaattctc gatgcagttg aagcaaaact caatttagag      960 aaaagaaat tggaagcaac taggcatgtg ttaagtgagt acggtaacat gtcaagtgca      1020
tgtgtgttgt ttattttgga tgagatgaga agaaatccc taaggggga aaaagccacc       1080 actggtgaag gattggattg gggagtacta tttggttttg gccaggcttt gaccatcgaa      1140
actgttgtgc tacatagcat tcctatggtt acaaattaag tgaag                     1185

<210> SEQ ID NO 98
<211> LENGTH: 1547
<212> TYPE: DNA
<213> ORGANISM: Vitis vinifera

<400> SEQUENCE: 98
cttcctcaac ttaatcttag gccttaattt gagtacgtag ctgggatcaa tggcttcagt       60
cgaggaaatt agaaacgctc aacgtgccaa gggtccggcc accatcctag ccattggcac      120
agctaccccc gaccactgtg tctaccagtc tgattatgct gatttctatt tcagggtcac      180
```

-continued

```
taagagcgag cacatgactg cgttgaagaa gaagttcaat cgcatatgtg acaaatccat      240
gatcaagaag cgttacattc atttgaccga agaaatgctt gaggagcacc caaacattgg      300
tgcttatatg gctccatctc ttaacatacg ccaagagatt atcactgctg aggtacccaa      360
gctcggtaag gaagcagcat tgaaggctct taaagagtgg ggtcagccta atcgaagat       420 cacccacctt gtatttgta ccacctcggg tgtagaaatg cctggtgcag attataaact       480
cgctaatctt ttaggtctcg aaccatccgt cagaagagtg atgttgtacc atcaagggtg      540
ctatgcaggt ggaactgtcc ttcgaaccgc taaggatctt gcagagaata atgcaggagc      600
acgagttctt gtggtgtgct ctgagatcac agttgttaca tttcgcggcc cttccgaaga      660
tgctttggac tctttagttg gccaagcccc ttttggtgat gggtctgcag ctgtaatcgt      720
aggatcagat ccggatatct caattgaacg accactcttc cagcttgtct cagcagccca      780
aacatttatt cctaattctg caggtgccat tgcaggaaac ttacgtgagg tgggactcac      840
ctttcatttg tggcccaatg tgcccacttt aatttctgaa acattgaga aatgtttgac       900 tcaggctttt gacccacttg gtattagcga ttggaactcc ttattttgga ttgctcaccc      960
aggtggccct gcaattcttg atgcagttga agcaaaactc aatttagata aaaagaaact     1020
cgaagcaacg aggcatgtgc taagtgagta tggaaacatg tcaagtgcat gtgtgttgtt     1080
tattttggat gagatgagaa agaaatccct taaggggggag agggccacca cgggtgaagg    1140
attggattgg ggagtattat tcggttttgg accaggcttg actattgaaa ctgttgtgtt     1200
gcatagcatt cctatggtga caaattaagt gaaggaaaag agaatggtcc cttcaatgtc     1260
ctattatgtt gaataggagt aaggtattta tctccgaaac taaattatac tcttatacta     1320
ttttattatt tttttctaaa tttagattgt aatctagtga ttgttagacc ctcttggtga     1380
gctcaaatga acggttgag tttcaagttc agactgtttt atcatcttga agattcccta      1440
aacattgtaa tgttgtgttc atatgaacat tattgaaaag taaataaaag aaatattgga     1500
ttttgataaa aaaaaaaaa aaaaaaaaa aaaaaaaaa aaaaaa                        1547
```

<210> SEQ ID NO 99
<211> LENGTH: 1170
<212> TYPE: DNA
<213> ORGANISM: Arachis hypogaea

<400> SEQUENCE: 99

```
atggtgtctg tgagtggaat tcgcaaggtt caaagagcag aaggtcctgc aaccgtatta       60
gcgattggca cagcaaatcc accaaactgt gttgatcaga gcacatacgc agattactat     120
tttagagtaa ccaatagcga gcacatgacc gacctcaaga agaaatttca gcgcatttgt     180
gagagaacac agatcaagaa cagacatatg tatctaacgg aagaaatact gaaggagaat     240
cctaacatgt gcgcatacaa agcaccgtcc ttggatgcaa gggaagacat gatgatcagg     300
gaggtaccaa gggttggaaa agaggctgca actaaggcaa tcaaggaatg gggtcagcca     360
atgtctaaga tcacacattt gatcttctgc accaccagcg tgttgcgtt gcctggcgtt      420 gattacgaac tcatcgtact cttagggctc gacccaagcg tcaagaggta catgatgtac     480
caccaaggct gcttcgctgg cggcactgtc cttcgtttgg ctaaggactt ggctgaaaac     540
aacaaggatg ctcgtgtgct tattgtttgt tctgaaaata cttcagtcac ttttcgtggt     600
cctagtgaga cagacatgga tagtcttgta ggacaagcat tgtttgccga tggagctgct     660
gcaattatca ttggttctga tcctgttcca gaggttgaga atcctctctt tgagattgtt     720
```

```
tcaactgatc aacaacttgt ccctaacagc catggagcca tcggtggtct ccttcgtgaa    780
gttggactta cattctatct taacaagagt gttccggata ttatttcaca aaacatcaat    840
gatgcactca gtaaagcttt tgatccacta ggtatatctg attataactc aatattttgg    900
attgcacatc ctggtggacg tgcaattttg gaccaagttg aagagaaggt gaacttgaag    960
ccagagaaga tgaaagccac cagagatgtg cttagcaatt atggtaacat gtcaagtgcg   1020
tgtgtgttct tcattatgga tttgatgaga aagaagtcac ttgaagcagg acttaaaacc   1080
accggagaag gacttgattg gggtgtactt tttggttttg gtcctggtct cactattgaa   1140
actgttgttc tccgcagcat ggccatataa                                    1170

<210> SEQ ID NO 100
<211> LENGTH: 1179
<212> TYPE: DNA
<213> ORGANISM: Cissus rhombifolia

<400> SEQUENCE: 100
atggcttcag ttgaggaatt tagaaacgct caacgtgcca agggtccagc taccatccta     60
gccattggca cagctactcc cgatcagtgt gtctaccagt ctgattatgc tgattactat    120
ttccgggtca ctaagagcga gcacatgact gagttgaaga agaagttcaa tcgcatatgt    180
gagaaatcaa tgatcaagaa gcgttacagt catttgaccg aagaaatgct cgaggagcac    240
ccaaacattg gtgcttatat ggctccatct cttaacatac gccaagagat tatcactgct    300
gaggtaccta agcttggtaa ggaagcagca ttgaaggctc taaaagagtg gggccagcca    360
aagtccaaga tcacccatct tgtatttgt acaacctccg gtgtagaaat gcctggtgca    420
gattacaaac tcgctaatct cttagggctt gaaacatcgg tcagaagagt gatgttgtac    480
catcaagggt gctatgcagg tggaactgtc ctccgaactg ctaaggatct tgcagagaat    540
aatgcaggag cacagttctc tgtggtgtgc tctgaaatca ctgttgttac attccgtggg    600
ccttctgaaa ccgctttgga ctctttagtt ggtcaagccc ttttggtga tgggtctgca    660 gctgtgatcg ttggatcaga tccagatatc ttgattgaac gaccgctctt ccaactcgtc    720
tcagcagccc aaacatttat tcctaattca gcaggtgcca ttgccgggaa cttacgtgag    780
gtgggactca ccttccattt gtggcccaat gtgcctactt taatttctga acatagag    840 aaatgcttga ctcaggcttt tgacccactt ggtattagcg attggaactc gttattttgg    900
attgctcacc caggtggtcc agctattctt gacgcggttg aagcaaaact cagtttagat    960
aaacaaaaac tcgaagcaac gaggcatgtg ctaagtgagt atggcaacat gtcaagtgca   1020
tgtgtgttgt ttattttga tgagatgaga aaaaaatccc ttaaggggga gaaggccacc   1080
acaggtgaag gattggattg gggagtatta ttcggttttg gcccaggttt gactattgag   1140
actgttgtgt tgcatagcat tcctatggtt acaaattaa                          1179

<210> SEQ ID NO 101
<211> LENGTH: 1179
<212> TYPE: DNA
<213> ORGANISM: Parthenocissus henryana

<400> SEQUENCE: 101
atggcttcag ttgaggaatt tagaaacgct caacgtgcca agggtccggc caccatccta     60
gccattggca cagctactcc cgaccagtgt gtctaccagt ctgattatgc tgattactat    120
tttagggtca ctaagagcga gcacatgact gagttgaaga agaagttcaa tcgcatatgt    180
gaaaaatcaa tgatcaagaa gcgttatatt catttgactg aaaagatgct tgaggagcac    240
```

| | |
|---|---|
| ccaaacattg gtgcttatat ggctccatct cttaacatac gccaagagat tatcactgcc | 300 |
| gaggtaccca agcttggtaa agaagcagca ttgaaggctc ttaaagagtg gggtcaaccc | 360 |
| aaatccaaga ttacccatct tgtatttgt accacctctg gtgtagaaat gcctggtgcc | 420 |
| gactataaac tcgctaatct cttaggcctc gaaacatctg ttagaagagt gatgttgtat | 480 |
| catcaaggtt gctatgcagg tggaactgtc cttcgaactg ctaaggatct tgcagagaat | 540 |
| aatgcaggag cacgagttct tgtggtgtgc tctgagatca ctgttgtcac attccgtgga | 600 |
| ccttccgaaa ctgctttgga ctctttagtt ggccaagccc tttttggtga tgggtctgca | 660 |
| gctgtgatcg ttggatcaga tccagatatc tcgattgaac aaccacttt tcaactcgtc | 720 |
| tcagcagccc aaacatttat tcctaattca gcaggtgcca ttgccgggaa cttacgtgag | 780 |
| gtgggactca catttcattt gtggcccaat gtgccaactt taatttctga aacatagag | 840 |
| aaatgcttga ctcaggcttt tgacccactt ggtattagcg attggaactc gttatttgg | 900 |
| attgctcacc caggtggccc tgcaattctt gatgcggttg aagcaaaact caatttagac | 960 |
| aaaaagaaac ttgaagcaac gaggcatgtg ttaagtgagt atggcaacat gtcaagtgca | 1020 |
| tgtgtgttgt ttattttgga tgagatgaga agaaatcac ttaaggggga aaggccacc | 1080 |
| acaggtgaag gattggattg gggagtatta tttggctttg gatcaggctt gactattgag | 1140 |
| actgttgtgt tgcatagcat tcctatggtt acaaattaa | 1179 |

<210> SEQ ID NO 102
<211> LENGTH: 1179
<212> TYPE: DNA
<213> ORGANISM: Parthenocissus quinquefolia

<400> SEQUENCE: 102

| | |
|---|---|
| atggcttcag ttgaggaatt tagaaacgct caacgtgcaa agggtccagc caccatccta | 60 |
| gccattggca cagctactcc cgacaactgt gtctatcagt cagattatgc tgatttctac | 120 |
| ttcagggtca ctaagagcga gcacatgact gagttgaaga agaagttcaa tcgcatatgt | 180 |
| gagaaatcaa tgatcaagaa gcgttacagt catttgaccg aagaaatgct cgaggagcac | 240 |
| ccaaacattg gtgcttatat ggctccatct cttaacatac gccaagagat tatcactgct | 300 |
| gaggtaccta agcttggtaa ggaagcagca ttgaaggctc taaaagagtg gggccagcca | 360 |
| aagtccaaga tcacccatct tgtatttgt acaacctccg gtgtagaaat gcctggtgca | 420 |
| gattacaaac tcgctaatct cttagggctt gaaacatcgg tcagaagagt gatgttgtac | 480 |
| catcaagggt gctatgcagg tggaactgtc ctccgaactg ctaaggatct tgcagagaat | 540 |
| aatgcaggag cacgagttct tgtggtgtgc tctgtaatca ctgttgttac attccgtggg | 600 |
| ccttctgaaa ccgctttgga ctctttagtt ggtcaagccc tttttggtga tgggtctgca | 660 |
| gctgtgatcg ttggatcaga tccagatatc ttgattgaac gaccgctctt ccaactcgtc | 720 |
| tcagcagccc aaacatttat tcctaattca gcaggtgcca ttgccgggaa cttacgtgag | 780 |
| gtgggactca ccttccattt gtggcccaat gtgcctactt taatttctga aacgtagag | 840 |
| aaatgcttga ctcaggcttt tgacccactt ggtattagcg attggaactc gttatttgg | 900 |
| attgctcacc caggtggtcc agctattctt gacgcggttg aagcaaaact cagtttagat | 960 |
| aaacaaaaac tcgaagcaac gaggcatgtg ctaagtgagt atggcaacat gtcaagtgca | 1020 |
| tgtgtgttgt ttattttgga tgagatgaga aaaaatccc ttaaggggga aaggccacc | 1080 |
| acaggtgaag gattggatag gggagtatta ttcggttttg gccaggtttt gactattgag | 1140 |

```
actgttgtgt tgcatagcat tcctatggtt acaaattaa                           1179
```

<210> SEQ ID NO 103
<211> LENGTH: 1618
<212> TYPE: DNA
<213> ORGANISM: Vitis riparia

<400> SEQUENCE: 103

```
gcttcaattt cattacgtat ctagcatcca tggcttcagt tgaggaattt agaaacgctc      60
aacgtgccaa gggtccggcc actatcctag ccattggcac agctactcct gaccactgta     120
tctaccagtc tgattatgct gattactatt tcagggtcac taagagcgag cacatgactg     180
agttgaagaa gaagttcaat cgcatatgta agtatattca tgcattaatt cttatataca     240
taacaattgt atgcatctaa gagtgtgagc tattaggtga ggctcacctc caagcgaatg     300
aatgttccaa cctttctaga gtaaagcttt tagataaatt agttcaggaa acttgaaaat     360
cattttactt cagtaaccaa tattcctttc atttgactgt aatggcttga agagctgttt     420
tttgaatcat atagcactgc tagctataat taagaatacc cttttatact ttcttcaatg     480
ttaaatgcat gttgatcatc ttgaacaata tactatatga cttgtcgatt ggtaaaacta     540
atgtgttcat gttacttcat ttacaggtga gaaatcaatg atcaagaagc gttacattca     600
cttgaccgaa gaaatgcttg aggagcaccc aaacatcggt gcttatatgg ctccatctct     660
taacatacgc caagagatta tcaccgctga ggtacctaga cttggtaggg atgcagcatt     720
gaaggctctt aaagagtggg gccaaccaaa gtccaagatc acccatcttg tgttttgtac     780
aacctccggt gtagaaatgc ccggtgcgga ttacaaactc gctaatctct taggtcttga     840
aacatcggtt agaagggtga tgttgtacca tcaagggtgc tatgcaggtg gaactgtcct     900
tcgaaccgct aaggatcttg cagaaaataa cgcaggagca cgagttcttg tggtgtgctc     960
tgagatcact gttgttacat tccgtgggcc ttccgaagat gctttggact ctttagttgg    1020
ccaagccctt tttggtgatg ggtcttcagc tgtgattgtt ggatcagatc cagatgtctc    1080
gattgaacga ccactcttcc gacttgtttc agcagcccaa acatttattc ctaattcagc    1140
aggagccatt gctggaaact acgtgaggt ggggctcacc tttcatttgt ggcccaatgt     1200
gcctactttg atttctgaga acatagaaa atgcttgacc caggcttttg acccacttgg    1260
tattagcgat tggaactcgt tattttggat tgctcaccca ggtggccctg caattctcga    1320
tgcagttgaa gcaaaactca atttagaaa aaagaaactt gaagcaacta ggcatgtgtt     1380
aagtgagtac ggtaacatgt caagtgcatg tgtgttgttt attttggatg agatgagaaa    1440
gaaatccttg aagggggaaa atgctaccac aggtgaagga ttggattggg gagtattatt    1500
cggttttggg ccgggcttga ccatcgaaac tgttgtgctg catagcattc ctacaattac    1560
aaattaagag aaataaaaga gaatggttta ccttataatg cactaatgta tcaaatag     1618
```

<210> SEQ ID NO 104
<211> LENGTH: 1618
<212> TYPE: DNA
<213> ORGANISM: Vitis labrusca

<400> SEQUENCE: 104

```
gcttcaattt cattacgtat ctagcatcca tggcttcagt tgaggaattt agaaacgctc      60
aacgtgccaa gggtccggcc actatcctag ccattggcac agctactcct gaccactgta     120
tctaccagtc tgattatgct gattactatt tcagggtcac taagagcgag cacatgactg     180
agttgaagaa gaagttcaat cgcatatgta agtatattca tgcattaatt cttatataca     240
```

-continued

```
tgacaattgt atgcatctaa gagtgtgagc tattaggtga ggctcacctc caagcgaatg    300
aatgttccaa cctttctaga gtaaagcttt tagataaatt agttcaggaa acttgaaaat    360
cattttactt cagtaaccaa tattcctttc atttgactgt aatggcttga agagctgttt    420
tttgaatcat atagcactgc tagctataat taagaatacc cttttatact ttcttcaatg    480
ttaaatgcat gttgatcatc ttgaacaata tactatatga cttgtcgatt ggtaaaacta    540
atgtgttcat gttacttcat ttataggtga gaaatcaatg atcaagaagc gttacattca    600
cttgaccgaa gaaatgcttg aggagcaccc aaacattggt gcttatatgg ctccatctct    660
taacatacgc caagagatta tcaccgctga ggtacctaga cttggtaggg atgcagcatt    720
gaaggctctt aaagagtggg gccaaccaaa gtccaagatc acccatcttg tattttgtac    780
aacctccggt gtagaaatgc ccggtgctga ttacaaactc gctaatctct taggtcttga    840
aacatcggtt agaagggtga tgttgtacca tcaagggtgc tatgcaggtg gaaccgtcct    900
tcgagccgct aaggatcttg cagaaaataa cgcaggagca cgagttcttg tggtgtgctc    960
tgagatcaca gttgttacat tccgtgggcc ttccgaagat gctttggact ctttagttgg   1020
ccaagccctt tttggtgatg ggtcttcagc tgtgattgtt ggatcagatc cagatgtctc   1080
gattgaacga ccactcttcc aacttgtttc agcagcccaa acatttattc ctaattcagc   1140
aggagccatt gccggaaact acgtgaggt ggggctcacc tttcatttgt ggcccaatgt   1200
gcctactttg atttctgaga acatagaaa atgcttgacc caggcttttg acccacttgg   1260
tattagcgat tggaactcgt tattttggat tgctcaccca ggtggccctg caattctcga   1320
tgcagttgaa gcaaaactca atttagaaa aagaaacttt gaagcaacta ggcatgtctt   1380
aagtgagtac ggtaacatgt caagtgcatg tgtgttgttt attttggatg agatgagaaa   1440
gagatccttg aagggggaaa atgctaccac aggtgaagga ttggattggg gagtattatt   1500
cggttttggg ccgggcttga ccatcgaaac tgttgtgctg catagcattc ctacagttac   1560
aaattaagag aaataaaaga gaatggttta cccttcaatg cagtaatgta tcaaatag    1618
```

<210> SEQ ID NO 105
<211> LENGTH: 1739
<212> TYPE: DNA
<213> ORGANISM: Vitis sp. cv. 'Norton'

<400> SEQUENCE: 105

```
tttgaagcca actaatcatt caaaacccaa attcaaatat ctaacattat ttattgaccg     60
ccaatagatg agagttggtg agacaagcta taaaagcccg gcacccacaa ccagctttct    120
caagccaact ctaagcactt gagttctctt tccttcctca acttaatctt aagcttcaat    180
ttcattacgt atctagcatc catggcttca gttgaggaat ttagaaacgc tcaacgtgcc    240
aagggtccgg ccactatcct aaccattggc acagctactc ctgaccactg tatctaccag    300
tctgattatg ctgattacta tttcagggtc actaagagcg agcacatgac tgagttgaag    360
aagaagttca tcgcatatg taagtatatt catgcattaa ttcttatata catgacaatt    420
gtatgcatct aagagtgtga gctattaggt gaggctcacc tccaagcgaa tgaatgttcc    480
aacctttcta gagtaaagct tttagataaa ttagttcagg aaacttgaaa tcattttac    540 ttcagtaacc aatattcctt tcatttgact gtaatggctt gaagagctgt ttttgaatc    600 atatagcact gctagctata attaagaata cctttttata cttcttcaa tgttaaatgc    660 atgttgatca tcttgaacaa tatactatat gacttgtcga ttggtaaaac taatgtgttc    720
```

```
atgttacttc atttataggt gagaaatcaa tgatcaagaa gcgttacatt cacttgaccg    780
aagaaatgct tgaggagcac ccaaacattg gtgcttatat ggctccatct cttaacatac    840
gccaagagat tatcaccgct gaggtaccta gacttggtag ggatgcagca ttgaaggctc    900
ttaaagagtg gggccaacca agtccaaga tcacccatct tgtattttgt acaacctccg     960
gtgtagaaat gcccggtgct gattacaaac tcgctaatct cttaggtctt gaaacatcgg   1020
ttagaagggt gatgttgtac catcaagggt gctatgcagg tggaaccgtc cttcgagccg   1080
ctaaggatct tgcagaaaat aacacaggag cacgagttct tgtggtgtgc tctgagatca   1140
cagttgttac attccgtggg ccttccgaag atgctttgga ctctttagtt ggccaagccc   1200 ttttggtga tgggtcttca gctgtgattg ttggatcaga ccagatgtc tcgattgaac    1260 gaccactctt ccaacttgtt tcagcagccc aaacatttat tcctaattca gcaggagcca   1320
ttgccggaaa cttacgtgag gtggggctca cctttcattt gtgcccaat gtgcctactt    1380 tgatttctga gaacatagag aaatgcttga cccaggcttt tgacccactt ggtattagcg   1440
attggaactc gttatttttgg attgctcacc caggtggccc tgcaattctc gatacagttg   1500
aagcaaaact caatttagag aaaaagaaac ttgaagcaac taggcatgtc ttaagtgagt   1560
acggtaacat gtcaagtgca tgtgtgttgt ttattttgga tgagatgaga aagaaatcct   1620
tgaaggggga aaatgctacc acaggtgaag gattggattg gggagtatta ttcggttttg   1680
ggccgggctt gaccatcgaa actgttgtgc tgcatagcat tcctacagtt acaaattaa    1739
```

<210> SEQ ID NO 106
<211> LENGTH: 1629
<212> TYPE: DNA
<213> ORGANISM: Cicer arietinum

<400> SEQUENCE: 106

```
atggatcttc tcctattgga aaagacccct ttagccctttt tcatcgccgc cactatcgcc     60
atcacaattt caaaactccg tggcaaaaga ttcaaacttc caccaggtcc aatcccagtc    120
cccgtcttcg gtaactggct tcaagtcggc gatgatctca ccaccgtaa tctcaccgac    180 ttagcaaaac ggttcggcga tatcttcctc cttcgtatgg gtcaaagaaa cctcgtcgta   240
gtttcatcac ctgaactcgc aaaagaggtt ctccacactc aaggtgtcga attcggttcc   300
cgaacaagga acgttgtttt cgatatcttc accggaaaag gacaggatat ggttttcacc   360
gtttacggaa cattggcgga aatgagaaga atcatgacgg tgccgttttt cacaaacaaa   420
gttgttcaac agtaccgttt tggatgggaa tttgaagctc agagtgttgt cgacgatgtt   480
aagaaaaatc cagaggcgtg ttcgagtgga attgttcttc ggagaagatt gcaacttatg   540
atgtataata ttatgtatag gattatgttt gatagaagat ttgagagtga agaggatcct   600
ttgtttgtga agcttaaagc tttgaatggt gaaagaagtc gtttggctca agctttgag    660 tataattatg gtgattttat tcctattttg agacccttt tgaaaggtta tttgaagctt   720
tgtaaagagg ttaaggatcg taggttgcag ctcttcaaag actatttcgt tgatgagaga   780
aagaaacttg gaagcaccaa gagcaccacc aatgaaggac tgaaatgtgc tattgatcac   840 atttggatg ctcaacagaa gggtgagatc aatgatgaca atgttcttta cattgttgag    900
aacatcaatg ttgctgcaat tgaaacaaca ttatggtcaa ttgaatgggg cattgctgag   960
ctagtgaatc accaaaagat ccaaaacaaa gtaagggaag aaattgatag agttcttgga   1020
ccaggacacc aagtaactga accagatctc caaaagctac cttacctaca gccgtaatc    1080 aaagaaacac ttcgtcttcg aatggcgatt ccactcctcg tcccacacat gaaccttcac   1140
```

```
gatgcaaagc tcagtggttt tgacatcccg gccgagagca agatattggt caatgcgtgg   1200
tggctcgcaa acaacccggc ccaatggaaa aagcccgagg aatttaggcc cgagaggttc   1260
ttagaggaag agtctcatgt cgaggctaat ggaaatgact ttaggtacct tccgttcggc   1320
gttggtagaa ggagttgtcc tggaattatt ctcgctttac cgatcctcgg tattactttg   1380
ggacgattgg ttcagaattt cgagcttttg cctcctccgg gacagtctaa gatcgacacg   1440
gctgagaaag gaggacaatt tagtttgcat atactcaaac attccaccat tgtttgtaag   1500
ccaagatcat ttaattaatt agtcctcaca tcaataatac cctttaattt gttttacttt   1560
actctacttt gtgtaatgca tatttcaatg attatgtggg aatgttggta ataaaaaaaa   1620
aaaaaaaaa                                                          1629
```

<210> SEQ ID NO 107
<211> LENGTH: 1518
<212> TYPE: DNA
<213> ORGANISM: Populus tremuloides

<400> SEQUENCE: 107

```
atggatctcc tactcctgga agaccctc ttgggttctt tcgttgccat tctcgttgcc    60
attctcgttt ctaaactacg tggcaaacgt tttaaactcc ctccaggtcc tttacctgtc   120
cccgtgtttg gaaactggct tcaagttggt gatgatttga accaccgtaa cctcaccgac   180
ttagccaaga aattcggtga catcctcctc cttcgcatgg gccaacgcaa tcttgtagtc   240
gtctcctcac ctgagctatc caagagtt ctgcacacac aaggtgttga gttcgggtcg   300
agaacaagaa atgttgtttt tgatatcttt actggaaagg gacaagacat ggtgttcact   360
gtctatggtg agcattggag gaagatgagg agaatcatga cagtcccttt ctttacaaac   420
aaggttgtcc aacaatatag gtatggatgg gaagaggaag cggctcaagt tgtcgaggat   480
gttaagaaaa accccggggc tgcaactcat gggattgttt tgaggaggag actgcaactg   540
atgatgtata caacatgta taggattatg tttgatagga gatttgagag cgaagaagat   600
cctttgttta taaacttaa ggctttgaat ggtgagagga gcagattggc tcagagtttt   660
gattataatt atggtgattt catccccatt ttgagacctt tcttgagagg ttacttgaag   720
atctgccagg aggttaagga gagaaggttg caactcttca aggactactt tgtcgatgag   780
aggaagaaac ttgcaagcac aaagaacatg tgcaatgaag ggttgaagtg cgcaatagac   840
catatcctgg atgctcaaaa gaagggagag atcaacgagg acaacgtcct ttacattgtt   900
gagaacatca acgtcgctgc aattgagaca acactatggt cgatcgagtg gggaattgct   960
gagcttgtga accatcctga aatccagaag aagttgcgcc atgagctcga taccttgctt  1020
ggacctggtc accaaatcac cgagcctgac acctacaagc tccctacct taacgctgtt  1080 gtcaaagaga cctccgact caggatggca attcctctac tcgtcccaca catgaacctt  1140
catgatgcca agcttggagg ctttgacatt ccagctgaga gcaagatctt ggtcaacgcc  1200
tggtggctcg ccaacaaccc tgcccactgg aaaaaccctg aagaattcag gccagagagg  1260
ttcttggaag aggaggccaa ggtcgaggcc aatggcaatg atttcaggta ccttccattt  1320
ggagttggga aaggagctg ccctgggatt attcttgcat tgccaattct tggcattact  1380
ctgggacgtc tggtacagaa tttcgagctc ttgcctcctc ctggacagtc aaagatcgac  1440
acctcagaga aggtggaca gttcagtttg cacatattga agcactccac tattgttgca  1500
aagccaaggt cctttaa                                                 1518
```

<210> SEQ ID NO 108
<211> LENGTH: 1602
<212> TYPE: DNA
<213> ORGANISM: Oryza sativa

<400> SEQUENCE: 108

| | | | | | |
|---|---|---|---|---|---|
| atggcggcct | ccgcgatgag | ggtggccatc | gccaccgggg | cgtcgttggc | ggtgcatttg | 60 |
| ttcgtcaagt | cgttcgtgca | ggcgcagcat | cctgctctca | ccttgctgct | gccagtggct | 120 |
| gtgtttgtcg | gcattgcggt | gggcgcgaag | ggcgggagcg | gtggtgacgg | aaggcgccg | 180 |
| ccggggccgg | cggccgtgcc | ggtgttcggc | aactggctgc | aggtgggcaa | cgacctgaac | 240 |
| caccggttcc | tcgcggcgat | gtcggcacgg | tacggtcccg | tgttccgtct | gcggctgggc | 300 |
| gtgcgcaacc | tggtggtggt | gtcggacccg | aagctggcga | cggaggtgct | gcacacgcag | 360 |
| ggcgtggagt | tcggctcccg | cccgcgcaac | gtcgtcttcg | acatcttcac | cgccaacggc | 420 |
| gccgacatgg | tgttcaccga | gtacggcgac | cactggcgac | gcatgcgccg | cgtcatgacg | 480 |
| ctgccgttct | tcacggcgcg | cgtcgtgcag | cagtacaagg | ccatgtggga | ggccgagatg | 540 |
| gacgccgtcg | tggacgacgt | gcgcggcgac | gcggtgcgc | agggcaccgg | cttcgtggtg | 600 |
| cgacgcaggc | tgcagctcat | gctgtacaac | atcatgtacc | ggatgatgtt | cgacgcgcgg | 660 |
| ttcgagtcgg | tggacgaccc | catgttcatc | gaggccacca | ggttcaactc | cgagcgcagc | 720 |
| cgcctcgcgc | agagcttcga | gtacaactac | ggcgacttca | tccccatcct | ccgtcccttc | 780 |
| ttgcggggct | acctcaacaa | gtgccgtgac | ctccagagca | ggaggctcgc | cttcttcaac | 840 |
| aacaactacg | tcgagaagag | aaggaaggtg | atggacactc | cgggagacag | gaacaagctc | 900 |
| cggtgcgcga | tcgaccatat | ccttgaggcg | gagaagaacg | cgcagctgac | ggcggagaac | 960 |
| gtgatctaca | tcgtggagaa | catcaacgtg | ccgccatcg | agacgacgct | ctggtccatc | 1020 |
| gagtgggcgc | tggccgaggt | cgtcaaccac | ccggcggtgc | agagcaaggt | ccgcgccgag | 1080 |
| atcaacgacg | tgctcggcga | cgacgagccc | atcaccgagt | ccagcatcca | aagctgact | 1140 |
| tacctgcagg | ccgtgatcaa | ggagacgctg | cggctgcact | ccccgatccc | gctgctggtg | 1200 |
| ccgcacatga | acctggagga | ggccaagctc | ggcgggtaca | ccatcccaa | gggatccaag | 1260 |
| gtggtggtga | acgcgtggtg | gctgccaac | aacccggcgc | tgtgggagaa | ccccgaggag | 1320 |
| ttccggcctg | agcggttctt | ggagaaggag | agcggcgtgg | acgccaccgt | cgccgggaag | 1380 |
| gtggacttca | ggttcctgcc | cttcggcgtg | ggccgccgca | gctgcccggg | gatcatcctg | 1440 |
| gcgctgccca | tcctggcgct | catcgtcggg | aagctggtga | ggagcttcga | gatggtgccg | 1500 |
| ccgccgggcg | tggagaagct | ggacgtgagc | gagaaaggcg | ggcagttcag | cctccacatc | 1560 |
| gccaagcact | ccgtcgtcgc | cttccacccc | atctctgcct | ga | | 1602 |

<210> SEQ ID NO 109
<211> LENGTH: 1173
<212> TYPE: DNA
<213> ORGANISM: Camellia sinensis

<400> SEQUENCE: 109

| | | | | | |
|---|---|---|---|---|---|
| atggtgttca | ctgtatacgg | tgagcactgg | aggaagatga | ggaggatcat | gacggttcct | 60 |
| tttttacca | acaaggtggt | gcagcagtac | aggttcgggt | gggaggacga | ggcgggtcgg | 120 |
| gtcgtggagg | atgtgaagaa | gaacccggaa | gcgaagacca | tgggatcgt | gctgaggagg | 180 |
| cggttgcagc | tgatgatgta | caataacatg | tacaggatta | tgtttgattc | gaggttcgag | 240 |
| agcgaggagg | acccgttgtt | cgtgaaattg | aaggcgttga | atggagagag | gagtaggttg | 300 |

```
gctcagagct tgagtataa ctacggcgat tttattccga ttttgaggcc gttcttgaga      360
gggtacttga agatctgcaa agaagttaaa gagaggaggt tgcagctttt caaggactat      420
tttgtcgatg aaaggaagaa gttagccaag ccacgaagag ccatggacac agttactcta      480
aaatgtgcga ttgatcatat tttggatgct caacaaaagg gagagatcaa cgaggacaac      540
gttctttaca tcgtggagaa cattaacgtc gctgcaattg agacaacatt atggtcgata      600
gaatggggca tagcagaact tgtaaaccac ccccaaatcc agaaaaagct tcggcacgaa      660
cttgacacca tgcttggcct tggagtccaa atcaccgagc agacaccta caaactcccc      720 tacctccaag ctgtagtcaa agagaccctc cgcctccgga tggcaattcc cctcttagtc      780
ccccacatga acctcacga tgcaaagctc tctggctatg acatccctgc tgagagcaaa      840
atcttggtaa acgcgtggtg gcttgcaaac aaccccgaca actggaagaa cccagaagag      900
ttcaggcccg agaggttctt ggaagaggag gctaaggttg aggccaatgg caatgacttt      960
aggtaccttc cgtttggtgt cggaaggagg agttgccctg gaattatcct tgctctgcca     1020
attctcggca tcactttggg aaggttggtt cagaatttcg agctcttgcc tcctccggga     1080
caggccaaga ttgatactgc tgagaagggg ggacagttca gcttgcatat tttgaagcac     1140
tcgaccattg ttctgaaacc aagatcgttc tga                                   1173

<210> SEQ ID NO 110
<211> LENGTH: 1766
<212> TYPE: DNA
<213> ORGANISM: Vigna radiata var. radiata

<400> SEQUENCE: 110
aatttaccac cgtcacgtca ccaaaatgga tctcctcctc ctggagaaga ccctcctcgg       60
cctcttccta gcggcggtgg tagccattgt tgtctccaag ctccgcggca agcgtttcaa      120
gctcccgccg ggcccactcc ccgtccccat cttcggcaac tggctccagg ttggcgacga      180
cctcaaccac cgcaacctca ctcaactcgc caagcgcttc ggcgacatct tcctcctccg      240
catggggcag cgcaacctgg tcgtggtttc ctcgccggac ctcgccaagg aggtgctgca      300
cacgcagggc gtggagttcg gctcccgcac ccgcaacgtt gtcttcgaca tcttcaccgg      360
cgagggccag gacatggtct tcaccgtcta cggcgagcac tggcgcaaga tgcgacgcat      420
catgaccgtg cccttcttca ccaacaaggt cgtccagcag taccgccacg gttgggaggc      480
cgaggccgcc gccgtcgtgg acgacgtcag gaagaatccc gacgcggccg tctccggcct      540
ggtcatccgc cgaaggctac agctcatgat gtacaacaac atgtaccgca tcatgttcga      600
ccggagattc gagagcgaag aagaccctct gttccagcgt ctgaaagcgc tgaacggcga      660
gaggagtcgc ttggctcaga gctttgagta aactatggc gatttcattc ccatcttgag      720
acccttcttg aagggttact tgaagatttg caaggaagtg aaagaaacca ggttgaagct      780
tttcaaggat tacttcgtcg acgagaggaa gaatattgga agcacgaaga gcactaacaa      840
cgaaggactt aaatgtgcta ttgatcacat tttggatgct gagaaaaagg gtgagatcaa      900
cgaagacaac gtgctttaca ttgttgagaa catcaacgtt gctgcaattg aaacaactct      960
ctggtcaatt gaatgggta ttgctgagct tgtgaaccat ccagatccc agcagaaagt     1020 gagggatgaa attgacagag ttcttggagt agggcatcag gtgactgagc cagatatcca     1080
aaagcttcca taccttcaag cagtggtgaa ggaaaccctt cgcctcagaa tggcaatccc     1140
tctccttgtc ccacacatga acctccatga tgctaagctt ggtggctatg acatcccagc     1200
```

```
tgaaagcaag attttggtga atgcatggtg gctggcgaac aaccctgcac actggaagaa    1260
gccagaagag ttcaggcctg agaggttctt cgaagaggaa tcgcatgtgg aagcgaatgg    1320
caatgacttc aggtaccttc cctttggtgt gggagaaga agctgccccg gaatcattct     1380
tgcattgccc attcttggca tcactttggg acgcttggtc caaaactttg agctcttgcc    1440 tcccctggg cagtcccaga ttgacaccag tgagaaagga ggacagttta gcttgcacat     1500
actaaagcat tccaccgttg ttgcaaagcc aaggtccttt tagacttcac cacatcatcg    1560
ttaccaatcc cctttattat tttttcttc ttattctccc tgtattatcg atgtttcaaa     1620
atggggttgc tccatgccat gtaataggg cctcctaatg ggtaggtggt gatgtatctc     1680
ttggtcccat tgtaattctc tcacaacttc aactcatgaa tgatcttgag atggttttgt    1740
aataaactta cactttttgt ctctaat                                        1766
```

<210> SEQ ID NO 111
<211> LENGTH: 1620
<212> TYPE: DNA
<213> ORGANISM: Helianthus tuberosus
<220> FEATURE:
<221> NAME/KEY: misc_feature
<222> LOCATION: (1588)..(1588)
<223> OTHER INFORMATION: n is a, c, g, or t
<220> FEATURE:
<221> NAME/KEY: misc_feature
<222> LOCATION: (1591)..(1591)
<223> OTHER INFORMATION: n is a, c, g, or t
<220> FEATURE:
<221> NAME/KEY: misc_feature
<222> LOCATION: (1593)..(1594)
<223> OTHER INFORMATION: n is a, c, g, or t
<220> FEATURE:
<221> NAME/KEY: misc_feature
<222> LOCATION: (1597)..(1597)
<223> OTHER INFORMATION: n is a, c, g, or t
<220> FEATURE:
<221> NAME/KEY: misc_feature
<222> LOCATION: (1599)..(1600)
<223> OTHER INFORMATION: n is a, c, g, or t
<220> FEATURE:
<221> NAME/KEY: misc_feature
<222> LOCATION: (1602)..(1602)
<223> OTHER INFORMATION: n is a, c, g, or t
<220> FEATURE:
<221> NAME/KEY: misc_feature
<222> LOCATION: (1604)..(1604)
<223> OTHER INFORMATION: n is a, c, g, or t
<220> FEATURE:
<221> NAME/KEY: misc_feature
<222> LOCATION: (1607)..(1608)
<223> OTHER INFORMATION: n is a, c, g, or t

<400> SEQUENCE: 111

```
aaatcacaca acaccaccac caccgtaacc atggacctcc tcctcataga aaaaccctc       60 gtcgccttat tcgccgccat tatcggcgca atactaatct ccaaactccg cggtaaaaaa     120
ttcaagctcc cacctggccc aatcccggtt ccaattttcg gcaactggct acaagttggc     180
gatgatttga accaccggaa cttaaccgat ctggctaaga ggtttggtga gatcttgctg     240
ctacgcatgg ggcagaggaa tctggtagtt gtgtcttcgc ctgagcttgc taaagaggtg    300
ttgcatacac aaggagtgga gtttggttcg agaacaagga atgttgtgtt cgatattttt     360
actgggaagg gtcaggatat ggtgtttacg gtttatggtg agcattggag gaagatgagg     420
aggatcatga ccgtacccct tttcaccaac aaagttgttc agcaatacag gtatgggtgg    480
gaggctgagg ccgcggcggt tgtggacgat gtgaagaaga atccggctgc agcaactgaa    540
ggaatcgtga tccgaagacg gttacaactc atgatgtata acaacatgtt cagaatcatg    600
```

```
ttcgacagac gattcgaaag tgaagatgat cccttgtttt tgaaactcaa ggcgttgaac    660
ggtgagagga gtcgattggc gcagagcttt gagtacaact atggcgattt catccctatt    720
ttgcggccgt ttttgagaaa ttatttgaag ttgtgcaagg aagttaaaga taaaaggatt    780
cagctcttca aggattactt cgttgacgaa aggaagaaga ttggaagcac taagaaaatg    840
gacaacaatc agttgaaatg tgccattgat cacattcttg aagctaaaga aagggtgag    900 atcaatgaag acaatgttct ttacattgtt gaaaacatca atgttgcagc aatcgagaca    960
actctatggt cgatcgaatg gggaattgcg gagctagtta accatcccga gatccaagcc   1020
aaactcaggc acgagctcga caccaagctc gggcccggtg tccagatcac cgagcccgac   1080
gtccaaaacc tcccttacct ccaagccgtg gtcaaggaaa ccctccgtct ccgtatggcg   1140
atcccgcttc tagtcccaca catgaacctc catgacgcta agctcggcgg gtttgacatc   1200
ccggccgaaa gcaagatctt ggtcaacgcg tggtggttag caacaaccc cgaccaatgg    1260 aagaaacccg aggagtttag gccagagagg ttttggaag aggaagcgaa ggttgaggct    1320
aacgggaatg attttaggta cttgccgttt ggagtcggga aaggagttg ccccgggatt    1380 attcttgcat tgccgatact tggtattaca atcgggcgtt tggtgcagaa tttcgagctg    1440
ttgcctccac cgggacagtc taagatcgat accgatgaga agggtgggca gtttagtttg    1500
catatcttga agcactctac tatcgtagct aaacctaggt cattttaagg attcttgttt    1560
atgttcttta ttgtatgata aaccaagngg ngnnggngnn gngngannaa aaaaaaaaaa   1620
```

<210> SEQ ID NO 112
<211> LENGTH: 1518
<212> TYPE: DNA
<213> ORGANISM: Camptotheca acuminata

<400> SEQUENCE: 112

```
atggatcttc tcctggtaga gaagaccctc ttggcactat tgctgccat tgttcttgct      60 atcaccatct ctaaactgcg tggtaagcgc tttaaactcc ctccgggtcc actacccgta    120
cccgtttttg gcaactggct ccaagtcggc gatgacttga accatcgaaa cctcacggat    180
ttggctaaga agttcggtga catgttcttg ctccgtatgg ccaacgcaa ccttgttgtg     240 gtttcgtctc cagaccttgc caaagaggtg ttacacactc agggtgtcga gttcgggtcc    300
cgaacccgaa acgttgtatt cgatattttc accggaaagg ggcaggacat ggtgttcacc    360
gtttatggtg agcactggag gaaaatgaga cgcatcatga ccgtcccttt cttcaccaac    420
aaggtggtcc agcagtaccg ttatgggtgg gaggaagagg cggcgcgcgt ggtcgaggat    480
gtgaagaaga tgccggaggc attgacgacg gggattgttt taagaaggcg gttgcaacta    540
atgatgtaca acaacatgta ccggatcatg ttcgatagga ggttcgagag tgaggacgac    600
ccgttgtttg tgaagcttaa ggcttttgaac ggagagagga gtcgattggc tcagagcttt    660
gagtacaatt atggtgattt cattcccatt ctgaggcctt tcttgagagg ttatttgaag    720
atctgtaagg atatcaagga gagaaggctt cagctctttta aggactattt tcttgacgaa    780
aggaagaagc tgacaagcac gaaaggcatg gacaactatg cctaaaatg tgccattgat    840 catattcttg aggcccaaca gaaggggag atcaacgagg acaatgttct ttacattgtt     900
gagaacatca acgttgccgc aattgaaaca acattgtggt cgatcgaatg gggcattgca    960
gaactcgtca accacccaga aatccagcag aagctgcggc atgagattca aactgtgctg   1020
ggacctggaa cccaagtcac cgagcctgaa gtccaaaaat tgcctatct ccaagcagta    1080
```

| | |
|---|---|
| gtcaaagaaa cccttcgact ccggatggca attcctcttc tggtgcctca catgaacctt | 1140 |
| catgatgcaa agctcggagg gtatgacgtg ccagccgaga gcaaaatctt agtcaatgcc | 1200 |
| tggtggctcg ccaacaaccc tgctcactgg cagaagccag aagaatttag gcccgagagg | 1260 |
| ttcttggaag aggagtctaa ggttgatgcc aatggcaatg acttccgata ccttccattt | 1320 |
| ggtgtcggaa gacgaagctg cccgggaatt atcctagccc tgccaattct tggcattact | 1380 |
| ttgggacgtt tggtgcagaa tttcgagctc ttgcctccac ccgggcagtc aaagatcgat | 1440 |
| acctcggaga agggtgggca gttcagtctg cacattttga agcattccac cattgttgca | 1500 |
| aaaccaatat cattttga | 1518 |

<210> SEQ ID NO 113
<211> LENGTH: 1727
<212> TYPE: DNA
<213> ORGANISM: Arabidopsis thaliana

<400> SEQUENCE: 113

| | |
|---|---|
| gccgacgatt ttctcaccgg aaaaaaacaa tatcattgcg gatacacaaa ctataatgga | 60 |
| cctcctcttg ctggagaagt ctttaatcgc cgtcttcgtg gcggtgattc tcgccacggt | 120 |
| gatttcaaag ctccgcggca agaaattgaa gctacctcca ggtcctatac caattccgat | 180 |
| cttcggaaac tggcttcaag tcggagatga tctcaaccac cgtaatctcg tcgattacgc | 240 |
| taagaaattc ggcgatctct cctcctccg tatgggtcag cgaaacctag tcgtcgtctc | 300 |
| ctcaccggat ctaacaaagg aagtgctcct cactcaaggc gttgagtttg atccagaac | 360 |
| gagaaacgtc gtgttcgaca ttttcaccgg aaaggtcaa gatatggtgt tcactgttta | 420 |
| cggcgagcat tggaggaaga tgaagaagaat catgacggtt cctttcttca ccaacaaagt | 480 |
| tgttcaacag aatcgtgaag gttgggagtt tgaagcagct agtgttgttg aagatgttaa | 540 |
| gaagaatcca gattctgcta cgaaaggaat cgtgttgagg aaacgtttgc aattgatgat | 600 |
| gtataacaat atgttccgta tcatgttcga tagaagattt gagagtgagg atgatcctct | 660 |
| tttccttagg cttaaggctt tgaatggtga gagaagtcga ttagctcaga gctttgagta | 720 |
| taactatgga gatttcattc ctatccttag accattcctc agaggctatt tgaagatttg | 780 |
| tcaagatgtg aaagatcgaa gaatcgctct tttcaagaag tactttgttg atgagaggaa | 840 |
| gcaaattgcg agttctaagc ctacaggtag tgaaggattg aaatgtgcca ttgatcacat | 900 |
| ccttgaagct gagcagaagg gagaaatcaa cgaggacaat gttctttaca tcgtcgagaa | 960 |
| catcaatgtc gccgcgattg agacaacatt gtggtctatc gagtggggaa ttgcagagct | 1020 |
| agtgaaccat cctgaaatcc agagtaagct aaggaacgaa ctcgacacag ttcttggacc | 1080 |
| gggtgtgcaa gtcaccgagc ctgatcttca caaacttcca taccttcaag ctgtggttaa | 1140 |
| ggagactctt cgtctgagaa tggcgattcc tctcctcgtg cctcacatga acctccatga | 1200 |
| tgcgaagctc gctggctacg atatcccagc agaaagcaaa atccttgtta atgcttggtg | 1260 |
| gctagcaaac aaccccaaca gctggaagaa gcctgaagag tttagaccag agaggttctt | 1320 |
| tgaagaagaa tcgcacgtgg aagctaacgg taatgacttc aggtatgtgc catttggtgt | 1380 |
| tggacgtcga agctgtcccg ggattatatt ggcattgcct attttgggga tcaccattgg | 1440 |
| taggatggtc cagaacttcg agcttcttcc tcctccagga cagtctaaag tggatactag | 1500 |
| tgagaaaggt ggacaattca gcttgcacat ccttaaccac tccataatcg ttatgaaacc | 1560 |
| aaggaactgt taaactttct gcacaaaaaa aaggatgaag atgactttat aaatgtttgt | 1620 |
| gaaatctgtt gaaatattcc cttgttttgc ttttgtgaga tgttttgtg taaaatgtct | 1680 |

<210> SEQ ID NO 114
<211> LENGTH: 1521
<212> TYPE: DNA
<213> ORGANISM: Ruta graveolens

<400> SEQUENCE: 114

```
atggatctcc tcttactgga gaaggccctc ctaggcctct tcgccgccgc ggtcgtagcg      60
attgctgttt ctaaactccg aggcaagcgc ttcaaactcc cgccggggcc cttcgggttc     120
ccggttttg gaaactggct tcaagtcggc gatgacttga accaacggaa acttgccaat     180
ttatccaaga aattcggaga tgtatacctt ctccgcatgg gccagcgcaa tctcgtcgtc     240
gtttcgtcgc cggaaatggc caaggaggtg ttgcatactc agggagtgga gttcggctct     300
cggacgagaa acgtcgtctt cgatatcttc accgggaaag gccaggacat ggtgttcacg     360
gtttacagtg agcactggcg gaagatgcgg aggatcatga ccgtcccttt cttcacaaac     420
aaagtcgtcc agcagcagag atttaactgg gaagacgagg cggccagggt cgtcgaggat     480
gtgaagaaag accccaggc ggcgaccact gggatcgttc tgaggcggcg gctgcagctc     540
ctgatgtaca caacatgta cagaatcatg ttcgatagga gattcgagag cgtcgacgat     600
ccttttgttca acaaattgaa ggccttgaat ggcgagagga gccgattggc tcagagcttc     660
gagtacaact acggtgattt cattcctatt ttgaggcctt tcttgagagg ttatttgaag     720
ctggtgaagg aagttaagga agaagactc aagcttttca aggactattt tgttgaagag     780
agaaagaaat taacaagcac aaagagcatg accgaggaaa acttcaaatg cgccattgat     840
catgtcttgg acgctcagca gaaggagaa atcaacgagg caacgttct gtacattgtc     900
gagaacatta tgttgcagc aattgagaca ctttgtggt ccatcgagtg gggtattgca     960
gagttggtga atcatccaga catccagaag aagctccgtg ctgaaattga cagagtcctc    1020
ggtcctgacc atcaaatcac cgagcctgac acccacaagc tcccctacct tcaggctgtg    1080
atcaaggaga ctctccgcct caggatggca attcctcttc ttgtaccaca catgaacctt    1140
aacgatgcta agcttgcagg ctacgacatt ccagctgaga gcaagatact ggtaaacgca    1200
tggtggctgg ccaacaaccc cgctcactgg aaagacccgc aagtattcag gccggagagg    1260
ttccttgagg aggagtctgg ggttgaggct aatggaaatg acttccgata cattcctttt    1320
ggtgtcggga gaagaagctg tcctggaatt atacttgctt tgccgattct cggaatcact    1380
attgggcgta tggtgcagaa ctttgagctg ttgcctcctc aggacagtc gaagattgat    1440
acttcagaga aggtgggca gttcagtttg ttcattctga accactccac gattgtgctc    1500
aagcctagat cttctgtcta a                                              1521
```

<210> SEQ ID NO 115
<211> LENGTH: 1521
<212> TYPE: DNA
<213> ORGANISM: Glycine max

<400> SEQUENCE: 115

```
atggatctcc tccttctgga aaagaccctc ataggtctct tcctcgctgc ggtggtcgcc      60
atcgccgtct ccaccctccg cggccggaaa ttcaagctcc accgggccc actcccgtc     120
ccaatcttcg gcaactggct ccaagtcggc gacgacctca accaccgcaa cctcaccgat     180
ttggccaaaa aattcggtga catcttcctc ctccgcatgg ggcagcgcaa cctcgtcgtg     240
```

| | |
|---|---|
| gtttcttccc ctgagctcgc caaagaggtt ctccacacgc agggcgtgga gttcggctcc | 300 |
| cgcacccgca acgtcgtctt cgacatcttc accggaaagg ccaagacat ggtcttcacc | 360 |
| gtctacggcg agcactggcg caaaatgcgc cgcatcatga ccgtccccct cttcaccaac | 420 |
| aaggttgtgc aacaataccg ccatggatgg gaatcggagg ctgccgccgt cgtcgaggac | 480 |
| gtcaagaaaa accccgacgc cgccgtctcc ggcaccgtca tccgccgccg ccttcagctc | 540 |
| atgatgtaca acaacatgta ccgcataatg ttcgaccgga ggttcgagag cgaggaggat | 600 |
| cccatcttcc agaggctaag agccttgaac ggagagagga gtcgcttggc gcagagcttt | 660 |
| gagtataact atggtgattt tattcccatc ttgagaccct tcttgaaggg ttacttgaag | 720 |
| atttgcaagg aggtgaagga gacgaggttg aagcttttca aggattactt cgttgacgag | 780 |
| aggaagaagc ttggaagcac caagagcacc aacaacaata tgaacttaa atgcgctatt | 840 |
| gaccacattt tggatgccca gagaaaaggc gagatcaacg aagacaacgt cctctacatt | 900 |
| gttgaaaaca tcaacgttgc tgcaattgaa acaactctat ggtcgattga gtggggcatt | 960 |
| gctgagcttg tgaaccaccc agagatccag caaaagttaa gggatgagat tgacagagtt | 1020 |
| cttggagcag gcaccaagt gactgagcca gacatccaaa agctcccata cctccaagca | 1080 |
| gtggtcaagg aaactcttcg tcttagaatg gcaatccctc tccttgtacc acacatgaac | 1140 |
| ctccacgacg caaagcttgg gggctatgat atcccagctg agagcaagat cttggtgaat | 1200 |
| gcatggtggc tggccaacaa ccctgcacac tggaagaagc cagaggagtt ccggcctgag | 1260 |
| aggttcttcg aggaggagtc gcttgttgaa gccaatggca atgactttag gtaccttccc | 1320 |
| tttggtgttg gcagaagaag ctgccctgga atcattcttg cattgccaat tcttggcatc | 1380 |
| actttgggac gtttggtcca aaactttgag ctcttgcctc ccctggcca gtcacagatt | 1440 |
| gacactagtg agaaaggagg gcaatttagc ttgcacatac tcaagcattc caccattgtg | 1500 |
| gcaaagccaa ggtcattta g | 1521 |

<210> SEQ ID NO 116
<211> LENGTH: 1611
<212> TYPE: DNA
<213> ORGANISM: Citrus sinensis

<400> SEQUENCE: 116

| | |
|---|---|
| atggcaaatc ttgttacaat ttcattcttt agcatccttc tcacaatctc actgctttcg | 60 |
| ttcaacaaat ctttaaatct tatatcaatc actctccctc ttgttcctct tattgcatac | 120 |
| gttttgaaat ccttttaaa atcttcgaaa gcctttttacc ctccaactcc tatctctatc | 180 |
| ccaatatttg gcaattggct ccaagttggc aatgaccta accacaggtt actagcatca | 240 |
| atggcacaaa tttacggccc cgtattccgt ctaaaacttg gttcaaaaaa tttaatagtg | 300 |
| gtatcagagc cagacctagc tacccaagta ctacacacgc aaggtgtaga attcggatcc | 360 |
| cgcccacgca acgtggtttt cgatatttc acgggcaatg acaggacat ggtgttcact | 420 |
| gtttatggtg agcattggcg caaaatgcgt aggattatga cactgccatt tttcaccaat | 480 |
| aaagttgtgc acaattacag tgacatgtgg gagcaggaaa tggacctagt ggtgcatgac | 540 |
| ttgaaaaatg attatgagag tgtgagcaca aagggattg ttattaggaa gcgtttgcag | 600 |
| ctcatgctat acaatattat gtataggatg atgtttgatg caaatttga gtcacaagag | 660 |
| gatcctttgt tcattgaagc aactaggttt aattctgaaa ggagtcggtt ggctcaaagt | 720 |
| tttgagtaca attatggaga ttttattcct tgctcaggc cattttttaag aggtacttg | 780 |
| aacaagtgca gagacttgca gtgtaggagg ttggctttct ttaacaacaa ttttgttgag | 840 |

```
aaaagaagga aaatcatggc tgccaatgga gagaagcaca agataagctg cgccattgat    900
cacataattg atgctcaaat gaaggggag atcactgaag aaaatgttat ttacattgtt    960
gagaacataa atgtggcggc aatagaaaca acactatggt ccatggaatg ggcaatagct   1020
gagttagtca atcacccaga ggttcaacag aagatccgtc gtgaaatctc gacagtcctt   1080
aaaggaaatc cggtcacaga atcaaacctg catgaattac cgtacctgca agccgcagta   1140
aaagaggtac taagattaca cactccaatt ccgttgttgg tgccacatat gaatctagaa   1200
gaagcaaaac ttggaggctt cacaattcct aaagagtcca aaattgtggt gaatgcatgg   1260
tggctagcaa acaaccccaa atggtgggaa aaacctgagg agtttcggcc agagagattc   1320
ttggaagagg aatgtaatat tgatgctgtt gctggtggtg gcaaagttga cttcaggtac   1380
ttgccttttg gcgtgggaag gcgaagctgc cctggaatca tacttgcatt accaatcttg   1440
gggcttgtga ttgcaaaact ggtgacatct tttgagatga agctccaca agggatagat   1500
aagattgacg tgagtgaaaa aggaggccaa ttcagcttgc acattgcaaa tcattcaact   1560
gttgtcttcg atccgataat ggaatcactt tcccaaccaa tgccacagta a           1611
```

<210> SEQ ID NO 117
<211> LENGTH: 891
<212> TYPE: DNA
<213> ORGANISM: Chromobacterium violaceum

<400> SEQUENCE: 117

```
atgaacgacc gcgccgactt tgtggtgccc gacatcacca cccgcaagaa tgtcggactg     60
agccacgacg ccaacgactt caccttgccg cagccgttgg atcgctactc tgcggaagat    120
cacgccacct gggccacgtt gtaccagcgc caatgcaagc tgctgcccgg ccgcgcctgc    180
gacgagtttc tggaaggcct ggagcgcctg gaagtggacg ccgacagggt gccggacttc    240
aataagctca cgagaagct gatggccgcc accggctgga agatcgtcgc ggtgccgggc    300
ctgattcccg acgacgtgtt cttcgagcac ctggccaacc gccgcttccc ggtcacctgg    360
tggctgcgcg agccgcacca gctcgactac ctgcaggagc cggacgtgtt ccacgacctg    420
ttcggccacg tgccgctgct gatcaatccg gtgttcgccg attacctgga ggcctacggc    480
aagggcgggg tgaaggcgaa ggcgctgggc gctgccgatg ctggcgcggc tgtactggta    540
cacggtggaa ttcggcctga tcaatactcc ggccggcatg cgcatctacg cgccggcat    600
cttgtccagc aagtcggaat ccatctactg cctggacagc gccagcccca accgcgtcgg    660
cttcgacctg atgcgcatca tgaacacgcg ctaccggatc gacaccttcc agaaaaccta    720
cttcgtcatc gacagcttca gcagctgttc gacgccacc gcgccggatt cgctccgct    780
atacttgcag ctggccgacg cgcaaccgtg gggcgcggcg acatcgcgcc ggacgacctg    840
gtgctgaatg ccggcgaccg ccaaggatgg gcggataccg aagacgtctg a             891
```

<210> SEQ ID NO 118
<211> LENGTH: 1200
<212> TYPE: DNA
<213> ORGANISM: Pseudomonas aeruginosa

<400> SEQUENCE: 118

```
atgagtcatt tcgccaaggt cgcccgcgta ccgggcgacc cgatcctggg cctgctcgac     60
gcctaccgca cgatccgcg cgcggacaag ctggacctcg cgtcggtgt ctacaaggat    120
gcccagggcc tgaccccgat cctgcgctcg gtgaaactcg ccgagcagcg cctggtcgag    180
```

| | |
|---|---|
| caggaaaacca ccaagagcta cgtcggcggc cacggcgatg cgctgttcgc cgcgcgcctg | 240 |
| gcggaactgg cgctcggcgc cgcctcgccg ctgttgctgg agcaacgcgc cgacgccacc | 300 |
| cagacgcccg gcggcaccgg cgccttgcgc ctggccggcg acttcatcgc ccattgcctg | 360 |
| cccggccgcg gcatctggct gagcgacccg acctggccga tccacgagac cctgttcgcc | 420 |
| gccgccggcc tgaaggtttc ccactacccc tacgtcagcg ccgacaaccg cctggatgtc | 480 |
| gaggcgatgc ttgctggcct ggagcgcatt ccccagggga cgtggtgct gctgcatgcc | 540 |
| tgctgccaca acccgaccgg tttcgacctg agccacgacg actggcgcag ggtgctcgac | 600 |
| gtggtgcgtc gccgcgagct gctgccgctg atcgacttcg cctaccaggg cttcggcgac | 660 |
| ggtctcgagg aagacgcctg gcggtacgc ctgttcgccg gcgaactgcc ggaggtgctg | 720 |
| gtcaccagtt cctgctcgaa gaacttcggc ctgtaccgcg accgcgtcgg tgcgctgatc | 780 |
| gtctgcgcgc agaacgccga gaagctcacc gacctgcgta gccaactggc cttcctcgcc | 840 |
| cgcaacctct ggtcgacccc gccggcgcat ggtgccgagg tggtcgcggc aatcctcggc | 900 |
| gacagcgagt tgaagggact ctggcaggaa gaggtcgaag gcatgcgctc gcgcatcgcc | 960 |
| agcctgcgca tcggcctggt cgaagccctg gcgccgcacg gcctggccga gcgcttcgcc | 1020 |
| catgtcggcg cgcaacgcgg gatgttttcc tataccggac tgagcccgca gcaggtcgct | 1080 |
| cggctgcgcg acgagcacgc cgtttacctg gtctccagcg gccgagccaa cgtcgccggt | 1140 |
| ctccacgcgc gccgcctcgg ccgcctggcg caagccatcg cccaggtctg cgcggactga | 1200 |

<210> SEQ ID NO 119
<211> LENGTH: 1353
<212> TYPE: DNA
<213> ORGANISM: Geodia cydonium

<400> SEQUENCE: 119

| | |
|---|---|
| atggatattg agcctccagc tacaaagaag agcaaaatgg acagcaatgg agaagcctcc | 60 |
| tacattcctg tacagactcc aacaggcgaa acagtgcaa acctgtcttt gatattttct | 120 |
| ctcaaagatg agcaaggatc tctagtcacg tcattgaagc ctttccagga tatgggtatc | 180 |
| aacatgaccc acttggagtc gagaccttcc aagtctaacc caggctctga gtatgacttc | 240 |
| tatgtcgact gtgtgtgccc tccagacaag aaagaagatc ttctctcttc tctcagagcc | 300 |
| aactcactca ctgtcaatat cctctccagg gaccctggag aggatgaagt gccttggttt | 360 |
| cctcgtaaga ttgctgaaat tgaccggttt gccaaccaag ttttgtccta tggagctgag | 420 |
| ttggactctg accaccctgg tttcactgat gcagtgtata gagcaaggag gaagcagttt | 480 |
| gcagacattg catttcactg caagcatggt caacccatac caagagtgga gtacacacct | 540 |
| caagagattg acacatggcg tacgatattc acgaaccttg tggacctctt ccaacgcat | 600 |
| gcctgcaaag aacacaacca tgtgttccct ctcttgcaag agaactgtgg atacagggaa | 660 |
| gacaacatac ctcaattgga ggaagtgtcc cagtacctcc aatcctgtac tggattcaga | 720 |
| ctgagacctg tggcaggtct tctgtcctca cgagacttct ggctggtct ggcctttaga | 780 |
| gtgttcact ccacacagta catacgtcac tactctcagc caaactacac accagaacct | 840 |
| gatgtgtgtc acgagctcat tggacatgtc cggtgttctg tgatcctctt tgcacagttt | 900 |
| tctcaggaga tcgattggc ttccctcgga gcaccagagg agtacgtaca caactggcc | 960 |
| acgctgtact ggttcacgat agagtttggc ctttgtaaac aagatggaca gacaaaggct | 1020 |
| tacggagctg gtctaatctc atcttttgga gagttacagt actgtctgtc agacaaacct | 1080 |
| gaagtccgtc ctctagatcc tttcaaaact tctcttcaaa catacccat cacagagatg | 1140 |

-continued
caacctgtct actttttggc caacagtttt gaggatgcca agcagaagct catggagttt 1200
gcccgtacca ttcctcgtcc tttctctgtg cgttacaacc cgtacactca gagtgtggac 1260
attataaagg acaagagctc cgtacagacc ttggtcaatg acatcagata tgaggtggac 1320
atactccagg acgccctacg taaacttgac taa 1353

<210> SEQ ID NO 120
<211> LENGTH: 891
<212> TYPE: DNA
<213> ORGANISM: Xanthomonas axonopodis
<400> SEQUENCE: 120
atgactaccg ctccgcaacg cgtcgaaaac cagctcaccg acaagggcta tgtcccggtc 60
tacaccactg cggtggtgga gcagccgtgg gacggctaca gcgccgacga ccacgccacc 120
tggggcacct tgtatcggcg ccagcgcgag ctgctggtcg gtcgcgcctg cgaggagttc 180
ctgcaggcgc aggatgcgat gggcatgggc cagacgcaca tcccgcgctt cgatgcgctc 240
aatcgcgtgc tgcaggcagc caccggctgg accctggtcg gcgtgcaggg cctgctgccg 300
gagctggatt tcttcgatca cctggccaac aggcgcttcc cggtgacctg gtggatccgc 360
cggcccgatc agatcgatta catcgccgaa cccgatctgt tccatgacct gttcgggcat 420
gtgccgttgt tgatgaaccc gctgtttgcc gacttcatgc aggcctatgg ccgcggcggg 480
gtcaaggcgc acggcatcgg cccggacgcg ctgcagaacc tcacccggct gtattggtac 540
acggtggaat tcggtctgat cgacacgccc cagggcctgc gcatctacgg tgccggcatc 600
gtgtcgtcca agggcgaatc gctgtattcg ctggaatcgc cggcacccaa ccgcatcggg 660
ttcgacctgc aacgcatcat gcgcacgcgc taccgcatcg acagctttca gaagacctat 720
ttcgtcatcg acagctttgc gcagttgatg gaagccactg cgccggactt caccccgatc 780
tatgccgagc ttgcacaaca gccgcagatg ccggcgggtg acgtgctgcc gggcgatcgg 840
gtgatccaac gcggcagcgg cgagggttgg agccgcgacg gcgacgtgtg a 891

<210> SEQ ID NO 121
<211> LENGTH: 891
<212> TYPE: DNA
<213> ORGANISM: Xanthomonas campestris
<400> SEQUENCE: 121
atgaacacag cgccgcgccg cgtcgagaac cagctcaccg acaagggcta tgtgccggtc 60
tacaccaccg cggtggtgga gcagccgtgg gatggttaca gcgccgacga ccatgccacc 120
tggggcacgc tgtaccggcg gcagcgcgcg ctgctggtcg ggcgggcctg cgatgagttc 180
ctgcaggcgc aggacgcaat gggcatggac gacacccaga ttccgcgctt cgacgcgctc 240
aacgcggtgc tgcaggcgac caccggctgg acgctggtcg gtgtggaagg gctgctgccg 300
gagctggatt tcttcgatca tctggccaac cggcgcttcc cggtgacctg gtggatccgc 360
cgcccggacc agatcgacta catcgccgaa ccggacctgt tccatgatct gttcgggcac 420
gtgccgctgc tgatgaatcc gctgtttgcc gacttcatgc aggcctatgg gcgcggtggc 480
gtcaaggcgc acggaattgg cccggacgcg ttgcaaaatc tcacccggct gtactggtac 540
acggtggaat tcggcctgat tgccacgccg caggggttgc gcatctacgg tgcgggcatc 600
gtctcgtcca agggcgaatc gctgcattcg ctggaatcgg cggcgccgaa ccgggtgggc 660
ttcgatctgc agcgggtgat gcgcacgcgc taccgcatcg acagtttcca aaagacctac 720

```
ttcgtcatcg acagctttac gcagctgatg gacgccaccg ccccggattt cacccgatc    780 tatgccgcgc tggcgcaaca gccgcaggtg ccggccggcg aggtgctggc aaccgaccac    840
gtcctgcagc gcggcagcgg cgaaggctgg agccgcgacg gcgacgtgtg a             891
```

<210> SEQ ID NO 122
<211> LENGTH: 900
<212> TYPE: DNA
<213> ORGANISM: Nocardia farcinica

<400> SEQUENCE: 122

```
ctagcctcgc gagccggacc cgacgcgccg cgcgcgcagc ggggtctcgt cgtccatctc     60
cgcgaagaac ccgccgatca cgtcctcgat ctggccgatc gactccgcgc agtacagcac    120
cggctgatag tgcgtgatgt cgtagggttc ggtgcccatc gcgaccacgt ccagcggacg    180
cagccgggcc cgccggaact cctcgatctc gccgaacgag gacagcagac ccgctccgta    240
acagcggatc tcgccgcgtt cccggaccac cccgaactcc atcgagaacc agaacacgtc    300
cgccaggaac ttcagcgccg cctcggtacg caggcgcgcc accgccgcgc cgacggtccg    360
gtagatcgcg gcgaaccgcg ggctggcgat ctggttcgcg tgcccgatga tctcgtggat    420
ggcgtccggc tcggggtgt acagcggtgc ggaatggtgg cggatgtact gggtggagtg     480
gaacaccgac tcggcgaagg agccgaagaa ctcccgcagc ggcaccagac cggcggcggg    540
gacgtaacgg aacccgctga gcggggccag cgccgcgctc acctcgtcga gctgcgggat    600
gtggtcggtg gcagggcga ggcgctcggc ggcggccagc acctcggcgc tggcgtaggt     660
gcggtgcttg cgcgccagct cggtcgagac catccgccag acccgctgct cctcctcggt    720
gtaatcgacc cggggaaggg ccgcgccggg cgtgtaaccc agcgccagcg cggcgatggc    780
gttgcgccgc gcccggtagt ccggatcgcg cacgccgggg tgctcgtcgc tcaggtgcac    840
cgtcaccgca ccgtctcggt cacgggtcac cggcgagtac agctgcgctt cggtgaacat    900
```

<210> SEQ ID NO 123
<211> LENGTH: 1341
<212> TYPE: DNA
<213> ORGANISM: Gallus gallus

<400> SEQUENCE: 123

```
atggatgcac agcactgcaa gatgaatgga gactccttcc aggaatccac atacactgaa     60 gagcccctcga acaaaaatgg tgtgatttct ttgattttct ctttgaaaga agaagttggg    120
gcactggcta agttctgcg cacatttgag gaaaaaggca taaatctgac tcacattgaa     180
tctcgacctt tcgtctcaa taaagatgag tatgaattct tcattaactt ggaaggcaag    240
aatgtcccag cactggacaa gatcatcaag tccttaagaa atgatattgg agtaacagtg    300
catgagcttt cacgaacaaa aagaaggac actgttccct ggttcccaag aagtatccag    360
gagctggaca gatttgccaa tcagatccta agctatggag cggagctgga tgctgaccat    420
cctgggttca agatcctgt gtaccgggcc cggaggaagg agtttgcaga catcgcctac    480
aactacagac atggtcaacc tattcctcga gttacctata cagaagaaga aaagaaaact    540
tggggcaccg tattcagaga gctgaagaat ctctatccaa tcatgcttg ttatgaacac    600 aaccatgtgt tcccactgct ggagaagtac tgtggctacc gggaggataa cattccccag    660
cttgaagatg tttcaaagtt cttgcagacc tgcactggat ttcgcctgcg tcctgttgca    720
ggcttgctct cctctcggga tttccttggct ggactggcat ccgagtatt tcactctaca    780 cagtatattc gccatgcatc caaacctatg tacacaccag agcctgatat ttgccatgag    840
```

```
ctactaggac atgtgcctct tttttgctgat cccagttttg ctcagttttc ccaggaaatt      900
ggactggcat ctctgggagc tccagatgat ttcatcgaga aacttgctac ggtttattgg      960
tttactgtgg aatttggact gtgtaaggaa ggagattcac taaaggcata tggtgctggg     1020
ctgctgtctt catttggaga gctgcagtac tgtttatcag gtaagcctga gattcggcct     1080
ctcgttctcg aaaacacttc tgtgcagaag tactctgtta ctgagttcca gcctacctac     1140
tttgttgctg aaagttttaa tgatgcaaaa gaaaagctaa ggaaatttgc tcaaacaatt     1200
cctcgtcctt tctctgttcg gtacaatccc tacacccaga ggatcgaagt cttggacaat     1260
gcaaagcagc tgaagaactt agctgacact atcaacagtg agatggggat cctctgcaat     1320
gccctccaga agatcaaatg a                                               1341

<210> SEQ ID NO 124
<211> LENGTH: 6702
<212> TYPE: DNA
<213> ORGANISM: Saccharomyces cerevisiae

<400> SEQUENCE: 124
ttatttcaaa gtcttcaaca attttctttt atcatcggta gataacatct tgataacttc       60
agataatcca tcaatagcat tgtcatggtc gcttctgatc ttttagcta agtcttgagc      120 gaatgactct aatttcaaac cctttagttt atcgtccaaa gttttgtagt tttcttcaat      180
ccatgttgcg acttgcctat catcttcatg gtccactgaa gcagggtacc acgatctaat      240
tcttgcgatc ttttctaatc ttgatgcttc gcctacctga tggctcaacc ttttaatcaa      300
atattcttcg ttcaatcttc ttctcaatct ccagaagaag aaacgacgtg cctcggtcca      360
ttccagttcc ttagaaataa cacccttggc caccatacgt gaagacctat cgtgcaaatc      420
agcaaattga agactgattt gtccgtaaat tggcaatagt tctctctcac gatcagctaa      480
ttgcttggat atttgctgat gtacttctgg agccaaactc ttgttggata attgagatct      540
caattctctg tacttgtcat ccaatctgtt catggtgtcc agcaattttt ctctacggaa      600
cttgatacca accataccttt gtggttccaa acaccagct ctagcgttga cgtcggcata      660
catttccatt tggtcagcgt tgatagttgg atcgacaaca acccatgaac cacctcttag      720
ttcaccggta ggtgggatat agataataat tggttgtttg taatccacca atgcgtcaac      780
aataaacgaa ccatacttca agacttcgtt gaacatatca cgttgaccac cagagaaacc      840
tctccagttg gccaaaatca tcattggcaa ttgttcaccg ttgttaaagt cattgatagc      900
ttgagcagtc ttgaaggcgg agtttggatg ccaaacttga ccaggttctt gaattaatgt      960
ttcagcacta tttggattag ctggatcagc aggaatcaag ttctcgacag ttcttgtttc     1020
aacaccaata cacccagtg gaataccacc aagacgggct ctaccaacga caacaccttt     1080
ggcccatcct gacaaagttt caagaaaga cccttttatca aacaaccat attcaaatcc     1140 actttcagtc tcacgacctt caatcatcca tcttacatcg taagtttcat cattagttgg     1200
agtgaaatca actggtctat cccatgtgtc tttagtttcc aagataggaa ctggcatatt     1260
acgcttggct ggaacataag acatccattc aacaatcttc tctacaccag ctaaatcgtc     1320
aacagcagtc aaatgtgaaa caccgttgtt atacatgatt tgagtaccac ccaattgtaa     1380
gttagaagta taaacttctc tacccagcat tttgttgatt gcaggagcac cagttaaaat     1440
aattggctgg ccttcgacct gaatagctct tgacccaaaa cgaaccaaat aagcaccgat     1500
accgacggat ctacaagtga ctaaggtgat agtgaagata tcgtggtaag cccttgacgt     1560
```

```
tgcaccagca attaaaccag atccacgtag acattcgaca cctaacccat cttcagaacc    1620
aataattgtc ttgatgacaa atctttcttc accgtttata acagtacgtt cagtgagaac    1680
agaattttct ttgtcaaatt tctttaaagt ttccatacct tcacttgtta agtataagta    1740
ttggaagccc ttgtccggat tggcagcatc attccatgca acttgaaata gtggaacaat    1800
ctcttcagcc ataccaattc tggcacctga gtttgcagcc aagtaaattc ttgggatacc    1860
acgctttcta gcatattcag taaccttatt gaagaattcg tcttcttgtg gaccaaagga    1920
accgatcttg aatgtgatat cgttagcaac aacaacaaat tgacggcctc ttggatattc    1980
aggagtcttt acagtaatct taaaggcaac cataccaata gcgttggcac caggttctct    2040
ttccacctca gttaattcgc cgttttcatc ttcaatcaac tcgttggaaa taaagaaatc    2100
atctgttaac ttaacatctg cagagaaatt tttccattgg gatgacgatg cttggcggaa    2160
taattctggg aagtcataga catatgtggt acccatcaag tgtgccttat aacgttttgg    2220
ttgcaaccat tccttaacag ggtaaggagt agcaataggc ttaaatgca tggatccagg     2280 tttacccaaa gacttaaata cccattcacc ttttgcgttc ttgacttcgg tgtacatttc    2340
tgttttgata acataaccag aaacgttatt gatcaaggca cgcaatggta ctggggcacc    2400
tgtttgagga tctttgatga tgattctaat ttcggcagaa gaaacacgca atctcaacaa    2460
tctcttacca aatctttcta agaaaccacc gaaggcggct tcgacatctt ctggagagat    2520
atcaaacacc gcaatgaagt tgatgaagat atgattcaaa tcagaatttg aagtgtcggt    2580
gacttctaaa ttatccaata tatcactcat caatctgtta gcttcagaag tcagatattc    2640
ttgaatagaa atgtcatcac ggatatgacc cgttctaata atacctcttg taaagaatct    2700
cttatccaat ggagaagtct tactaacagc ttcgtagaca tggatgtttc tattatcagt    2760
gaaaattggt ttaatgttga agttggacaa tcttcctaat tccagttgga aggccaaagc    2820
cggctcaatg tgacgaattg tttcattttc gttataattt ggaccgttaa aagtataata    2880
ctttggataa gacccatctt taaaaccgaa cataaatgtg atacgacgga tagaagcatt    2940
gattaattcc tgcttattca aatccaaaat ttctctcaac cttaccaaaa tttcctcttc    3000
agattcgaaa ccttctgtag aagcaacaca acattagca acattactca acgatgcgga    3060
gctaccagaa cgatcaggag caggtccgtt agaagaagat tggtgacgag gaataacttc    3120
caaactttgt gacaaaattt catcaacatc atctaaatga tccacagcca tcaaaatacc    3180
ttctcttaac ggagatgact gactgtttgc aacatatgac aaatctgaaa cagaaacagc    3240
cctgttcata cccatttag atttaacagt tggaaaggtg gagaacgcag ctgaaggtag     3300
ttggaatttc cattcaacaa ttggaactgt gacaccttcg tgaactctaa tatctcctat    3360
ggtgtaagca cgataagcac gacgaatata gacttgagca gctgcagcag tcacaactgg    3420
gtcttgatgg gttaggaatt gaagtaaaac atcgaacaca acgtaattag aatcgatcaa    3480
gtccttcaag atattcaaat ctggttcaga gcgctttgga ttggatgagc ataggcaac    3540 cttcacaaca gaggatttta agatatgttc aatttgttca gttctttcct tgaccgaagg    3600
taaagcgcct tgaatcaaaa tttctcttgc ttgtagagcg accttagcgg tagccttaga    3660
ttctagttca acaatatgtt gtagaggagt agagaaaatg gcagaaactt tagaagataa    3720
cttgcacaat ggttgataat gtttcaagat agctaggatc aggttattct tcgctgaaac    3780
tttcgaatga gacaaaacag ttagcgcaac tttatctaga tctttagggt tttcatcacg    3840
caatttcaga atgatatttt cctcacgaac atttggacca ttgaataact tttcaacttc    3900
gtaatattct tccaagaaat ggacaaatat agaatgttca tgggcttcta acccgttaga    3960
```

```
gtacttatga gcaatatccg ccaatggttc cacgacggcg cccagcaatt tgtcggggtt    4020
gtattcagga ttcttcacgg ccatatcaat caatttactt aattgtctag ctgggaaaac    4080
agcaccacgt ctcaaagaac gtgcaactaa ctcttccatt tgttcatcta gcttagcagg    4140
caatcttgaa tgtaaagcag agatgtgtag tttccattct gagtaaggca gttttggatt    4200
tctcaaaacc tctatcaatt gttgcaagga agcgttcata ataacttggt tgtcataacc    4260
cttcaaaatg ttttccaaag tagacactaa tgacttgaat ttataggcag gtttggttcc    4320
ttcgataact ggagaaccaa aatctggcag cataccttca aatggtagag cgtgcttgac    4380
cttggatgga tcgtcaagag tcataatagc catgatatca cctgcaacaa tggtagaacc    4440
aggttgcttt aataactgga cgataccatt ttcttgagaa accaaaggca tttgcattt    4500 cataacttca atttctgcat atggttggcc cttgataatg tgttcaccat tttccaccaa    4560
gaatttaacc aatttaccag gggatggagt acgcaactgg gttggatcgt tttcaacttc    4620
caacaaagta gtcatagagt caacggataa tcttgtagca gcaacttctt ctttccaata    4680
gatggtatgc gatttaccgc ctatggcaat caaaagacca ccatcagata gttgacgcag    4740
tatgatatca catttagaac cattgataaa taatgtgtaa cggtcattac cggatttagc    4800
tacggtgaac ttgtatcttt taccctcatg gataaaatct acaggaaaca tagtttgcag    4860
taggtcttta gatagaactt gtccctttg taaggattcg atatacttgt ggcgggcttc    4920
ttcagatgct aagaaagcct ttgtagcggc accgcaaatg acggcaagag ttggatcagg    4980
cttttcagcg gtcattttat gagtaatcaa atcgtccaac caaccggtgg taatagtgtt    5040
atcctcgaaa tcttcagttt ccaaaagttt gatcaagtat tccacagtag ttctgaaatc    5100 accccctaatg gacaattcct tcagggcaac aaccatgtgt ttcctggaag cttgtctatt    5160
ttcaccaaaa gcaaaaatat ggccgaactg agagtccgaa aaggagtgaa tattaccatt    5220
gttacccacg gagaagtaac cccaaacatt agaggaagaa cggaagttta gttcatgcaa    5280
agtaccaccc gatggcttga atccatcgtt tggatcttct gatgtgatac gacaagcggt    5340
acaatgaccc tttggaatag gtcttctttg tttcttggtg gcatcttgag ttttgaattc    5400
gaaatcgatt tctgaggcag aatgaggatt cataccatat aaagttctaa tgtcacttat    5460
tctatgcata gggatacccc tagcgatttg taattgagct gcaggtaagt taacaccgga    5520
gaccatttcc gttgttggat gctcgacttg taatcttggg ttcaattcta aaagtagaa    5580 ttttccatca tcatgagaat atagatactc cacggtaccg gcagagacat aaccgactag    5640 tttcccagt ctgacggcag ccttttccat ctcgtgaaat gtttcagcct tggcaattgt    5700
aactggtgct tcttcgataa ttttttgatg acgtctctga acggaacagt ctctaccgaa    5760
caaggaaata tttgtaccgt actgatctgc tagcagttga acttccaagt gacgcgctct    5820
accggccaac ttcatgatga aaatggggga gcctggaatt tcgttggctg cctggtggta    5880
taaagcgatg aaatcttctt cacgttcaac ttgtctgata cctttaccac caccaccttc    5940
ggatgcctta atcatgacag gaaaaccaat acgcttggcc ttttgtaaac catcttcagg    6000
agaggtacaa caacccttt gatagatgtc atcgtcgaca gagaccagac cggtttctc    6060 gtccacgtga acggtgtcaa caccggtacc agaccatgga atacatggga ctttagcact    6120
ttgagcgaca atggtagagg agattttatc acctaaagac ctcatggcgt tacctggagg    6180
cccaataaag atgacttttcc tcttagactg ggacaatttt tcaggcaata gtggattctc    6240
ggaggcgtga ccccagccag cccatacggc gtctacgtct gctctttcgg cgatgtctac    6300
```

-continued

```
gatcaagtct acgttagcgt agttgttatt attagtacca cctggcactt caatgtattg    6360
atcggccata cggatatatt ctgcgttggc ctccagatct tctggggtgg ccatggcgac    6420
gaattggacg gttctgtcat cgccgaacgt ctcgtatgcc cattttctga cggatctaat    6480
ttctttcacg gcggcaatac cattatttgc tatcaggatc ttggatatga ccgtgtgacc    6540
accgtgactc ttaacaaagt cccttaacgg ggactcctct agtttatcta ctgtattgag    6600
gccaatgaaa tgacctggaa gttctgtatg tctttctgag tagtttgtaa tttcgtactc    6660
catcttctgt ggagaagact cgaataagct ttcttcgctc at                       6702
```

<210> SEQ ID NO 125
<211> LENGTH: 8413
<212> TYPE: DNA
<213> ORGANISM: Saccharomyces cerevisiae

<400> SEQUENCE: 125

```
gtcgacatgc attccaccag gacctgatat tatgttattg atgtttggct cgaaacctaa      60
actctgcttc aacgatagtt ccttaggctt ggttgtatct tggccgccca cggcagcatt     120
cgcatcatcg gtaggtgtct tatctccaaa aagccacgac atgattgtgt gtgatctgtt     180
aaacaagtat acctatatta tcttggttat tttttttttt tctatctgct tttgttaacg     240
ctataacgtg tagtatgtac aggcaaagag agtagaagag gaaaatggtc tttttttttt     300
tttttttctg caatggaggg cgaatgcaat aacctattat ttctattaat taaacgcaac     360 aaatgttttcc cttttgctct acgtaaaggt tcctttctct cttttttttg tcggtgtctt    420 tttttttttca gtattttctc ttttttttcaa tgaatcgtcg atttcctttt cttccttttg    480
cgattaaatt attttttaccc agctttagca agccagttcg tacgcagcga ctagcaaaca    540
gccgggtaac tcacattttg tttgcacact taaaatacccc atacagaacc attatatatg    600
ttgggttgaa ttgggaccta atgtgctgct caggtgccgc gtatatcatg acacttatac    660
ttggtgggga atcgcccgtc aggcctgaac gcaacgaacc cgcgcatgca tcgacgtcac    720
agtgagctca ggccgcatca cggctgtacg ccctccagag tcaccacgac tgcgactagt    780
atcatccgtc aagaagaaca agaacaagaa caagaacaag aacaacaaac tccgggcaca    840
tctctcggct tcagtcgctt tcgctcattg cctgtaggtt ggcccgatat gcgttgacgt    900
tatccaaagg ggaatgcttc atcttgttga acaacgccca acaatttcca ctgcccaccg    960
aatcgttgcg cccgttaaaa tcttcacatg gcccggccgg cgcgcgcgtt gtgccaacaa   1020
gtcgcagtcg aaattcaacc gctcattgcc actctctcta ctgcttggtg aactaggcta   1080
tacgctcaat cagcgccaag atatataaga agaacagcac tccagtcgta tctggcacag   1140
tatagcctag cacaatcact gtcacaattg ttatcggttc tacaattgtt ctgctctctt   1200
caattttcct ttccttattc tactcttttt atcccttttcg tacagtttac ctgaagataa   1260
aaaacaacaa agccaattcc ctaatttgca atcgccattt gcatctatat atatatattt   1320
gttgtgccat ttttttatcc tctgtgagtg atcggtgcat gtgtttataa agtttattc    1380 attctactat acgaactttt ccctctgccc ttccctcccg cttcatcctt attttttggac   1440 aataaactag agaacaattt gaacttgaat tggaattcag attcagagca agagacaaga   1500
aacttccctt tttcttctcc acatattatt atttattcgt gtattttctt ttaacgatac   1560
gatacgatac gacacgatac gatacgacac gctactatac tatacaaata taatagtata   1620
ataaccgatt cgtcttctag cttaatttt ttccgttccc gaaacagcgc agaaaattag    1680
aaaaaatcaa gtttctacca tgagcgaaga aagcttattc gagtcttctc cacagaagat   1740
```

```
ggagtacgaa attacaaact actcagaaag acatacagaa cttccaggtc atttcattgg    1800
cctcaataca gtagataaac tagaggagtc cccgttaagg gactttgtta agagtcacgg    1860
tggtcacacg gtcatatcca agatcctgat agcaaataat ggtattgccg ccgtgaaaga    1920
aattagatcc gtcagaaaat gggcatacga gacgttcggc gatgacagaa ccgtccaatt    1980
cgtcgccatg gccaccccag aagatctgga ggccaacgca gaatatatcc gtatggccga    2040
tcaatacatt gaagtgccag gtggtactaa taataacaac tacgctaacg tagacttgat    2100
cgtagacatc gccgaaagag cagacgtaga cgccgtatgg gctggctggg gtcacgcctc    2160
cgagaatcca ctattgcctg aaaaattgtc ccagtctaag aggaaagtca tctttattgg    2220
gcctccaggt aacgccatga ggtctttagg tgataaaatc tcctctacca ttgtcgctca    2280
aagtgctaaa gtcccatgta ttccatggtc tggtaccggt gttgacaccg ttcacgtgga    2340
cgagaaaacc ggtctggtct ctgtcgacga tgacatctat caaagggtt gttgtacctc    2400
tcctgaagat ggtttacaaa aggccaagcg tattggtttt cctgtcatga ttaaggcatc    2460
cgaaggtggt ggtggtaaag gtatcagaca agttgaacgt gaagaagatt tcatcgcttt    2520
ataccaccag gcagccaacg aaattccagg ctcccccatt ttcatcatga gttggccgg    2580
tagagcgcgt cacttggaag ttcaactgct agcagatcag tacggtacaa atatttcctt    2640
gttcggtaga gactgttccg ttcagagacg tcatcaaaaa attatcgaag aagcaccagt    2700
tacaattgcc aaggctgaaa catttcacga gatggaaaag gctgccgtca gactggggaa    2760
actagtcggt tatgtctctg ccggtaccgt ggagtatcta tattctcatg atgatggaaa    2820
attctacttt ttagaattga acccaagatt acaagtcgag catccaacaa cggaaatggt    2880
ctccggtgtt aacttacctg cagctcaatt acaaatcgct atgggtatcc ctatgcatag    2940
aataagtgac attagaactt tatatggtat gaatcctcat tctgcctcag aaatcgattt    3000
cgaattcaaa actcaagatg ccaccaagaa acaaagaaga cctattccaa agggtcattg    3060
taccgcttgt cgtatcacat cagaagatcc aaacgatgga ttcaagccat cgggtggtac    3120
tttgcatgaa ctaaacttcc gttcttcctc taatgtttgg ggttacttct ccgtgggtaa    3180
caatggtaat attcactcct tttcggactc tcagttcggc catattttg cttttggtga    3240
aaatagacaa gcttccagga aacacatggt tgttgccctg aaggaattgt ccattagggg    3300
tgatttcaga actactgtgg aatacttgat caaacttttg gaaactgaag atttcgagga    3360
taacactatt accaccggtt ggttggacga tttgattact cataaaatga ccgctgaaaa    3420
gcctgatcca actcttgccg tcatttgcgg tgccgctaca aaggctttct tagcatctga    3480
agaagcccgc cacaagtata tcgaatcctt acaaaaggga caagttctat ctaaagacct    3540
actgcaaaact atgttccctg tagattttat ccatgagggt aaaagataca agttcaccgt    3600
agctaaatcc ggtaatgacc gttacacatt atttatcaat ggttctaaat gtgatatcat    3660
actgcgtcaa ctatctgatg gtggtctttt gattgccata ggcggtaaat cgcataccat    3720
ctattggaaa gaagaagttg ctgctacaag attatccgtt gactctatga ctactttgtt    3780
ggaagttgaa aacgatccaa cccagttgcg tactccatcc cctggtaaat tggttaaatt    3840
cttggtggaa aatggtgaac acattatcaa gggccaacca tatgcagaaa ttgaagttat    3900
gaaaatgcaa atgcctttgg tttctcaaga aaatggtatc gtccagttat taagcaacc    3960
tggttctacc attgttgcag gtgatatcat ggctattatg actcttgacg atccatccaa    4020
ggtcaagcac gctctaccat ttgaaggtat gctgccagat tttggttctc cagttatcga    4080
```

```
aggaaccaaa cctgcctata aattcaagtc attagtgtct actttggaaa acattttgaa    4140
gggttatgac aaccaagtta ttatgaacgc ttccttgcaa caattgatag aggttttgag    4200
aaatccaaaa ctgccttact cagaatggaa actacacatc tctgctttac attcaagatt    4260
gcctgctaag ctagatgaac aaatggaaga gttagttgca cgttctttga dacgtggtgc    4320
tgttttccca gctagacaat taagtaaatt gattgatatg gccgtgaaga atcctgaata    4380
caaccccgac aaattgctgg gcgccgtcgt ggaaccattg gcggatattg ctcataagta    4440
ctctaacggg ttagaagccc atgaacattc tatatttgtc catttcttgg aagaatatta    4500
cgaagttgaa aagttattca atggtccaaa tgttcgtgag gaaaatatca ttctgaaatt    4560
gcgtgatgaa aaccctaaag atctagataa agttgcgcta actgttttgt ctcattcgaa    4620
agtttcagcg aagaataacc tgatcctagc tatcttgaaa cattatcaac cattgtgcaa    4680
gttatcttct aaagtttctg ccattttctc tactcctcta caacatattg ttgaactaga    4740
atctaaggct accgctaagg tcgctctaca agcaagagaa attttgattc aaggcgcttt    4800
accttcggtc aaggaaagaa ctgaacaaat tgaacatatc ttaaaatcct ctgttgtgaa    4860
ggttgcctat ggctcatcca atccaaagcg ctctgaacca gatttgaata tcttgaagga    4920
cttgatcgat tctaattacg ttgtgttcga tgttttactt caattcctaa cccatcaaga    4980
cccagttgtg actgctgcag ctgctcaagt ctatattcgt cgtgcttatc gtgcttacac    5040
cataggagat attagagttc acgaaggtgt cacagttcca attgttgaat ggaaattcca    5100
actaccttca gctgcgttct ccaccttccc aactgttaaa tctaaaatgg gtatgaacag    5160
ggctgtttct gtttcagatt tgtcatatgt tgcaaacagt cagtcatctc cgttaagaga    5220
aggtattttg atggctgtgg atcatttaga tgatgttgat gaaattttgt cacaaagttt    5280
ggaagttatt cctcgtcacc aatcttcttc taacggacct gctcctgatc gttctggtag    5340
ctccgcatcg ttgagtaatg ttgctaatgt ttgtgttgct tctacagaag gtttcgaatc    5400
tgaagaggaa attttggtaa ggttgagaga aattttggat ttgaataagc aggaattaat    5460
caatgcttct atccgtcgta tcacatttat gttcggtttt aaagatgggt cttatccaaa    5520
gtattatact tttaacggtc caaattataa cgaaaatgaa acaattcgtc acattgagcc    5580
ggctttggcc ttccaactgg aattaggaag attgtccaac ttcaacatta aaccaatttt    5640
cactgataat agaaacatcc atgtctacga agctgttagt aagacttctc cattggataa    5700
gagattcttt acaagaggta ttattagaac gggtcatatc cgtgatgaca tttctattca    5760
agaatatctg acttctgaag ctaacagatt gatgagtgat atattggata atttagaagt    5820
caccgacact tcaaattctg atttgaatca tatcttcatc aacttcattg cggtgtttga    5880
tatctctcca gaagatgtcg aagccgcctt cggtggtttc ttagaaagat ttggtaagag    5940
attgttgaga ttgcgtgttt cttctgccga aattagaatc atcatcaaag atcctcaaac    6000
aggtgcccca gtaccattgc gtgccttgat caataacgtt tctggttatg ttatcaaaac    6060
agaaatgtac accgaagtca gaacgcaaa  aggtgaatgg gtatttaagt ctttgggtaa    6120
acctggatcc atgcatttaa gacctattgc tactccttac cctgttaagg aatggttgca    6180
accaaaacgt tataaggcac acttgatggg taccacatat gtctatgact cccagaatt     6240
attccgccaa gcatcgtcat cccaaggaaa aaatttctct gcagatgtta agttaacaga    6300
tgatttcttt atttccaacg agttgattga agatgaaaac ggcgaattaa ctgaggtgga    6360
aagaaacct ggtgccaacg ctattggtat ggttgccttt aagattactg taaagactcc    6420
tgaatatcca agaggccgtc aatttgttgt tgttgctaac gatatcacat tcaagatcgg    6480
```

```
ttcctttggt ccacaagaag acgaattctt caataaggtt actgaatatg ctagaaagcg    6540
tggtatccca agaatttact tggctgcaaa ctcaggtgcc agaattggta tggctgaaga    6600
gattgttcca ctatttcaag ttgcatggaa tgatgctgcc aatccggaca agggcttcca    6660
atacttatac ttaacaagtg aaggtatgga aactttaaag aaatttgaca agaaaaattc    6720
tgttctcact gaacgtactg ttataaacgg tgaagaaaga tttgtcatca agacaattat    6780
tggttctgaa gatgggttag gtgtcgaatg tctacgtgga tctggtttaa ttgctggtgc    6840
aacgtcaagg gcttaccacg atatcttcac tatcacctta gtcacttgta gatccgtcgg    6900
tatcggtgct tatttggttc gtttgggtca aagagctatt caggtcgaag ccagccaat    6960 tatttggtat cggtgcttat taactggtgc tcctgaatca acaaatgctg gtagagaagt    7020
ttatacttct aacttacaat gggtggtac tcaaatcatg tataacaacg gtgtttcaca    7080
tttgactgct gttgacgatt tagctggtgt agagaagatt gttgaatgga tgtcttatgt    7140
tccagccaag cgtaatatgc cagttcctat cttggaaact aaagacacat gggatagacc    7200
agttgatttc actccaacta atgatgaaac ttacgatgta agatggatga ttgaaggtcg    7260
tgagactgaa agtggatttg aatatggttt gtttgataaa gggtctttct ttgaaacttt    7320
gtcaggatgg gccaaaggtg ttgtcgttgg tagagcccgt cttggtggta ttccactggg    7380
tgttattggt gttgaaacaa gaactgtcga gaacttgatt cctgctgatc cagctaatcc    7440
aaatagtgct gaaacattaa ttcaagaacc tggtcaagtt tggcatccaa actccgcctt    7500
caagactgct caagctatca atgactttaa caacggtgaa caattgccaa tgatgatttt    7560
ggccaactgg agaggtttct ctggtggtca acgtgatatg ttcaacgaag tcttgaagta    7620
tggttcgttt attgttgacg cattggtgga ttacaaacaa ccaattatta tctatatccc    7680
acctaccggt gaactaagag gtggttcatg ggttgttgtc gatccaacta tcaacgctga    7740
ccaaatggaa atgtatgccg acgtcaacgc tagagctggt gttttggaac cacaaggtat    7800
ggttggtatc aagttccgta gagaaaaatt gctggacacc atgaacagat tggatgacaa    7860
gtacagagaa ttgagatctc aattatccaa caagagtttg gctccagaag tacatcagca    7920
aatatccaag caattagctg atcgtgagag agaactattg ccaatttacg gacaaatcag    7980
tcttcaattt gctgatttgc acgataggtc ttcacgtatg gtggccaagg gtgttatttc    8040
taaggaactg aatggaccg aggcacgtcg tttcttcttc tggagattga aagaagatt    8100 gaacgaagaa tatttgatta aaaggttgag ccatcaggta ggcgaagcat caagattaga    8160
aaagatcgca agaattagat cgtggtaccc tgcttcagtg gaccatgaag atgataggca    8220
agtcgcaaca tggattgaag aaaactacaa aactttggac gataaactaa aggggtttgaa    8280 attagagtca ttcgctcaag acttagctaa aaagatcaga agcgaccatg acaatgctat    8340
tgatggatta tctgaagtta tcaagatgtt atctaccgat gataaagaaa aattgttgaa    8400
gactttgaaa taa                                                      8413
```

<210> SEQ ID NO 126
<211> LENGTH: 6696
<212> TYPE: DNA
<213> ORGANISM: Kluyveromyces lactis

<400> SEQUENCE: 126

```
atgagtgagg aaaatctttc tgaggtttca atctctcaaa gtaaacaata cgaaattact      60
gaatatagcg atagacattc caagttggct tctcatttca ttggtctgaa cactgtggat    120
```

-continued

```
aaggcagatg attctccatt gaaagagttt gtcaaatcac atggtggtca tactgtgatc      180
tcaaaggttt tgatcgctaa caatggtatc gcagccgtta agaaatcag atcggttcgt      240
aaatgggcct atgaaacctt cggcgatgaa agaactgttc aattcgtggc catggccact      300
ccagaagatc ttgaagccaa cgcagaatac attcgtatgg ctgatcaata tatcgaagtt      360
cccggtggta ccaacaataa caattatgca acgttgacc taattgttga agttgccgaa       420
agagctgatg tagatgcagt ttgggcaggt tggggtcatg cttcagaaaa cccactactc      480
cctgaaaggc tagccgcttc tcacagaaag attatattta ttggtccacc aggaaatgcc      540
atgagatctc tcggtgataa gatctcgtcc actatcgttg cccaacacgc taaggttcct      600
tgtatcccat ggtctggtac tggtgtcgat gaagttcatg ttgataaaga aactaacttg      660
gtctctgtcg aagataaagt ataccaagaa ggttgttgtt cgtctccaga agacggtcta      720
aagaaagcca aggaaattgg tttcccaatt atggtcaagg cttccgaagg tggtggtggt      780
aaaggtatca gaaaagtcga aaatgaagat gagttcctgt ctttgtacca acaagctgct      840
aatgaaattc ctggttctcc aatttttatt atgaagttgg ctggtaaggc tcgtcatttg      900
gaagttcaac ttttggctga tcaatatggt accaacatct ctctatttgg tcgtgattgt      960
tctgttcaaa gacgtcatca aaagattatc gaagaagctc ctgtaactat cgctaagcca     1020
gataccttca ctgaaatgga aaagcagcc gtcagattag gtcaattggt tggttacgtt      1080
tctgctggta ccgtcgaata tttatattct catgatgaag acaagttcta cttcttggag     1140
ttgaacccaa gattacaagt tgaacatcca accacagaaa tggttactgg tgttaacttg      1200
ccgtctgccc agttacaaat cgctatgggt attccaatgc acagaatcag agatattaga     1260
ttgttatacg gtgtcgatcc aaaatctgca tccgaaattg actttaactt ctctacacct     1320
gagtctgcta aaactcaaag aaaaccaact cctaaaggtc actgtactgc ctgccgtatc     1380
acatccgaag atccaaatga gggtttcaaa ccatctggcg gtgctttaca cgaattgaac     1440
ttccgttctt cttccaacgt tgggggttat ttctctgttg gtaataatgg tggtatccat     1500
tcattctctg actctcaatt cggtcatatc ttcgccttcg gtgaaaacag acaagcttca     1560
aggaaacata tggttgttgc tttgaaggaa ttatctatca gaggtgattt cagaactacg     1620
gttgaatatt taatcaaatt attggaaacc gaagacttcg aagacaatac catcacgact     1680
gggtggttgg atgatttgat ttctcagaaa atgacagctg aaaagcctga tagaacccta     1740
tctgtcattt gtggtgccgc taccaaggct catattgcct cccaaaaagc cagagaagat     1800
tacatctcat ctttgaagag aggccaagtt ccaaacaaat cattactaca aacaatgtac     1860
ccaattgaat ttattcatga tggtatgaga tatagattta ctgttgctaa atcagccgac     1920
gatcgttata ctctattcat taacggttcc aagtgcgaag ttggcgtaag gaagttatct     1980
gatggtggtt tgttgattgc cgttggtggt aaatcacaca ccatttactg gaaggaagaa     2040
gttgctgcta ccagattatc aatcgactct aagacaactc tactagaggt tgaaaatgat     2100
ccaacacaac tcagaactcc atctcctggt aaattggtca gttttttggt cgaaaacggt     2160
gatcatgtta ttgctggcca accatatgcc gaagttgaag ttatgaagat gcaaatgcca     2220
ttgatttctc aagaaaatgg tgtcgttcag ttattgaaac aaccaggctc tactctggcc     2280
gccggtgaca ttctagccat cttaactcta gatgacccta gtaaagtcaa acatgctaag     2340
ccttacgaag gcatgctacc agaattgggt gctccaatcg ttgaaggtac caagcctgca     2400
tacaaattta atctttggt cactactttg gaaaacatct gaagggata cgacaatcaa      2460
gttattatga atgcttcatt gcagcaatta attgaagtgt tgagacaacc agaattacca     2520
```

```
tactctgaat ggaaattaca agtttctgct ttacattcaa gattaccacc taagttagac    2580
gaaatgcaag aacaattggt cacccgttca ttcaagagaa atgcggattt cccagcaaga    2640
caactagaaa agatgttaga agctgcctta aatgatccta acgttgaccc attgtttagc    2700
actaccattg aaccacttgt tgatattact acccgttact ctaagggact tgctgctcat    2760
gaacattttg tctttgccac tttcttagaa aactattaca atgtcgaaaa attgttctct    2820
gggccaaaca ttcgggaaga agacgtcatc ttaaaattgc gtgatgagaa ccctgacgac    2880
ttggagaagg ttgttttaac cgtcctagct cactccagag tatcagccag aaacaacctg    2940
atccttgcca ttttgaagca ttatcaaccg ctatgcaaat tgagctctga ggtagccgct    3000
gctatcgaac aaccattgaa acacatcgtc gaattagaat ctaaggccac cgctaaggtt    3060
gctctacaag ccagagaaat tttgattcaa ggtgctttgc catctatcaa ggagagaaca    3120
gatcaagttc aatacattct taagtcatct gttttaagca cttcatatgg ttcatccgaa    3180
acgaagcgca caaaacctga tttagaagtt ttaaaggact tgatcgattc caactatgtt    3240
gttttcgatg tgttggccca attcttgaca aatccagatg atgccgtttc tgctgctgct    3300
gccgaggtct acattagaag agcatacaga gcgtacacta ttggtgattt gaagcatcaa    3360
aagtcttctg gatcacctgt agttgagtgg aagttccaac ttccatctgc tgcattcacc    3420
tcattgccac aggttaagag taaattgggt atgaacagac tatttctgt ctctgatttg    3480
acttatgtct ctgacggtga aaaccaacca ttaagaactg gtttgttgat tcctgctaga    3540
catctagatg atgttgatgg tatttttgtcg tcagctctat cttttaattcc ttctcatcat    3600
atgtctactg gccctgtccc agacagatct ggctcttcag ccagcttgtc taatgttgcc    3660
aatgttgttg tgtcttcaac tgaaggattt gaatctgagt cggatgtttt aaagagactc    3720
agagagatac tcgatttaaa caagcaatca ttagttgact ctgctattcg tcgtattacc    3780
ttcgtgtttg gatacagtga tggtacatat ccaaagtact ataccttccg tggtccaaat    3840
tacaatgaag atgaaacaat tcgtcacatt gaaccagctc tagcttttcca acttgaacta    3900
ggtaagatgt cgaacttcaa tatcagacaa atatttactg agaacagaaa cattcatgtc    3960
tatgaggccg ttggtaaaaa ctctccggtt gacaagagat tctttaccag aggtattatc    4020
agaacaggtc gtattagtga cgacatttcc atccatgaat atttgacttc agaagctaac    4080
agattaatga gtgacatttt ggacaactta gagatcattg acacttctaa ctcagatctt    4140
aaccatattt tcattaactt ctctgctgta tttgacattt cgccagaagc tgttgaagct    4200
gcctttggcg gtttcttgga aagatttggc agaagattgc tcagattacg tgttgccgct    4260
gctgaaatca gaattattat caaggaccct caaactggca ccccggttcc aatcagagcg    4320
ttgatcaaca acgtctcggg ctttgttgtg aagactgaat tgtatacaga gatcaagaat    4380
gcacaaggtg aatggatttt caaatcttta gataaaccag tgctatgca tttgagacct    4440
attgccactc cttatcctgc aaaggagtgg ttacagccaa aacgttacaa ggctcatttg    4500
atgggaacca catacgttta cgatttccca gagctattcc gtcaagccac cgtggcacaa    4560
tggaagaaac actctccaaa gaccaagttg tcagacgatt ttttcattgc aaatgaattg    4620
attgaagatg aaaatggtga attaactgaa gttgatcgtg aacttggtgc taataacatc    4680
ggtatggttg cattcaaggt tactgcaaaa actccagaat actctcatgg ccgtcaattt    4740
gtcatagtcg ccaatgatat cactttcaaa attggttcgt tcggtccaca ggaagatgcc    4800
ttcttcaaca aggttactga atatgcaaga aagcgtggta tcccaagaat atacttatct    4860
```

```
gccaattcag gtgcaagaat tggtattgcc aagagcttg ttccattgtt ccagattgct    4920
tggaatgatg aaaaagatcc agcaaagggt ttccaatact tatggttgtc agatgagtct    4980
cttgaagaac tcaaatctaa gggtaaagac aatgctgttg ttaccgaatg tgttgttgaa    5040
gaaggtaagg tcagaaacgt cattactgct attatcggtt cggaagatgg tcttggtgtt    5100
gagtgtttga agggatccgg tttaattgca ggtgccactt caagagcgta caaggatatc    5160
ttcacgatca ccttagttac ttgtaggtct gtgggtatcg gtgcttatct agtcagatta    5220
ggtcaaagag ccattcaaat cgaagcacag ccaatcattt taaccggtgc tcctgccatc    5280
aataagcttc ttggtagaga agtttactct tcaaacttgc aattgggtgg tactcagatc    5340
atgtacaaca atggtgtttc acacttaact gctccagatg atttggctgg tgttgaaaag    5400
atcatggact ggttatctta cattcctgcc aaacgtgatc taccggttcc tattttggaa    5460
tctgaagata aatgggacag aaaaattgac tatgctccat ctttaaacga acagtacgat    5520
gttaggtgga tgattgcagg tcgtgaatct gccgatggtt cgaatatgg tcttttcgat    5580 aaaggttcct tccaagaaac cttgtctggt tgggccaagg gtgttgttac aggtagagcc    5640
cgtttaggtg gtattccatt aggtgttatt gccgttgaaa caagaattgt cgaaaatttg    5700
attcctgctg atcctgctaa tcctgattct accgaaatgt tgattcaaga agccggccaa    5760
gtttggtatc caaattccgc gttcaagaca gcccaggcta tcaatgactt caatcatggt    5820
gaacaattgc cattaatgat cctagccaac tggagaggtt tctctggtgg acaacgtgat    5880
atgtacaacg aagttttgaa gtatggttct ttcatcgttg atgcattggt tgattacaaa    5940
cagcctataa ttacatacat tcctccaact ggtgaactaa gaggtggttc ttgggttgtt    6000
gttgatccaa ctatcaatgc tgaccaaatg gaaatgtatg ctgatataaa ctcaagagct    6060 ggtgtttttgg aaccagaagg tatggtcggt atcaaatacc gtagagaaaa attgttggct    6120
actatggcaa gattagatga caagtacaga gagttgaaag ccaagttggc cgattccact    6180
ttgactccag aagaacatca agaagtatca aagcagcttg ctatccgtga aagcaattg    6240 ttgccaattt accatcaaat tacagtacag tttgctgact tgcatgatag atccggtcgt    6300
atgttggcaa agggtgtgat caaaaaggaa ttggactggc cagaagctcg tcgcttcttt    6360
ttctggagat taagaagaag attaaacgaa gaatatttga tgagaagatt aaataacgag    6420
ctaggatctg cttctagact agagaaaatg gcaagaatca tatcatggta cccagcttct    6480
gtgagccaag ataacgacag agaagttgct acttggatcg aagaaaacta ccaattcttg    6540
gatgaacaag ttaagagtct gaagttggaa gctttcgcac aaaatttggc aaaatctatc    6600
agaaacgacc gtgaaaattc catcaatggt ttggcggaag ttttgaaatt attgtctgcc    6660
aaagacaaag aaaagcttca aaaagctttg gaatga                              6696
```

<210> SEQ ID NO 127
<211> LENGTH: 6894
<212> TYPE: DNA
<213> ORGANISM: Debaryomyces hansenii

<400> SEQUENCE: 127

```
atgagcgcca tttgtgccaa attgaaaaaa cttacaacta acatttcact caataggtta     60
ctatttccaa atcttaattt acgtcatcaa tatagaaat taaagtatat tccagttaaa    120
cgacttaata gatacatcaa ctacaacagt gtcaacacta ctaataacga caccaacgat    180
aacaaactaa agaataccat tgataataaa tataggatgt ctgacgtaac aacagaggtg    240
agaaattaca ctcaaatgca tcagaaatta gctgaccact ttaaagggtt gaactcggca    300
```

```
gataatgctg agccaggtaa ggtgacggac tttgtaagat cgcacgaagg tcacacggta    360
atttcgagag ttttaattgc aaataacggt attgctgccg tcaaggagat cagatcggtt    420
agaaaatggg cctacgagac attcggtgat gaaagggcca ttcaattcac tgtgatggct    480
accccagaag atttggaagc taatgcggag tacattcgta tggcggacca atttatcgag    540
gttccaggtg gaactaacaa taataattat gccaacgttg agttgatcgt ggaaattgcc    600
gaaagaacca atgttgacgc tgtctgggcc ggatgggggtc atgcttcaga aaacccatta   660
ttaccagaaa tgttagctgc ctctccaaag aaaatcttgt ttataggggcc tccgggatct   720
gctatgagat ctttaggaga taagatttct tctactatcg tagctcaaca cgcagatgtt    780
ccatgtattc catggtccgg tactggcgtt agggaagtta agattgacga agaaactaac    840
ttggtttcgg tttccgacgc tgtttacgcc aagggttgtt gcacaagtcc agaagatggt    900
cttgttaagg caaagaaaat tggtttccca gtcatgatca agcttctga aggtggtggt     960
ggtaaaggta ttagaaaagt cgataacgaa aaagacttta ttgccttata caagcaagct   1020
tcgaacgaaa ttccaggatc tcctattttc attatgaagt tagccggtga tgctagacat   1080
ttggaagttc aattattagc cgatcaatac ggtacgaata tttctctttt tggaagagat   1140
tgttccgttc aaagaagaca tcaaaagatc attgaagagg ctccagtcac tattgccaaa   1200
aaagaaagtt ccacgccat ggaaaacgct gccgtaaggt taggtaaatt agttggctat    1260
gtttctgcag gtacagttga ataccttta t tcgcatagtg aagataaatt ctatttctta  1320
gaattgaatc caagattaca agttaacat ccgactactg aaatggtcac tggggttaat    1380
ttaccagctg cccaattaca aattgctatg ggtattccaa tgcaccgtat tagggatatt   1440
aggtcattat acggtgtaga ccctcacact tctaccgaaa ttgattttga atttaagact   1500
gaaagttcat tagttagtca gcgtcgtcct gttccaaagg ccacactac tgcatgtcgt    1560
attacttcag aagatccagg tgaaggattt aagccttctg ggggttcgtt acatgaattg   1620
aattttagat catcttctaa tgtctgggt tatttctctg tcggtaatca atcttctatt    1680
cattcttttct ccgattcgca attcggtcat atttttgcct ttggtgaaaa ccgttctgct  1740
tcaagaaaac atatggttgt tgcttttgaaa gaattatcta ttagaggtga ttttagaact  1800
accgtggaat atttaattaa attattagaa acaccagatt ttgaagacaa tacaatcact   1860
actggatggt tagacgaatt aatttcaaag aaattaacgt ccgaaagacc tgatcatatt   1920
gttgcagttg tgtgtggtgc cgctaccaaa gcccatattc aatccgaaga agatagaaaa   1980
gagtatatcc aatcattgga gaaaggtcaa gttccaaaca aagctttatt aaggactatt   2040
tatccaattg aattcatttta tgaaggatat agatataaat tcaccgcaac caagtcatct   2100
aatgattctt atactttatt cttaaatggt acaagaggag ttgttggtgt tcgttcatta   2160
tctgatggtt ggttattatg tgcaattgac gggaaatctc attctattta ttggaaagaa   2220
gagcctgctg caaccagatt atcagtgaat ggtaaaacct gcttattaga agctgaaaac   2280
gatccaacac aactaagaac accatctcca ggtaagttag tgaagtactt aattgaaagt   2340
ggtgaacatg ttaattccgg agaagtttat gctgaggttg aagttatgaa aatgtgtatg   2400
ccattaattg cccaagacaa tggtgttgtt caattaataa aacagcctgg ctctacagtg   2460
aatgctggtg atattttagc tatttagag ttagatgacc catctaaggt taaacatgct    2520
atgccttacg aaggaacctt acctccatta ggtgatcctg tcgttagagg taccaaatca   2580
gcacatgctt ccaacattta tactaatat tttgagaaata tcttagcagg gtttgataat   2640
```

```
caagttatca tgaattcaac tttgaagagc ttaattgaga tcttaaaaaa caaagacttg   2700
ccctactcag aatggaatca gtatgcctct gcattacact caagattacc aattaagtta   2760
gatgaagcat tgtcagcttt gattgaaaga accaatcga gaggtgctga gttcccagct   2820
cgtcaaatct tgaagcagat tcaaaaattc actaccgatc catcgatcga tgcaagtgtt   2880
aatgaagtgg ttaaaccatt aattgatatt gcgactagat actctaacgg tcttgttgag   2940
cacgagtatg aatttttctc aaatttgatc aatgaatact ttgaaattga aaacttattc   3000
tctggtacaa atgttcgtga ggatgatgtt gttttgaaat taagggatga aaacaaagct   3060
gatttaaata aagttattag tattgtatta tctcattcca gagtcagctc aaaaaacaat   3120
ttagttttgg ctattttaga tgaataccaa ccactattac agtcatcttc aatacagct   3180
aacggaatta gaaatgcatt gaaggatatt gttgaattgg atactagagg cgcggctaag   3240
gtggctttga agcaaggga atgttaatt caatgctctt tgccatcaat tcaagaaaga   3300
tcagatcaat tagaacatat cttgagatcc tccgtgcttc aaacttctta tggtgagatc   3360
tatgctaatc accgtactcc aagattagat attattcgcg aggttgtcga ttccaaacac   3420
acagtctttg acgtgttgcc tcaattttta gtcaaccaag atgaatgggt ttctattgcg   3480
gctgcagaag tctatgttcg tcgttcatat agggcatact ccttgggacc gatcacttat   3540
gacttccatg acaaattacc gatcattgaa tggaaattcc aattaccaag tcttaactca   3600
tcccagttaa ctggtgttca acaaactcag aatccagatc aacctgctat gaaccgtgcg   3660
gcatctgttt ctgatttgtc ttttgtcgtc gatcaaaaca agaacaaaa gacaagaatt   3720
ggtgtcttag taccttgtag acatcttgat gatgtggatg aaatgattac tgcagcatta   3780
gaaaagatcc aaccttctga cggtattacg tttaaggcta aagagtcgga ggaatctaaa   3840
gcttcttatt taaatgtttt caacatcgtc gtaacgaata ttgatggtta caataatgaa   3900
gaggaagtat tggcccgggt tcatgaaatt ctcgatgaat ttaaggaaga ccttaagtca   3960
gcttctattc gtcgtatcac tttcgtattt gctaataaga ttggtgttta tcctaaatac   4020
tttactttta ccgcaccaga ttatgttgaa acaaggtta tccgtcatat tgagcctgca   4080
ttggcattcc aattggaatt gggaagatta ataactttg acattaagcc gatatttacc   4140
gacaacagaa atattcatgt ttatgaagct gttggtaaga actctccatc tgataagaga   4200
ttctttacaa gaggtatcat taggactgga attattcgta atgatataag tattagtgaa   4260
tacttgattg ccgaatctaa tcgtttgatg tcaagcattt tggatgcact tgaggttatt   4320
gatacttcta attcagatct taatcatatc ttcatcaact tttctgctgt atttaatgtc   4380
ttgcctgagg aggttgaagc cgcttttggc tcatttttag agagattcgg tagaagattg   4440
tggagattac gtgtgactgg ggctgaaatt agaattgcat gtactgatcc aaatactggt   4500
aattctttcc cattgcgcgc aattatcacc aatgtctcag ttacgttgt taaatctgag   4560
ttgtatatgg aagttaaaaa cactaagggt gaatgggttt tcaaatccat tggttctacg   4620
ggttccatgc acttgagacc aatttcaact ccttatccag cgaaggaatc gttgcaacca   4680
aaacgttata aggctcataa tatgggtact acgtacgttt atgatttccc agaattattc   4740
cgccaggcta ctctttctca atggaaaaat catccgaaag aaaaagttcc taaggaaatc   4800
tttacgtctt tagaattaat ttctgacgag aatggagatt tgacggcagt agaacgtgat   4860
cctggcagca acaagattgg tatggttgga ttcaaggtaa ctgccaaaac cccagaatat   4920
cctcgcggcc gtcaatttat tattgttgcc aatgatatta cccataaaat tggttcattt   4980
ggtccagaag aagatgaatt cttcaacaaa tgtactcaat tagctagaaa attaggaatt   5040
```

-continued

```
ccaagaattt atctttcagc taattccggt gccagaattg gtattgctga tgaattggtt    5100
ccacttttca atgttgcttg gaatgttgaa ggttctccag ataagggttt cagatactta    5160
ttcttgaccc ctgaagataa aagagcatt gatgaagctg aaaatctga tacaattgtc    5220 actgaaagaa tcgttgaaga aggccaggaa agatatgtca tcaagtcgat cgttggagaa    5280
gaagatggtt taggtgttga atgtcttaaa ggatctggtt tgattgctgg tagtacctcg    5340
agggcctata aggatatttt cactattacc ttagtgactt gtagatcagt tggtattggt    5400
gcttacttgg ttagattagg tcaaagagcc attcaagttg aaggtcaacc aatcattta    5460 actggtgctc ccgctattaa taagttatta ggtagagatg tctattcgtc taacttgcaa    5520
ttaggtggta ctcaaattat gtatcgtaat ggtgtttccc atcttacagc ttcagatgat    5580
ttagcgggag ttgagaagat tatggaatgg atgtcttatg ttccggctaa gcgtgatatg    5640
ccaattccaa ttttgaaag tgaagacagc tgggatagag aggttgaata tgttccacct    5700
aaggatgaac catatgatgt tcgttggatg atagaaggaa aacagttaga taatggtgaa    5760
ttcgaatcag gttatttga taagaattct ttccaagaaa cattatccgg ttgggccaaa    5820
ggtgttgttg ttggtagagc acgtcttggt ggtataccaa ttggtgtcat tggtgtcgaa    5880
acaagaacta tagacaactt agtacctgct gatcctgcta atccagagtc cactgaaatg    5940
atgattcaag aagctggtca agtttggtat ccaaactctg ctttcaagac tgctcaagcg    6000
attaacgatt tcaaccatgg tgaacaattg ccattaatga ttttggctaa ctggagaggt    6060
ttctctggtg gtcaacgtga tatgttcaat gaagttctta aatacggttc ttttattgtt    6120
gatgcgttag ttgactttaa gcaaccaatt ttcacttata ttccaccaaa tggtgaatta    6180
agaggtggtt catgggttgt tgttgaccca accattaatg ctgatatgat ggaaatgtat    6240
gctgatgtca attccagagc tggtgttttg gaacccgagg gaatggttgg tattaaatac    6300
agacgtgaca agttattatc tactatagaa agattagatc caacatacag ggaccttaaa    6360
aagcaattaa acgaaagcaa attatcacca gaagaacatg cccaaatttc tgctaagttg    6420
actactcgtg aaaaggcatt gttaccaatt tatgcccagg tttcagttca atttgctgac    6480
ctccacgata gatctggtcg tatgttagcc aagggtgtca ttagaaaaga aatcaactgg    6540
ccagaagcac gtcgtacctt tttctggcgt ttacgtcgtc gtttgaatga agaatacttg    6600
ttgaaactta ttggtgaaca aatcaaatca gacaacaaat tagaaaaggt tgccaggttg    6660
aagagttgga tgccaacagt tgactatgac gacgatatgg ctgtcagcaa ttggatcgaa    6720
cagaaccact ctaagttgca gaagagaatt gaagaattga acacgaatc cgctcgtcaa    6780 aacttagtta atatcttgag agaggaccct aaaagctcgg tttccgttat taaagatttc    6840
ttatctaacc ttccagagga ccaaagatca gaatttgcgg catccttaaa atag         6894
```

<210> SEQ ID NO 128
<211> LENGTH: 6801
<212> TYPE: DNA
<213> ORGANISM: Yarrowia lipolytica

<400> SEQUENCE: 128

```
atgcgactgc aattgaggac actaacacgt cggttttca gtatggcttc aggatcttca      60
acgccagatg tggctcccttt ggtggacccc aacattcaca aaggtctcgc ctctcatttc    120
tttggactca attctgtcca cacagccaag ccctcaaaag tcaaggagtt tgtggcttct    180
cacggaggtc atacagttat caacaaggtc ctcatcgcta caacgggtat tgccgcagta    240
```

```
aaggagatcc gttcagtacg aaaatgggcc tacgagacct ttggcgacga gcgagcaatc    300
tcgttcaccg tcatggccac ccccgaagat ctcgctgcca acgccgacta cattagaatg    360
gccgatcagt acgtcgaggt gcccggagga accaacaaca acaactacgc caacgtcgag    420
ctgattgtcg acgtggctga gcgattcggc gtcgatgccg tgtgggccgg atggggccat    480
gccagtgaaa atcccctgct ccccgagtcg ctagcggcct ctccccgcaa gattgtcttc    540
atcggccctc ccggagctgc catgagatct ctgggagaca aaatttcttc taccattgtg    600
gcccagcacg caaaggtccc gtgtatcccg tggtctggaa ccggagtgga cgaggttgtg    660
gttgacaaga gcaccaacct cgtgtccgtg tccgaggagg tgtacaccaa gggctgcacc    720
accggtccca gcagggtct ggagaaggct aagcagattg gattccccgt gatgatcaag    780
gcttccgagg aggaggagg aaagggtatt cgaaaggttg agcgagagga ggacttcgag    840
gctgcttacc accaggtcga gggagagatc cccggctcgc ccatcttcat tatgcagctt    900
gcaggcaatg cccggcattt ggaggtgcag cttctggctg atcagtacgg caacaatatt    960
tcactgtttg gtcgagattg ttcggttcag cgacggcatc aaaagattat tgaggaggct   1020
cctgtgactg tggctggcca gcagaccttc actgccatgg agaaggctgc cgtgcgactc   1080
ggtaagcttg tcggatatgt ctctgcaggt accgttgaat atctgtattc ccatgaggac   1140
gacaagttct acttcttgga gctgaatcct cgtcttcagg tcgaacatcc taccaccgag   1200
atggtcaccg tgtcaacct gcccgctgcc cagcttcaga tcgccatggg tatcccccte   1260
gatcgaatca aggacattcg tctcttttac ggtgttaacc ctcacaccac cactccaatt   1320
gatttcgact tctcgggcga ggatgctgat aagacacagc gacgtcccgt cccccgaggt   1380
cacaccactg cttgccgaat cacatccgag gaccctggag agggtttcaa gccctccgga   1440
ggtactatgc acgagctcaa cttccgatcc tcgtccaacg tgtggggtta cttctccgtt   1500
ggtaaccagg gaggtatcca ttcgttctcg gattcgcagt ttggtcacat cttcgccttc   1560
ggtgagaacc gaagtgcgtc tcgaaagcac atggttgttg ctttgaagga actatctatt   1620
cgaggtgact tccgaaccac cgtcgagtac ctcatcaagc tgctggagac accggacttc   1680
gaggacaaca ccatcaccac cggctggctg gatgagctta tctccaacaa gctgactgcc   1740
gagcgacccg actcgttcct cgctgttgtt tgtggtgctg ctaccaaggc ccatcgagct   1800
tccgaggact ctattgccac ctacatggct tcgctagaga agggccaggt ccctgctcga   1860
gacattctca agacccttt ccccgttgac ttcatctacg agggccagcg gtacaagttc   1920
accgccaccc ggtcgtctga ggactcttac acgctgttca tcaacggttc tcgatgcgac   1980
attggagtta gacctctttc tgacggtggt attctgtgtc ttgtaggtgg gagatcccac   2040
aatgtctact ggaaggagga ggttggagcc acgcgactgt ctgttgactc caagacctgc   2100
cttctcgagg tggagaacga ccccactcag cttcgatctc cctctcccgg taagctggtt   2160
aagttcctgg tcgagaacgg cgaccacgtg cgagccaacc agcccatgc cgagattgag   2220
gtcatgaaga tgtacatgac tctcactgct caggaggacg gtattgtcca gctgatgaag   2280
cagcccggtt ccaccatcga ggctggcgac atcctcggta tcttggccct tgatgatcct   2340
tccaaggtca agcatgccaa gcccttgag ggccagcttc ccgagcttgg accccccact   2400
ctcagcggta acaagcctca tcagcgatac gagcactgcc agaacgtgct ccataacatt   2460
ctgcttggtt tcgataacca ggtggtgatg aagtccactc ttcaggagat ggttggtctg   2520
ctccgaaaacc ctgagcttcc ttatctccag tgggctcatc aggtgtcttc tctgcacacc   2580
cgaatgagcg ccaagctgga tgctactctt gctggtctca ttgacaaggc caagcagcga   2640
```

```
ggtggcgagt tcctgccaa gcagcttctg cgagcccttg agaaggaggc gagctctggc    2700
gaggtcgatg cgctcttcca gcaaactctt gctcctctgt ttgaccttgc tcgagagtac    2760
caggacggtc ttgctatcca cgagcttcag gttgctgcag gccttctgca ggcctactac    2820
gactctgagg cccggttctg cggacccaac gtacgtgacg aggatgtcat tctcaagctt    2880
cgagaggaga accgagattc tcttcgaaag gttgtgatgg cccagctgtc tcattctcga    2940
gtcggagcca agaacaacct tgtgctggcc cttctcgatg aatacaaggt ggccgaccag    3000
gctggcaccg actctcctgc ctccaacgtg cacgttgcaa agtacttgcg acctgtgctg    3060
cgaaagattg tggagctgga atctcgagct tctgccaagg tatctctgaa agcccgagag    3120
attctcatcc agtgcgctct gccctctcta aaggagcgaa ctgaccagct tgagcacatt    3180
ctgcgatctt ctgtcgtcga gtctcgatac ggagaggttg gtctggagca ccgaactccc    3240
cgagccgata ttctcaagga ggttgtcgac tccaagtaca ttgtctttga tgtgcttgcc    3300
cagttctttg cccacgatga tccctggatc gtccttgctg ccctggagct gtacatccga    3360
cgagcttgca aggcctactc catcctggac atcaactacc accaggactc ggacctgcct    3420
cccgtcatct cgtggcgatt tagactgcct accatgtcgt ctgctttgta caactcagta    3480
gtgtcttctg gctccaaaac ccccacttcc ccctcggtgt ctcgagctga ttccgtctcc    3540
gacttttcgt acaccgttga gcgagactct gctcccgctc gaaccggagc gattgttgcc    3600
gtgcctcatc tggatgatct ggaggatgct ctgactcgtg ttctggagaa cctgcccaaa    3660
cggggcgctg gtcttgccat ctctgttggt gctagcaaca agagtgccgc tgcttctgct    3720
cgtgacgctg ctgctgctgc cgcttcatcc gttgacactg gcctgtccaa catttgcaac    3780
gttatgattg gtcgggttga tgagtctgat gacgacgaca ctctgattgc ccgaatctcc    3840
caggtcattg aggactttaa ggaggacttt gaggcctgtt ctctgcgacg aatcaccttc    3900
tccttcggca actcccgagg tacttatccc aagtatttca cgttccgagg ccccgcatac    3960
gaggaggacc ccactatccg acacattgag cctgctctgg ccttccagct ggagctcgcc    4020
cgtctgtcca acttcgacat caagcctgtc cacaccgaca accgaaacat ccacgtgtac    4080
gaggctactg gcaagaacgc tgcttccgac aagcggttct tcacccgagg tatcgtacga    4140
cctggtcgtc ttcgagagaa catccccacc tcggagtatc tcatttccga ggctgaccgg    4200
ctcatgagcg atattttgga cgctctagag gtgattggaa ccaccaactc ggatctcaac    4260 cacatttttca tcaacttctc agccgtcttt gctctgaagc ccgaggaggt tgaagctgcc    4320
tttggcggtt tcctggagcg atttggccga cgtctgtggc gacttcgagt caccggtgcc    4380
gagatccgaa tgatggtatc cgaccccgaa actggctctg ctttccctct gcgagcaatg    4440
atcaacaacg tctctggtta cgttgtgcag tctgagctgt acgctgaggc caagaacgac    4500
aagggccagt ggatttttcaa gtctctgggc aagcccggct ccatgcacat gcggtctatc    4560
aacactccct accccaccaa ggagtggctg cagcccaagc ggtacaaggc ccatctgatg    4620
ggtaccacct actgctatga cttccccgag ctgttccgac agtccattga gtcggactgg    4680
aagaagtatg acggcaaggc tcccgacgat ctcatgactt gcaacgagct gattctcgat    4740
gaggactctg gcgagctgca ggaggtgaac cgagagcccg cgccaacaa cgtcggtatg    4800 gttgcgtgga agttttgaggc caagacccccc gagtaccctc gaggccgatc tttcatcgtg    4860
gtggccaacg atatcacctt ccagattggt tcgtttggcc ctgctgagga ccagttcttc    4920
ttcaaggtga cggagctggc tcgaaagctc ggtattcctc gaatctatct gtctgccaac    4980
```

| | |
|---|---|
| tctggtgctc gaatcggcat tgctgacgag ctcgttggca agtacaaggt tgcgtggaac | 5040 |
| gacgagactg acccctccaa gggcttcaag tacctttact tcaccccctga gtctcttgcc | 5100 |
| accctcaagc ccgacactgt tgtcaccact gagattgagg aggagggtcc caacggcgtg | 5160 |
| gagaagcgtc atgtgatcga ctacattgtc ggagagaagg acggtctcgg agtcgagtgt | 5220 |
| ctgcggggct ctggtctcat tgcaggcgcc acttctcgag cctacaagga tatcttcact | 5280 |
| ctcactcttg tcacctgtcg atccgttggt atcggtgctt accttgttcg tcttggtcaa | 5340 |
| cgagccatcc agattgaggg ccagcccatc attctcactg gtgcccccgc catcaacaag | 5400 |
| ctgcttggtc gagaggtcta ctcttccaac ttgcagcttg gtggtactca gatcatgtac | 5460 |
| aacaacggtg tgtctcatct gactgcccga gatgatctca acggtgtcca agatcatg | 5520 |
| cagtggctgt catacatccc tgcttctcga ggtcttccag tgcctgttct ccctcacaag | 5580 |
| accgatgtgt gggatcgaga cgtgacgttc cagcctgtcc gaggcgagca gtacgatgtt | 5640 |
| agatggctta tttctggccg aactctcgag gatggtgctt tcgagtctgg tctctttgac | 5700 |
| aaggactctt tccaggagac tctgtctggc tgggccaagg tgttgttgt tggtcgagct | 5760 |
| cgtcttggcg gcattccctt cggtgtcatt ggtgtcgaga ctgcgaccgt cgacaatact | 5820 |
| accctgccg atcccgccaa cccggactct attgagatga gcacctctga gccggccag | 5880 |
| gtttggtacc ccaactcggc cttcaagacc tctcaggcca tcaacgactt caaccatggt | 5940 |
| gaggcgcttc ctctcatgat tcttgctaac tggcgaggct tttctggtgg tcagcgagac | 6000 |
| atgtacaatg aggttctcaa gtacggatct ttcattgttg atgctctggt tgactacaag | 6060 |
| cagcccatca tggtgtacat ccctcccacc ggtgagctgc gaggtggttc ttgggttgtg | 6120 |
| gttgacccca ccatcaactc ggacatgatg gagatgtacg ctgacgtcga gtctcgaggt | 6180 |
| ggtgtgctgg agcccgaggg aatggtcggt atcaagtacc gacgagacaa gctactggac | 6240 |
| accatggctc gtctggatcc cgagtactcc tctctcaaga gcagcttga ggagtctccc | 6300 |
| gattctgagg agctcaaggt caagctcagc gtgcgagaga agtctctcat gcccatctac | 6360 |
| cagcagatct ccgtgcagtt tgccgacttg catgaccgag ctggccgaat ggaggccaag | 6420 |
| ggtgtcattc gtgaggctct tgtgtggaag gatgctcgtc gattcttctt ctggcgaatc | 6480 |
| cgacgacgat tagtcgagga gtacctcatt accaagatca atagcattct gccctcttgc | 6540 |
| actcggcttg agtgtctggc tcgaatcaag tcgtggaagc ctgccactct tgatcagggc | 6600 |
| tctgaccggg gtgttgccga gtggtttgac gagaactctg atgccgtctc tgctcgactc | 6660 |
| agcgagctca agaaggacgc ttctgcccag tcgtttgctt tcaactgag aaaggaccga | 6720 |
| cagggtactc tccagggcat gaagcaggct ctcgcttctc tttctgaggc tgagcgggct | 6780 |
| gagctgctca aggggttgtg a | 6801 |

<210> SEQ ID NO 129
<211> LENGTH: 9251
<212> TYPE: DNA
<213> ORGANISM: Aspergillus nidulans

<400> SEQUENCE: 129

| | |
|---|---|
| gcagcggtaa agccgacaat cttattggca gattggtgcg taagtcaaat cagactttat | 60 |
| tcggtactga ctagctcgac cttccccccc ggtctagact gtctagccga cggaaaacgg | 120 |
| gcgctacgtg cttcaagaga gatcgatcgt ctctgcagaa tgtctccgcg agccttgggg | 180 |
| ctagggcatt gcaaaaaatc gaatttcctg ctactcaagc ccaactaagt gcaaaagaca | 240 |
| tccgttcaat gatactagag acggcggaaa aagctaccgt ctcatttgaa gtcaaagggg | 300 |

-continued

```
gctccctacc gtggggcaga ggctgccaca tcctgatttt ctgctgatca agcaagaacc    360
agcgcccgat tgttacttac tacagtttat agtcgtgacc tcgtgggttt caagacttgc    420
acctcagaat acccgccata ccacatatgg ttagttgcca ggcgatttgc tgaggccgat    480
cctctcccga ggaccaactc cccaacgtga gcttcatatc cgaagattgt gattggtggg    540
atacttgacc ggtgccaaca tgtccgaagg cggctagtat atttctgctc tcgataccac    600
caccgtttat tggttatcgt acgtattgat cttacaggtt gaaacctcga tggctggact    660
acggaggatt ttaagagtat caacaggcca tggttgcttt cctgatgtat accattggga    720
acttgacaag aaagttattg agatgttact tttgaacgaa ttgccggcgg cggtgcaaaa    780
ccggacttct tggaatcctt tgaggacaga cttgtaggaa taaaactccc gagccgacac    840
ttactccgga acaggttccg tacaaacttg gcctatgaaa tactatcgaa atcttactgt    900
actccgcata ctccggccaa caagcagtca gcttatactc cggagaggta agcagataag    960
atgaagagac tcctgtagcg atataaaggt tgccataaat tcccagctga atgatccatt   1020
gatacgatcc acgcgtggta gaggtcgttc gacgcagctg agattcaatc tgtctatgcg   1080
gatatttcaa acgcagcctt atactccgta aaaatactgt actctgcgta attaccgaac   1140
accacctgac tggaaaacca aaaagccaa ctccagcttt cggagcggag tattaatatt    1200
ttggggccaa atggacgtca ttgggagttg gcacgctata tgagacacta aggattctga   1260
aattgcatag gcaggcatac acagtaaaac ggggcaaaaa agtggtggga agagtgcggg   1320
cggcccaaca atgcagtcaa tggggtggga atcctggacc cggactccga agaagattca   1380
ttactgccgc gtatccagat tacgttcctg atccagctcg gtcttttcct cacgttctcc   1440
tcgcctctgt atcatattct tttcccccta gggataaaag aagaagaata ttaggattca   1500
tttttcctct tgttcatttc agatttcttc ttctgactct ctttgaccgg tggtggtaag   1560
tactgcgaat ccttccgttc ctggcgcgct gtaccgccgt ttgcgactga ggcgagtaca   1620
gtagctttcg atttttctgg gacccttcag gttaacgttg cgttctgtca gcccagctct   1680
ttctctcttc atcctccttc cggcacgaat gctctctcct gcctaattga cttatcctgg   1740
ctcttctctt ctgattctcc aacccgggct tatctcacac ccttgtcgtt tcacgaattg   1800
aacgaagccc gtattctccc cttctctctg gaccttcggg ctgttccgc cgactttcct    1860 actttccccc cgaacttctt ttcgagctgc gcattaatat atatcgcatg ggaagcgttt   1920
aatacataat actcaaacag ccactgcaaa tatgggcgtc ccagacggta caacaaacgg   1980
ccacggaggc tctcgagccg ccaaacacaa cctcccctca catttcattg gtggcaacca   2040
cttagacgct gctgccccaa gcagcgtcaa ggactttgtc gctaaccatg aaggtcactc   2100
cgtcatcacc tcggtgagtt tagcctggcg actattgaag aataatttag aggcggtcgg   2160
accggcgact aactagaact ctcactttca ggtccttatc gcgaataacg gtattgcggc   2220
cgtcaaggag attcgatctg tccgaaaatg ggcctacgag acattcggca acgagcgtgc   2280
cattcaattc acagtgatgg caaccccaga agatctggcg gcgaacgccg actatatccg   2340
tatggctgat caatatgttg aggtatggaa acgcctttcg gatgattcgg agtgtatata   2400
atataggtca aatttgttaa atctcctcgc aggtccctgg tggtacgaat aacaacaact   2460
acgccaacgt cgagctgatt gtggatgtgg ctgaacggat ggacgttcac gccgtctggg   2520
ccggttgggg tcacgcctct gagaaccccc ggtaccaga atctctagcc gcttctccca    2580
aaaagatcat ctttattgga cctcccgcct ctgcgatgcg atctcttggt gacaagattt   2640
```

```
cctctactat cgtcgctcag cacgctcagg taccgtgcat tccgtggtct ggaaccggtg   2700
tagatgaggt gaaggttgat gagaacggca tcgttacggt ggaggaagag gtttacaaca   2760
agggatgcac attctctccg gaagagggtc tagagaaagc caagcagatt ggattccccg   2820
tcatgattaa agcctccgag ggtggcggtg gtaagggtat ccgtaaggtt gagaaggaag   2880
aggactttat caacctgtac aatgctgcgg cgaatgagat tcctgggtca cctatcttca   2940
tcatgaagct tgccggtaac gcccgccact tggaagtgca gttgttggct gaccagtacg   3000
gtaacaatat ttcgcttttc ggtcgtgact gttccgtgca gcgacggcac cagaagatta   3060
ttgaggaggc gccagtaacc attgcgaacc ctacaacttt ccaggccatg gaacgtgccg   3120
ccgtgagctt gggtaagctt gtcggttacg tctccgccgg tacggttgag tacctgtact   3180
ctcacgctga tgacaaattt tacttcctgg agctcaaccc cgtctgcag gtcgagcatc   3240
ccaccactga aatggtcact ggtgtcaact tgcccgctgc ccagctccag attgccatgg   3300
gtatccctct gcaccgtatc cgtgacattc gtctgcttta tggcgttgac cccaatacat   3360
cggcggagat agacttcgac ttttccagcg aagagagctt caagactcag cgccgtcctc   3420
agcccaaggg cacaccacc gcttgccgta tcacttccga agatcctggt gagggtttca   3480
agccctctag cggaaccatg cacgagttga acttccgaag ttcatctaac gtttggggtt   3540
acttctctgt cggaacagcg ggtggtatcc acagtttctc cgacagccag ttcggtcaca   3600
tcttcgcgta cggagagaac cgctccgcct cgcgaaagca catggtcatt gccctgaaag   3660
aattgagcat tcgtggtgat ttccggacga caattgagta cctgatcaag ctcttggaga   3720
cgccagcttt tgaggaaaac aagatcacca ctggttggtt ggatcagctg atttccaaca   3780
agctgactgc agagcgtccc gatacaacga tcgctgtgct ctgcggtgct gtcactaaag   3840
cccatcaggc tagcgaggcg cgccttgaag agtaccgtaa cggcattcag aagggtcagg   3900
ttccctctaa ggatgtcctg aaaaccgtct tccccgtgga cttcatctac gagggtaagc   3960
ggtacaagtt cactgccacc cgtgccggtc ttgacagcta tcacctcttc atcaacggtt   4020
ctaagtgctc gattggtgtg cgtgccttgg ctgacggtgg actactcgtc ctcctcaacg   4080
gtcggagcca taacgtatac tggaaggagg aggccgctgc tacccgtatt agtgtggacg   4140
gcaagacttg cttgctcgag caggagaatg atcctactca acttcgtact ccctctcccg   4200
gaaagttggt caagttcacc gtcgagaacg gagagcatgt ccgcgccggt cagccttttg   4260
ctgaagttga agtcatgaag atgtacatgc ctctgatcgc ccaggaggac ggtattgtcc   4320
agctcatcaa gcagcccggt gccacccttg aggctggtga cattcttggt atccttgccc   4380
ttgacgatcc atcccgtgtc aagcatgctc agccgttcac cgagcagctt ccccaattg   4440
gacccctca ggtcgttggt aataagcctg ctcaacgatt tttcctcttg cacagcattt   4500
tggagaacat cttgaagggt ttcgacaacc aggttattat gaactctact ctcaaggagc   4560
tcatcgaggt ccttcgcgac cccgagttgc cttacgcga tggaacgcc cagtcttccg   4620
ccctccactc ccgcatgccc cagaaattgg atgctcagct caaaacatt gttgaccgcg   4680
ctcggtcacg caaggccgag tttccggcca ggcagctgca gaagactatg gtccgattca   4740
ttgaagagaa tgtcaacccct gctgacgccg agatcctgaa gactacactt cttcctttgg   4800
ttcaggttat taataactac atcgaaggct tgaaggcgca cgaatacaag gtgttcgttg   4860
gacttctcga gcagtactac gctgtggaga agctgttctc tggcagcaaa gctcgatatg   4920
aggatggtat cctcgccctc cgtgaggagc acaaggatga tgttgccact attgtgcaga   4980
tcgccctgtc tcacagccgc atcggcgcca agaacgacct catcctcgcg atcctgtcga   5040
```

```
tctaccgtcc caaccagcct ggaatggcca atgtgggcca gtacttcaag tcgattctga    5100
agaaactgac tgaaattgag tcgcgtgctg cggccaaggt caccctgaag gctcgtgaag    5160
tcctcattca gtgcgctctg ccttcgctgg aggagcgtct ttctcagatg gagctcattc    5220
tgcgctcctc tgttgcggag tctcagtacg gcgagaccgg ctgggcccac cgtgagcccg    5280
atctcggtgc cctcaaggag gttgtcgatt ccaaatacac cgtgttcgac gttctgccac    5340
gcttctttgt tcacaaggat gcgtgggtca ctttggcggc tctcgaagtc tatgtgcgcc    5400
gcgcctaccg tgcttactca attcagggta tccagtatca ccacgagggc gagccagcat    5460
tcctgtcttg ggacttcaca atgggcaagc tgggtcagcc tgagttcggt tccatgactg    5520
ctgtcaccca cccctccacg ccaagcacgc ctaccactga atcaaacccc ttcaagcgcg    5580
tctcctcaat cagtgacatg tccaacttgc taaatgacag ccccaacggg actcccagaa    5640
agggtgtcat ccttcctgta cagtacctcg aagatgccga agagtacctc accaaggctt    5700
tggaagtgtt cccaagggct ggcactagga agcctagcga ccatggccta attgcctctc    5760
ttgaggggaa gcgccgtccg gctcccgtg ctgacagtga gtctactgag ctgaccggag    5820
tcttaaacat cgccatccgt gacatcgagg agcttgatga tgcccagatc gttgcccaga    5880
tcagtaagct cgtttctagc ttcaaggacg agttccttgc gcgccgcatt cgtcgtgtga    5940
cgttcatctg cggcaaggat ggtgtctacc ccagctacta caccttcaga ggtcccaact    6000
acgaagagga tgagagtatc cgccacagcg agcctgccct ggccttccag ctcgaactca    6060
accgtctttc caagttcaag atcaagcccg tattcacaga gaacaggaac atccatgtct    6120
acgaggcgat tggcaagggg cctgagaacg ataaggcttt ggacaaacgg tacttcgttc    6180
gcgctgtcgt ccgtcccggc cgactccgtg acgatatccc cactgcggag taccttacct    6240
cggaagctga ccgtttgatg aacgacattc ttgatgccct tgaggtcatt ggcaacaaca    6300
actccgatct caaccacatc ttcatcaact tctcccccgt cttcaactta cagcccaaag    6360
atgtggaaga ggcattagca ggcttcttgg atcgcttcgg ccttcgcctt tggcgccttc    6420
gtgtcactgg tgccgagatc cgcattctat gcaccgatcc cgccactggc atgccatacc    6480
ctctgcgtgt gatcattagc aacactgttg gctatatcat ccaggttgag ctttacattg    6540
agaaaaagtc cgagaaggc gagtggcttc ttcacacgat tggtggcact aacaagcttg    6600
gatccaacca cttgcgtccg gtttccaccc cttaccctac caaggagtgg ctgcagccta    6660
agcgctacaa ggctcacgtc atgggtactc aatatgtgta cgacttccct gagctcttcc    6720
gtgaagcttt ccagaactcg tggaccaagg ccatagagaa gagcccgagc ttgatcgagc    6780
gtcgtcctcc tcttggcgag tgcatggaat acagcgagct tgtcttagac gatactgaca    6840
acctggttga gatttctcgc ggcctggca ccaacaccca cggtatggtt ggatggatag    6900
ttactgctcg caccccgag tatcccgagg gcagacgctt catcattgtt gcgaatgaca    6960
ttaccttcca gatcggttcg ttcggtccat ggaagacaa gttcttccac aaatgtaccg    7020
aattggctcg taagctcgga atccctcgtg tctacctttc tgccaactct ggtgctcgca    7080
ttggtatggc ggatgagctc atcccatact tctccgttgc ttggaacgac cctgctaagc    7140
ctgaggctgg cttcaagtac ctttacctca cacctgaggt gaagaagaag ttcgacgcaa    7200
gcaagcagaa ggaggttatc actgaactga ttcacgatga gggtgaggag cgccacaaga    7260
tcaccaccat tatcgtgcc aaggatggtc ttggagtcga gtgtcttaag ggttctggtc    7320
tcattgctgg tgccacttcc cgcgcttacg aagacatttt taccattact ctcgtcacct    7380
```

| | |
|---|---|
| gccgttcagt cggtattggt gcctaccttg tccgtcttgg acaaagagct attcaggttg | 7440 |
| agggccagcc tatcattctt actggtgctc ctgccatcaa caagctgcta ggaagagagg | 7500 |
| tctatacttc caacctgcag cttggtggta ctcagatcat gtacaggaac ggtgtttctc | 7560 |
| acatgaccgc tgctaacgac ttcgatggtg tcgagaaaat tgtcgactgg cttgccttcg | 7620 |
| tccccgaaaa gaagggctct ctgccaccca tccgaccact cgccgaccct tgggatcgtg | 7680 |
| acgtttctta ccaccctcct gcaaagcaag cctacgatgt ccgttggctc atcaatggta | 7740 |
| aggaagacga ggaaggcttc ctccctggtc tttttgacgc cggctccttc gaggaggctc | 7800 |
| ttggtggctg ggctcgcact gtcgttgttg gtcgtgctag acttggtggc atccccatgg | 7860 |
| gtgttatcgc tgtcgagaca cgctctgtgg agaacgttac tccggctgat cctgctaacc | 7920 |
| ccgactctat ggaaatgatc acccaggaag cgggcggtgt ctggtaccct aactcgtcct | 7980 |
| tcaagactgc ccaggccctc cgggacttca acaacggcga gcagcttccc gttatgatat | 8040 |
| tggctaactg gagaggtttc tctggtggac aacgtgacat gtacaacgag gttctgaagt | 8100 |
| acggttccta catcgtggat gctctcgtca aatacgagca gcctattttc gtgtacattc | 8160 |
| ctccgttcgg tgaactccgt ggtggttctt gggtcgttgt cgaccctacc atcaaccccg | 8220 |
| accagatgga aatgtacgcc gatgaggagg cccgtggtgg tgtcctggag cccgagggta | 8280 |
| tcgttaacat caaattccgc cgcgacaagc agttggagac catggctcgt ttggacccta | 8340 |
| cttacggaga acttcgccgc gctcttcagg acaagaacct cagcaaggag aaactttccg | 8400 |
| acatcaagga caaaatggcg gcacgcgagg agcaactcct tcctgtttac atgcagattg | 8460 |
| cattgcagtt tgccgatctg cacgatcgtg ctggccgcat gcaagccaag aacaccatcc | 8520 |
| gccaagccct ctcctggaag aacgctcgtc gcttcttcta ctggcgtgtt cgccgccgta | 8580 |
| ttagcgagga gtacattatc aagcgcatgc tcaccgcatg ccctgctcct gttcagggtg | 8640 |
| aaggcagcgg agctgtcgcc cagggtgtgt cgcctgcccc tagcgactcc cctcgcacca | 8700 |
| cccatctccg cactttgcac tcatggactc ccttccttga gaacgaggtt gagaatgacg | 8760 |
| accgtcgcgt cgccgtctgg tatgaggaga caaggagct tatccaggag aagattgaag | 8820 |
| ctctcaagtc tcaagccatc gcttcccaga tctccgacgt cctcttcagc aaccgcgaaa | 8880 |
| gcggcctcaa gggcattcag caggctctca gcttcctccc tgttgaagag aaagagtcca | 8940 |
| ttctcaaata cctcggatcc aactagattc acggagtccc ccattgtctc tacgaagaac | 9000 |
| aaacctactc cttgtgaaga attgattat tgcattacta ctatcttctt ttaaagcgcc | 9060 |
| ttgttctttt ctttacattc ttcagatcca gactccttta aggcgacgat tactgattgc | 9120 |
| ttgacggtgg cttgttatgt ttgctttgac tgggttagaa ggcacatgat atggaatggt | 9180 |
| ttggattttg catatactgt tgcgtctttg ttatttagct tttacgtctc attgaatgga | 9240 |
| acatttcata g | 9251 |

<210> SEQ ID NO 130
<211> LENGTH: 7795
<212> TYPE: DNA
<213> ORGANISM: Schizosaccharomyces pombe

<400> SEQUENCE: 130

| | |
|---|---|
| gtcgacattt gagattaaga gatttaaat ttacaagaca tcaaattaga atacaattat | 60 |
| taaaatctat gtatttttag aaaagttgga tgcgtgggaa ctcaaaaaca cgggacttac | 120 |
| catgcgccag agcgttacct cttcctcttc ctgtagcaag ctctacgcga taaaagcaac | 180 |
| catttccctt ccacgactct tttaccgtag actgagaact atggctcctc gtgtagcctc | 240 |

```
ccattttctg ggtatgttat attaatcatt tgatgtagga attgcttgta gaaagttttg    300
agatattgct gagcgtctgc ggatgaaatg ggttgttgtc gaacggtcag aagactagct    360
tttttcgttg ataatttggc aaaaacgagt tagataaact tctttactat gtatacagta    420
attgctagtc tcatttcctc taaaatgaca ctgtgtgcaa aatcgaatgt tcttcatgc     480
ggaacttgct gcccatgttt atcacttttc aagcactagc tgtttgtttt ttccttagaa    540
accattcttt cacgattatt catagaggat acattgtttc tttacgcgta gatttcaaac    600
atggatttgt gtgtctctgc tgttgactgg catgatttta ctcgctcaat ttttaactgt    660
tcgttaagca tgtttaccca cgatacataa ttacttatat tcttacaact ttttcctcat    720
ttcctttgca atcagtcgtc tctgcttttc cttctctccc aatcaagggg ttctttttt     780
aacggttcat ttttattgac gttcttctta tctcgcaact ttcgatttca agcttttctt    840
ttttcatttt gtactttatt aaccatattt taggaggcaa ttccttagat aaagcacctg    900
caggaaaggt gaaagattat attgcatcac acggaggaca cactgttatc acgtctattc    960
ttattgctaa taatggtatt gcggccgtga agaaatccg aagcattcga aaatgggctt    1020
atgaaacctt caataatgaa agagctatca agtttactgt tatggcaacg ccagatgatt    1080
taaaagttaa tgccgattat attcgtatgg ccgatcagta tgtcgaagta cctggcggct    1140
caaataacaa taattatgct aatgtcgaac ttatcgttga cattgctgaa cgtatgaacg    1200
tccatgctgt ttgggctggt tggggacacg catctgaaaa ccctaaattg cctgagatgc    1260
tttctgccag tagtaagaaa atcgttttta ttggtcctcc aggtagcgca atgcgtagtc    1320
ttggtgacaa aattagttct acaatcgttg ctcaaagtgc tcgtgtacct tgtatgtctt    1380
ggtccggtaa tgaactcgac caagtacgta ttgatgaaga gacaaacatt gttactgttg    1440
acgatgatgt ttatcaaaaa gcctgtattc gctctgcaga agaaggtatt gccgtagccg    1500
agaagattgg ttattccgtc atgattaagg cctctgaagg gggtggtggt aaaggtattc    1560
gtcaagttac ttcaaccgaa aagtttgctc aagcattcca acaagtactt gatgaactcc    1620
ctggatctcc cgttttttgtt atgaaacttg ctggacaagc acgccatttg gaagttcaaa    1680
ttttagctga tcaatatggt aataatattt ctcttttttgg tcgtgattgt tccgttcaac    1740
gccgtcatca aaaaatatta gaggctcctg ttaccatcgc acctgccgct accttccatg    1800
aaatggagcg tgccgccgtg cgtttaggtg aattggtcgg ttacgcttct gctggtacca    1860
ttgagtatct ttatgagcca gagaatgaca ggttctattt ccttgaactg aaccctcgtt    1920
tacaggtcga gcatccaact accgaaatgg tttctggcgt taatttaccc gctgcacaac    1980
ttcaagttgc tatgggtttg cctcttagtc gtattccaca cattcgtgag ctctatggct    2040
taccacgtga tggtgactct gaaatcgatt ttttctttca aaatcccgaa tcttttaaag    2100
tacagaaggt ccctactcct aaaggccatt gtgttgcctg tcgtattacg tctgaagatc    2160
ccggcgaagg atttaaacca tcgagcggta tgattaaaga tctcaacttt cgttcttcta    2220
gcaatgtgtg gggttatttc tctgttggta ctgctggtgg aattcatgag ttttcggatt    2280
cccaattcgg tcatattttt tcatttacag aatctcgtga atcctctcgc aaatcgatgg    2340
tggttgcgtt aaaagaatta tctattcgtg gtgattttag aactactgtc gaatatctcg    2400
tgcgtctcct tgaaactaag gagttttctg aaaatgagtt taccacagga tggctagatc    2460
ggcttattgc acaaaaagtt acatctgctc gtcccgacaa gatgcttgct gttgtatgtg    2520
gtgctcttgt ccgtgctcat gctactgccg atactcagta ccgtgctttc aaatcctacc    2580
```

```
ttgaacgcgg tcaagtaccg tcccgtgaat ttttgaaaaa tgtgtatgat attgaattta    2640
tttatgataa cactcgctat cgttttaccg catctcgttc ttctccaggc tcttatcatt    2700
tgtttttaaa tggttctcgt tgtactgctg gtgtccgttc tttgactgat ggtggattgt    2760
tagttttgct aaacggacat tcctatacag tatactatcg tgatgaggta actggtactc    2820
gtatatctat cgataacctt tcttgtatgc tggaacaaga aaatgatcct actcaattaa    2880
gaactccttc ccctggcaag ttggttcgtt tcttggttga acaggtgag catattaaag     2940 ccggtgaagc gtatgcagag gtagaagtta tgaaaatgat tatgccttta gtagcaaccg    3000
aagatggtgt tgttcaattg ataaagcaac ccggtgcatc tttagacgcc ggtgatattc    3060
ttggaatact cacgcttgat gatcctagcc gtgtcaccca tgcattacca tttgatggtc    3120
agcttcctaa ttggggtgag cctcaaattg cgggaaataa gccttgtcaa cgctatcatg    3180
ctcttttgtg tattcttttg gacattctaa agggatatga taaccaaatc attctcaaca    3240
gtacctacaa tgaatttgtt gaagtccttc gtaatcatga attgccctat agcgaatgga    3300
gtgctcatta ttcagcattg gttaatagaa tctctcctgt acttgataag cttttgtat    3360 ctataatcga aaaagccaga tctcgtaaag ctgaatttcc tgccaaacag cttgaggttg    3420
ctattcagac ttattgtgat ggtcaaaatt tggcgacgac tcaacaatta aaggtccaaa    3480
ttgcacctct ccttaaaatc atatctgact acaaagacgg cctcaaagtt catgaataca    3540
atgttattaa aggtttgctc gaagaatatt ataatgttga aaagttgttc tctggaatta    3600
ataagcgaga agaagatgtt attcttcgtc tacgtgacga aaataaagat gatgttgata    3660
aagttattgc gttggcttta tctcattctc gtataggatc taagaataac ttgttaatta    3720
caattcttga tctaatgaag tccgaaccat caacttttgt ttctctgtac tttaatgaca    3780
ttttgaggaa gcttacagat ttggattcaa gggttacttc taaagtgtct ctaaaggctc    3840
gtgagttgtt aattacatgt gctatgcctt ctcttaatga gcgattctct caaatggagc    3900
acatattgaa atcgtctgta gttgaaagtc attatggtga tgctaaattc tcacaccgta    3960
caccatcttt agacattctg aaagaattga ttgattctaa atatacagtc tttgatgttt    4020
tacctgcttt cttttgtcac accgacccat ggtattcttt agctgctctt gaggtatatg    4080
ttagacgtgc ttatcgtgcc tactctgttc ttgaaatcaa ctatcatacc gaggccggaa    4140
ctccgtatgt actcacgtgg cgttttcagc ttcattcaag tggtgctccg ggtttgggtg    4200
ccaactcaac taatggttcc aatttccctg caagcactac tccttcatac gaaaacagca    4260
atcgacgcct gcagtctgtt agtgatcttt cttggtatgt caataaaaca gactctgagc    4320
cattccgttt tggtacaatg attgccgcag aaactttcga tgaattggaa ataaccttg    4380 cccttgcaat cgaccgttta ccactttctc gtaattactt taatgctggt ttaacgttgg    4440
atggcaattc ttcttcagct aacgataaca ctcaagaatt aactaatgta gtgaacgttg    4500
cgttaacctc aactggtgat ttggatgatt ctgctattgt tagcaagctt aaccaaatcc    4560
ttagtgattt ccgtgatgat ttgcttgagc ataatgttag aagagtgaca attgttggtg    4620
gcagaattaa caagtctgct tatccttcct actatactta tcgtgtttcc gctgaacaaa    4680
aagacggcaa tcttgtacac tataacgaag atgagcgtat tcgtcatatt gaacctgcat    4740
tggcattcca attagaattg ggtcgtctat cgaacttcaa tattgaaccc gttttcaccg    4800
ataatcataa cattcatgtt tattcggcta ccgccaaaaa tatggataca gataagcgat    4860
tctttactcg tgcattagtt agaccaggaa gattacgtga cgagataccct actgctgagt    4920 atcttatatc cgaaacccat cgtttaatta atgatatttt ggatgctttg gaagttatcg    4980
```

```
gtcatgaaca aacagacttg aatcatattt tcattaactt tacaccagcc tttggtcttg   5040
ctcctaagca agttgaagct gccctcggag aattttttgga acgttttggc agtcgtttat   5100
ggcgcttgag agtaactgca gctgaaattc gtattatttg cacggaccca tcaactaaca   5160
ctttgtttcc tcttcgtgtc attatttcta atgtttctgg atttgttgtg aacgttgaaa   5220
tttattctga agtcaagact gagaataatt cttggatatt taagagtatc ggacaacctg   5280
gatccatgca tcttcgcccc atcagtacac cttatcctac caaagaatgg cttcaacctc   5340
gtcgttacaa agctcaatta atgggcacta cttttcgttta tgacttccca gaattattcc   5400
gtcgcgcctt caccgatagc tggaaaaagg ttccaaatgg gcgatccaaa gttactatac   5460
cccagaatat gtttgaatgt aaggagcttg ttgctgacga acatggtgta ttacaggaag   5520
tcaataggga gcctggaact aactcctgtg gtatggtagc atggtgcatt actgttaaga   5580
cgcctgaata tcctaatgga cgaaaaatta tcgtagtggc taacgacatc actttccaaa   5640
ttggttcttt tgggccccaa gaggatgaat acttttataa agttactcaa ttggcacgtc   5700
aacgcggtat tcctcgtatt tacctcgctg ccaattccgg tgcacgtatt ggagttgctg   5760
atgaaatcgt ccctctttc  aatattgctt gggtcgatcc cgatagtcca gaaaagggtt   5820
ttgattatat ctatcttact ccagaggcat atgagcgtct tcagaaagaa atcccaata   5880 ttctcaccac tgaggaggtt gttactgaaa ctggggaact tcgccataag attaccacaa   5940
tcattggctc aagcgagggt cttggtgttg aatgtttgcg tggatccggt ctgattgctg   6000
gtgtcacatc tcgcgcatac aatgacattt ttacatgtac tttggtcact tgtcgtgctg   6060
ttggtattgg cgcgtacttg gttcgtctcg gccaaagagc tgtacaaatc gaaggccaac   6120
caattattct aacaggtgca cccgccctta caaggttttt aggccgtgag gtctatacct   6180
ccaacttgca attaggtggt actcaagtta tgcatagaaa tggtatatcc catcttacta   6240
gtcaagatga ttttgatggc atttcgaaaa ttgtaaactg gatttcctat atccccgata   6300
aacgtaacaa tccagtacca atttcaccat catcagatac atgggatcgt gatgtggagt   6360
tctatccttc tcaaaatggt tacgatcctc gttggttaat tgccggaaag gaagatgaag   6420
attctttctt gtatggtttta tttgacaaag gatctttcca ggaaactttg aatggctggg   6480
ccaagactgt tgttgttggt cgtgctagaa tgggcggaat tcctactggt gtgattgctg   6540
tcgagactcg tactattgaa aacactgtac cggctgatcc agctaaccct gactctactg   6600
aacaagtatt aatggaggct ggtcaagttt ggtatcccaa ctcagccttc aagactgctc   6660
aagcaatcaa tgacttcaac catggtgaac agttacctct tttattctt gctaattggc   6720 gtggattttc tggtggtcaa cgtgatatgt ttaatgaggt actcaaatat ggttcttata   6780
tcgtagatgc tttggcttct tataaacaac ctgtatttgt atacattcct ccattcagtg   6840
aacttagagg tggctcttgg gttgtagtag atccaaccat caatgaggat caaatgaaaa   6900
tgtacgcaga tgaagagagt agagctggtg ttttggaacc tgaaggtatg gtcagtatta   6960
aattcagacg tgaaaagttg ctttctttga tgcgacgctg tgatcataaa tatgcatcat   7020
tgtgcaatga gcttaaaaga gatgatttga gtgctgatga cctttcaact ataaaggtca   7080
agttgatgga acgcgaacag aagcttatgc caatttatca acaaattagt attcattttg   7140
ccgacttgca tgatcgtgtt ggtcgtatgg ttgcaaagaa ggttgtccgt aaaccgttga   7200
aatggacaga agctagacgt ttcttttact ggcgtctccg cagacgtttg aatgaacatt   7260
atgctcttca aaagattacc cagctcattc cttccttgac tatccgtgaa tctcgtgagt   7320
```

```
atctccagaa atggtatgaa gagtggtgtg gaaagcaaga ttgggatgaa tctgataagt    7380
ctgttgtttg ttggattgag gaacataacg acgatttgag taagagaact caggaactta    7440
agagtactta ttacagtgag cgtctttcta aactccttcg ttcagatagg aagggaatga    7500
tagacagcct tgcacaagtt tgaccgagc tcgacgaaaa tgaaagaaa gaattggccg      7560 gaaaactcgc gtcggttaat taagagtgcg atgatgattt ttattcttca ttctataaca    7620
tctacatatc ggtcttcaca tgcttgaaaa aatgagatta atagatatgt ttttagataa    7680
ctaagtgcta tgagccttaa tagtaaaagc ccagtcttgc gttacccagc ttttgatttt    7740
taggatggag gtacgttcct ttccttttga tatatactag gtatttgaac tgcag         7795

<210> SEQ ID NO 131
<211> LENGTH: 7874
<212> TYPE: DNA
<213> ORGANISM: Ustilago maydis

<400> SEQUENCE: 131
ggatccaaac tgcgctccag ccaagtcgga aaatctctca tgctccaagc tggaagtctg     60
ggagtgtgcc gctagttccg cctggccggt gcatgggtat tcgcgtgtgt agaggtgtgt    120
gtgtgtgctt tcttccaagt tttttggttt tgcctcgacc atctcccatc ccatcggtcg    180
tccagcactt gatctcacaa accttgactg tgttggctct tccagagaaac gtcgggtctt    240 actgttatca ttcctggcgg tgcgtgccct tcttgcttcc tcaccatcac tatcgtcatc    300
ttcatcctca tccctccttc ctgtgacctc tcagtccaac atctgtccgc caacaccatc    360
ctctggcctt ccgactacgg ctctccgcac ctctttccag ccgcatcgtt ctcaaggttt    420
ccctcaccct tgactatttg ttgcagctcc tacaccacct ctctctcccc gctttacttt    480
cgagctgtca gtgttagtcg agcagacgtt actctcgacc tactcttcga ctcaccagag    540
aatcacgtct aaatccctct cgggctcact ttttctcggac acgctctcgc ttccttcgtc    600
gtcttcgagc tcccctctctc gaacgccgat cgagttgcca cgtaacactc gttcaatcct    660
cgatcgagaa gttttgttct aaagacccaa gcgttctgtc ttgacctatt ccccgaatcc    720
tctgcaagcg cagctcttat ttttacgcac gtaaagaatc agacaaccgt cagaatgccg    780
cctccggatc acaaggcagt cagccagttt atcggtaagt ttgaatgtaa aagtcttgta    840
tttaccctac aagttggcgc tgaccccaact cccaactgcg ctatgcgact acaggcggca    900
acccgcttga aaccgctccc gccagccctg ttgccgactt tattcgcaaa cagggtggtc    960
acagtgtcat caccaaggtc ctcatttgca acaacggtat cgccgccgtc aaggagattc   1020
gctccatccg aaaatgggcc tacgagacct ttggcgatga gcgtgccatt gaatttaccg   1080
tcatggccac ccctgaggac ctcaaagtca atgccgacta catccgcatg gccgaccaat   1140
acgtcgaggt acccggtggc tctaacaaca caaactacgc taacgtcgac ctcatcgtcg   1200
atgtcgctga gcgagccggc gttcacgccg tatgggctgg ctggggtcac gcctccgaga   1260
acccacgcct acctgaatcg ctcgccgcct ccaagcacaa gatcatcttt atcggtcccc   1320
ccggctccgc catgcgctcg cttggtgaca agatctcgtc caccatcgtc gcacagcacg   1380
ccgacgtgcc atgcatgccc tggtccggta ccggcatcaa ggagaccatg atgagcgatc   1440
agggtttcct gaccgtctcg gacgacgtct accaacaggc ctgcatccac accgctgaag   1500
aaggtcttga gaaggccgaa aagatcggct accccgtcat gatcaaggcc tccgaaggtg   1560
gaggaggaaa gggtatccga aagtgtacca acggcgaaga attcaagcag ctctacaacg   1620
ccgttctcgg tgaagtgccc ggctcgcccg tttttcgttat gaaactcgcc ggccaggcgc   1680
```

-continued

```
gtcatctcga ggtgcagctg ctggccgatc agtacggcaa cgccatcagc atctttggtc    1740
gtgactgctc tgtccagcgt cgtcaccaaa agatcatcga ggaggctcct gtcactatcg    1800
ctcctgagga tgcccgcgag tccatggaga aggctgccgt gcgtctcgcc aaactggtcg    1860
gctacgtctc tgccggtacc gtcgaatggc tctactctcc cgagtcgggc gagtttgcct    1920
tcctcgagct caaccccgt cttcaggtcg agcaccctac taccgagatg gtctcggtg     1980
tcaacattcc cgctgcccag cttcaggtcg ccatgggtat ccctctctac tcgatccgcg    2040
acatccgaac cctttacggc atggaccctc gcggtaatga ggtcatcgac tttgacttct    2100
ctagccccga gtcgttcaag acccagcgca agcctcagcc ccagggccac gtagtcgcct    2160
gccgtatcac tgccgaaaac cccgacaccg gcttcaagcc tggcatgggt gccctcactg    2220
agctcaactt ccgctccagc acctccacct ggggttactt ctccgtcgca ccagcggtg     2280
ctctccacga gtacgccgat cgcagttcg gacacatctt tgcctatggt gccgaccgat     2340
ccgaggcgcg aaaacagatg gtcatctcgc tcaaggagct ctccattcgc ggtgacttcc    2400
gtaccaccgt cgaataccte atcaagttgc tcgagaccga cgccttcgag tccaacaaga    2460
tcaccactgg atggctcgat ggtctcattc aggaccgtct cactgccgaa cgacctcctg    2520
cggacctcgc tgtcatttgc ggtgctgccg tcaaggctca tctccttgcg cgtgagtgcg    2580
aggacgagta caagcgcatc ttgaatagag gtcaggtccc tcctcgcgac accatcaaga    2640
ccgtcttctc gatcgacttc atctacgaga acgtcaagta caactttact gccacgcgca    2700
gctccgtctc cggctgggtc ctctacctca acggtggacg tacgctggtg cagctccgac    2760
cccttaccga cggaggtctg ctcattggtc tttcgggcaa gtcgcacccc gtctactggc    2820
gtgaggaggt cggcatgacc cgtctcatga tcgactccaa gacctgcctc atcgagcagg    2880
agaatgaccc cacccagatc cgctcgccct cgcccggtaa gctcgttcgc ttcttggtgg    2940
attcgggcga ccacgtcaag gccaaccagg ccattgcaga gatcgaggtc atgaagatgt    3000
acttgcctct cgttgccgcc gaggacggcg tcgtctcgtt tgtcaagacc gccggtgttg    3060
ctctcagccc tggagacatt atcggtattc tctcgcttga tgaccctagc cgtgtccagc    3120
acgctaaacc cttgctggc cagctgcccg acttttggaat gcccgtcatc gttggcaaca    3180
agcctcacca gcgttacacg gcccttgtcg aggtactcaa cgatatcctc gatgcttacg    3240
accagagctt ccgcatgcag gcggtcatca aggagctcat cgagacgctc cgcaacccg     3300
agctgcccta cggtcaggcc tcccagattc tgtccagctt gggcggccgt atccctgcca    3360
ggctcgagga tgtggtgcgc aacacaattg agatgggcca ctcgaagaac attgagttcc    3420
ccgctgctcg tctgcgcaag ctcaccgaga acttcctccg tgacagcgtc gaccctgcta    3480
tccgcggaca ggtgcaaatc accattgctc ctctctacca gctcttcgag acctacgctg    3540
gcggcctcaa ggctcatgag ggcaacgtgc ttgcttcgtt cctccaaaag tactacgaag    3600
ttgagtccca gtttaccggt gaggctgacg tcgttctcga gcttcgtctc caggccgacg    3660
gcgacctcga caaggttgtg gccctgcaga cttcgcgcaa tggcatcaac cgcaaaaacg    3720
ctctgctgct caccttgctt gacaagcaca tcaagggcac ctcgcccgtc tcgcgtacta    3780
gcggtgctac catgatcgag gctctgcgca agcttgcctc gcttcagggc aagtcgactg    3840
cccccatcgc cctcaaggct cgtgaggtct cgctcgacgc cgacatgccc agtcttgccg    3900
accgatcagc tcagatgcag gccattcttc gtggctccgt cacctcgtcc aagtatggtg    3960
gtgatgatga gtaccatgct ccctcgcttg aggttctccg cgagctcagc gactcacagt    4020
```

```
acagcgtgta cgatgtgctg cacagcttct tcggtcaccg cgagcaccat gtcgcctttg    4080
ccgcgctctg cacctacgtc gtccgcgcct accgagctta cgagattgtc aacttcgact    4140
atgccgttga ggactttgac gtcgaagaac gcgctgtgct cacctggcag ttccagctgc    4200
ctcgaagcgc ttcttcgctc aaggagcgtg agcgtcaggt gtctatcagc gacctcagca    4260
tgatggataa caacaggagg gctcgcccca tccgcgagct gcgcactggt gccatgacca    4320
gctgcgccga tgtggccgac attcctgaac ttctccctaa ggttctcaag ttcttcaagt    4380
cttctgccgg tgccagtgga gcgcccatca atgtgctaaa cgttgctgtt gtcgaccaga    4440
ctgactttgt cgacgccgaa gtgcgaagcc agcttgccct gtacaccaat gcctgcagca    4500
aggagttttc cgctgctcgt gtccgccgtg tcacctacct cctttgccag cccggcttgt    4560
atcccttctt cgccaccttc cgtcccaacg agcaggcat ctggtccgaa gagaaggcga    4620
ttcgcaacat cgaacccgcg cttgcctacc agcttgagct cgacagggtc agcaagaact    4680
ttgagctcac ccccgttccg gtctcgtcgt ccacgatcca tctctacttt gctcgtggta    4740
tccagaactc ggccgatacc cgattctttg ttcgctcact cgtccgtccc ggccgcgtgc    4800
agggcgacat ggctgcatac ctcatctccg aatcggaccg cattgtcaac gatattctca    4860
acgtcatcga ggtagctctt ggccagcccg agtaccgcac cgccgatgct tcgcacatct    4920
tcatgtcttt catctaccag ctggatgtca gcctcgtgga tgtgcagaag gctattgccg    4980
gcttccttga gcgacacggc acccgcttct tccgtctccg catcacaggt gccgagatcc    5040
gcatgattct aaacggtccc aacggcgagc ccgcccgat ccgagccttt gtcaccaacg    5100
agaccggtct ggtcgtccga tacgagacat acgaggagac tgtcgccgat gacggctctg    5160
tgattctgcg cggcatcgag ccccagggca aggatgccac gctcaatgcc cagagcgcac    5220
acttccctta cacaaccaag gtggcactgc agtcgcgacg atctcgtgcc cacgctttgc    5280
agaccacctt cgtctacgac tttatcgatg tgcttggtca ggccgtgcgt gcgtcgtgga    5340
gaaaggttgc tgccagcaag attcccggtg atgtcatcaa gtcggccgtc gagttggtct    5400
ttgacgagca ggagaacctg cgtgaggtca agcgtgctcc tggtatgaac aacatcggca    5460
tggttgcttg gctcgtcgag gtgctcaccc ccgagtaccc cgctggccgt aagctcgttg    5520
tcatcgggaa cgacgtcacc atccaggctg gctcgttcgg ccccgttgag gaccgcttct    5580
tcgctgctgc ctccaagctc gcccgtgagc ttggtgtgcc gcgcctctac atctcggcca    5640
attcgggtgc ccgtatcggc ttggcaactg aggcgctcga cctgttcaag gtcaagttcg    5700
tcggcgacga ccctgccaag ggtttcgagt acatctacct cgacgacgag tcgctccaag    5760
ccgtccaggc caaggcgccc aacagtgtca tgaccaagcc cgtccaggcc gctgatggca    5820
gcgtccataa catcatcacc gatatcatcg gcaagcctca gggggtctc ggtgtcgagt    5880
gtctgtcggg cagtggtctc attgccggtg agaccagccg tgcaaaggac cagatcttca    5940
ctgccaccat catcacggga cgaagtgtcg gtatcggtgc ctatcttgct cgtctgggcg    6000
agcgtgtaat ccaggtcgag ggctcgccct tgatcctcac tggttatcag gcactcaaca    6060
agctgctggg tcgtgaggtc tatacctcga acctacagct cggtggtcct cagatcatgt    6120
acaagaacgg tgtttctcac ctcactgctc aggacgacct cgacgctgtc aggtcgtttg    6180
tcaactggat atcatacgtt cctgctcagc gtggtgacc tctgccgatc atgcccacca    6240
ccgatagctg ggaccgagcg gtcacatacc agcctcctcg tggtccttac gacccacgat    6300
ggctcatcaa cggtaccaag gccgaagacg gcaccaagct caccggtctt ttcgatgaag    6360
gctcatttgt cgagacgctt ggcggctggg ccacttcggt agtcactggt cgtgctcgcc    6420
```

```
tgggcggcat ccctgtcggt gtgatcgctg tcgagacgcg cacgctcgag cgtgttgttc    6480
cggccgaccc tgcgaacccc aactcgaccg agcagcgcat catggaagcc ggccaggtgt    6540
ggtaccccaa ctcagcgtac aagactgccc aagccatctg ggactttgac aaagagggtc    6600
tgcctttggt catccttgcc aactggcgtg gattttcggg tggccagcag gacatgtacg    6660
acgagatcct caagcagggc tccaagatcg tcgacggtct gtcgtcgtac aagcagcccg    6720
tgtttgttca cattccacct atgggtgagc ttcgcggtgg ttcgtgggtc gtggtcgact    6780
ctgcgatcaa cgacaacggt atgatcgaga tgtcggccga tgtcaacagc gcacgaggtg    6840
gtgtgctgga agcctcaggt ctggtcgaga tcaagtaccg tgccgacaag caacgtgcta    6900
ccatggagcg actcgacagc gtctatgcca agttgagcaa ggaagctgcc gaagcgaccg    6960
acttcaccgc gcagaccacc gctcgtaagg cgttggcaga gcgagagaag cagctcgcac    7020
ctatctttac ggcgatcgct accgagtatg cagatgcaca cgaccgtgca ggacgcatgc    7080
ttgcgactgg agtgctgcga tcggcgctgc catgggagaa cgcgcgtcga tacttctact    7140
ggcgtctcag gagaaggttg accgaggtcg ctgctgaacg cacggttggc gaggccaacc    7200
cgacgctgaa gcatgttgag aggctggctg tattgcgaca gtttgttggt gctgctgcga    7260
gcgatgacga caaggcggtg gctgagcact tggaggcttc ggccgaccag ctgttggccg    7320
catccaaaca gttgaaggca cagtacatct tggctcagat ctcgacattg gaccctgaac    7380
tgcgcgctca actagccgct tcgctcaagt aatggacgtg actcttgcaa gaattcgttc    7440
tccaggcgcc aggcgatcgt tggcgcgatt gacatcggat tgagggatcc acatgccatt    7500
ctccttcacg agcacctggc tttacgttga acgaattttt acgatgcaga cctcattacg    7560
ctctgcatga gcgctcttct ggaatcagat ctctcaaaga ccactgaggg gtggtctgcg    7620
aacctcttag aagtagcgca cgcactgggc gatggtccct gtcaattgtt cttgttcttg    7680
ttcttgtttt ggttttgat tatgttcttt tcagcgttta aatgtcccg tggctgcgca    7740 atcgtgaagg ttgattttcg gctgatgtgg gcgcgacgtg tggccgaact agcataattc    7800
tctcttgcac acgagagctt ggtctgcaga gtgctggcgg cgattggaga gagtcacgag    7860
atcaagtagt cgac                                                     7874
```

<210> SEQ ID NO 132
<211> LENGTH: 7367
<212> TYPE: DNA
<213> ORGANISM: Gallus gallus

<400> SEQUENCE: 132

```
catcgccgcg cccccagcac cgccgctgcc ctgcaccagg ccgggggccc gcggcgcctc      60
caccgcgccc ggcaccctga gttcattttg gaagtggata actgctcaga ttgcaagaat     120
aacaagagtg ctgagagctc aatttgggga gccatggaag agtcttccca acctgctaaa     180
cccctggaga tgaaccctca ctctcgcttt attattggtt ccgtgtcaga ggataactca     240
gaagatgaga cgagctcctt ggtgaaactt gacctgctgg aggagaaaga gaggtctctg     300 tccccctgttt ctgtctgctc ggattccctt tcggatttgg gacttcctag tgctcaagat     360
ggtttggcaa accatatgag gcccagcatg tctggtttgc acctcgtaaa gcaaggccgg     420
gacaggaaga agttgacgt gcagcgggat ttcactgtgg cttctccagc agaatttgtt     480
actcgttttg gagggaacag agttattgag aaggtcctga tagccaacaa tgggattgca     540
gcagtgaaat gcatgaggtc gatccggcgc tggtcctatg agatgttccg aaacgagcgg     600
```

```
gcaatcagat tgttgtcat ggtgactcct gaggacctga aagcaaatgc agagtacatt      660
aaaatggcag atcactacgt gccagttcca ggaggaccaa caacaacaa ctatgcaaat       720 gtggaactca ttctcgatat tgcaaaacgc attccagtgc aggctgtttg ggctggctgg     780
ggccatgcct ccgagaaccc aaaactacca gaacttctcc acaaaatgg gattgctttc      840 atgggtcctc caagccaagc aatgtgggct taggagata aaattgcgtc gtcaatagtg      900
gctcagactg ctggcatccc aactcttcct tggaatggca gtggtcttcg agtggattgg    960
caggagaatg atcttcagaa gcgtatcctg aatgttcctc aggagctgta tgaaaaaggc   1020
tatgtgaaag atgcagacga tggcctgcgg gctgctgagg aagttggcta ccctgtcatg   1080
atcaaggcct ctgaaggagg aggagggaag ggaattagga aagtcaataa tgcggatgac   1140
ttccccaacc tatttagaca ggttcaggct gaagtcccag gctctccgat ctttgtaatg   1200
aggctagcca acagtcccg ccacttggag gtgcagatcc tggcagacca gtatggcaat     1260
gccatctctc tctttggtcg ggattgctcc gtgcaacgca ggcatcagaa gattattgaa   1320
gaagcacctg cttctattgc aacttcggtg gtatttgagc acatggaaca gtgtgcagtg   1380
aagcttgcaa aaatggtggg gtatgtgagt gcgggcactg tggaataccct gtacagccag   1440 gatggcagct tctactttct ggagttgaat ccccgtctgc aagtggagca ccctgcacc     1500 gagatggtag ctgatgttaa tcttcctgca gcacagctcc agattgccat ggggattcca   1560
ctccaccgta tcaaggatat ccgagtgatg tatggtgttt ccccatgggg agatggatct   1620
attgattttg agaattcagc ccatgtcccc tgtccacgtg gccatgttat tgctgcacgt   1680
atcaccagtg agaatcctga tgagggattt aagcccagtt ctggtacagt ccaggaactg   1740
aatttccgca gcaataagaa tgtttggggc tatttcagtg ttgctgctgc aggagggctg   1800
catgaatttg ctgattctca gtttggtcac tgcttctctt ggggagagaa tcgtgaagaa   1860
gccatctcaa acatggtggt ggctttgaag gagctgtcca tccgagggga tttccgaacc   1920
actgttgaat acttgataaa actgttggaa acagaaagct tccagcagaa ccgcattgac   1980
actggctggt tggatcggct tattgctgag aaagtgcagg ctgaaaggcc tgataccatg   2040
ctaggagtgg tatgtggagc tcttcatgtg gctgatgtga gctttcgaaa cagcgtctca   2100
aacttcctgc actctttaga aaggggccaa gtcctgcctg ctcatacttt gctaaacact   2160
gtggatgtgg aactcatcta tgaaggacgg aaatatgtgt tgaaggtgac ccgacagtct   2220
cccaattcct acgtggtcat catgaacagc tcttgtgtgg aagttgatgt gcacagactg   2280
agcgatggag ggctgctcct atcttacgat ggtagcagct acaccaccta catgaaagaa   2340
gaagtggaca ggtatcgcat cactataggt aacaagacct gtgtgtttga aaaggaaaat   2400
gatccttcta ttctgcgctc accttcggct gggaagctta ccagtatgt ggtggaggat     2460 gggggacacg tgtttgcagg ccaatgcttt gcagaaatag aggtgatgaa aatggtgatg   2520
acactaacag caggagagtc aggctgcatc cattatgtca aacgccccgg ggcagtgctg   2580
gatccaggct gtgtgattgc caaactccag ctggatgatc ccagcagggt tcagcaggct   2640
gaactgcaca caggcacctt gccacagatc cagagcacag cacttcgagg cgaaaaactc   2700
catcgcatct tccattatgt cctggataac ctggtcaacg tgatgaatgg gtactgcctg   2760
ccagagccct actttagcag caaggtgaag ggctgggttg agcgactaat gaagacactg   2820
agagatccat ctttgcctct gctggaactt caggacatca tgaccagtgt ttctggacgg   2880
attccaccca atgtggagaa gtccatcaag aaggagatgg cccaatatgc cagcaacatc   2940
acgtcagtcc tttgccagtt tcccagccaa cagattgcca atatcttgga tagccatgca   3000
```

```
gccaccttga accgcaaatc agagcgtgag gtcttttca tgaacactca gagtattgtg    3060
cagcttgtac agaggtaccg gagtggtatt cggggtcaca tgaaagcagt ggtcatggat    3120
ttgctccgtc aatatctgaa ggtggagact cagtttcagc atggtcacta tgacaagtgt    3180
gtctttgccc ttcgggaaga gaataaaagc gacatgaatg ctgtattgaa ctacatcttc    3240
tcacatgctc aggtcaccaa gaagaacctg cttgtcacaa tgctcattga ccagctctgt    3300
ggccgtgacc ccaccctgac agatgagctg atcaatattc tgacagagct gacccagctc    3360
agcaagacaa ccaacgccaa agtggcgctg cgggcacggc aggttctcat tgcttcccat    3420
ttgccgtcct acgagctgcg tcacaaccag gtggagtcca tcttcctatc tgctattgac    3480
atgtatggac accagttctg cattgagaac ctgcagaaac tcattttgtc agagacatcc    3540
atctttgatg tgctacccaa cttttttctac cacagtaatc aggtggtgag aatggcagct    3600
ttggaggtgt acgttcgaag ggcgtacatt gcctacgagc tgaacagcgt ccagcaccgc    3660
cagctgaagg acaacacctg cgtggtggag ttccagttca tgctgccacc ctcccaccca    3720
aacagaatgt ccttctcttc aacctcaat cactacggga tggtccacgt agccagtgtg    3780
agtgacgtgc tgctggacaa ctcgttcact ccccccgtgcc agcggatggg agggatggtc    3840
tctttccgca cgtttgaaga ttttgtcaga atctttgatg aagtgatgag ttgttttgc    3900
gactctcctc cccagagccc aaccttccct gaagctggcc atgcttccct ctatgatgaa    3960
gacaaggctg cccgtgagga gcccattcac attcttaatg tcgctattaa aactgatggg    4020
gacgtggatg atgatgggct ggcagccatg ttcagagagt tcacacaaag caagaaatca    4080
gtcctgattg agcatggcat ccggaggctg acattccttg tggcacagaa gagggaattt    4140
ccaaagttct tcacgttccg tgccaggat aagtttgaag aagacagaat ctaccgccat    4200
ctggagccag ctctggcttt ccagctggag ctgaaccgaa tgcggaactt tgacctcact    4260
gccattccat gtgccaacca taaatgcat ctctacctgg agcagctaa agttgaagta    4320
ggaacagaag tgacagacta caggttcttt gtgagggcca ttataaggca ttcagacctt    4380
gttaccaagg aagcctcctt cgagtacctg caaaacgagg gagagcgatt gcttttggaa    4440
gccatggatg agttggaggt ggcatttaat aataccaacg tgcgcacgga ctgcaatcac    4500
atcttcttaa attttgtgcc tactgtcatc atggacccat ccaagatcga ggaatccgtg    4560
cggagcatgg tgatgcgcta cgggagccgc ctgtggaagc tccgcgtcct ccaggccgag    4620
ctgaagatca acattcggct gacaccgaca ggaaaggcca tccccattcg tctcttcctg    4680
accaacgagt cgggctacta cctggacatc agcctgtaca aagaggtgac ggattccagg    4740
acagggcaga ttatgttcca ggcctatggg gataaacagg gaccacttca cgggatgctg    4800
ataaatacc catacgtgac caaggacctt cttcagtcca agagattcca ggcacagtct    4860
ttagggacat cctatgtcta tgacattcct gagatgtttc ggcagtcttt aattaaactc    4920
tgggattcta tgaatgaaca tgcattcctg ccaacaccgc cgctgccgtc tgacatactg    4980
acatacactg aattggtgct ggatgatcag ggccagctcg tgcacatgaa caggctgcca    5040
ggaggaaacg agattgggat ggtagcctgg aaaatgaccc tcaagacccc ggagtatccc    5100
gaaggccgtg atatcatcgt cattggcaat gacattacgt accggatagg ttctttgggg    5160
cctcaggagg acgtgctgtt cctgagggct tcagagcttg ctcgaactca tggcatcccc    5220
cgcatctacg tggctgccaa cagcggagcc aggattggtt tggctgagga gatccggcac    5280
atgttccatg ttgcgtggga agatccagat gacccataca aaggatacaa gtacttgtat    5340
```

```
ctgacacctc aagactataa gaaagtcagc gctctgaact cagttcactg tgaacacgtg    5400
gaggacaacg gagagtccag gtataagata acagatatta tcggaaagga agacggactt    5460
ggaatagaga acctcagagg atctggcatg attgctggag aatcatcttt agcctacgag    5520
agtattatca ccatcaactt ggttacgtgt cgggcaattg gaattggagc ttacctcgtt    5580
cggttagggc agaggactat ccaggttgag aactctcaca taatcctgac tggctgtgga    5640
gccctcaaca aggtgctggg acgggaggtg tacacctcca caaccagct gggcgggatc     5700 cagatcatgc acaacaacgg ggtgacccac ggcaccgtgt gcgacgattt gaaggagtc     5760 tacactatcc tgctgtggct ttcctacatg cccaagagcg tatacagccc tgttcctatc    5820
ctcaaggtca aggatcctat agacagaacc atagacttcg ttcctaccaa gactccctat    5880
gatcctcgct ggatgctggc tggacgccca aatccaagtc aaaaagggca atggcagagc    5940
ggtttctttg acaatggctc gttcctggag atcatgcagc cctgggcaca gacggttgtg    6000
gttggcagag caaggctggg aggaatacct gtaggagtag ttgccgtaga aaccagaaca    6060
gtggagctga gcatccctgc tgatcccgcc aacctggact cggaggccaa gataatccag    6120
caggctggtc aggtgtggtt ccccgactct gcctttaaga cagcccaggc catcaacgac    6180
ttcaacagag aagggctgcc tctgatggtc tttgccaact ggagaggctt ctctggtggc    6240
atgaaagaca tgtacgacca ggtgctcaag tttggtgcct acatcgtgga cggcctgcgg    6300
gagtaccggc agcccgtgct catctacatc ccaccgcagg cggagctcag gggcggctcc    6360
tgggctgtca tcgaccccac catcaacccc aggcacatgg agatgtacgc ggaccgtgaa    6420
agcagagggg gaatcctgga gccggagggg acggtggaaa tcaagttccg caggaaggac    6480
ctggtgaaga caatgaggag agtggacccc gtctacatgc ggctggccga gcggctgggt    6540 accccctgagc tgagtgctgc cgaccgaaaa gacctggaga gcaaactgaa ggagcgggag    6600
gaattcctga ttcccatttta ccaccaggtg gccatgcagt ttgctgacct gcacgacaca    6660
cccggccgca tgcaggagaa gggtgccatc acggacattc tggactggaa aacgtctcgg    6720
accttcttct actggaggct gagacgtctt cttctggaag atgtggtcaa aaagaagatc    6780
catgatgcca accctgagct gaccgacggg cagatccagg ccatgctgcg acgctggttt    6840
gtggaagtgg aggggacggt aaaggcgtac ctgtgggaca gcaataagga cctggtggag    6900
tggctggaga agcagctgat ggaggaggag ggggttcgct cggttgtgga tgagaacatt    6960
aagtacatct ccagggatta catcctgaag cagatccgca gcctggtcca ggccaatccc    7020
gaggttgcca tggattcgat cgtgcacatg acccagcata tatcacccac ccagcgagcc    7080
gagatcgtgc ggatcctctc cacaatggac tctccttctt caacgtaaga gcatcgattt    7140
cctgtactcc cccctgctcg gtacagtgga ggggaagaaa aaagaaaaa aagctcagaa     7200 ttgcccttt tctgctcaac tgcgaccgct gtaccgagac ggggaggctc agggaaacgc     7260
tggaagagtg acagttttag tttttttcaaa ccagactgac cagaggaagt cgctttggcc    7320
ggagacacga ggaagatgta taaacacggg ccctgcagga ttgagtt                  7367
```

<210> SEQ ID NO 133
<211> LENGTH: 1359
<212> TYPE: DNA
<213> ORGANISM: Mesoplasma florum

<400> SEQUENCE: 133

```
atgttaaaat tcctaaaaaa ttttcacatc ggtgcttcaa tgagtgctat gcaaacagaa      60
ggaaaaggaa ttactgaaat aggtgattta acttttgatg catatttcaa agaaaatccg     120
```

```
gaattgtttt accatggtgt tgggccagat ctgacaagtg atattacaag acactataaa      180
gatgatattg aaaaatttaa atacatcgga ttagattcag ttagaacagg ttttcttga       240 gctagattat ttccagatgg tattaatcta aacaaagaag cagtaaagtt ctatcatgac      300
tatatcgatg agtatttaaa aatgatatt gaaattatta tgactttatt tcactttgac      360
atgcctttat gagcacatga attaggtggt tgagagagca gagaagttat tgaaaaattt      420
ataagttatt gtgaatttgt attcaaggaa tatggatcaa aaataaatta ttttgttacc      480
ttcaatgaac cacttgttcc tgtatttgaa ggatatgtag gtaaaatgca ctatcccgca      540
aaggatagtc ccaaagaagc tgtagctcaa gcatatggaa ttttcctagc tcatgctaaa      600
gcagtaaagt tatttaaaga attaaaaatt gattcaaaaa taggagttgt ttataactga      660
aactttacat tcccattttc agattcagca gaagataaaa tttcagctga aatctatgat      720
gcttatgtaa atagaggacc attaaacatt atgtataatg gaaatattaa cccaattatt      780
ataaaaacct tagaagaata taacataact ccatttcaca caagcgaaga aattgaaata      840
attaaacaaa ctgaaattga ttttttagga gttaattatt atttccttg tagagttaaa       900 acaaatgaaa atgtaaaaaa tagatgagct ttagatcaaa tgcatattga aattcctgca      960
gatgcaaaaa ttaatccttt tagagggtga gaaatttatc ctgaagggct atatgatata    1020
tctatagcaa ttaaaaaga gttaaataac attccatgat acattgctga aatggtatg       1080 ggtgttgaaa atgaagatag atttagaaat gaaaatggac aaatagatga tgattacaga    1140 attgagttt tagaaactca tatgtctgaa ttaaaaagag gtttagatgc tggatcaaat     1200
tgttttggtt accacatttg agctgccatt gactgctgaa gctttagaaa tgcttataaa     1260
aatagatatg gtttaattga agttgattta aagaccaat ctagaaagtt taaaaaatca     1320
gcttactgat ataagaact aatagaaaat aaggagtaa                            1359

<210> SEQ ID NO 134
<211> LENGTH: 1152
<212> TYPE: DNA
<213> ORGANISM: Oryza sativa

<400> SEQUENCE: 134
atgataaatg agctagtaaa agcaggtatt cagattcatg ctgttctgta ccatatagat       60
cttccacaga gccttcaaga tgagtacggt ggatgggtta gccccaaagt tgtggatgac      120
ttcgcagcat acgctgatgt gtgcttccgc gagttcggtg acagagtcgc gcattggaca      180
acttccattg agccaaatgt catggctcaa tctggctatg acgatgggta tctcccgcca      240
aatcgttgct cgtatccgtt tggcagaagc aactgcacac taggaaattc cacggttgag      300
ccatacttgt tcatacacca caccctgcta gctcatgctt cagctgttag actttacagg      360
gaaaagcacc aagctgcaca gaagggcgtt gtcggcatga acatatactc catgtggttc      420
tacccactca cagagtcaac tgaagatatt gctgccactg aaagagtaaa ggatttcatg      480
tatggatgga tcttgcatcc tttggtgttt ggagattacc cagagaccat gaagaaggcc      540
gccggttccc gtcttccatt attctctgac tacgaatctg agctggttac taatgcgttc      600
gacttcattg ggttgaatca ttatacctca aattatgtga gcgataatag taacgcagta      660
aaggcgccgc tacaggatgt cactgacgat atttcttctt tgttctgggc cagcaagaat      720
agcacaccta ctcgagagtt tctaccaggg acctcattag atcctcgggg gctagagctc      780
gcgcttgaat atcttcagga aaagtatgga aatttgctgt tttatatcca ggaaaacggt      840
```

| | |
|---|---|
| agtggatcaa atgcaaccct ggatgatgtg gggaggattg actgcttgac acaatacatt | 900 |
| gcagccacgc tgcgatccat caggaatggc gccaacgtga agggatactg cgtgtggtca | 960 |
| ttcatggatc agtacgagat gtttggcgat tacaaggcgc atttcggcat tgttgccgtc | 1020 |
| gattttggca gcgaagaact gacaaggcag cccaggcgct ctgctagatg gtactcggac | 1080 |
| ttcttgaaga acaatgctgt catcaaggtg gatgatggtt ctgtctccac agccttccat | 1140 |
| gctcagcttt ga | 1152 |

<210> SEQ ID NO 135
<211> LENGTH: 2292
<212> TYPE: DNA
<213> ORGANISM: Pseudomonas putida

<400> SEQUENCE: 135

| | |
|---|---|
| tcaaagcaat tcaaagctct gctgctgcac cgcctgggaa tccagcccta cctggacatt | 60 |
| gaactcccct ggttcggcaa cccgctgcaa ctggccattg tagaacttca ggtcgtcctc | 120 |
| gctgatgcgg aaggtcaacg tgcgggtttc acccggttca agcatcagct tctggaagtt | 180 |
| tttcagctct tcactgggc ggctcatcga cgccgacaca tcctgcaggt acagctgcac | 240 |
| caccgtctcg cctgcaacct tgccggtgtt cttgaccgtt accttggcat ccagcgtatc | 300 |
| gccgcgcttg agatccttgc tgacaggtt caggcctgac agctcgaagc tgctgtagct | 360 |
| caagccatag ccgaacggat aaagcggccc gttgggttct tcgaagtatt gcgaggtgta | 420 |
| gttgcccggc ttgcccggcg tgaacggccg ccgatgcgg gtgtggttgt agtacatcgg | 480 |
| gatctgcccc accgaccgtg ggaaggtaat ggccagcttg ccggagggt tgtagtcgcc | 540 |
| aaacagcacg tcggcgatgg cattgccgcc ttcggtgccg cgaaccagg tttccaggat | 600 |
| ggcgtcggcc tgctcgcgct cccagctgat cgacagcggc cggccgttca tcagcaccag | 660 |
| caccagcggt ttgccggtgg ccttgagcgc cttgatcagc tcgcgctggc tggccgggat | 720 |
| ctccagggtg gtgcggctcg acgactcgtg ggacatgccg cgggactcgc cgaccactgc | 780 |
| gaccacgacg tcggattgct tggctgcctt gattgcttca tcgatcagca ccgcaggcgg | 840 |
| gcgtgggtcg tcgacgattt ccggggcatc gaagttgagg aagttcaggt aatcgaagat | 900 |
| cgccttgtcg cccgtgacgt tggagccttt ggcgtagacc agcttggcct tgccttccac | 960 |
| ggcgcggcgc aagccttcgc gcacggtcac cgagtggacg ggtttaccgt cggcggccca | 1020 |
| gctgcccatc atgtcgatcg gagcatcggc cagcgggccg accaaggcaa tggtgccggc | 1080 |
| cttttttcagc ggcagggtct ggttgcggtt ttccagcagc accaggctgc ggcgtgccac | 1140 |
| gtcgcgcgca gcttcgcggt gcaggcgtc gttgccgtag tagtccttca gatcggtttc | 1200 |
| ggccttgccg atgcgcacgt acgggtcctt gaacaggccc atgtcgtact ggcacccag | 1260 |
| cacttcacgc accgcctggt ccagctcgcg ctgggtcacc tgccggact tcagcaggcc | 1320 |
| cggcagctct tcgccgtaca gggtatcgtt catgctcatg tcgatgccgg ccttgatcgc | 1380 |
| cagcttggcg gcttcacggc cgtcacgggc gacgccgtgg cgaatcagct cctggatggc | 1440 |
| accgtggtcg ctgatggtca cgcccttgaa gccccactcc ttgcgcagca ggtcgttcat | 1500 |
| cagccaggtg ttggaggtgg ccggtacgcc gttgatcgag ttcagcgcca ccatcacgcc | 1560 |
| accggcaccc gcatcgagcg cggcgcgata gggtggcagg tagtcgttgt acattttcgg | 1620 |
| caggctcata tcgaccgtgt tgtagtcgcg cccgccttcc acggcgccat acaaggcgaa | 1680 |
| atgcttgacg atggccatga tgctgtcggg gttggccggg ctgctgccct ggaacgagcg | 1740 |
| caccattacc tggccgattc tcgaagtcag gtaggtgtct tcgccgaaac cttcgcttgt | 1800 |

```
gcggccccag cgcgggtcac gggcgatatc caccattggc gcgaacgtca tgtccagggc   1860
gtcggccgag gcttcgatcg cggcggtgcg gccgaccttg gcgacggcct ccatgtccca   1920
ggtcgcggcc atgcccaggc cgatcgggaa gatggtgcgc tcgccgtgga cggtgtcgta   1980
ggcgaagaac atcgggatct tcaggcggct gcgcatggcc gcgtcctgca tcggccggtt   2040
ttcgggggca gtgcgtgagt tgaaggtgcc accgatacgg ccggcggcga tttcctcgcg   2100
gatcttgtcg cggggcattt ccgggccgat gctgatcagg cgcaactggc cgattttttc   2160
ggcttcggtc atctggctga tcagatgctc gataaaggcc tgcttgtcct gtaggggcgg   2220
ggcggtgggg gcggcgaggg ccgcctgact ggcaaggccc atggccaggc ccagcaaaga   2280
cagtttcatc at                                                       2292
```

<210> SEQ ID NO 136
<211> LENGTH: 2742
<212> TYPE: DNA
<213> ORGANISM: Pseudomonas syringae

<400> SEQUENCE: 136

```
atgaacaagc gaaagatgat aggcgcgcac tcggcgctgg ccttgctggc actggccgtt     60
tctcaggtgc acgccgctga tccgactgtg cagcagggac gtgaagaccg cgctgaaaaa    120
gccgcgcaaa agaccctggc gaaaatgacc atggaagaaa gctggcctat catcggcggc    180
accggcggct gggatgtgaa gccgctgacc aactacggcg ttccgcagat tcacggcgct    240
gacggcggcg tgggcgtgcg ttacaccagc gaaggcaacg atcagggcgt ggtctatccg    300
tccggcccta acctggcagc caccttcaac ccgcgtcgcg ccatcgacct gggccgtgct    360
ctgggttatg acactgcgac cggcggctac cagttcatca caggtccagg tgtaaacctg    420
taccgcatgc cttacggcgg ccgtgcattc gaatacctttc cggtgaagaa tccgttcctg    480
ggcgccagcc tggcaccggg tgtcatcaac ggtatccagt cccgtggtgt gtgggccaac    540
gccaagcact acgcggccaa cgaccaggaa agcaaccgtt tcaatcttga ccagaagatg    600
cccgagcgcg tactgcgtga atgtcgctg cctgcgttcg agtcgtcgtc gaaaaacggc    660
aatgttgcga tgatgatgtg cgccttccag aaagtgaacg gtgatttcgc ctgcgaaagc    720
gagcacctga tcgcccagat cctgaagaag gaatgggggct acaaaggctt cgtgcagagc    780
gactacaacg ctgtggtgca cggctttgaa gctgcccgcg ccggtaccga tctggacatg    840
atgggctacc agatgaacag ctccgtgctc aagccgcacc tggacgccgg tgacctgagc    900
gctgcgacca tcgatgacaa ggtgcgccgc atcctcaagc agatctacct gtacaagttc    960
gacagcaagg caccgctgac cacccacaac atgaacagct cgaccagcaa caaggtcgct   1020
ctgaatgctg cgcgtgaagg catcgtgctg ctgaaaaacc agggcgatct gttgccactg   1080
gacaagcaga aggtcaagaa aatcgccgtc gtcggcaccc tggccaaata tgcaccaccg   1140
accggtttcg gtagcgccaa tgtcatggcc agccattacg tcagcgagtt gagcggcctg   1200
cagcaaatgg cacccaacgc caaggtcgag ttcatcgatg gcctgtcgct ggacccaagc   1260
acctctgcct ggaacaccac tgacgccgct ggcaacagtg ttcagggcat gaaggtcgaa   1320
tacttcagca acaccaactg gtctggcgat gcagcggtca cccgtaccga gcagcacgtt   1380
gacctggact gggccaacga caagaacctg ccgttcgaga gcaacacctc aacgtccgat   1440
ccgtacacca ccaaaggctc gaccgctggt gagctgaacg gtgacacgtc ttcgacctcg   1500
atccgctaca ccggcaagat cacccccgacc cagagcggcg aacaggtgtt caaggtgcgt   1560
```

```
gccgacggcg ctgtgcgcct gtgggtcaac ggcaagaaaa tcatcgacaa cggtgacggc     1620
aagccattgc cgggcaacag catcccgccg accattccag agttcgccaa gatcaatctg     1680
gaagcaggcc agtcctacga cgtgaagctt gagtactcgc gtcgcgccgg gtacctgtcg     1740
accatgggtg gtctggtcgg tgtgcagttg agctccgctt cgctgaacgc gcctcaggac     1800
ctgtccggtt atgacgcggt tgtgcttgca gtgggtaaca gcaacgaata cgaaggtgaa     1860
ggtttcgacc acagcttcga tctgcccgag ttccagaacg aactgatcca gaacatcgcc     1920
aaggtcaacc cgaacaccgt ggtgaccatg tatggcggta ccggcctgaa gatgagcgac     1980
tggatcgaac aggttccggt agcgctgcac gccttctacc cgggtcagaa cggtggtcag     2040
gccctggccg aaattctgtt cggcaagatc aacccgtcgg gcaagctgcc gatcagtatc     2100
gaacgcaaca tcgaagacaa cccggcctac gcctccttcc cgaaattcga caaccagaac     2160
acgctggctg aaatggatta caaggatgac ctgatgctgg gttatcgcgg ttacgagaag     2220
aaaggcatca agccgcttta cccgttcggt tacggcctgt cgtacaccac gttcggctac     2280
agcaacatca aagtcacgcc aggcgtcgcg gtgggcaata cgccgatcaa ggtgtccttc     2340
gacctgacca acaccggcaa ggtcggcggt tcggaagttg cacagctgta cgttggccag     2400
cagaacccga agtcgagcg tccgatcaag gaactcaaag gctacaagaa ggtgttcctc     2460
aagccgggtg aaagcaagcg cgtgaccatc gagctcaatg accgctcgct ggcctacttc     2520
gacgtgaaaa ccaaccagtg ggtggttgac gccgacacct tcaacctgtc gctgggtggc     2580
tcgtcgcagg acattcgcct gaacgccaag ctggtcaact cgttccgcca ggaactgtcg     2640
accactacca gcaacccgct gccacgttcg gcgctgaact cggtgctggt cgagaagcca     2700
ccggtcaaga ccggtggtgt gttccagcag actgtcgagt aa                       2742
```

<210> SEQ ID NO 137
<211> LENGTH: 2580
<212> TYPE: DNA
<213> ORGANISM: Streptomyces coelicolor

<400> SEQUENCE: 137

```
gtggggacga gtgacgaaga gatcgaccgg ctgctcggca agctgacacc acgcgcccgc       60
gcactgctgc tgaacggcgc cacgacctgg cgcacgaggg cggaaccagc ggtggagctg      120
agggagttgg tgatgtcgga cggtccggcg ggcgtacggg gcgaggcctg ggacgagcgg      180
agcacctctc tcctgctgcc ctccgcctcg gcgctcgccg ccacctggga cgaggcgctg      240
gtcgaagacc tcggtggcct gctcgccgcc gaggcccggc gcaagggcgt ggacgtcctc      300
ctcgccccga ccctcaacct gcaccgcagc ccgctgggcg gccggcactt cgagtgcctc      360
tccgaggacc ccgagctgac cggccggatc ggcgccgcgc tggtccgcgg gatccaggcg      420
cacggcgtgg ccgccaccgc caagcactac gtggccaacg actccgagac cgaccgcctc      480
accgtcgacg tgcgggtggg cgaacggcg ctgcagaggg tctacctcgc cccttcgag       540 gcggcggtgg ccgccggggt ccggctcgtc atggcggggt acaacgcggt caacggcacc      600
acgatgaccg cgaacgccct cctcaccgac ccgctgaaga gcgagtgggg cttcgacggc      660
gtcgtcgtgt ccgactgggg cgcggtgcgc ggcacgaccg gcaccgcccg gccggtctc       720 gacctcgcca tgccgggtcc cgacggcccc tgggcgaagg cgctggcccg cgcggtggcc      780
gagggcgcgg tgccgaacc ggccgtcgac gacaaggcac ggcgcctgct gcgactcgcg       840
gcgtggctgg gcgcgctggg cgggcgcgac gtgtcccgt cgccggtccc gggcaggccg       900
gccgactcgc cgggtgcgga gggtgcggac ggtgggcgg gcgctggccc gtcgtccggt       960
```

-continued

```
gcggagggcc tcccgggccg gggcccggcg cacggtgcga agccgtccgg gccccgaccg    1020
cggcgtgccg gggacgggcg ggcgctggcc cgtcgtgccg tcgccgccgg ggccgtgctg    1080
ctggccaaca aggacgtcct gccactcgac cccgagcacc tcgggacggt cgccgtgatc    1140
ggcgcgcacg ccgcgcggac ccgtacccag ggcggcggca gcgcgggcgt cttcccgcgg    1200
ggcgaggtgt ccgtcctcga cggcatccgg gccgaactgc gcggccgggc ccgcgtcgtg    1260
cacgtcccgg gcccccggcc ggacggcccc gcgcccccac tggacccgga cacatgcacc    1320
gacccgcgct cggggctgcc cggcgtcctg ctgcggatgc tcgacgcgga cggccgcgag    1380
ctgtacgccg aacggcgccg cggcgggcgc ctgctggagc cccgcctggt gccgggcgcg    1440
cacaccgtcg agatccgcgc ccggctgtgt cccgcaccg gcggctcctg gtccctgggc    1500
gtggccgggt tcggccggat gagcctgacg acggacggac gcaccctgct ggaggggac    1560 ttcccgccgt ccaccgacga tccgcggtg atgcacgtca acccgcccgc ccagtacgcc    1620
accgccgacc tcaccgccgg ccgggacacc ctgctggtgg cccggcgcga gctggcaccc    1680
ggcaccggcc gggcgaccgt cctcgtcgcg gccccgcccg ccccgacgt gaccgcgtcg    1740 ctcgccgagg ccgtccgcgc ggccggtgcg gcggacgccg cggtcgtggt cgtcggcacc    1800
accgagcacg gggagtcgga gggctacgac cgtacggacc tggcgctcgg cgccacccag    1860
gacgcgctgg tccgcgccgt cgcggccgcc aaccccgcgca ccgtcgccgt cgtcaacagc    1920
ggcggcccgg tggaactgcc gtggcggag caggcgggtg cggtgctgct ggcctggttt    1980 cccgacagg agggcggcgg tggactggcc gacgtgctct cgggcacgc cgagccgggc    2040 ggacgactgc ccaccacctg gccggccgtc ctcgccgacg ccccggtcac ccgcacccgc    2100
cccgacggcg gccgctcga ctacgacgag ggactgcacc tcggtcaccg gggctggctg    2160
cgccatcacc gcacgcccgc ctactggttc ggacacgggc tcggctacac gacgtggcgg    2220
tacgaggagc tgaccgtccc gccggtgacc cgggcgggcg acggcctcac cgtgcgcgtg    2280
cgggtgcgca acaccggtgc gcgagcgggc cgggaggtcg tccaggtgta cctggcccgg    2340
cccgcgtcgg ccctcgaccg tcccgcgcgt tggctcgccg ggtacacggc ggtgcgggcg    2400
cgcccggggg agacggtgac ggcgacggtg cgcgtcccgg cgcgggccct cgccactgg    2460 tcggtggcg agcacgcgtg gcgtaccgag gcggggccct gccgggtgct ggccgggcgg    2520
tcggcggggg acgtgccgct ggccgcggag gtggaggtgg tgcctacggc ttccgcgtga    2580
```

<210> SEQ ID NO 138
<211> LENGTH: 1410
<212> TYPE: DNA
<213> ORGANISM: Caulobacter crescentus

<400> SEQUENCE: 138

```
tcagggggag gacggcaagg tcccggtctg cgccaaggcc ttgaaccagc cgtaggacgc      60
cttcgggatc ctacggccgc tggcggcttc catcgtcgtg atcccaaact cgaggtgta     120 gcccaggtcc cactcgaaat tgtcgatcag ggtccactcg aaataccccc ggacgtcaca     180
acccgcctcg cgggccgcca gcaccgcctc aaggtggcgg cgcaagtact tgatgcggaa     240
ggtgtcatcc aagatcgctg gaccgctgct gaacgggtcg gaacatccgt tctcggtcac     300
cagcatcttg ggcgcgccgt actcgcggcg cacacgatcc agaacctcga acaggccgga     360
cggatctatg tgccgccga acgcgtcctg ctcggcgcta ttgggcgcgg cggcggcggc     420
gatcttgctg ggcgccgaca gatccagccg cacgtaggcc ggcgcgtagt agttcacccc     480
```

```
caggaaatca acaggctggc gcgtggtctt caagtcgccg tcgcgaacca cgcccttgag    540
cggctcctcc atcgccttgg ggtaggttcc cttgaacagc gggtcgagcc aggcaaggtt    600
ccagatctcg tccagaccat ccgacgccag ccggttccag aacgccaatg cccacccgc     660 cggccggcac ggctgaagcg ccatcgtggt gcctaccgaa aggtcgctcc gcgccgcgcg    720
cagagcctgg atcgccagac cctggcccag attcatatgg tgcgtgactg gacccagcag    780
cgcagcgtcc ttgagccccg gcgcatgatc gcccagcacg tggccgaaca cggtatggac    840
cgccgcctca ttgagaatga tgtagttctt cagccggtcg cccagccgct cgaccacggc    900
gcgcgcatag tccgccagac gctgggccgt gtcgcggttc gcccagccgc ccttgtcctg    960
caggccttgc ggcaggtccc aatgaaacag ggtggcgtag ggcgtgatcc ccttggccag   1020
cagcgcgtcg accagccgcg aatagtgatc gaggcctgcg gcgttcaccg cgcccgcccc   1080
ggtcggcaga atccgcgacc agctcatcga gaaccgataa gcgctcaggc tggcgccggc   1140
gatcaggtcg acatcgtcct ggtagcgccg atagctgtcg gtggcgtccg cagcggtgtc   1200
gccattcttg acgtggcccg gaactctctc gaacacgtcc cagatgctgg gcccgcgccc   1260
gtcggcggtt tgcgaacctt cggtctggaa agcggccgta gccacgcccc agacaaagtc   1320
cttcggaaac tgccgaccct tgggggtcag gtccgtttcg cccggcccct cgcacgccga   1380
tagccccaga gccgcgccgc ccagggccaa                                    1410

<210> SEQ ID NO 139
<211> LENGTH: 2158
<212> TYPE: DNA
<213> ORGANISM: Candida wickerhamii

<400> SEQUENCE: 139
gaattcaatt gaagtcatga tgtttgcatt ttgccaattt gtcagtttac ttagaatttc     60
attatttaaa tgatactttt tgcctttgtg gaagtatttg aaattttatc aattaaaaac    120
tgttaagaaa agatgttctc acaaaagtat ctttttatcat tagctgcaat aattgcaatc    180
gctaaagcag ctccagctga tgacgcttct aaaccaggta ttgggaaatt tgcaccaggt    240
caattaggtt tccgttatta tatcgacacc accaccgagt acgcaactcc tgccactgct    300
actgctcctg caagttccac tacgtacgct gcaccatatg ctgaattgtc atccttggtt    360
ggaaacttgt ccacgacgac atgggtaat tggtatcctg acgctaccga ggctgccacg    420
gatactgatg acccatatgg acaatacgca tggtctcaat tatgggaagc taccactttc    480 ccaaattta ctcgtggtat ttacagtacc acggtggatc caacaccgat cccaaccgag    540
agtttagttg tgccaccaga tgacccagtc aagagggcat tccaagattt gggaatcaaa    600
ttccctctgg gtttcattca aggtgttgcc ggttccgctg ctcaaattga aggtgccgtc    660
gccgatgaag gtagatcacc aactaattta gaagttagtt ccgctagtag acatttacct    720
gaagatttcg tcactaatga aaattattat ctttacaaac aagatatcac cagattagca    780
gctatcggcg ttgaatacta ttcgttcact atcccatgga ctagaatctt accattcgcc    840
tatcccggtt ctcctgtgaa tcaacaaggt ttagatcatt atgacgactt gatcaacact    900
gtcttagcat atggaatgaa accaattgtc acattgatcc atttcgattc accattacaa    960
cttgtcgact tcaatgccac attggaattg ggactgccag gtggatacga aggtgaagat   1020
ttcgtcgagg catttgtcaa ttacggtaaa atcgtcatga cccatttcgc tgatcgtgtc   1080
ccattatgga tcatctttaa tgaacctgtc caattcgcca ctaatggact cggtgtcaaa   1140
catgtcgtcc aagccacggc tcaattatac gatttctacc ataacgagat caacgggtcc   1200
```

-continued

```
ggtaagattg gtatgaagtt cagtcacatc ttcgggttcc ctgaggatcc aactaaccca    1260
gaacatgttg ctgccgcaga cagatcaaat gaattgcaat taggtctctt tgctgatcca    1320
ttgttcttag gtgaagacta cccagacagt ttcaagacca cattattgaa aacgcagcca    1380
gcactggctt ggacactgga tgaattagcc gctgttaagg gtaaatgtga tttcttcggt    1440
gttgatccat acacttataa cactatcaag ccattggata acggtactgc atcatgtgaa    1500
gccaacgtca ccgacactta ctggccaacg tgtgtcaatg tcaccgttac tgaagctgat    1560
aactggagta tcggttaccg ttcccaatcc tatgtctaca tcacaccaag acaattaaga    1620
gtctcgttga actacatctg gcaacactgg cacgttccta tcttcatcac ggaatttggt    1680
ttccctgaat ggagagaagg tgagaaactc ttagttgacc aagtccaaga tttggacaga    1740
tccatttact acagatcttt cttgactgca gcattagagg catctcagta cgacggtgtc    1800
gagataatgg gtgccttggc ttggagtttt gccgataatt gggaattcgg tgattataac    1860
caacaattcg gtttacaagt cgttaataga actactcagg agagattcta taagaagagt    1920
ttctttgatt ttgtcggttt tattaatgat aatagagctt gagatcccta atccatttat    1980
gattatattt tttaaaaaac tttctatgat gactattatt tctttaatga cattactaca    2040
ctaaatgtca atttctttac ttacgcttct tttattttat aacccagaaa agttgatata    2100
caatttactt gtcttttacc aatttaaata aaaaattaaa taaataaaat tcaagctt     2158
```

METHOD FOR THE PRODUCTION OF RESVERATROL IN A RECOMBINANT OLEAGINOUS MICROORGANISM

This application claims the benefit of U.S. Provisional Application No. 60/682,651 filed May 19, 2005.

FIELD OF THE INVENTION

The invention is in the field of molecular biology and microbiology. Specifically, the invention relates to production of resveratrol in a recombinant oleaginous microorganism. More specifically, a method to produce resveratrol is exemplified in a recombinant oleaginous yeast (*Yarrowia lipolytica*). Expression of genes involved in the phenylpropanoid pathway along with a resveratrol synthase gene enables production of resveratrol at concentrations exceeding 0.01% dry cell weight.

BACKGROUND OF THE INVENTION

Resveratrol (trans-3,4',5-trihydroxystilbene) and/or its corresponding glucoside (piceid) are stilbene compounds reported to have many beneficial health effects. Resveratrol is a potent antioxidant, decreasing low density lipid (LDL) oxidation, a factor associated with the development of atherosclerosis (Manna et al., *J. Immunol.*, 164:6509-6519 (2000)). It is also reported to lower serum cholesterol levels and the incidents of heart disease. This effect as been attributed to a phenomenon known and the "French Paradox". French citizens that regularly consume red wine tend to have lower incidents of heart disease and serum cholesterol levels even though this same group tends to consume foods high in both fat and cholesterol. There is also evidence that resveratrol may have other cardiovascular protective effects including modulation of vascular cell function, suppression of platelet aggregation, and reduction of myocardial damage during ischemia-reperfusion (Bradamante et al., *Cardiovasc. Drug. Rev.*, 22(3):169-188 (2004)). Resveratrol is reported to have anti-inflammatory effects associated with the inhibition of the cyclooxygenase-1 (Cox-1), an enzyme associated with the conversion of arachidonic acid to pro-inflammatory mediators. It may also aid in the inhibition of carcinogenesis (Schultz, J., *J Natl Cancer Inst.*, 96(20):1497-1498 (2004); Scifo et al., *Oncol Res.*, 14(9):415-426 (2004); and Kundu, J. and Surh, Y., *Mutat Res.*, 555(1-2):65-80 (2004)).

Resveratrol is classified as a phytoalexin due to its antifungal properties. It appears that some plants produce resveratrol as natural defense mechanism against fungal infections. For example, red grapes have been reported to produce resveratrol in response to fungal infections. Fungal cell wall components can stimulate local expression of the resveratrol synthase gene in grapes. The antifungal property of resveratrol has been applied to plants that do not naturally produce the compound. Transgenic plants modified to express the resveratrol synthase gene exhibit improved resistance to fungal infections. Furthermore, it has been reported that treatment of fresh fruits and vegetables with an effective amount of resveratrol will significantly increase shelf life (Gonzalez-Urena et al., *J. Agric. Food Chem.*, 51:82-89 (2003)).

Use of resveratrol in commercial products (e.g., pharmaceuticals, personal care products, antifungal compositions, antioxidant compositions, dietary supplements, etc.) is limited due to the current market price of the compound. Methods to extract resveratrol from plant tissues such as red grape skins, peanuts or the root tissue of *Polygonum cuspidatum* are not economical. Means to produce resveratrol by chemical synthesis are difficult, inefficient, and expensive. There is a need for an efficient and cost effective method to synthesize resveratrol.

Resveratrol and/or resveratrol glucoside are naturally produced in a variety of herbaceous plants (Vitaceae, Myrtaceae, and Leguminosae). The resveratrol biosynthesis pathway is well known. In plants, a single type III polyketide synthase (resveratrol synthase; E.C. 2.3.1.95) catalyzes three consecutive Claisen condensations of the acetate unit from malonyl CoA with the phenylpropanoid compound p-coumaroyl CoA, which is succeeded by (1) an aldol reaction that forms the second aromatic ring, (2) cleavage of the thioester, and (3) decarboxylation to form resveratrol.

Industrial microbial production offers a possible means to economically produce commercial quantities of resveratrol. Microbial production requires functional expression of the resveratrol synthase gene in the presence of suitable quantities of malonyl CoA and p-coumaroyl CoA. Cost-effective microbial production generally requires host cells having the ability to produce both malonyl CoA and p-coumaroyl CoA in suitable quantities from a relatively inexpensive carbon substrate.

Many naturally occurring microorganisms, such as *E. coli* and *Saccharomyces cerevisiae*, produce malonyl CoA, albeit in relatively low quantities ranging from barely detectable levels up to about 30 µM (Davis et al., *J. Biol. Chem.*, 275: 28593-28598 (2000) and Subrahmanyam, S, and Cronan, J., *J. Bacteriol.*, 180:45964602 (1998)). Since malonyl CoA is involved in fatty acid biosynthesis, a host cell capable of synthesizing significant amounts of oil (e.g., an oleaginous microorganism) may produce suitable quantities of malonyl CoA (or may exhibit the ability to accommodate high-flux malonyl CoA production).

Recombinant microbial production of resveratrol also requires the substrate p-coumaroyl CoA. This phenylpropanoid compound is ubiquitously produced in plants, but is found in relatively low quantities (if at all) in many microbial host cells. As such, the microbial host cell selected for resveratrol production should be engineered to produce p-coumaroyl CoA.

The enzyme coumaroyl CoA ligase (E.C. 6.2.1.12) catalyzes the conversion of para-hydroxycinnamic acid (pHCA) to p-coumaroyl CoA. In the past, coumaroyl CoA ligases were generally considered to only exist in plants, however a coumaroyl CoA ligase was recently reported in the filamentous bacterium *Streptomyces coelicolor* (Kaneko et al., *J. Bacteriol.*, 185(1):20-27 (2003)). Recombinant microbial expression of coumaroyl CoA ligase has been reported (Becker et al., *FEMS Yeast Research*, 4(1):79-85 (2003)); Keneko et al., supra; Watts et al., *Chembiochem*, 5:500-507 (2004); and Hwang et al., *Appl. Environ. Microbiol.*, 69(5): 2699-2706 (2003)).

Recombinant biosynthesis of coumaroyl CoA requires a suitable source of pHCA. The source of pHCA may be supplied exogenously to the host cell or it may be produced within the host cell. Preferably, the host cell can be engineered to produce suitable levels of pHCA when grown on an inexpensive carbon source, such as glucose. Recombinant microbial host cells engineered to produce and/or accumulate phenylpropanoid-derived compounds (I.e., p-hydroxycinnamic acid) have been reported (U.S. Pat. Nos. 6,368,837, 6,521,748, U.S. application Ser. Nos. 10/138,970, 10/439, 479, 10/621,826; and Schroder, J. and Schroder, G., Z. Naturforsch, 45:1-8 (1990)). Recombinant expression of a coumaroyl CoA ligase in cells engineered to produce para-hydroxycinnamic acid (pHCA) results in the production of p-coumaroyl CoA (p-coumaric acid).

Microbial expression of enzymes involved in the phenylpropanoid pathway to produce the flavanone narigenin is described by Watts et al. (supra) and Hwang et al. (supra). Specifically, Watts et al. describe the simultaneous expression of a phenylalanine ammonia lyase, a tyrosine ammonia lyase, a cinnamate 4-hydroxylase (C4H), a coumaroyl CoA ligase, and a chalcone synthase (E.C. 2.3.1.74) in *E. coli* to produce narigenin and phloretin up to 20.8 mg/L. However, Watts et al. were not able to actively express cinnamate-4-hydroxylase (C4H) in *E. coli* and had to supply exogenous p-coumaric acid or 3-(4-hydroxyphenyl)propionic acid to obtain significant concentrations of the desired products. Watts et al. do not describe recombinant microbial production of resveratrol.

Hwang et al. describe recombinant bacterial (*E. coli*) production of the flavanones pinocembrin and narigenin by simultaneously expressing phenylalanine ammonia lyase, coumaroyl CoA ligase, and a chalcone synthase (E.C. 2.3.1.74). The bacterial coumaroyl CoA ligase used by Hwang et al. was able to convert both cinnamic acid to cinnamoyl CoA and p-coumaric acid to p-coumaroyl CoA, resulting in the production of pinocembrin (from phenylalanine) and naringenin (from tyrosine) as the PAL used also exhibited tyrosine ammonia lyase activity, resulting in the production of pHCA. In the absence of exogenously supplementing the medium with excess L-phenylalanine and/or L-tyrosine, only small amounts of each flavanone are produced (<0.3 µg/L). Hwang et al. do not describe recombinant microbial production of resveratrol.

Becker et al. (supra) describe recombinant expression of several phenylpropanoid pathway genes in *Saccharomyces cerevisiae* FY23 for the production of resveratrol. Genes encoding a coumaroyl CoA ligase and a resveratrol synthase were recombinantly expressed in *S. cerevisiae* in a culture medium supplemented with pHCA, producing resveratrol in amounts up to 1.45 µg/L in the culture volume. Becker et al. report that experiments supplementing the culture medium with additional precursors necessary for resveratrol production do not produce significantly more resveratrol. Becker et al. do not illustrate a method to produce significant quantities of resveratrol in a recombinant host cell, including production of resveratrol from a commonly used (and economical) fermentable carbon source (e.g., glucose).

The problem to be solved is to provide a method for recombinant microbial production of resveratrol in significant amounts.

SUMMARY OF THE INVENTION

The stated problem has been solved by engineering an oleaginous microorganism (e.g., oleaginous yeast) to produce resveratrol. The recombinant host cell (*Yarrowia lipolytica*) was genetically modified to produce resveratrol by introducing several genes from the phenylpropanoid pathway in combination with a suitable resveratrol synthase gene. The recombinant host cell produced p-coumaroyl CoA through recombinant expression of at least one nucleic acid molecule encoding an enzyme providing phenylalanine/tyrosine ammonia lyase activity and at least one nucleic acid molecule encoding an enzyme providing coumaroyl CoA ligase. This, in combination with the oleaginous host cell's natural ability to produce a suitable amount of malonyl CoA enabled production of resveratrol in significant quantities (at least 0.03% dry cell weight).

Accordingly the invention provides a method for the production of resveratrol comprising:
  a) providing an oleaginous microbial host cell comprising:
    1) at least one nucleic acid molecule encoding an enzyme having resveratrol synthase activity;
    2) a source of malonyl CoA and coumaroyl CoA;
  b) growing the oleaginous microbial host of (a) under conditions where malonyl CoA and coumaroyl CoA are reacted to form a product selected from the group consisting of resveratrol and resveratrol glucoside; and
  c) optionally recovering the product of step (b).

In other embodiments the invention provides methods of the invention which additionally make use of nucleic acid molecules encoding various other enzymes and their corresponding substrates such as coumaroyl CoA ligase/p-hydroxycinnamic acid; tyrosine ammonium lyase/tyrosine; cinnamate-4-hydroxylase/cinnamic acid; phenylalanine ammonium lyase/phenylalanine.

In another embodiment the invention provides a recombinant oleaginous microorganism comprising at least one nucleic acid molecule encoding an enzyme having resveratrol synthase activity which produces a product selected from the group consisting of resveratrol and resveratrol glucoside. Optionally the recombinant oleaginous microorganism of the invention may also comprise at least one nucleic acid molecule encoding an enzyme having an activity selected from the group consisting of; coumaroyl CoA ligase, tyrosine ammonium lyase, cinnamate-4-hydroxylase and phenylalanine ammonium lyase.

In another embodiment the invention provides a composition selected from the group consisting of antioxidants, anti-inflammatory agents, antifungal/antimicrobial agents, cosmetics, cosmeceuticals, nutritional/dietary supplements, feed additives, and pharmacological agents comprising 0.1 to 99 wt % recombinant oleaginous microbial biomass having at least 0.01% (dry cell weight) resveratrol and/or resveratrol glucoside.

BRIEF DESCRIPTION OF THE FIGURES SEQUENCE DESCRIPTIONS

The invention can be more fully understood from the following detailed description, the figures, and the accompanying sequence descriptions that form a part of this application.

FIG. 1. The resveratrol biosynthetic pathway. Phenylalanine (Phe) or tyrosine (Tyr) can be converted into para-hydroxycinnamic acid (pHCA). Phenylalanine can be converted into tyrosine using an enzyme having phenylalanine hydroxylase activity. The tyrosine is then converted into pHCA using an enzyme have PAL/TAL activity. Optionally, phenylalanine can be converted into cinnamic acid (CA) using an enzyme having PAL/TAL activity. A cytochrome P450/P450 reductase system (cinnamate 4-hydroxylase activity) converts cinnamic acid to pHCA. The pHCA is converted into p-coumaroyl CoA by coumaroyl CoA ligase. Malonyl CoA (naturally produced in suitable quantities in the oleaginous. microorganisms) and p-coumaroyl CoA are converted into resveratrol by resveratrol synthase (stilbene synthase).

Figure 2:
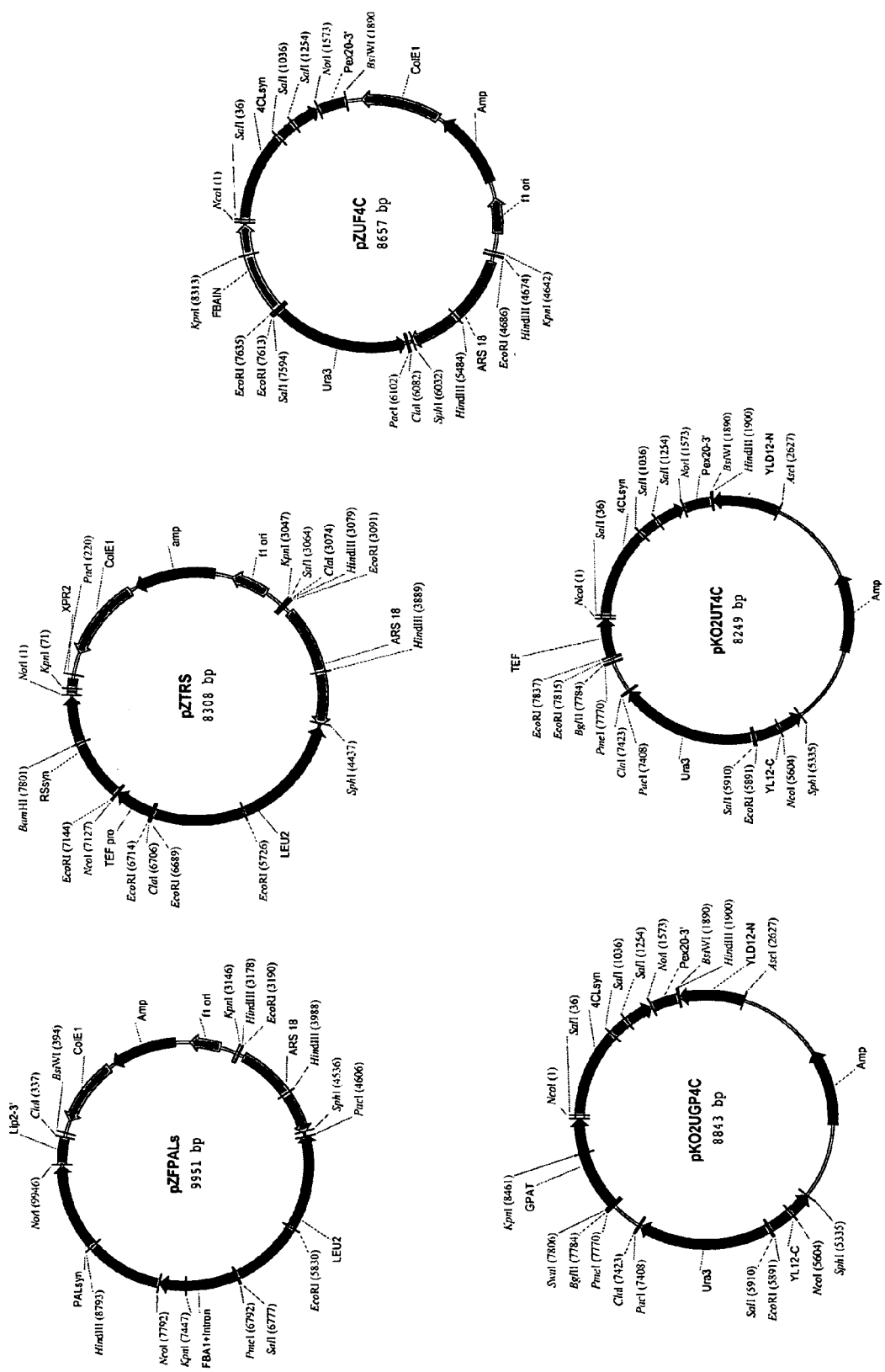

FIG. 2. Plasmid maps for pZFPALs, pZTRS, pZUF4C, pKO2UGP4C, and pKO2UT4C.

Figure 3:
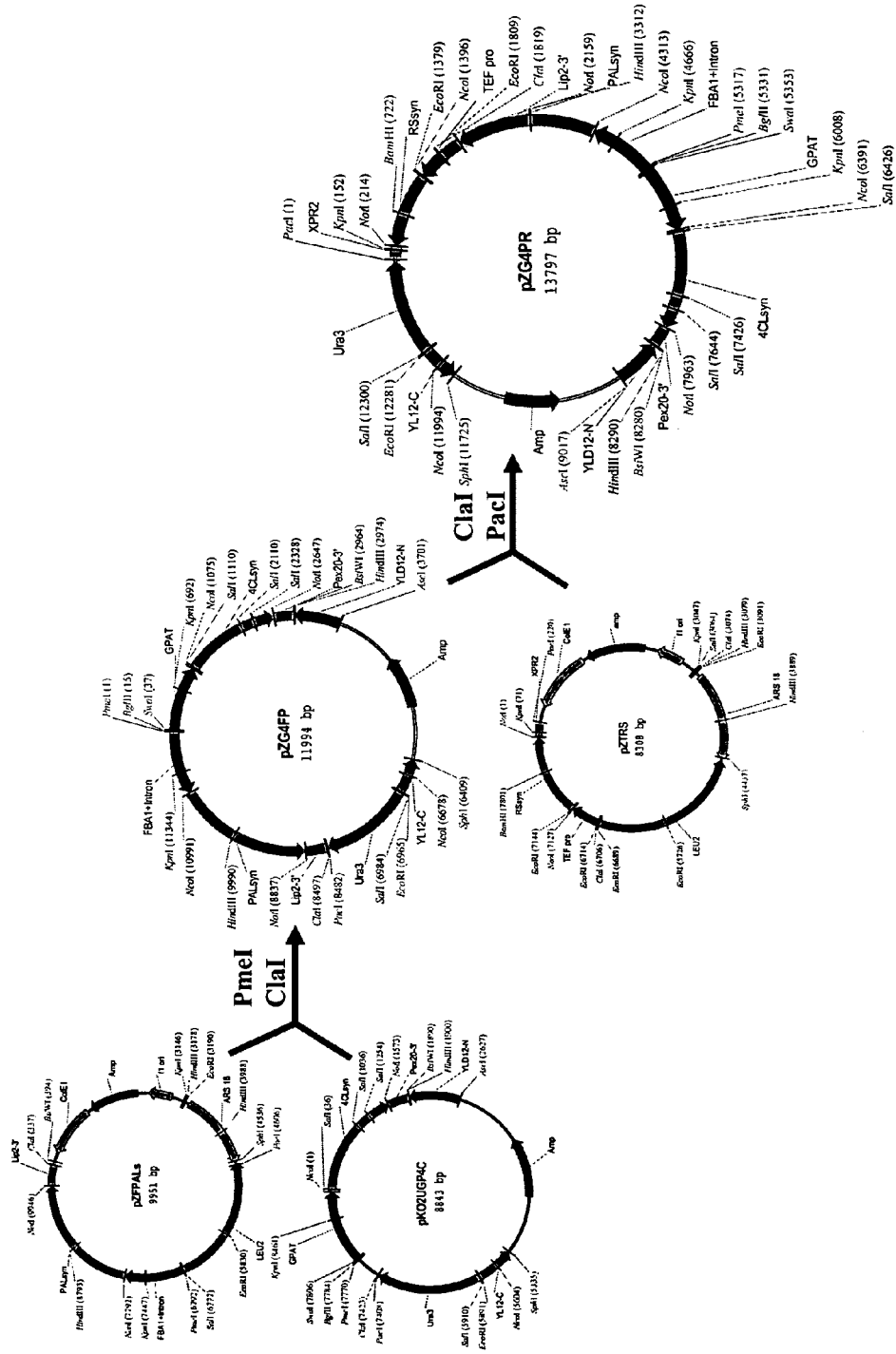

FIG. 3. Plasmid maps for plasmids used to create plasmid pZG4PR.

Figure 4:
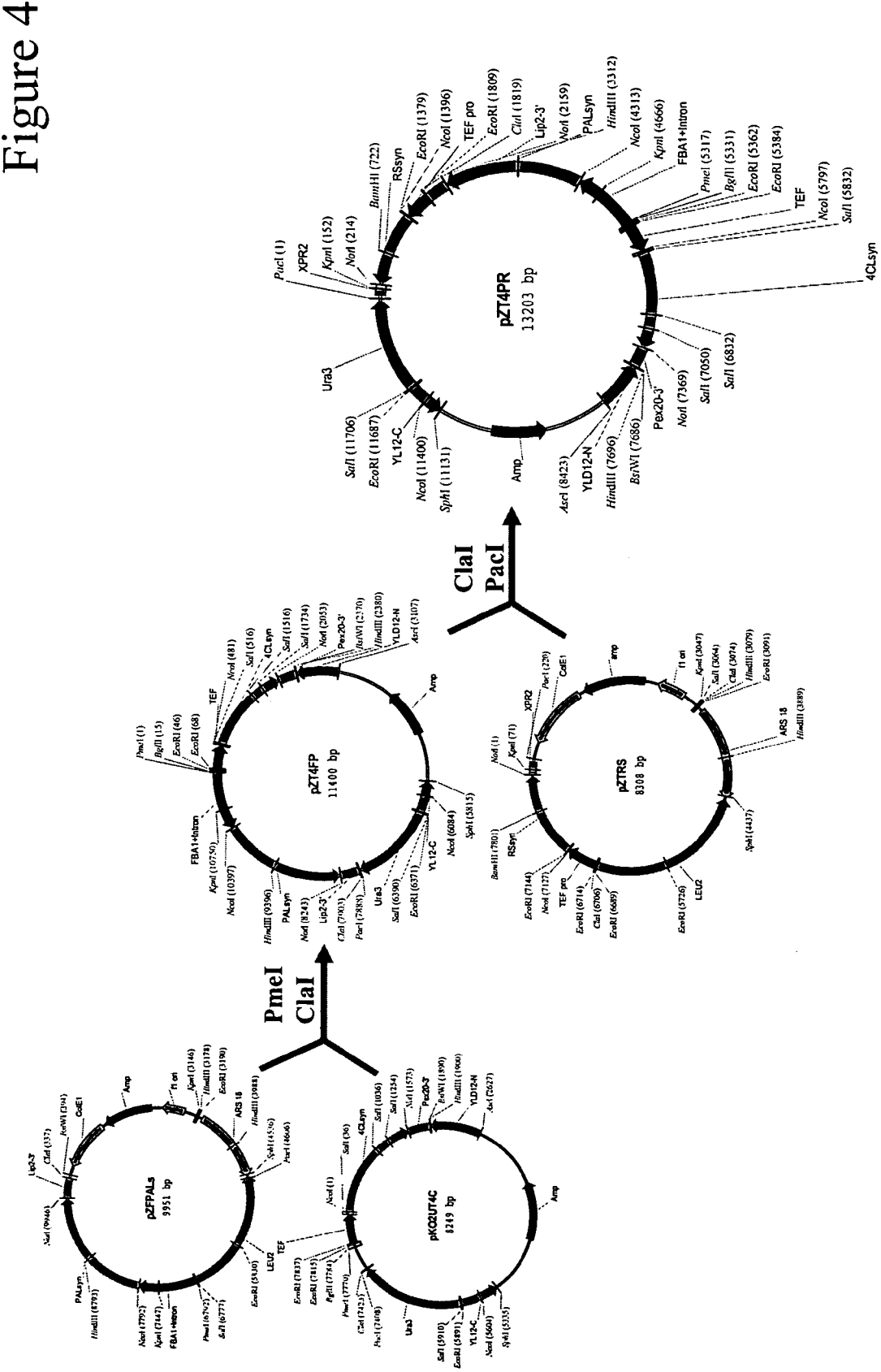

FIG. 4. Plasmid maps for plasmids used to create plasmid pZT4PR.

Figure 5:
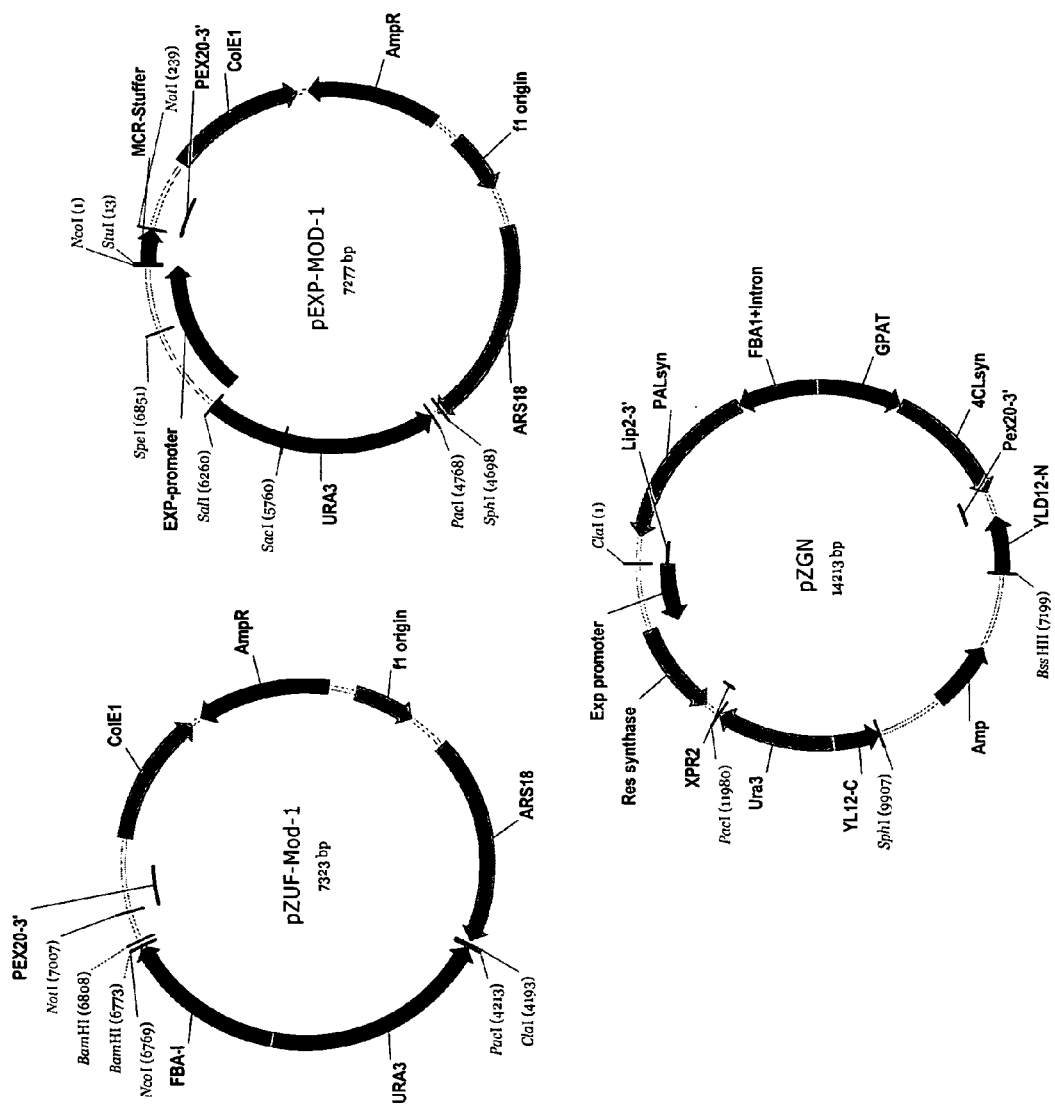

FIG. 5. Plasmid maps for plasmids for pZUF-Mod-1, pEXP-MOD-1, and pZGN.

Figure 6:
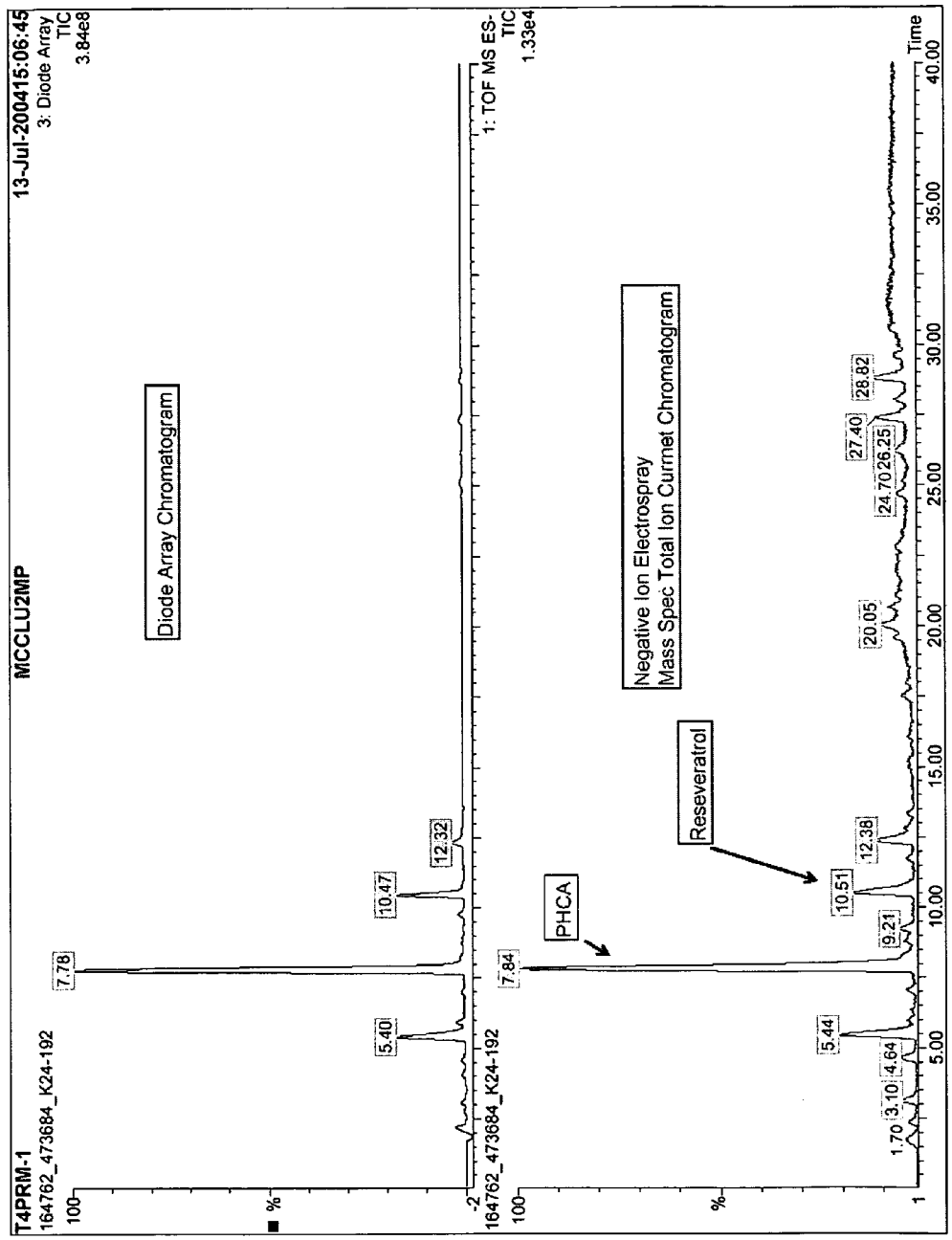

FIG. 6. Mass analysis of pZGN transformed 20362U1 cells. Using negative ion electrospray mass spectroscopy, a peak at 10.51 min contains the molecular ion of 227 that matches the molecular weight of resveratrol (top). The peak at 7.84 min contains the molecular ion of 163 that matches the molecular weight of pHCA (bottom).

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the European Patent Convention (EPC) and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1—Sequence Listing" and "Copy 2 Sequence listing" The discs contain the following file: CL2033 US NA.ST25 having the following size: 379,000 bytes and which was created May 16, 2006.

SEQ ID NO:1 is the nucleotide sequence of the phenylalanine ammonia lyase coding sequence from *Rhodotorula glutinis* (herein also referred to as *Rhodosporidium toruloides*; GenBank® Accession No. X12702).

SEQ ID NO:2 is the deduced amino acid sequence of the phenylalanine ammonia lyase from *Rhodotorula glutinis* (GenBank® Accession No. X12702).

SEQ ID NO:3 is the nucleotide sequence of the phenylalanine ammonia lyase coding sequence from *Rhodotorula glutinis* (GenBank® Accession No. X12702) codon-optimized for expression in *Yarrowia lipolytica*.

SEQ ID NO:4 is the nucleotide sequence of the coumaroyl CoA ligase coding sequence from *Streptomyces coelicolor* (GenBank® Accession No. AL939119).

SEQ ID NO:5 is the deduced amino acid sequence of the coumaroyl CoA ligase from *Streptomyces coelicolor* (GenBank® Accession No. AL939119).

SEQ ID NO:6 is the nucleotide sequence of the coumaroyl CoA ligase coding sequence from *Streptomyces coelicolor* (GenBank® Accession No. AL939119) codon-optimized for expression in *Yarrowia lipolytica*.

SEQ ID NO:7 is the nucleotide sequence of a resveratrol synthase coding sequence isolated from *Vitis* sp.

SEQ ID NO:8 is the deduced amino acid sequence of a resveratrol synthase isolated from *Vitis* sp.

SEQ ID NO:9 is the nucleotide sequence of a resveratrol synthase coding sequence isolated from *Vitis* sp. codon-optimized for expression in *Yarrowia lipolytica*.

SEQ ID NO:10 is the nucleotide sequence of the FBAIN promoter from *Yarrowia lipolytica* (U.S. Ser. No. 10/987, 548).

SEQ ID NO:11 is the nucleotide sequence of primer pY331.

SEQ ID NO:12 is the nucleotide sequence of primer pY332.

SEQ ID NO:13 is the nucleotide sequence of primer TEF5'.
SEQ ID NO:14 is the nucleotide sequence of primer TEF3'.
SEQ ID NO:15 is the nucleotide sequence of the XPR2 transcriptional terminator.
SEQ ID NO:16 is the nucleotide sequence of primer XPR5'.
SEQ ID NO:17 is the nucleotide sequence of primer XPR3'.
SEQ ID NO:18 is the nucleotide sequence of 5' end part of the codon-optimized coumaroyl CoA ligase gene.
SEQ ID NO:19 is the nucleotide sequence of primer YL539.
SEQ ID NO:20 is the nucleotide sequence of primer YL540.
SEQ ID NO:21 is the nucleotide sequence of the FBAIN promoter::4CL::Pex20 chimeric gene (GenBank® AF054613).
SEQ ID NO:22 is the nucleotide sequence of primer YL27.
SEQ ID NO:23 is the nucleotide sequence of primer YL28.
SEQ ID NO:24 is the nucleotide sequence of primer YL61.
SEQ ID NO:25 is the nucleotide sequence of primer YL62.
SEQ ID NO:26 is the nucleotide sequence of the *Mortierella alpina* Δ 5 desaturase gene (U.S. Pat. No. 6,075,183).
SEQ ID NO:27 is the nucleotide sequence of primer YL11.
SEQ ID NO:28 is the nucleotide sequence of primer YL12.
SEQ ID NO:29 is the nucleotide sequence of primer YL224.
SEQ ID NO:30 is the nucleotide sequence of primer YL225.
SEQ ID NO:31 is the nucleotide sequence of primer YL232.
SEQ ID NO:32 is the nucleotide sequence of primer YL233.
SEQ ID NO:33 is the nucleotide sequence of primer YL101.
SEQ ID NO:34 is the nucleotide sequence of primer YL102.
SEQ ID NO:35 is the nucleotide sequence of primer YL95.
SEQ ID NO:36 is the nucleotide sequence of primer YL266.
SEQ ID NO:37 is the nucleotide sequence of primer YL263.
SEQ ID NO:38 is the nucleotide sequence of primer YL265.
SEQ ID NO:39 is the nucleotide sequence of primer YL285.
SEQ ID NO:40 is the nucleotide sequence of primer YL286.
SEQ ID NO:41 is the nucleotide sequence of primer YL259.
SEQ ID NO:42 is the nucleotide sequence of primer YL260.
SEQ ID NO:43 is the nucleotide sequence of the *Yarrowia* GPAT promoter (U.S. Ser. No. 11/225,354; hereby incorporated by reference).
SEQ ID NO:44 is the nucleotide sequence of primer YL497
SEQ ID NO:45 is the nucleotide sequence of primer YL498
SEQ ID NO:46 is the nucleotide sequence of primer YL103
SEQ ID NO:47 is the nucleotide sequence of primer YL104
SEQ ID NO:48 is the nucleotide sequence of plasmid pKO2UFkF2.
SEQ ID NO:49 is the nucleotide sequence of 730-bp 5' part of the *Yarrowia* Δ12 desaturase gene.
SEQ ID NO:50 is the nucleotide sequence of 573-bp 3' part of the *Yarrowia* Δ12 desaturase gene.
SEQ ID NO:51 is the nucleotide sequence of a modified FBAIN promoter designated as the FBAINm promoter.
SEQ ID NO:52 is the nucleotide sequence of Δ12 desaturase gene (Δ12DS) from *Fusarium moniliforme*.
SEQ ID NO:53 is the nucleotide sequence of the Pex20 terminator sequence of the *Yarrowia* Pex20 gene (GenBank® AF054613).

SEQ ID NO:54 is the nucleotide sequence of *Yarrowia* Ura3 gene (GenBank® AJ306421).

SEQ ID NO: 55 is the nucleotide sequence of plasmid pZG4PR.

SEQ ID NO: 56 is the nucleotide sequence of plasmid pZT4PR.

SEQ ID NO: 57 is the nucleotide sequence of plasmid pZUF-MOD-1.

SEQ ID NO: 58 is the nucleotide sequence of primer pZUF-mod1.

SEQ ID NO: 59 is the nucleotide sequence of primer pZUF-mod2.

SEQ ID NO: 60 is the nucleotide sequence of the multiple cloning site used in making pZUF-MOD-1.

SEQ ID NO: 61 is the nucleotide sequence of the EXP promoter from *Yarrowia lipolytica* gene YALI-CDS5725.1.

SEQ ID NO: 62 is the nucleotide sequence of primer EP-Promoter-F.

SEQ ID NO: 63 is the nucleotide sequence of primer EP-Promoter-R.

SEQ ID NO: 64 is the nucleotide sequence of plasmid pEXP-MOD-1.

SEQ ID NO: 65 is the nucleotide sequence of plasmid pZGN.

SEQ ID NO: 66 is the nucleotide sequence comprising a phenylalanine ammonia lyase coding sequence from *Rhodotorula mucilaginosa*.

SEQ ID NO: 67 is the nucleotide sequence comprising a phenylalanine ammonia lyase coding sequence from *Amanita muscaria*.

SEQ ID NO: 68 is the nucleotide sequence comprising a phenylalanine ammonia lyase coding sequence from *Ustilago maydis*.

SEQ ID NO: 69 is the nucleotide sequence comprising a phenylalanine ammonia lyase coding sequence from *Arabidopsis thaliana*.

SEQ ID NO: 70 is the nucleotide sequence comprising a phenylalanine ammonia lyase coding sequence from *Rubus idaeus*.

SEQ ID NO: 71 is the nucleotide sequence comprising a phenylalanine ammonia lyase coding sequence from *Medicago sativa*.

SEQ ID NO: 72 is the nucleotide sequence comprising a phenylalanine ammonia lyase coding sequence from *Rehmannia glutinosa*.

SEQ ID NO: 73 is the nucleotide sequence comprising a phenylalanine ammonia lyase coding sequence from *Lactuca savita*.

SEQ ID NO: 74 is the nucleotide sequence comprising a phenylalanine ammonia lyase coding sequence from *Petroselinium crispum*.

SEQ ID NO: 75 is the nucleotide sequence comprising a phenylalanine ammonia lyase coding sequence from *Prunus avium*.

SEQ ID NO: 76 is the nucleotide sequence comprising a phenylalanine ammonia lyase coding sequence from *Lithospernum erythrorhizon*.

SEQ ID NO: 77 is the nucleotide sequence comprising a phenylalanine ammonia lyase coding sequence from *Citrus limon*.

SEQ ID NO: 78 is the nucleotide sequence comprising a phenylalanine ammonia lyase coding sequence from *Rhodotorula glutinis*.

SEQ ID NO: 79 is the nucleotide sequence comprising a phenylalanine ammonia lyase coding sequence from *Rhodobacter sphaeroides*.

SEQ ID NO: 80 is the nucleotide sequence comprising a phenylalanine ammonia lyase coding sequence from *Trichosporon cutaneum* (U.S. Pat. No. 6,951,751).

SEQ ID NO: 81 is the nucleotide sequence comprising a coumaroyl CoA ligase coding sequence from *Streptomyces coelicolor*.

SEQ ID NO: 82 is the nucleotide sequence comprising a coumaroyl CoA ligase coding sequence from *Allium cepa*.

SEQ ID NO: 83 is the nucleotide sequence comprising a coumaroyl CoA ligase coding sequence from *Streptomyces avermitilis*.

SEQ ID NO: 84 is the nucleotide sequence comprising a coumaroyl CoA ligase coding sequence from *Populus tremuloides*.

SEQ ID NO: 85 is the nucleotide sequence comprising a coumaroyl CoA ligase coding sequence from *Oryza sativa*.

SEQ ID NO: 86 is the nucleotide sequence comprising a coumaroyl CoA ligase coding sequence from *Amorpha fruticosa*.

SEQ ID NO: 87 is the nucleotide sequence comprising a coumaroyl CoA ligase coding sequence from *Populus tomentosa*.

SEQ ID NO: 88 is the nucleotide sequence comprising a coumaroyl CoA ligase coding sequence from *Nicotiana tabacum*.

SEQ ID NO: 89 is the nucleotide sequence comprising a coumaroyl CoA ligase coding sequence from *Pinus taeda*.

SEQ ID NO: 90 is the nucleotide sequence comprising a coumaroyl CoA ligase coding sequence from *Glycine max*.

SEQ ID NO: 91 is the nucleotide sequence comprising a coumaroyl CoA ligase coding sequence from *Arabidopsis thaliana*.

SEQ ID NO: 92 is the nucleotide sequence comprising a coumaroyl CoA ligase coding sequence from *Arabidopsis thaliana*.

SEQ ID NO: 93 is the nucleotide sequence comprising a coumaroyl CoA ligase coding sequence from *Rubus idaeus*.

SEQ ID NO: 94 is the nucleotide sequence comprising a coumaroyl CoA ligase coding sequence from *Lithospermum erythrorhizon*.

SEQ ID NO: 95 is the nucleotide sequence comprising a coumaroyl CoA ligase coding sequence from. *Zea mays*.

SEQ ID NO: 96 is the nucleotide sequence comprising a resveratrol synthase (stilbene synthase) coding sequence from *Vitis* sp.

SEQ ID NO: 97 is the nucleotide sequence comprising a resveratrol synthase (stilbene synthase) coding sequence from *Vitis vinifera*.

SEQ ID NO: 98 is the nucleotide sequence comprising a resveratrol synthase (stilbene synthase) coding sequence from *Vitis vinifera*.

SEQ ID NO: 99 is the nucleotide sequence comprising a resveratrol synthase (stilbene synthase) coding sequence from *Arachis hypogaea*.

SEQ ID NO: 100 is the nucleotide sequence comprising a resveratrol synthase (stilbene synthase) coding sequence from *Cissus rhombifolia*.

SEQ ID NO: 101 is the nucleotide sequence comprising a resveratrol synthase (stilbene synthase) coding sequence from *Parthenocissus henryana*.

SEQ ID NO: 102 is the nucleotide sequence comprising a resveratrol synthase (stilbene synthase) coding sequence from *Parthenocissus quinquefolia*.

SEQ ID NO: 103 is the nucleotide sequence comprising a resveratrol synthase (stilbene synthase) coding sequence from *Vitis riparia*.

SEQ ID NO: 104 is the nucleotide sequence comprising a resveratrol synthase (stilbene synthase) coding sequence from *Vitis labrusca*.

SEQ ID NO: 105 is the nucleotide sequence comprising a resveratrol synthase (stilbene synthase) coding sequence from *Vitis* sp. cv. "Norton".

SEQ ID NO: 106 is the nucleotide sequence comprising a cinnamate 4-hydroxylase coding sequence from *Cicer arietinum*.

SEQ ID NO: 107 is the nucleotide sequence comprising a cinnamate 4-hydroxylase coding sequence from *Populus tremuloides*.

SEQ ID NO: 108 is the nucleotide sequence comprising a cinnamate 4-hydroxylase coding sequence from *Oryza sativa*.

SEQ ID NO: 109 is the nucleotide sequence comprising a cinnamate 4-hydroxylase coding sequence from *Camellia sinensis*.

SEQ ID NO: 110 is the nucleotide sequence comprising a cinnamate 4-hydroxylase coding sequence from *Vigna radiata*.

SEQ ID NO: 111 is the nucleotide sequence comprising a cinnamate 4-hydroxylase coding sequence from *Helianthus tuberosus*.

SEQ ID NO: 112 is the nucleotide sequence comprising a cinnamate 4-hydroxylase coding sequence from *Camptotheca acuminata*.

SEQ ID NO: 113 is the nucleotide sequence comprising a cinnamate 4-hydroxylase coding sequence from *Arabidopsis thaliana*.

SEQ ID NO: 114 is the nucleotide sequence comprising a cinnamate 4-hydroxylase coding sequence from *Ruta graveolens*.

SEQ ID NO: 115 is the nucleotide sequence comprising a cinnamate 4-hydroxylase coding sequence from *Glycine max*.

SEQ ID NO: 116 is the nucleotide sequence comprising a cinnamate 4-hydroxylase coding sequence from *Citrus sinensis*.

SEQ ID NO: 117 is the nucleotide sequence comprising a phenylalanine hydroxylase coding sequence from *Chromobacterium violaceum*.

SEQ ID NO: 118 is the nucleotide sequence comprising a phenylalanine hydroxylase coding sequence from *Pseudomonas aeruginosa*.

SEQ ID NO: 119 is the nucleotide sequence comprising a phenylalanine hydroxylase coding sequence from *Geodia cydonium*.

SEQ ID NO: 120 is the nucleotide sequence comprising a phenylalanine hydroxylase coding sequence from *Xanthomonas axonopodis*.

SEQ ID NO: 121 is the nucleotide sequence comprising a phenylalanine hydroxylase coding sequence from *Xanthomonas campestris*.

SEQ ID NO: 122 is the nucleotide sequence comprising a phenylalanine hydroxylase coding sequence from *Nocardia farcinica*.

SEQ ID NO: 123 is the nucleotide sequence comprising a phenylalanine hydroxylase coding sequence from *Gallus gallus*.

SEQ ID NO: 124 is the nucleotide sequence comprising a acetyl CoA carboxylase coding sequence from *Saccharomyces cerevisiae*.

SEQ ID NO: 125 is the nucleotide sequence comprising a acetyl CoA carboxylase coding sequence from *Saccharomyces cerevisiae*.

SEQ ID NO: 126 is the nucleotide sequence comprising a acetyl CoA carboxylase coding sequence from *Kluyveromyces lactis*.

SEQ ID NO: 127 is the nucleotide sequence comprising a acetyl CoA carboxylase coding sequence from *Debaryomyces hansenii*.

SEQ ID NO: 128 is the nucleotide sequence comprising a acetyl CoA carboxylase coding sequence from *Yarrowia lipolytica*.

SEQ ID NO: 129 is the nucleotide sequence comprising a acetyl CoA carboxylase coding sequence from *Aspergillus nidulans*.

SEQ ID NO: 130 is the nucleotide sequence comprising a acetyl CoA carboxylase coding sequence from *Schizosaccharomyces pombe*.

SEQ ID NO: 131 is the nucleotide sequence comprising a acetyl CoA carboxylase coding sequence from *Ustilago maydis*.

SEQ ID NO: 132 is the nucleotide sequence comprising a acetyl CoA carboxylase coding sequence from *Gallus gallus*.

SEQ ID NO: 133 is the nucleotide sequence comprising a β-glucosidase coding sequence from *Mesoplasma florum*.

SEQ ID NO: 134 is the nucleotide sequence comprising β-glucosidase coding sequence from *Oryza sativa*.

SEQ ID NO: 135 is the nucleotide sequence comprising a β-glucosidase coding sequence from *Pseudomonas putida*.

SEQ ID NO: 136 is the nucleotide sequence comprising β-glucosidase coding sequence from *Pseudomonas syringae*.

SEQ ID NO: 137 is the nucleotide sequence comprising a β-glucosidase coding sequence from *Streptomyces coelicolor*.

SEQ ID NO: 138 is the nucleotide sequence comprising β-glucosidase coding sequence from *Caulobacter crescentus*.

SEQ ID NO: 139 is the nucleotide sequence comprising a β-glucosidase coding sequence from *Candida wickerhamii*.

DETAILED DESCRIPTION OF THE INVENTION

The present invention describe a method for microbial production of resveratrol and/or resveratrol glucoside (piceid) in a recombinant oleaginous microorganism. In another embodiment, the present invention provides microorganisms genetically modified to produce resveratrol and/or resveratrol glucoside. Both compounds can be isolated and purified for a variety of commercial applications. In one aspect, resveratrol can be obtained from resveratrol glucoside by removing the glucose moiety using chemical or enzymatic hydrolysis to release the aglycone (i.e., non-glycosylated resveratrol).

In one aspect, the recombinant host cell is oleaginous microorganism that produces suitable amounts of malonyl CoA. In a preferred aspect, the recombinant host cell is oleaginous yeast that produces suitable amounts of malonyl CoA. In another preferred aspect, the recombinant oleaginous yeast is engineered to product both resveratrol/resveratrol glucoside and at least one ω-3 polyunsaturated fatty acid. In a further aspect, the recombinant host cell is *Yarrowia lipolytica*.

In the following disclosure, a number of terms and abbreviations are used. The following definitions are provided.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably with 5% of the reported numerical value.

As used herein the term "invention" or "present invention" is not meant to be limiting to any specific aspect or embodiment of the invention but shall be read to refer to all embodiments of the invention as described in the claims and the specification.

As used herein, the term "resveratrol" is used to describe the compound 3,4',5-trihydroxystilbene as shown below.

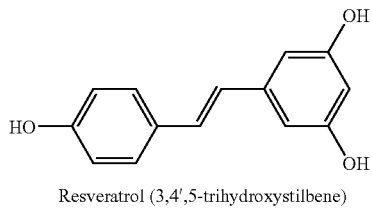

Resveratrol (3,4',5-trihydroxystilbene)

As used herein, the term "comprising" means the presence of the stated features, integers, steps, or components as referred to in the claims, but that it does not preclude the presence or addition of one or more other features, integers, steps, components or groups thereof.

As used herein, the terms "para-hydroxycinnamic acid", "p-hydroxycinnamic acid", and "4-hydroxycinnamic acid" are used interchangeably and are abbreviated as "pHCA".

As used herein, "resveratrol glucoside" and "piceid" are used interchangeably to describe resveratrol 3-O-β-D-glucoside. In many eukaryotic host cells, compounds produced during secondary metabolism are glycosylated using an endogenous glycosyl transferase. As used herein, "resveratrol glycosylating activity" and "endogenous resveratrol glycosylating activity" will be used to describe the endogenous enzymatic activity observed in many host cells that adds at least one sugar moiety to resveratrol. In one aspect, the endogenous resveratrol glycosylating activity adds a single glucose moiety to resveratrol. In another aspect, the glucose moiety can be chemically hydrolyzed and/or enzymatically hydrolyzed to produce the aglycone (free resveratrol).

As used herein, the terms "trans-cinnamic acid", "cinnamic acid", and "trans-cinnamate" are used interchangeably.

As used herein, the terms "phenylalanine" and "L-phenylalanine" are used interchangeably.

As used herein, the terms "tyrosine" and "L-tyrosine" are used interchangeably.

As used herein, the terms "stilbene synthase" and "resveratrol synthase" are used interchangeably arid are abbreviated as RS. Resveratrol synthase is a type III polyketide synthase (E. C. 2.3.1.95) that condenses one molecule of p-coumaroyl CoA with 3 molecules of malonyl CoA to produce 1 molecule of resveratrol.

As used herein, the terms "para-coumaroyl CoA" and "p-coumaroyl CoA" are used interchangeably.

As used herein, the term "coumaroyl CoA ligase" is used to described an enzyme that converts pHCA into p-coumaroyl CoA (E.C. 6.2.1.12).

As used herein, the term "phenylalanine hydroxylase" is abbreviated PAH. The term "PAH" activity" or "PAH enzyme" refers to an enzyme that hydroxylates phenylalanine to produce tyrosine (E.C. 1.14.16.1).

As used herein, the term "cinnamate 4-hydroxylase" is used to describe one or more enzymes having an enzyme activity (E.C. 1.14.13.11) that converts trans-cinnamic acid to p-hydroxycinnamic acid and is abbreviated C4H.

As used herein, the term "tyrosine ammonia lyase" or "TAL enzyme" is abbreviated TAL (EC 4.3.1.). As used herein, the term "TAL activity" refers to the ability of a protein to catalyze the direct conversion of tyrosine to p-hydroxycinnamic acid (pHCA). "taf" represents a gene that encodes an enzyme with TAL activity. TAL enzymes typically have some PAL activity.

As used herein, the term "phenylalanine ammonia-lyase" or "PAL enzyme" is abbreviated PAL (EC 4.3.1.5). As used herein, the term "PAL activity" refers to the ability of a protein to catalyze the conversion of phenylalanine to trans-cinnamic acid. "pal" represents a gene that encodes an enzyme with PAL activity. The phenylalanine ammonia lyase used in the present examples has significant TAL activity. As used herein, the term "phenylalanine ammonia lyase" will be also be referred to as a "phenylalanine/tyrosine ammonia lyase", "phenylalanine/tyrosine enzyme", "an enzyme having phenylalanine/tyrosine ammonia lyase activity", and "PAL/TAL enzyme". In one aspect, the PAL/TAL enzyme has a ratio of TAL specific activity:PAL specific activity ranging from 0.001 to 1000, preferably 0.1 to 100.

As used herein, "phenylalanine/tyrosine ammonia lyase activity" and "PAL/TAL activity" refers to an enzyme that has both PAL activity and TAL activity, converting phenylalanine to trans-cinnamic acid and tyrosine to p-hydroxycinnamic acid.

As used herein, the term "modified PAL/TAL" or "mutant PAL/TAL" refers to a protein which has been derived from a wild type PAL enzyme which has greater TAL activity than PAL activity (U.S. Pat. No. 6,368,837; hereby incorporated by reference). As such, a modified PAL/TAL protein has a greater substrate specificity (or at least greatly improved in comparison to the non-modified enzyme from which it is derived) for tyrosine than for phenylalanine.

As used herein, the terms "significant amount" and "significant amount of resveratrol" are used to describe the amount of resveratrol and/or resveratrol glucoside produced using the present method. In one aspect, a significant amount produced by the present method is a resveratrol titer of at least 0.5 mg/L within the culture volume, preferably at least 1 mg/L within the culture volume, and most preferably at least 1.4 mg/L within the culture volume. In one aspect, "significant amount" is defined as at least 0.01% dry cell weight (dcw), preferably at least 0.03% (dcw) and more preferably at least 0.1% (dcw), and most preferably at least 1.0% (dcw).

As used herein, the terms "suitable amount" and "suitable substrate amount" are used to describe an amount of available substrate that enables recombinant microbial production of resveratrol and/or resveratrol glucoside at concentrations exceeding 0.01% (dcw) within the culture volume using the present method. In another aspect, the suitable amount enables production of resveratrol and/or resveratrol glucoside at concentrations exceeding 0.03% (dcw) within the culture volume using the present method. In yet another aspect, the suitable amount enables production of resveratrol and/or resveratrol glucoside at concentrations of about 0.1% (dcw) or more within the culture volume. In still yet another aspect, the suitable amount enable production of resveratrol and/or resveratrol glucoside at concentrations of at least 1.0% (dcw). In one aspect, the recombinant microbial host cell can produce suitable amounts of the necessary substrates for resveratrol production from the fermentable carbon source supplied to the fermentation media. In another aspect, one or more substrates useful for the biosynthesis of resveratrol may be exogenously supplemented to the fermentation media to enable production resveratrol and/or resveratrol glucoside in significant quantities. In yet another aspect, the exogenously supplied substrate is selected from the group consisting of acetate, malonate or malonic acid, phenylalanine, tyrosine, p-hydroxycinnamic acid, and trans-cinnamic acid. In a preferred aspect, the exogenously supplied substrate is p-hydroxycinnamic acid.

As used herein, the terms "P450/P-450 reductase system" and "cytochrome P450/P450 reductase system" refers to a protein system responsible for the catalytic conversion of trans-cinnamic acid to pHCA. The P450/P450 reductase system is one of several enzymes or enzyme systems known in the art that performs a cinnamate 4-hydroxylase function. As used herein, the term "cinnamate 4-hydroxylase" will refer to the general enzymatic activity that results in the conversion of trans-cinnamic acid to pHCA, whereas the term "P450/P450 reductase system" will refer to a specific binary protein system that has cinnamate 4-hydroxylase activity.

As used herein, the term "aromatic amino acid biosynthesis" means the biological processes and enzymatic pathways internal to a cell needed for the production of an aromatic amino acid (i.e., L-phenylalanine and/or L-tyrosine).

As used herein, the term "oleaginous" or "oleaginous microorganism" refers to those microorganisms that tend to store their energy source in the form of lipid (Weete, In: *Fungal Lipid Biochemistry*, 2nd Ed., Plenum, 1980). In one aspect, oleaginous microorganisms are those microorganisms that store lipids/oils in amounts greater than 20% of their dry cell weight. Many species of oleaginous microalgae, oleaginous diatoms and oleaginous fungi have the ability to store lipids to >20% of the dry cell weight. Examples of oleaginous microorganisms include those belonging to the genera *Mortierella, Conidiobolus, Pythium, Phytophathora, Penicillium, Porphyridium, Coidosporium, Mucor, Fusarium, Aspergillus, Rhodotorula*, and *Entomophthora*. Within the genus *Porphyridium*, of particular interest is *P. cruentum*. Within the genus *Mortierella*, of particular interest are *M. elongata, M. exigua, M. hygrophila, M. ramanniana* var. *angulispora*, and *M. alpina*. Within the genus *Mucor*, of particular interest are *M. circinelloides* and *M. javanicus*.

As used herein, the term "oleaginous yeast" refers to those microorganisms classified as yeasts (and modified versions thereof) that can accumulate at least 20% of their dry cell weight as oil. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Liopmyces starkeyii, L. lipoferus, Candida revkaufl, C. pulcherrima, C. tropicalis, C. utilis, Trichosporon pullans, T. cutaneum, Rhodotorula glutinis, R. graminis*, and *Yarrowia lipolytica* (formerly classified as *Candida lipolytica*). In another aspect, the oleaginous yeast is *Yarrowia lipolytica*; and, in a further aspect, the *Y. lipolytica* strains are designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)). In a preferred aspect, the oleaginous yeast is capable of producing at least one ω-3 polyunsaturated fatty acid (PUFA). In a further preferred aspect, the oleaginous yeast is a *Yarrowia lipolytica* strain genetically modified to produce at least one ω-3 PUFA select from the group consisting of eiscosatetraenoic acid (ETA), eicosapentaenoic acid (EPA), docasapentaenoic acid (DPA), and docasahexaenoic acid (DHA).

As used herein, the term "fermentable carbon substrate" refers to a carbon source capable of being metabolized by host organisms of the present invention and particularly carbon sources selected from the group consisting of monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate, carbon-containing amines) for which metabolic conversion into key biochemical intermediates has been demonstrated. Hence, it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons and mixtures thereof.

As used herein, the term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, "gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

As used herein, an "nucleic acid molecule" is a polymer of RNA or DNA that is single- or double-stranded, optionally containing synthetic, non-natural or altered nucleotide bases. A nucleic acid molecule in the form of a polymer of DNA may be comprised of one or more segments of cDNA, genomic DNA or synthetic DNA.

As used herein, "coding sequence" refers to a DNA sequence that codes for a specific amino acid sequence.

As used herein, "suitable regulatory sequences" refer to nucleotide sequences located upstream (5' non-coding sequences), within, or downstream (3' non-coding sequences)

of a coding sequence, and which influence the transcription, RNA processing or stability, or translation of the associated coding sequence. Regulatory sequences may include promoters, translation leader sequences, introns, and polyadenylation recognition sequences.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

As used herein, the term "FBA1" refers to a fructose-bisphosphate aldolase enzyme (E.C. 4.1.2.13) encoded by the fba1 gene and which converts D-fructose 1,6-bisphosphate into dihydroxyacetone phosphate (DHAP) plus D-glyceraldehyde 3-phosphate (U.S. Ser. No. 10/987,548; hereby incorporated by reference).

As used herein, the term "FBA promoter" or "FBA promoter region" refers to the 5' upstream untranslated region in front of the 'ATG' translation initiation codon of fba1 and that is necessary for expression (U.S. Ser. No. 10/987,548).

As used herein, the term "FBAIN promoter" or "FBAIN promoter region" or "FBAIN" refers to the 5' upstream untranslated region in front of the 'ATG' translation initiation codon and that is necessary for expression, plus a portion of 5' coding region that has an intron of a fba1 gene (U.S. Ser. No. 10/987,548). An example of a suitable FBAIN promoter region is provided as SEQ ID NO: 10, but this is not intended to be limiting in nature.

As used herein, the term "FBAINm promoter" or "FBAINm promoter region" or "FBAINm" refers to a modified version of the FBAIN promoter (U.S. Ser. No. 10/987,548) as represented by SEQ ID NO: 51.

As used herein, the term "promoter activity" will refer to an assessment of the transcriptional efficiency of a promoter. This may, for instance, be determined directly by measurement of the amount of mRNA transcription from the promoter (e.g., by Northern blotting or primer extension methods) or indirectly by measuring the amount of gene product expressed from the promoter.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, "introns" are sequences of non-coding DNA found in gene sequences (either in the coding region, 5' non-coding region, or 3' non-coding region) in most eukaryotes. Their full function is not known; however, some enhancers are located in the introns (Giacopelli, F. et al., Gene Expr., 11:95-104 (2003)). These intron sequences are transcribed, but removed from within the pre-mRNA transcript before the mRNA is translated into a protein. This process of intron removal occurs by self-splicing of the sequences (exons) on either side of the intron.

As used herein, the term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

As used herein, "transformation" refers to the transfer of a nucleic acid molecule into the genome of a host organism, resulting in genetically stable inheritance. Host organisms containing the transformed nucleic acid fragments are referred to as "transgenic" or "recombinant" or "transformed" organisms. In the present application, the nucleic acid molecule(s) transferred into the genome of host organism are operably linked to suitable regulatory sequences (e.g., promoters, terminators, etc.) that facilitate expression in the host.

As used herein, the terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, "pQZ-PAL" refers to the name of the plasmid comprised of the codon optimized phenylalanine ammonia lyase coding sequence (SEQ ID NO: 3) inserted into plasmid pUC57 (GenScript Corporation, Piscataway, N.J.).

As used herein, "pQZ-4CL" refers to the name of the plasmid comprised of the codon optimized coumaroyl CoA ligase coding sequence (SEQ ID NO: 6) inserted into plasmid pUC57 (GenScript Corporation, Piscataway, N.J.).

As used herein, "pQZ-R$^S$" refers to the name of the plasmid comprised of the codon optimized resveratrol synthase coding sequence (SEQ ID NO: 9) inserted into plasmid pUC57 (GenScript Corporation, Piscataway, N.J.).

As used herein, "pZT4FP" refers to the name of a plasmid comprised of codon-optimized versions of the resveratrol synthase, phenylalanine ammonia lyase, and coumaroyl CoA ligase genes.

As used herein, "pZT4PR" refers to the name of a plasmid comprised of codon-optimized versions of the chimeric resveratrol synthase, phenylalanine ammonia lyase, and coumaroyl CoA ligase genes.

As used herein, "pZUF-MOD-1" refers to an vector comprising the FBA-1 promoter, a multiple cloning site (MCS also referred to herein as "MCR-stuffer"), and the Pex20 terminator.

As used herein, "pEXP-MOD-1" refers to an vector comprising the EXP promoter, a multiple cloning site (MCS or "MCR-stuffer"), and the Pex20 terminator.

As used herein, "pZGN" refers to a vector comprising comprised of codon-optimized versions of the chimeric resveratrol synthase, phenylalanine lyase, and coumaroyl CoA ligase genes. Transformation of the oleaginous microorganism using the pZGN vector resulted in the production of resveratrol.

As used herein, the term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in WO2004/101757. "PUFAs" can be classified into two major families (depending on the position (n) of the first double bond nearest the methyl end of the fatty acid carbon chain). Thus, the "ω-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "co-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

As used herein, the terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell. "Microbial oils" or "single cell oils" are those oils naturally produced by microorganisms during their lifespan.

As used herein, "percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

As used herein, the term "amino acid" will refer to the basic chemical structural unit of a protein or polypeptide. The following abbreviations will be used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "chemically equivalent amino acid" will refer to an amino acid that may be substituted for another in a given protein without altering the chemical or functional nature of that protein. For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gin;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, alanine, a hydrophobic amino acid, may be substituted by another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Additionally, in many cases, alterations of the N-terminal and C-terminal portions of the protein molecule would also not be expected to alter the activity of the protein.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS at 65° C. followed by 0.1×SSC, 0.1% SDS at 65° C., for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one aspect the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

As used herein, a "substantial portion" of an amino acid or nucleotide sequence is that portion comprising enough of the amino acid sequence of a polypeptide or the nucleotide sequence of a gene and/or a nucleic acid fragment to putatively identify that polypeptide or gene and/or nucleic acid fragment, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The instant specification teaches partial or complete amino acid and nucleotide sequences encoding one or more particular proteins and promoters. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*, 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

In one aspect, suitable nucleic acid fragments encode polypeptides that are at least about 70% identical to the amino acid sequences reported herein. In another aspect, the nucleic acid fragments encode amino acid sequences that are about 85% identical to the amino acid sequences reported herein. In a further aspect, the nucleic acid fragments encode amino acid sequences that are at least about 90% identical to the amino acid sequences reported herein. In yet a further aspect, the nucleic acid fragments encode amino acid sequences that are at least about 95% identical to the amino acid sequences reported herein. In even yet a further aspect, the nucleic acid fragments encode amino acid sequences that are at least 99% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

Likewise, suitable promoter regions encode promoter regions that are at least about 70% identical to the nucleotide sequences reported herein. In one aspect, the nucleic acid fragments are about 85% identical to the nucleotide sequences reported herein, in another aspect they are at least about 90% identical, and in a further aspect the nucleic acid fragments are at least about 95% identical to the nucleotide sequences reported herein. In yet a further aspect, the promoter regions are at least 99% identical to the nucleic acid sequences reported herein. Suitable promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell. In one aspect, the recombinantly expressed genes are codon optimized for expression in the oleaginous microorganism. In another aspect, the recombinantly expressed genes are codon optimized for expression in an oleaginous yeast strain. In yet another aspect, the recombinantly expressed genes are codon optimized for expression in *Yarrowia lipolytica* (Table 2).

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); and 4:) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized.

Standard recombinant DNA and molecular cloning techniques used here are well known in the art and are described by Sambrook, J., Fritsch, E. F. and Maniatis, T. *Molecular Cloning: A Laboratory Manual*, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Engineering pHCA Production in a Recombinant Host Cell

The present method describes production of pHCA in the recombinant host. In one embodiment, p-hydroxycinnamic acid can be produced by expressing a phenylalanine ammonia lyase in combination with a cinnamate 4-hydroxylase (C4H), harnessing the endogenous production of the aromatic amino acid phenylalanine to produce pHCA (FIG. 1). Phenylalanine ammonia lyase (EC 4.3.1.5) is widely distributed in plants, fungi, yeast, and *Streptomyces*, but it has not been found in *Escherichia coli* or mammalian cells. PAL catalyzes the removal of the (pro-3S)-hydrogen and $—NH_3^+$ from L-phenylalanine to form trans-cinnamic acid. Subsequently, the enzyme cinnamic acid 4-hydroxylase (C4H; E.C. 1.14.13.11) catalyzes the conversion of trans-cinnamic acid to 4-hydroxycinnamate. Coumaroyl CoA ligase (4CL) converts 4-hydroxycinnamate (and other substituted cinnamic acids) into the corresponding CoA thiol esters (i.e., p-coumaroyl CoA), which are used for the biosynthesis of flavonoids, isoflavonoids, lignin, suberins, and coumarins (Ehlting et al., *Plant J.*, 19(1):9-20 (1999)).

L-tyrosine can also be converted to para-hydroxycinnamic acid by using an enzyme having tyrosine ammonia lyase activity ("TAL"; EC 4.3.1.-). A tyrosine ammonia lyase directly converts L-tyrosine to pHCA without the intermediacy of cinnamate (trans-cinnamic acid).

Phenylalanine ammonia lyases will, to some extent, also accept tyrosine as a substrate, converting tyrosine directly to p-hydroxycinnamic acid. As such, PAL enzymes (especially those exhibiting significant TAL activity) can alternatively be referred to a phenylalanine/tyrosine ammonia lyases (Rosier et al., *Plant Physiol.*, 113:175-179 (1997); Hwang et al., supra). Conversely, naturally-occurring TAL enzymes will have some PAL activity, converting L-phenylalanine to trans-cinnamic acid (Kyndt et al., *FEBS Letters*, 512:240-244 (2002); Watts et al., supra). Enzymes having PAL and/or TAL activity are defined by the substrate preference of the enzyme. TAL enzymes are defined as those that preferentially use L-tyrosine as a substrate. The source of the TAL in the present invention can be obtained or derived from any naturally-occurring source. In one aspect, an enzyme having TAL activity can be obtained by mutating a naturally-occurring PAL gene into one that encodes an enzyme that preferentially uses L-tyrosine as a substrate (U.S. Pat. No. 6,368,837, hereby incorporated by reference; Kyndt et al., supra). In another aspect, L-phenylalanine is converted to L-tyrosine using an enzyme having phenylalanine hydroxylase (PAH) activity. The L-tyrosine produced using a phenylalanine hydroxylase is then subsequently converted to pHCA using an enzyme having tyrosine ammonia lyase activity (Watts et al., supra; FIG. 1).

In one embodiment, pHCA is exogenously supplemented to the fermentor medium and/or produced by the recombinant host cell. In a further aspect, L-phenylalanine and/or trans-cinnamate can be exogenously supplied to a recombinant host cell expressing a phenylalanine ammonia lyase and/or a cinnamate 4-hydroxylase.

In another aspect, a phenylalanine hydroxylase (PAH) can be recombinantly expressed in a host cell capable of producing phenylalanine to increase L-tyrosine production in the recombinant host cell (assuming that a tyrosine ammonia lyase activity is present to convert the tyrosine into pHCA). In another aspect, the host cell is engineered to recombinantly express genes required to convert a portion of the aromatic amino acids endogenously produced by the host cell (L-phenylalanine and/or L-tyrosine) into pHCA by recombinantly expressing genes in the phenylpropanoid pathway. One of skill in the art will recognize that there is a need to balance the carbon flow from aromatic amino acid production into pHCA production (and eventually resveratrol production) so that a decrease in concentration of the free aromatic amino acids is not detrimental to the viability or health of the recombinant host cell. In another aspect, L-phenylalanine and/or L-tyrosine can be exogenously supplemented to the culture medium to increase resveratrol and/or resveratrol glucoside production. In yet another aspect, the genes involved in aromatic amino acid biosynthesis can be upregulated to increase the production of L-phenylalanine and/or L-tyrosine.

Microbial expression of a phenylalanine ammonia lyase and/or a tyrosine ammonia lyase is known in the art. Use of an enzyme having PAL/TAL activity in the present methods is exemplified by recombinant expression of the *Rhodotorula glutinis* (also referred to herein as *Rhodosporidium toruloides*) PAL (SEQ ID NOs: 2 and 3) in an oleaginous yeast. Other PAL/TAL genes are publicly available and known in the art (for example, see Table 1). One of skill in the art can select and recombinantly express one or more genes encoding enzyme(s) having PAL/TAL activity using the present methods.

Production of p-Coumaroyl CoA from pHCA

The pHCA produced by the recombinant host cell is converted into p-coumaroyl CoA by expressing an enzyme having coumaroyl CoA ligase activity. The coumaroyl CoA ligase can be endogenous to the host cell or can be recombinantly expressed within the host cell to increase p-coumaroyl CoA production. Microbial expression of plant and/or bacterial coumaroyl CoA ligases has previously been reported. The coumaroyl CoA ligase presently exemplified was isolated from *Streptomyces coelicolor*(SEQ ID NOs: 5 and 6). However, one of skill in the art can select and recombinantly expression any of the publicly available coumaroyl CoA ligases (see for example, Table 1 for a non-limited list). In one aspect, the coumaroyl CoA ligase is chosen based on its ability to convert pHCA into p-coumaroyl CoA. In another aspect, a plurality of coumaroyl CoA ligases are coexpressed to increase the production of resveratrol and/or resveratrol glucoside. In yet another aspect, the coumaroyl CoA ligase activity is derived from *Streptomyces coelicolor* or Acinectobactersp. ADP1.

Production of Malonyl COA

Resveratrol synthase (stilbene synthase) catalyzes the formation of resveratrol by combining 3 molecules of malonyl CoA with 1 molecule coumaroyl CoA. In one aspect, the recombinant host cell endogenously produces suitable amounts of malonyl CoA (for example, oleaginous microorganisms, presently exemplified by an oleaginous yeast). In another aspect, the host cell is engineered to produce increased amounts of malonyl CoA by recombinantly expressing acetyl CoA carboxylase (Davis et al., *J. Biol. Chem.*, 275:28593-28598 (2000)).). Acetyl CoA carboxylase catalyzes the production of malonyl CoA from acetyl CoA. Acetyl CoA carboxylases are known in the art (Table 1; Davis et al., supra).

In yet another aspect, the host cell is capable of high flux biosynthesis of fatty acids. The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate (Smith, S., *FASEB J.*, 8(15):1248-59 (1994)). Since malonyl CoA is used as precursor for fatty acid biosynthesis, organisms capable of producing significant amounts of fatty acids (oleaginous microorganisms) have the capability to produce significant amounts of malonyl CoA. In yet a further aspect, the host cell is an oleaginous yeast, capable of producing suitable amounts of malonyl CoA (i.e., an organism capable of high flux malonyl CoA production). In another aspect, the oleaginous yeast is a *Yarrow* sp. In a further aspect, the oleaginous yeast is *Yarrowia lipolytica*.

In another embodiment, the recombinant host cell is engineered to recombinantly express an enzyme having malonyl CoA synthetase activity (E.C. 6.2.1.-). Malonyl CoA synthetases catalyzes the synthesis of malonyl CoA from malonate and CoA (Kim and Yang, Biochem. J. 297:327-333 (1994)). Genes encoding enzymes having malonyl CoA synthetase activity are known in the art. Recombinant expression of malonyl CoA synthetases has been reported (An, J. H., and Kim, Y. S., *Eur. J. Biochem.* 257:395-402 (1998)). In one embodiment, the recombinant host cell recombinantly expresses at least one malonyl CoA synthetase in order to produce suitable amounts of malonyl CoA when grown on an inexpensive carbon source (i.e., the cell produces malonate and CoA). In another embodiment, malonic acid or malonate is supplemented to the fermentation medium to increase resveratrol production.

Uptake of exogenous supplied malonic acid/malonate may be improved by coexpressing at least one nucleic acid molecule encoding an enzyme having dicarboxylate carrier protein activity. Dicarboxylate carrier proteins are membrane bound proteins that facilitate cellular update of dicarboyxlates. Interestingly, malonyl CoA biosynthesis operons have been reported to contain coding regions for both malonyl CoA synthetase (matB) and a dicarboxylate carrier protein (malonate transporter; matC). Recombinant expression of matB and matC genes has been reported (An, J. H., and Kim, Y. S., supra). In one embodiment, host cells grown in the presence of endogenously supplemented malonate/malonic acid recombinantly express at least one nucleic acid molecule encoding a protein having dicarboxylate carrier protein (malonic acid transporter) activity.

In one embodiment, the recombinant host cell engineered for resveratrol production expresses at least one nucleic acid molecule encoding an enzyme having malonyl CoA synthetase activity and at least one nucleic acid molecule encoding a dicarboxylate carrier protein.

Hydrolysis of Resveratrol Glucoside to Free Resveratrol

The recombinant host cell is engineered to produce resveratrol in significant amounts. In one aspect, the host cell endogenously glycosylates the resveratrol to produce resveratrol glucoside (piceid). The glucose moieties (one or more) attached to the resveratrol glucoside can hydrolyzed to produce free resveratrol (i.e., the aglycone). In one aspect, the glucose moieties are removed from the piceid using a non-enzymatic process such as acid or base hydrolysis (Jencks, William, P., in *Catalysis in Chemistry and Enzymology*, Dover Publications, New York, 1987). In another aspect, the recombinantly produced glycoside is treated with a α-glucosidase (E.C. 3.2.1.21) to release the sugar moieties bound to resveratrol (Example 8). In a further aspect, the gene(s) encoding the endogenous glucosyltransferase(s) is/are disrupted to block the production of the resveratrol glycoside (assuming this is not detrimental to the growth characteristics and/or viability of the host cell). In yet another aspect, a β-glucosidase is recombinantly expressed in the host cell to increase production of the aglycone.

In one aspect, the resveratrol and/or resveratrol glycoside is accumulated within the recombinant host cell. In this instance, the resveratrol and/or resveratrol glycoside can be purified from the recombinant host cells. In a further aspect, the recombinant host cell can be further modified so that the resveratrol (or resveratrol glycoside) produced is secreted from the host cell into the fermentation medium where it can be purified in batch or continuously removed from the fermentation medium.

In yet another aspect, the resveratrol glycoside produced by the recombinant host cell is the desired end product (i.e., for use in personal care products). Resveratrol glycoside may be the produced using the present methods by simply omitting the final hydrolysis step used to produce the aglycone.

Genes Useful for Resveratrol Biosynthesis

The key enzymatic activities used in the present invention are encoded by a number of genes known in the art. The principal enzymes used in the conversion of L-phenylalanine and/or L-tyrosine into resveratrol are phenylalanine/tyrosine ammonia lyases (PAL/TAL), cinnamate 4-hydroxylase (when converting phenylalanine to cinnamate using PAL activity), coumaroyl CoA ligase, and resveratrol synthase (FIG. 1). Additional enzymes useful for the production of resveratrol in the transformed microorganisms may also include acetyl CoA carboxylase (carboxylates acetyl CoA to make malonyl CoA), phenylalanine hydroxylase (used to convert phenylalanine to tyrosine), malonyl CoA synthetase (catalyzes formation of malonyl CoA from malonate and CoA), and β-glucosidase (used to remove sugar moieties from resveratrol glycoside) (FIG. 1). In another aspect, the genes useful to produce resveratrol and/or resveratrol glycoside by the present methods are expressed in multiple copies, optionally having divergent amino acid and/or nucleic acid sequences to create a more genetically stable production host (i.e., reduce or eliminate probability of homologous recombination events). In yet another aspect, the one or more of the genes used to produce resveratrol and/or resveratrol glucoside are chromosomally expressed. In another aspect, one or more of the genes used to produced resveratrol and/or resveratrol glucoside are expressed extrachromosomally (i.e., on an expression vector).

The current methods are exemplified using genes isolated from specific sources. However, one of skill in the art recognizes that homologs for each of the exemplified genes are known in the art as illustrated by the non-limited list provided in Table 1.

TABLE 1

Examples of Alternative Sources for Genes Useful for Recombinant Production of Resveratrol

| Gene | GenBank ® Accession No., Source Organism | SEQ ID NO.: |
|---|---|---|
| pal, tal (phenylalanine ammonia lyases and/or tyrosine ammonia lyases) | X13094, *Rhodotorula mucilaginosa* | 66 |
| | AAJ10143, *Amanita muscaria* | 67 |
| | XM397693, AF306551, *Ustilago maydis* | 68 |
| | AY079363, *Arabidopsis thaliana* | 69 |
| | AF237955, *Rubus idaeus* | 70 |
| | X58180, *Medicago sativa* | 71 |
| | AF401636, *Rehmannia glutinosa* | 72 |
| | AF299330, *Lactuca savita* | 73 |
| | P14913, *Petroselinium crispum* | 74 |
| | AF036948, *Prunus avium* | 75 |
| | D83075, *Lithospernum erythrorhizon* | 76 |
| | U43338, *Citrus limon* | 77 |
| | AAP01719, *Rhodotorula glutinis* from U.S. Pat. No. 6,521,748 | 78 |

TABLE 1-continued

Examples of Alternative Sources for Genes Useful for Recombinant Production of Resveratrol

| Gene | GenBank ® Accession No., Source Organism | SEQ ID NO.: |
|---|---|---|
| | ZP_00005404, *Rhodobacter sphaeroides* | 79 |
| | AR722988, *Trichosporon cutaneum* from U.S. Pat. No. 6,951,751 | 80 |
| Coumaroyl CoA ligase (4CL) | CAB95894, AL939119, for *Streptomyces coelicolor* | 81 |
| | AY541033, *Allium cepa* | 82 |
| | AP005036, *Streptomyces avermitilis* | 83 |
| | AF041049, *Populus tremuloides* | |
| | XM_482683, *Oryza sativa* | 84 |
| | AF435968, *Amorpha fruticosa* | 85 |
| | AY043495, *Populus tomentosa* | 86 |
| | D43773, *Nicotiana tabacum* | 87 |
| | U12013, *Pinus taeda* | 88 |
| | AF279267, *Glycine max* | 89 |
| | NM_113019, *Arabidopsis thaliana* | 90 |
| | AY376731, *Arabidopsis thaliana* | 91 |
| | AF239687, *Rubus idaeus* | 92 |
| | D49367, *Lithospermum erythrorhizon* | 93 |
| | | 94 |
| | AY566301, *Zea mays* | 95 |
| Resveratrol Synthase (RS) (Stilbene synthase) | S63225, *Vitis* sp. | 96 |
| | AF274281, *Vitis vinifera* | 97 |
| | X76892.1, *Vitis vinifera* | 98 |
| | AB027606, *Arachis hypogaea* | 99 |
| | AY094616.1, *Cissus rhombifolia* | 100 |
| | AY094615.1, *Parthenocissus henryana* | 101 |
| | AY094617.1, *Parthenocissus quinquefolia* | 102 |
| | AB046373.1, *Vitis riparia* | 103 |
| | AB046374.1, *Vitis labrusca* | 104 |
| | AF418566, *Vitis* sp. cv. "Norton" | 105 |
| Cinnamate 4-hydroxylase (C4H) | O81928, AJ007449, *Cicer arietinum* | 106 |
| | O24312, U47293, *Populus tremuloides* | 107 |
| | XP_465542, *Oryza sativa* | 108 |
| | AAT68775, AY641731, *Camellia sinensis* | 109 |
| | P37115, L07634, *Vigna radiata* | 110 |
| | Q04468, Z17369, *Helianthus tuberosus* | 111 |
| | AAT39513, AY621152, *Camptotheca acuminata* | 112 |
| | P92994, U71081, *Arabidopsis thaliana* | 113 |
| | AAN63028, AF548370, *Ruta graveolens* | 114 |
| | Q42797, X92437, *Glycine max* | 115 |
| | AAF66065, AF255013, *Citrus sinensis* | 116 |
| Phenylalanine hydroxylase (PAH) | AAA23115, M55915, *Chromobacterium violaceum* | 117 |
| | AAA25938, M88627, *Pseudomonas aeruginosa* | 118 |
| | CAA76184, Y16353, *Geodia cydonium* | 119 |
| | AAM35066, AE011641, *Xanthomonas axonopodis* | 120 |
| | AAM39475, AE012111, *Xanthomonas campestris* | 121 |
| | BAD55786, AP006618 *Nocardia farcinica* | 122 |
| | NP_001001298, *Gallus gallus* | 123 |
| Acetyl CoA carboxylase | NP_014413, NC_001146, *Saccharomyces cerevisiae* | 124 |
| | M92156, *Saccharomyces cerevisiae* | 125 |
| | XM_455355, *Kluyveromyces lactis* | 126 |
| | XM_457211, *Debaryomyces hansenii* | 127 |
| | XM_501721, *Yarrowia lipolytica* | 128 |
| | Y15996, *Aspergillus nidulans* | 129 |

TABLE 1-continued

Examples of Alternative Sources for Genes Useful
for Recombinant Production of Resveratrol

| Gene | GenBank ® Accession No., Source Organism | SEQ ID NO.: |
|---|---|---|
| | D78169, *Schizosaccharomyces pombe* | 130 |
| | Z46886, *Ustilago maydis* | 131 |
| | J03541, *Gallus gallus* | 132 |
| β-Glucosidase | YP_053668, NC_006055 *Mesoplasma florum* | 133 |
| | AAV32242, AC135927 *Oryza sativa* | 134 |
| | NP_743562, NC_002947 *Pseudomonas putida* | 135 |
| | NP_793101, NC_004578 *Pseudomonas syringae* | 136 |
| | NP_630676, NC_003888 *Streptomyces coelicolor* A3(2) | 137 |
| | NP_420939, NC_002696 *Caulobacter crescentus* | 138 |
| | 2107160A, U13672, *Candida wickerhamii* | 139 |

In one embodiment, the present method comprises at least one nucleic acid molecule encoding an enzyme providing resveratrol synthase activity is selected from the group consisting of:
 (1) a nucleic acid molecule encoding a polypeptide having resveratrol synthase activity, said polypeptide having an amino acid sequence SEQ ID NO: 8;
 (2) a nucleic acid molecule encoding a polypeptide having resveratrol synthase activity, said polypeptide having 95% identity to SEQ ID NO: 8; and
 (3) a nucleic acid molecule that hybridizes with (1) under the following hybridization conditions: 0.1×SSC, 0.1% SDS, 65° C. and washed with 2×SSC, 0.1% SDS, at 65° C.; followed by 0.1×SSC, 0.1% SDS, at 65° C.

In another embodiment, the present method comprises at least one nucleic acid molecule encoding an enzyme providing coumaroyl CoA ligase activity is selected from the group consisting of:
 (1) a nucleic acid molecule encoding a polypeptide having coumaroyl CoA ligase activity, said polypeptide having an amino acid sequence SEQ ID NO: 5;
 (2) a nucleic acid molecule encoding a polypeptide having coumaroyl CoA ligase activity, said polypeptide having 95% identity to SEQ ID NO: 5; and
 (3) a nucleic acid molecule that hybridizes with (1) under the following hybridization conditions: 0.1×SSC, 0.1% SDS, 65° C. and washed with 2×SSC, 0.1% SDS, at 65° C.; followed by 0.1×SSC, 0.1% SDS, at 65° C.

In another embodiment, the present method optionally comprises at least one nucleic acid molecule encoding an enzyme providing phenylalanine/tyrosine ammonia lyase activity is selected from the group consisting of:
 (1) a nucleic acid molecule encoding a polypeptide having phenylalanine/tyrosine ammonia lyase activity, said polypeptide having an amino acid sequence SEQ ID NO: 2;
 (2) a nucleic acid molecule encoding a polypeptide having phenylalanine/tyrosine ammonia lyase activity, said polypeptide having 95% identity to SEQ ID NO: 2; and
 (3) a nucleic acid molecule that hybridizes with (1) under the following hybridization conditions: 0.1×SSC, 0.1% SDS, 65° C. and washed with 2×SSC, 0.1% SDS, at 65° C.; followed by 0.1×SSC, 0.1% SDS, at 65° C.

In another embodiment, the present invention provides a resveratrol-producing and/or resveratrol glucoside-producing recombinant oleaginous microorganism comprising at least one isolated nucleic acid molecule encoding an enzyme having resveratrol synthase activity and at least one isolated nucleic acid molecule encoding an enzyme providing coumaroyl CoA ligase activity and optionally at least one nucleic acid molecule encoding an enzyme having phenylalanine/tyrosine ammonia lyase activity. In a further embodiment, the recombinant oleaginous microorganism further comprises at least one nucleic acid molecule encoding an enzyme having phenylalanine/tyrosine ammonia lyase activity. Preferably, the enzyme having phenylalanine/tyrosine ammonia lyase activity will have a tyrosine ammonia lyase activity to phenylalanine ammonia lyase activity (TAL specific activity: PAL specific activity) of at least 0.1, more preferably at least 1, even more preferably at least 10, and most preferably at least 1000.

In yet another embodiment, an isolated recombinant oleaginous microorganism capable of producing resveratrol or resveratrol glucoside is provided comprising:
 a) at least one nucleic acid molecule encoding an enzyme having resveratrol synthase activity selected from the group consisting of:
  i) a nucleic acid molecule encoding a polypeptide having an amino acid sequence SEQ ID NO: 8;
  ii) a nucleic acid molecule encoding a polypeptide having 95% identity to SEQ ID NO: 8; and
  iii) a nucleic acid molecule that hybridizes with (a)(i) under the following hybridization conditions: 0.1× SSC, 0.1% SDS, 65° C. and washed with 2×SSC, 0.1% SDS, at 65° C.; followed by 0.1×SSC, 0.1% SDS, at 65° C.;
 b) at least one nucleic acid molecule encoding an enzyme having coumaroyl CoA ligase activity selected from the group consisting of:
  i) a nucleic acid molecule encoding a polypeptide having an amino acid sequence SEQ ID NO: 5;
  ii) a nucleic acid molecule encoding a polypeptide having 95% identity to SEQ ID NO: 5; and
  iii) a nucleic acid molecule that hybridizes with (b)(i) under the following hybridization conditions: 0.1× SSC, 0.1% SDS, 65° C. and washed with 2×SSC, 0.1% SDS, at 65° C.; followed by 0.1×SSC, 0.1% SDS, at 65° C.; and
 c) optionally at least one nucleic acid molecule encoding an enzyme having phenylalanine/tyrosine ammonia lyase activity selected from the group consisting of:
  i) a nucleic acid molecule encoding a polypeptide having an amino acid sequence SEQ ID NO: 2;
  ii) a nucleic acid molecule encoding a polypeptide having 95% identity to SEQ ID NO: 2; and
  iii) a nucleic acid molecule that hybridizes with (c)(i) under the following hybridization conditions: 0.1× SSC, 0.1% SDS, 65° C. and washed with 2×SSC, 0.1% SDS, at 65° C.; followed by 0.1×SSC, 0.1% SDS, at 65° C.

In another embodiment, the present invention provides an isolated oleaginous microbial biomass comprising at least 0.03 wt % (dcw) resveratrol and/or resveratrol glucoside for inclusion in an animal feed, a pharmaceutical composition, an antifungal composition, or a dietary supplement.

Phenylalanine Ammonia Lyase (PAL) and Cinnamate 4-hydroxylase (C4H)

Phenylalanine ammonia-lyase (PAL) (EC 4.3.1.5) is widely distributed in plants (Koukol et al., *J. Biol. Chem.*, 236:2692-2698 (1961)), fungi (Bandoni et al., *Phytochemistry*, 7:205-207 (1968)), yeast (Ogata et al., *Agric. Biol. Chem.*, 31:200-206 (1967)), and *Streptomyces* (Emes et al., *Can. J. Biochem.*, 48:613-622 (1970)), but it has not been found in *Escherichia coli* or mammalian cells (Hanson and Havir In *The Enzymes*, 3rd ed.; Boyer, P., Ed.; Academic: New York, 1967; pp 75-167). PAL is the first enzyme of phenylpropanoid metabolism and catalyzes the removal of the (pro-3S)-hydrogen and —$NH_3^+$ from L-phenylalanine to form trans-cinnamic acid. In the presence of a P450 enzyme system (cinnamate 4-hydroxylase activity), trans-cinnamic acid can be converted to para-hydroxycinnamic acid (pHCA), which serves as the common intermediate in plants for production of various secondary metabolites such as lignin and isoflavonoids. In microbes however, trans-cinnamic acid (not pHCA) acts as the precursor for secondary metabolite formation.

Phenylalanine ammonia lyases will, to some extent, also accept tyrosine as a substrate, converting tyrosine directly to p-hydroxycinnamic acid. As such, PAL enzymes (especially those having a PAL/TAL activity ratio of at least 0.1) can alternatively be referred to an phenylalanine/tyrosine ammonia lyases. Preferably, phenylalanine/tyrosine ammonia lyases having significant tyrosine ammonia lyase activity are used in the present methods to converted tyrosine directly to p-hydroxycinnamic acid. In one embodiment, the TAL specific activity of the PAL/TAL enzyme is at least $0.02\ S^{-1}$, preferably at least $0.1\ s^{-1}$, more preferably at least $0.5\ S^{-1}$, even more preferably at least $1\ S^{-1}$, and most preferably at least $3\ S^{-1}$.

Tyrosine Ammonia LVase (TAL) to Convert Tyrosine to pHCA

Another biosynthetic pathway leading to the production of pHCA is based on the use of an enzyme having tyrosine ammonia lyase activity. Instead of the two enzyme reactions used to convert phenylalanine to pHCA, an enzyme tyrosine ammonia lyase activity converts L-tyrosine directly into pHCA. A coumaroyl CoA ligase then converts pHCA into p-coumaroyl CoA. In one aspect, an enzyme classified as a tyrosine ammonia lyase can be recombinantly expressed in the host cell. The classification of tyrosine ammonia lyases and phenylalanine ammonia lyases is primarily determined by the enzyme's activity towards each substrate, where classification is assigned based on the preferred substrate. However, these enzymes normally accept both L-tyrosine and L-phenylalanine as substrates, albeit to varying degrees. As such, an in another embodiment as defined herein, tyrosine ammonia lyases will also be referred to as "phenylalanine/tyrosine ammonia lyases". One exception is bacterial tyrosine ammonia lyases from *Rhodobacter capsulatus* and *Rhodobacter sphaeroides*. These TAL enzymes are specific towards tyrosine, with very low activity towards phenylalanine. But these TAL enzymes have relatively low overall activity, e.g., *Rhodobacter sphaeroides* TAL has a kcat of 0.02 S-1. Kyndt et al. (supra) report the TAL activity for *Rhodobacter capsulatus* is $27\ S^{-1}$, but we were unable to reproduce this data (actually measured activity was $0.02\ S^{-1}$; unpublished results).

Mutating Phenyalanine Ammonia Lyase to Create Tyrosine Ammonia Lyase (TAL)

In nature, genes encoding phenylalanine ammonia-lyase are known to convert phenylalanine to trans-cinnamate which may then be converted to para-hydroxycinnamic acid (pHCA) via a p450/p450 reductase enzyme system (FIG. 1). Phenylalanine ammonia lyases have dual substrate specificity, acting on L-phenylalanine principally, but also having some affinity for L-tyrosine. For example, the PAL enzyme isolated from parsley (Appert et al., *Eur. J. Biochem.*, 225:491 (1994)) and corn ((Havir et al., *Plant Physiol.*, 48:130 (1971)) both demonstrate the ability to use tyrosine as a substrate. Similarly, the PAL enzyme isolated from Rhodosporidium (Hodgins D S, *J. Biol. Chem.*, 246:2977 (1971)) also may use L-tyrosine as a substrate. Such enzymes are referred to herein as "PAL/TAL" enzymes or activities. Where it is desired to create a recombinant organism expressing a wild type gene encoding PAL/TAL activity, genes isolated from maize, wheat, parsley, *Rhizoctonia solani*, *Rhodosporidium*, *Sporobolomyces pararoseus*, and *Rhodosporidium* may be used as discussed in Hanson and Havir, *The Biochemistry of Plants;*

Academic: New York, 1981; Vol. 7, pp 577-625.

It is possible to increase the substrate specificity of the PAL/TAL enzyme via various forms of mutagenesis and protein engineering. In one aspect, a phenylalanine ammonia lyase can be protein engineered to have increased activity towards L-tyrosine as a substrate for the production of pHCA (U.S. Pat. No. 6,521,748; hereby incorporated by reference). A variety of approaches may be used for the mutagenesis of the PAL/TAL enzyme. Suitable approaches for mutagenesis include error-prone PCR (Leung et al., *Techniques*, 1:11-15 (1989) and Zhou et al., *Nucleic Acids Res.*, 19:6052-6052 (1991) and Spee et al., *Nucleic Acids Res.*, 21:777-778 (1993)), in vitro mutagenesis, and in vivo mutagenesis. Protein engineering may be accomplished by the method commonly known as "gene shuffling" (U.S. Pat. Nos. 5,605,793; 5,811,238; 5,830,721; and 5,837,458), by recombinogenic methods as described in U.S. Ser. No. 10/374,366, or by rationale design based on three-dimensional structure and classical protein chemistry.

The process of protein engineering an enzyme classified as a phenylalanine ammonia lyase into an mutant enzyme with increased activity for L-tyrosine as a substrate (hence tyrosine ammonia lyase activity) has previously been reported (U.S. Pat. No. 6,368,837; hereby incorporated by reference).

Phenylalanine Hydroxylase (PAH) to Increase Tyrosine Production

In another aspect, phenylalanine hydroxylase (PAH) activity can be endogenous or introduced into the host cell to increase production of tyrosine (FIG. 1). The PAH enzyme hydroxylates L-phenylalanine to produce L-tyrosine. This enzyme is well known in the art and has been reported in *Proteobacteria* (Zhao et al., In *Proc. Natl. Acad. Sci. USA*, 91:1366 (1994)). For example *Pseudomonas aeruginosa* possesses a multi-gene operon that includes phenylalanine hydroxylase which is homologous with mammalian phenylalanine hydroxylase, tryptophan hydroxylase, and tyrosine hydroxylase (Zhao et al., supra). The enzymatic conversion of L-phenylalanine to L-tyrosine is known in eukaryotes. Human phenylalanine hydroxylase is specifically expressed in the liver to convert L-phenylalanine to L-tyrosine (Wang et al., *J. Biol. Chem.*, 269 (12): 9137-46 (1994)). Although any gene encoding a PAH activity will be useful, and genes isolated from Proteobacteria will be particularly suitable A PAH gene encoding such activity has been isolated from *Chromobacterium violaceum* and recombinantly expressed (U.S. Ser. No. 10/138,970; hereby incorporated by reference).

Coumaroyl CoA Ligase (4CL) for the Synthesis of p-Coumaroyl-CoA from pHCA

Coumaroyl CoA ligases catalyze the conversion of 4-coumaric acid (pHCA) and other substituted cinnamic acids into the corresponding CoA thiol esters. In the present invention, coumaroyl CoA ligase is used to convert pHCA into p-coumaroyl CoA, one of the substrates used by resveratrol synthase to make resveratrol. Coumaroyl CoA ligases are well-known in the art and have been recombinantly expressed in microorganisms (Watts et al., supra; Hwang et al., supra; and Kaneko et al., supra). A non-limited list of additional, publicly available coumaroyl CoA ligases is provided in Table 1.

Resveratrol Synthase (Stilbene Synthase)

Resveratrol synthase, also referred to as stilbene synthase, catalyzes the formation of resveratrol from p-coumaroyl CoA and malonyl CoA. Specifically, resveratrol is formed by three consecutive Claisen condensations of the acetate unit from malonyl CoA with p-coumaroyl CoA, which is succeeded by an aldol reaction that forms the second aromatic ring, cleaves the thioester, and decarboxylates to produce resveratrol.

The present methods were exemplified using the resveratrol synthase isolated from *Vitis* sp. (SEQ ID NOs: 8 and 9). However, resveratrol synthases appear to be highly conserved in both structure and function based on comparisons to publicly available sequences. As such, one of skill in the art would expect that the present method is not limited to the particular resveratrol synthase exemplified in the present examples. A non-limited list of additional, publicly available, resveratrol synthases is provided in Table 1.

Synthesis of Malonyl CoA

Synthesis of resveratrol and/or resveratrol glucoside is dependent upon an available pool of malonyl CoA. In one aspect, the oleaginous host cell produces a suitable amount of malonyl CoA. In another aspect, the selected host cell is genetically modified to increase the amount of available malonyl CoA. In yet a further aspect, the host cell is engineered for increased expression of acetyl CoA carboxylase (Davis et al., supra). A non-limited list of additional, publicly available acetyl CoA carboxylases is provided in Table 1.

Microbial Hosts—Oleaginous Microorganisms

Many species of oleaginous microalgae, oleaginous diatoms, and oleaginous fungi/yeasts have the ability to store lipids (i.e. oils) to >20% of the dry cell weight. In one aspect, suitable oleaginous microorganisms useful for the present methods include oleaginous microalgae, oleaginous diatoms, and oleaginous fungi/yeast. In another aspect, suitable oleaginous microorganisms useful for the present methods include oleaginous fungi. Examples of oleaginous microorganisms include those belonging to the genera *Mortierella, Conidiobolus, Pythium, Phytophathora, Penicillium, Porphyridium, Coidosporium, Mucor, Fusarium, Aspergillus, Rhodotorula, Yarrowia,* and *Entomophthora.* Within the genus *Porphyridium,* of particular interest is *P. cruentum.* Within the genus *Mortierella,* of particular interest are *M. elongata, M. exigua, M. hygrophila, M. ramanniana* var. *angulispora,* and *M. alpina.* Within the genus *Mucor,* of particular interest are *M. circinelloides* and *M. javanicus.* The fungus *Mortierella alpina,* for example, can accumulate oil to more than half it weight, as can the yeast *Yarrowia lipolytica.* For an organism to produce large quantities of oil, the flux through the fatty acid biosynthetic pathway must be substantially higher than non-oleaginous organisms. Thus, these organisms have the ability to produce substantial amounts of malonyl-CoA Since the biosynthesis of resveratrol requires malonyl-CoA, oleaginous microorganisms have a clear advantage over non-oleaginous microorganisms when producing resveratrol, especially if one can genetically engineer the organism such that the production of fatty acid is reduced, redirecting the accumulated malonyl-CoA towards resveratrol biosynthesis.

Oleaginous Yeasts

In one aspect, the production host is an oleaginous yeast.

Oleaginous yeasts are defined as those organisms (and derivatives thereof) that are naturally capable of oil synthesis and accumulation, wherein oil accumulation ranges from at least about 20% of the cellular dry weight. These oleaginous organisms are naturally capable of oil synthesis and accumulation, wherein the oil can comprise greater than about 20% of the cellular dry weight, more preferably greater than 25% of the cellular dry weight, even more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon,* and *Lipomyces.* More specifically, illustrative oil-synthesizing yeasts include: *Rhodosporidium toruloides, Liopmyces starkeyii, L. lipoferus, Candida revkaufi, C. pulcherrima, C. tropicalis, C. utilis, Trichosporon pullans, T. cutaneum, Rhodotorula glutinus, R. graminis,* and *Yarrowia lipolytica* (formerly classified as *Candida lipolytica*).

In one particular aspect, the oleaginous yeast is *Yarrowia lipolytica.* In a further aspect, the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.,* 82(1):43-9 (2002)) are used. In yet a further aspect, the *Yarrowia lipolytica* strains is an ω-3 and/or ω-6 polyunsaturated fatty acid-producing derivative of ATCC #20362, ATCC #8862, ATCC #18944, ATCC #76982 and/or LGAM S(7).

The technology for growing oleaginous yeast with high oil content is well developed (for example see EP 0 005 277B1; Ratledge, C., *Prog. Ind. Microbiol.* 16:119-206 (1982)). In addition, these organisms have been commercially used for a variety of purposes in the past. For example, various strains of *Yarrowia lipolytica* have historically been used for the manufacture and production of: isocitrate lyase (DD259637); lipases (SU 1454852, WO2001083773, DD279267); polyhydroxyalkanoates (WO2001088144); citric acid (RU2096461, RU2090611, DD285372, DD285370, DD275480, DD227448, PL160027); erythritol (EP770683); 2-oxoglutaric acid (DD267999); γ-decalactone (U.S. Pat. No. 6,451,565, FR2734843); γ-dodecalactone (EP578388); and pyruvic acid (JP09252790). Most recently, the natural abilities of oleaginous yeasts have been enhanced by advances in genetic engineering, resulting in organisms capable of producing polyunsaturated fatty acids ("PUFAs"). Specifically, is has demonstrated that *Yarrowia lipolytica* can be engineered for production of ω-3 and ω-6 fatty acids, by introducing and expressing genes encoding the (ω-3/ω-6 biosynthetic pathway (U.S. Ser. Nos. 10/840,579, 10/840,478, 10/840,579, 10/840,325, 10/869,630, 10/882,760, 10/985,109, 10/985, 691, 10/987,548, 11/024,545, 11/024,544, 11/166,993, 11/183,664, 11/185,301, 11/190,750, 11/198,975, 11/225, 354, 11/251,466, 11/254,173, 11/253,882, 11/264,784, 11/264,737, and 11/265,761; each hereby incorporated by reference).

Recombinant Microbial Expression

Microbial expression systems and expression vectors containing regulatory sequences that direct high level expression of foreign proteins are well known to those skilled in the art. Any of these could be used to construct chimeric genes for production of resveratrol and/or resveratrol glucoside. These chimeric genes could then be introduced into appropriate microorganisms via transformation to allow for expression of high level of the enzymes.

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the relevant genes in the desired host cell are numerous and familiar to those skilled in the art. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. Virtually any promoter capable of driving these genes is suitable for the present invention including, but not limited to FBAIN, FBAINm, EXP, FBA1, GPAT, CYC1, HIS3, GAL1, GAL10, ADH1, PGK, PHO5, GAPDH, ADCI, TRP1, URA3, LEU2, ENO, TPI; AOXI (particularly useful for expression in *Pichia*); and lac, trp, $IP_L$, $IPR_R$, T7, tac, and trc (particularly useful for expression in *Escherichia coli*).

In another aspect, when the host cell is yeast, transcriptional and translational regions functional in yeast cells are provided, particularly from the host species (e.g., see U.S. Ser. No. 11/265,761 and WO 2004/101757 for preferred transcriptional initiation regulatory regions for use in *Yarrowia lipolytica*). The transcriptional initiation regulatory regions can be obtained, for example, from: 1.) genes in the glycolytic pathway, such as alcohol dehydrogenase, glyceraldehyde-3-phosphate-dehydrogenase (U.S. Ser. No. 10/869,630, hereby incorporated by reference), glyceraldehyde-3-phosphate O-acyltransferase (U.S. Ser. No. 11/225,354;hereby incorporated by reference), phosphoglycerate mutase (U.S. Ser. No. 10/869,630), fructose-bisphosphate aldolase (U.S. Ser. No. 10/987,548, hereby incorporated by reference), phosphoglucose-isomerase, phosphoglycerate kinase, etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, as demonstrated in *Yarrowia lipolytica*, one can determine the consensus translation initiation sequence in the host and engineer this sequence into heterologous genes for their optimal expression in the host of interest.

Termination control regions may also be derived from various genes native to the preferred hosts. Optionally, a termination site may be unnecessary, however, it is most preferred if included. The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. In one embodiment, the terminator is the terminator is selected from the group consisting of LIP2, PEX20, and XPR2.

Suitable Coding Regions of Interest

Coding regions of interest to be expressed in the recombinant yeast host may be either endogenous to the host or heterologous and must be compatible with the host organism. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides.

The coding regions of the present invention are those encoding proteins useful for the production of resveratrol and/or resveratrol glucoside. The coding regions of interest may be optionally codon-optimized using the preferred codon usage of the host cell selected. The present methods are exemplified using specific genes as described by the accompanying sequence listing. However, many of the genes used to recombinantly produce resveratrol and/or resveratrol glucoside are available from alternative sources. For example, a non-limited list of alternative, publicly available genes of the present invention are provided in Table 1. One of skill in the art can operably link a suitable coding region of interest to suitable regulatory sequences. In a further aspect, one or more of the genes used to recombinantly produce resveratrol can be optionally codon optimized using the preferred codon usage of the host cell selected. In yet a further aspect, the genes selected for recombinant expression in *Yarrowia lipolytica* can be optionally codon optimized using the preferred codon usage described in Table 2.

Components of Vectors/DNA Cassettes

Vectors or DNA cassettes useful for the transformation of suitable host cells are well known in the art. The specific choice of sequences present in the construct is dependent upon the desired expression products, the nature of the host cell, and the proposed means of separating transformed cells versus non-transformed cells. Typically, however, the vector or cassette contains sequences directing transcription and translation of the relevant gene(s), a selectable marker, and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

As one of skill in the art is aware, merely inserting a chimeric gene into a cloning vector does not ensure that it will be successfully expressed at the level needed. In response to needs for high expression rates, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention as means to further optimize expression of a chimeric gene.

Transformation of Yeast Cells

Once an appropriate chimeric gene has been constructed that is suitable for expression in a yeast cell, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination with the host locus (Example 8). Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising a coding region of interest may be introduced into a host cell by any standard technique. These techniques include transformation (e.g., lithium acetate transformation [Guthrie, C., *Methods in Enzymology*, 194:186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. No. 4,880,741, U.S. Pat. No. 5,071,764, and Chen, D. C. et al. (*Appl Microbiol Biotechnol.*, 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct.

Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Preferred for use herein are resistance to kanamycin, hygromycin and the aminoglycoside G418, as well as ability to grow on media lacking uracil or leucine.

Industrial Production Using Transformed Oleaginous Microorganisms Expressing Suitable Coding Regions of Interest In general, media conditions which may be optimized for high-level expression of a particular coding region of interest include the type and amount of carbon source, the type and amount of nitrogen source, the carbon-to-nitrogen ratio, the oxygen level, growth temperature, pH, length of the biomass production phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source for the production of resveratrol and/or resveratrol glucoside. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate, carbon-containing amines) for which metabolic conversion into key biochemical intermediates has been demonstrated. Hence, it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins, and other components known to those skilled in the art suitable for the growth of the microorganism.

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Host cells comprising a suitable coding region of interest operably linked to the promoters of the present invention may be cultured using methods known in the art. For example, the cell may be cultivated by shake flask cultivation, small-scale or large-scale fermentation in laboratory or industrial fermentors performed in a suitable medium and under conditions allowing expression of the coding region of interest.

Where commercial production of resveratrol and/or resveratrol glucoside is desired a variety of fermentation methodologies may be applied. For example, large-scale production of a specific gene product over-expressed from a recombinant host may be produced by a batch, fed-batch or continuous fermentation process.

A batch fermentation process is a closed system wherein the media composition is fixed at the beginning of the process and not subject to further additions beyond those required for maintenance of pH and oxygen level during the process. Thus, at the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high growth log phase and finally to a stationary phase, wherein the growth rate is diminished or halted. Left untreated, cells in the stationary phase will eventually die. A variation of the standard batch process is the fed-batch process, wherein the source is continually added to the fermentor over the course of the fermentation process. A fed-batch process is also suitable in the present invention. Fed-batch processes are useful when catabolite repression is apt to inhibit the metabolism of the cells or where it is desirable to have limited amounts of source in the media at any one time. Measurement of the source concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates Sunderland, Mass.; or Deshpande, Mukund V., *Appl. Biochem. Biotechnol.*, 36:227 (1992).

Commercial production of resveratrol and/or resveratrol glucoside may also be accomplished by a continuous fermentation process, wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Methods to Isolate Resveratrol and/or Resveratrol Glucoside

Resveratrol can be extracted from plant or other sources by extraction with organic solvents, such as methanol or methanol/water (80:20) (Adrian et al., *J. Agric. Food Chem.*, 48:6103-6105 (2000)) and methanol:acetone:water:formic acid (40:40:20:0.1) (Rimando et al., *J. Agric. Food Chem.*, 52:4713-4719 (2004)). Dried or freeze-dried extracts are dissolved in methanol, or water, or acetone, before reverse phase HPLC analysis. In one study in which resveratrol glucoside is produced in transgenic alfalfa (Hipskind, J. D., and Paiva, N. L, *Molecular plant-microbe interactions*, 13(5):551-562 (2000)), resveratrol and other metabolites are extracted in 100% acetone, followed by drying completely in nitrogen, and dissolving in 70% methanol in water. The extract is then analyzed by reverse phase HPLC. It is also possible to extract resveratrol using ethanol, dimethylsulfoxide, or other polar solvents. In the study in which resveratrol is produced in the yeast *Saccharomyces cerevisiae* at ~1.4 µg/L (Becker et al., supra), resveratrol was extracted by breaking cells open by glass beads in 100% ice cold methanol and incubating at 37° C. for a few hours. Upon glycosidase treatment, the sample was dried and dissolved in 50% acetonitrile and analyzed by HPLC and mass spectroscopy. It is also possible to extract resveratrol using ethanol, dimethylsulfoxide, acetonitrile or other polar solvents. Resveratrol or resveratrol glucoside can also be detected by $^1$H-NMR.

Uses of Resveratrol and/or Resveratrol Glucoside

The microbially produced resveratrol and/or resveratrol glucoside of the present invention may be used as an antioxidant, anti-inflammatory agent, antimicrobial/antifungal agent, a dietary supplement, or as a pharmacological agent used to treat such conditions as hypercholesterolemia or cancer, to name a few. The resveratrol and/or resveratrol glucoside can be used for formulating cosmetics, cosmeceuticals, nutritional supplements, one or more components of a pharmaceutical composition, compositions applied fresh foods and or agricultural crops to deter and/or inhibit microbial/fungal growth. In another embodiment, the isolated resveratrol-producing and/or resveratrol glucoside-producing microbial biomass is used as an additive in a composition selected from the group consisting of antioxidants, anti-inflammatory agents, antifungal/antimicrobial agents, cosmetics, cosmeceuticals, nutritional/dietary supplements, feed additives, and pharmacological agents, to name a few. The isolated oleaginous biomass may be in the form of whole cells, homogenized cells, or partially-purified cell extracts.

In one aspect of the invention, a composition selected from the group consisting of antioxidants, anti-inflammatory agents, antifungal/antimicrobial agents, cosmetics, cosmeceuticals, nutritional/dietary supplements, feed additives, and pharmacological agents is provided comprising 0.1 to 99 wt %, preferably from 0.1 to 30 wt %, recombinant oleaginous microbial biomass comprising at least 0.01% (dry cell weight) resveratrol and/or resveratrol glucoside.

In another embodiment, resveratrol and/or resveratrol glucoside is used as an antioxidant to stabilize other antioxidants such as carotenoids (including xanthophylls) and polyunsaturated fatty acids, especially ω-3 polyunsaturated fatty acids. In one embodiment, the recombinantly produced stilbene is added to compositions comprising at least one ω-3 PUFA. In a preferred embodiment, the oleaginous microorganism is engineered to produce both resveratrol/resveratrol glucoside and at least one ω-3 polyunsaturated fatty acid whereby either compounds, preferably the ω-3 PUFA, exhibits increased stability to oxidation.

EXAMPLES

The present invention is further defined in the following Examples. It should be understood that these Examples, while indicating preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Unless otherwise specified, all referenced United States patents and patent applications are hereby incorporated by reference.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "sec" means second(s), "min" means minute(s), "h" or "hr" means hour(s), "psi" means pounds per square inch, "nm" means nanometers, "d" means day(s), "μL" means microliter, "mL" means milliliters, "L" means liters, "mm" means millimeters, "nm" means nanometers, "mM" means millimolar, "M" means molar, "mmol" means millimole(s), "pmole" mean micromole", "g" means gram, "μg" means microgram and "ng" means nanogram, "U" means units, "mU" means milliunits, "U mg$^{-1}$" means units per mg, "PEG" mean (poly)ethylene glycol, and "DTT" means dithiothreitol.

Example 1

Determining the Preferred Codon Usage in *Yarrowia lipolytica*

Approximately 100 genes of *Yarrowia lipolytica* were found in the National Center for Biotechnology Information public database. The coding regions of these genes, comprising 121,167 bp, were translated by the EditSEQ program of DNAStar to the corresponding 40,389 amino acids and were tabulated to determine the *Y. lipolytica* codon usage profile shown in Table 2. The column titled "No." refers to the number of times a given codon encodes a particular amino acid in the sample of 40,389 amino acids. The column titled "%" refers to the frequency that a given codon encodes a particular amino acid. Entries shown in bold text represent the codons favored in *Yarrowia lipolytica*.

TABLE 2

Codon Usage in *Yarrowia lipolytica*

| Codon | Amino Acid | No. | % |
|---|---|---|---|
| GCA | Ala (A) | 359 | 11.4 |
| GCC | Ala (A) | 1523 | 48.1 |
| GCG | Ala (A) | 256 | 8.1 |
| GCU | Ala (A) | 1023 | 32.3 |
| AGA | Arg (R) | 263 | 13.2 |
| AGG | Arg (R) | 91 | 4.6 |
| CGA | Arg (R) | 1133 | 56.8 |
| CGC | Arg (R) | 108 | 5.4 |
| CGG | Arg (R) | 209 | 1.0 |
| CGU | Arg (R) | 189 | 9.5 |
| AAC | Ans (N) | 1336 | 84.0 |
| AAU | Ans (N) | 255 | 16.0 |
| GAC | Asp (D) | 1602 | 66.8 |
| GAU | Asp (D) | 795 | 33.2 |
| UGC | Cys (C) | 268 | 53.2 |
| UGU | Cys (C) | 236 | 46.8 |
| CAA | Gln (Q) | 307 | 17.0 |
| CAG | Gln (Q) | 1490 | 83.0 |
| GAA | Glu (E) | 566 | 23.0 |
| GAG | Glu (E) | 1893 | 77.0 |
| GGA | Gly (G) | 856 | 29.7 |
| GGC | Gly (G) | 986 | 34.2 |
| GGG | Gly (G) | 148 | 5.1 |
| GGU | Gly (G) | 893 | 31.0 |
| CAC | His (H) | 618 | 65.5 |
| CAU | His (H) | 326 | 34.5 |
| AUA | Ile (I) | 42 | 2.1 |
| AUC | Ile (I) | 1106 | 53.7 |
| AUU | Ile (I) | 910 | 44.2 |
| CUA | Leu (L) | 166 | 4.7 |
| CUC | Leu (L) | 1029 | 29.1 |
| CUG | Leu (L) | 1379 | 38.9 |
| CUU | Leu (L) | 591 | 16.7 |
| UUA | Leu (L) | 54 | 1.5 |
| UUG | Leu (L) | 323 | 9.1 |
| AAA | Lys (K) | 344 | 14.8 |
| AAG | Lys (K) | 1987 | 85.2 |
| AUG | Met (M) | 1002 | 100 |
| UUC | Phe (F) | 996 | 61.1 |
| UUU | Phe (F) | 621 | 38.9 |
| CCA | Pro (P) | 207 | 9.6 |
| CCC | Pro (P) | 1125 | 52.0 |
| CCG | Pro (P) | 176 | 8.2 |
| CCU | Pro (P) | 655 | 30.2 |
| AGC | Ser (S) | 335 | 11.3 |
| AGU | Ser (S) | 201 | 6.8 |
| UCA | Ser (S) | 221 | 7.5 |
| UCC | Ser (S) | 930 | 31.5 |
| UCG | Ser (S) | 488 | 16.5 |

TABLE 2-continued

Codon Usage in *Yarrowia lipolytica*

| Codon | Amino Acid | No. | % |
|---|---|---|---|
| UCU | Ser (S) | 779 | 26.4 |
| UAA | Term | 38 | 46.9 |
| UAG | Term | 30 | 37.0 |
| UGA | Term | 13 | 16.1 |
| ACA | Thr (T) | 306 | 12.7 |
| ACC | Thr (T) | 1245 | 51.6 |
| ACG | Thr (T) | 269 | 11.1 |
| ACU | Thr (T) | 595 | 24.6 |
| UGG | Trp (W) | 488 | 100 |
| UAC | Tyr (Y) | 988 | 83.2 |
| UAU | Tyr (Y) | 200 | 16.8 |
| GUA | Val (V) | 118 | 4.2 |
| GUC | Val (V) | 1052 | 37.3 |
| GUG | Val (V) | 948 | 33.6 |
| GUU | Val (V) | 703 | 24.9 |

For further optimization of gene expression in *Y. lipolytica*, the consensus sequence around the 'ATG' initiation codon of 79 genes was examined. The 'A' of the ATG translation codon is referenced as the +1 position. Seventy seven percent of the genes analyzed had an "A" in the −3 position, indicating a strong preference for "A" at this position. There was also preference for 'A' or 'C' at the −4, −2 and −1 positions, an 'A', 'C' or 'T' at position +5, and a 'G' or 'C' at position +6 (see FIG. 4 of U.S. Ser. No. 10/840,478; hereby incorporated by reference).

Example 2

Design of A Codon-optimized Phenylalanine Ammonia Lyase Gene

The phenylalanine ammonia lyase gene of *Rhodotorula glutinis* (SEQ ID NO:1-2) is 2151 bp in length (GenBank® Accession No: X12702). As with other phenylalanine ammonia lyases, the enzyme encoded by the phenylalanine ammonia lyase gene also has tyrosine ammonia lyase activity, converting tyrosine into pHCA. A codon-optimized phenylalanine ammonia lyase gene was designed, based on the *R. glutinis* DNA sequence, according to the *Yarrowia* codon usage pattern, the consensus sequence around the ATG translation initiation codon, and the general rules of RNA stability (Guhaniyogi, G. and J. Brewer, *Gene,* 265(1-2):11-23 (2001)). In addition to modifying the translation initiation site, 357 bp of the 2151 bp coding region corresponding to 342 codons were also codon-optimized. The GC content was reduced from 64.8% of the wild type coding region to 56.4% of the codon optimized coding region (SED ID NO: 3) of the phenylalanine ammonia lyase gene.

None of the modifications in the codon-optimized gene changed the amino acid sequence of the encoded protein (SEQ ID NO:2). The codon optimized gene was synthesized and inserted into pUC57 by GenScript Corparation (Piscataway, N.J.) to generate pQZ-PAL.

Example 3

Design of A Codon-optimized Coumaroyl CoA Ligase Gene

The coumaroyl CoA ligase gene of *Streptomyces coelicolor* (SEQ ID NOs:4-5) is 1569 bp in length (GenBank® Accession No: AL939119). A codon-optimized coumaroyl CoA ligase gene was designed, based on the *Streptomyces* DNA sequence, according to the *Yarrowia* codon usage pattern, the consensus sequence around the ATG translation initiation codon, and the general rules of RNA stability (Guhaniyogi, G. and J. Brewer, supra). In addition to modifying the translation initiation site, 278 bp of the 1569 bp coding region corresponding to 260 codons were also codon-optimized. The GC content was reduced from 72.7% of the wild type coding region to 59% of the codon optimized coding region (SED ID NO. 6) of the coumaroyl CoA ligase gene. None of the modifications in the codon-optimized gene changed the amino acid sequence of the encoded protein (SEQ ID NO:5), except the first codon from GTG (SEQ ID NO: 4) to ATG (SEQ ID NO. 6). The codon optimized gene was synthesized and inserted into pUC57 by GenScript Corparation (Piscataway, N.J.) to generate pQZ-4CL.

Example 4

Design of A Codon-optimized Resveratrol Synthase Gene

The resveratrol synthase gene of grape (SEQ ID NOs:7-8) is 1179 bp in length (clone: vlb1c.pk013.c4; E. I. du Pont de Nemours and Company, Inc., Wilmington, Del.). A codon-optimized resveratrol synthase gene was designed, based on the grape DNA sequence, according to the *Yarrowia* codon usage pattern, the consensus sequence around the ATG translation initiation codon, and the general rules of RNA stability (Guhaniyogi, G. and J. Brewer, supra). In addition to modifying the translation initiation site, 229 bp of the 1179 bp coding region corresponding to 203 codons were also codon-optimized. The GC content was increased from 45.4% of the wild type coding region to 56% of the codon optimized coding region (SED ID NO. 9) of the resveratrol synthase gene. None of the modifications in the codon-optimized gene changed the amino acid sequence of the encoded protein (SEQ ID NO:8). The codon optimized gene was synthesized and inserted into pUC57 by GenScript Corparation (Piscataway, N.J.) to generate pQZ-RS

Example 5

Construction of Chimeric Genes for Expression of Resveratrol Biosynthesis Genes in *Yarrowia lipolytica*

In general, codon-optimized genes were either isolated by restriction digestion or amplified by PCR and inserted into appropriate vectors for expression. Each PCR amplification was carried out in a 50 µL total volume, comprising PCR buffer containing: 10 ng template, 10 mM KCl, 10 mM $(NH_4)_2 SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µL of PfuTurbo DNA polymerase (Stratagene, San Diego, Calif.). Amplification was carried out as follows (unless otherwise specified): initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C.

Construction of pZFPAL plasmid containing FBAIN:: PAL::Lip2 chimeric gene The 2154 bp NcoI/NotI fragment of pQZ-PAL which contains the codon-optimized coding region of phenylalanine ammonia lyase gene was inserted into the NcoI/NotI sites of pZF17T to generate PZFPAL (FIG. 2).

pZF17T is a derivative plasmid of pDMW214 (U.S. Ser. No. 10/987,548), which contains a FBAIN promoter::codon optimized coding region of *Saprolegia diclina* Δ17 desaturase (U.S. Ser. No. 10/840,579)::terminator of *Yarrowia* lipase2 gene (GenBank® AJ012632).

The FBAIN promoter (U.S. Ser. No. 10/987,548, SEQ ID NO: 10) includes 826 bp upstream DNA sequence and 169 bp downstream sequence from the putative translation start codon of *Yarrowia* fructose-bisphosphate aldolase gene (fba1). There is a 102 bp intron located between +60 and +163 nucleotides of the 169 bp downstream sequence from the translation start codon (the nucleotide A of the ATG translation codon was designated as +1 position).

Construction of pZTRS Plasmid Containing TEF::RS::XPR2 Chimeric Gene

The 1179 bp NcoI/NotI fragment of PQZ-RS which contains the codon-optimized coding region of resveratrol synthase gene was inserted into the NcoI/NotI sites of pY54-PCB to generate pZTRS (FIG. 2). pY54-PCB is a derivative plasmid of pY54-PC (U.S. Ser. No. 10/840,579). A SbfI site was introduced into pY54-PC to generate pY54-PCB by in vitro mutagenesis using pY331 (SEQ ID NO: 11) and pY332 (SEQ ID NO: 12) as primers. Plasmid pZTRS contains a TEF promoter:RS::XPR2 chimeric gene. The TEF promoter (Muller, S., et al., *Yeast,* 14: 1267-1283 (1998)) was amplified from *Yarrowia lipolytica* genomic DNA by PCR using TEF5' (SEQ ID NO: 13) and TEF3' (SEQ ID NO: 14) primers. The XPR2 transcriptional terminator (SEQ ID NO: 15) was amplified by PCR using pINA532 (a gift from Dr. Claude Gaillardin, Institut National Agronomics, Centre de Biotechnologie Agro-Industrielle, laboratoire de Genetique Moleculaire et Cellularie INRA-CNRS, F-78850 Thiverval-Grignon, France (U.S. Ser. No. 10/840,579)) as template and XPR5' (SEQ ID NO: 16) and XPR3' (SEQ ID NO: 17) as primers.

Construction of PZUF4C Plasmid Containing FBAIN::4CL::Pex20 Chimeric Gene

The 788 bp of the 5' end part of the codon-optimized 4CL gene (SEQ ID NO: 18) was amplified by PCR using pQZ-4CL as template, YL539 (SEQ ID NO: 19) and YL540 (SEQ ID NO: 20) as primers. The 5' end of the Primer YL539 contains a NcoI site, The 5' end of YL540 has an XmnI site. The PCR product was digested with NcoI/XmnI, and the fragment was isolated after separation of agarose gel electrophoresis. Plasmid pQZ4CL was also digested with XmnI/NotI, and the 792 bp XmnI/NotI fragment was isolated after separation by agarose gel electrophoresis. The gel purified NcoI/XmnI digested fragment and the XmnI/NotI digested fragment were then ligated with NcoI/NotI digested pZUF17 to generate pZUF4C. The pZUF4C (FIG. 2) contains a FBAIN promoter:4CL::Pex20 (GenBank® AF054613) chimeric gene (SEQ ID NO: 21).

Construction of pZUF17

*Yarrowia* ura3 gene (GenBank® AJ306421; SEQ ID NO: 54) was amplified using genomic DNA as template and oligouncleotides YL27 (SEQ ID NO: 22) and YL28 (SEQ ID NO: 23) as primers. The PCR product was digested with SalI/PacI, and then inserted into SalI/PacI-digested pY5-9 (U.S. Ser. No. 10/840,579) to generate pY21(Ura). A Bs/WI site was introduced into pY21 (Ura) to generate pY22(Ura) by in vitro mutagenesis using pY21 as template and oligonucleotides YL61 (SEQ ID NO: 24) and YL62 (SEQ ID NO: 25) as primers. The M. alpina Δ5 desaturase gene (SEQ ID NO: 26; U.S. Pat. No. 6,075,183; hereby incorporated by reference) was amplified by PCR using oligonucleotides YL11 and YL12 (SEQ ID NOs: 27, 28) as primers and plasmid pCGR4 (U.S. Pat. No. 6,075,183) as template. The 1357 bp PCR product was digested with NcoI/NotI and ligated to NcoI/NotI-digested pY5-2 to generate pYMA5. The NcoI/NotI fragment of pYMA5 was used to replace the NcoI/NotI fragment of pY22(Ura) to generate pYZT5U. A SwaI was introduced into pYZT5U to generate pYZT5U-S by in vitro mutagenesis using pZYT5U as template and oligonucleotides YL224N/YL225 as primers (SEQ ID NOs. 29 and 30). A ClaI site was introduced into pYZT5U-S to generate pYZT5U-SC by in vitro mutagenesis using pZYT5U-S as template and oligonucleotides YL232/YL233 (SEQ ID NO. 31, 32) as primers.

pYSD17S-C was a derivative plasmid of pYSD17S (U.S. Ser. No. 10/840,579; incorporated herein by reference). A ClaI site was introduced into pYSD17S to generate pYSD17S-C by in vitro mutagenesis using pYSD17S as template and oligonucleotides YL101/YL102(SEQ ID NO. 33, 34) as primers. The GPM promoter was amplified by PCR using pT-GML as template and oligonucleotides YL95 and YL266 (SEQ ID NOs. 35 and 36) as primers. The PCR product was digested with PmeI/NcoI, and then used to replace the PmeI/NcoI fragment of pYSD1 7S-C to generate pZGM17S. The transcriptional terminator of Lip2 gene (GenBank®#: AF054613) was amplified by PCR using *Yarrowia* genomic DNA as template and oligonucleotides YL263 and YL265 (SEQ ID NOs. 37 and 38) as primers. The PCR product was digested with NotI/ClaI, and then used to replace the NotI/ClaI fragment of pZGM17S to generate pZGM17T. pZGM17T-S was produced by elimination of the SphI site in the Lip2 terminator of pZGM17T through in vitro mutagenesis using pZGM17T as template, oligonucleotides YL285 and YL286 (SEQ ID NOs. 39 and 40) as primers. The PmeI/NcoI fragment containing the FBAIN promoter of pDMW214 (U.S. Ser. No. 10/987,548), NcoI/NotI fragment containing the coding region of synthetic Δ17 desaturase gene of pZGM17S and the PmeI/NotI digested pZGM17T-S vector, were three way directionally ligated together to produce pZF17T. The transcriptional terminator of Pex20 gene (SEQ ID NO: 53) was PCR amplified using *Yarrowia* genomic DNA as template and oligonucleotides YL259 and YL260 (SEQ ID NO. 41, 42) as primers. The PCR product was digested with NotI/BsiWI. The pZUF17 was then produced by three way ligation using MfeI/NotI digested pYZT5U-SC as vector, MfeI/NotI fragment containing FBAIN::D17 of pZF17T and the NotI/BsiWI fragment containing Pex20 terminator (GenBank® AF054613).

Example 6

Construction of Plasmids PZG4PR and pZT4PR

Construction of pZG4PR

The *Yarrowia* GPAT promoter (SEQ ID NO: 43) was PCR amplified using pYGPAT-GUS (U.S. Ser. No. 11/225,354) as template, and oligonucleotides YL497 and YL498 (SEQ ID NOs. 44 and 45) as primers. The PCR product was digested with SwaI/NcoI. The SwaI/NcoI fragment containing the GPAT promoter, the NcoI/NotI fragment of pZUF4C, and the SwaI/NotI-digested pKO2UFkF2 were directionally ligated together to produce pKO2UGP4C. The PmeI/ClaI fragment of pZFPAL was used to replace the PmeI/ClaI fragment of pKO2UGP4C to generate pZG4FP. The ClaI/PacI fragment of pZTRS was used to replace the ClaI/PacI fragment of pZG4FP to produce pZG4PR (SEQ ID NO: 55; FIG. 3).

Construction of pZT4PR

A PmeI site was introduced into pYSD17S-C to generate pYSD17S-CP by in vitro mutagenesis using oligonucleotides YL103 and YL104 (SEQ ID NOs. 46 and 47) as primers. The PmeI/NcoI fragment of pYSD17S-CP, the NcoI/NotI fragment of pZUF4C, and the SwaI/NotI-digested pKO2UFkF2 (FIG. 4) were directionally ligated together to produce pKO2UT4C. Plasmid pKO2UFkF2 (SEQ ID NO. 48) contained the following components as described in Table 3:

TABLE 3

Description of Plasmid pKO2UFkF2

| Restriction Enzyme Sites And Nucleotides Within SEQ ID NO: 48 pKO2UF2PE | Description Of Fragment And Chimeric Gene Components |
|---|---|
| AscI/BsiWI (92459-1722) | 730 bp 5' part of *Yarrowia* Δ12 desaturase gene (SEQ ID NO: 49) |
| SalI/SphI (5742-5167) | 556 bp 3' part of *Yarrowia* Δ12 desaturase gene (SEQ ID NO: 50) |
| SwaI/BsiWI/ (7638-1722) | FBAINm::*F. moniliforme* Δ12DS::Pex20, comprising: FBAINm promoter (SEQ ID NO: 51) *F moniliforme*.b12 DS: *Fusarium moniliforme* Δ12 desaturase gene (SEQ ID NO: 52) Pex20: Pex20 terminator sequence (SEQ ID NO. 53) of *Yarrowia* Pex20 gene (GenBank® AF054613) |
| SalI/PacI (5742-7240) | *Yarrowia* Ura3 gene (GenBank® AJ306421; SEQ ID NO. 54) |

The PmeI/ClaI fragment of pZFPAL was used to replace the PmeI/ClaI fragment of pKO2UT4C to generate pZT4FP. The ClaI/PacI fragment of pZTRS was used to replace the ClaI/PacI fragment of pZT4FP to produce pZT4PR (SEQ ID NO: 56; FIG. 4).

Example 7

Construction of Plasmids Containing Strong Promoters and Suitable for the Coordinate Expression of Multiple Resveratrol Biosynthesis Pathway Genes in *Yarrowia lipolytica*

Construction of pZUF-MOD-1 pZUF-MOD-1 (SEQ ID NO: 57; FIG. 5) was prepared as follows. First, primers pzuf-mod1 (5'-GATCCCATGGATCCAGGCCTGTTMCGG-3'; SEQ ID NO: 58) and pzuf-mod2 (5'-GATCGCGGCCGCAGACATGATAAGATACATTG-3'; SEQ ID NO: 59) were used to amplify a 253 bp DNA fragment containing multiple cloning sites (MCS, SEQ ID NO: 60) using pDNR-LIB (ClonTech, Palo Alto, Calif.) as template. The reaction mixture contained ~50 ng of template DNA in 1 μL, 1 μL of 20 μM stock solution of each primer, 22 μL of water and 25 μL of 2× premix of TaKaRa ExTaq polymerase mix (TaKaRa Bio, Inc., Mountain View, Calif.). The PCR condition was as follows: 94° C. for 1 min, 30 cycles of 94° C. 30 sec, 55° C. 30 sec and 72° C. 30 min, finish with an additional 5 min at 72° C. The amplified fragment was purified with a QIAquick PCR purification kit (Qiagen, Valencia, Calif.). This fragment was digested with NcoI-/NotI, and ligated at room temperature overnight into similarly digested pZUF17 vector (wherein the ligation consisted of 0.5 μg of the digested PCR fragment and 0.3 μg of ~7079 bp digested pZUF17 vector (Example 6) fragment with 2 μL of 10×T4 ligase buffer and 3 units of T4 DNA ligase (Promega, Madison, Wis.) in a total volume of 20 μL. The resulting ligation mixture was used to transform *E. coli* Top10 cells (Invitrogen, Carlsbad, Calif.). Plasmid DNA was purified from 4 resulting colonies, using a Qiagen QIAprep Spin Miniprep kit. The purified plasmids were digested with NcoI and NotI to confirm the presence of the ~250 bp fragment. The resulting plasmid was named "pZUF-MOD-1" (FIG. 5; Table 4).

TABLE 4

Description of Plasmid pZUF-MOD-1

| Restriction Enzyme Sites And Nucleotides Within SEQ ID NO: 57 pZUF-MOD-1 (7323 bp) | Description Of Fragment And Chimeric Gene Components |
|---|---|
| MfeI/NcoI (5798-6769) | 971 bp part of *Y. lipolytica* FBAIN promoter |
| NcoI/NotI (6769-7007) | 239 bp part of the multiple cloning site region (MCS) |
| NotI/BsiWI/ (7007-1) | 316 bp fragment containing terminator region of *Y. lipolytica* PEX20 gene (GenBank® AF054613) |
| SalI/PacI (4213-5705) | *Yarrowia* Ura3 gene (GenBank® AJ306421; SEQ ID NO. 54) |

Construction of pEXP-MOD1

The promoter region of the *Y. lipolytica* gene YALI-CDS5725.1 (EXP promoter; SEQ ID NO: 61), encoding a homolog of the non-classic export protein of *S. cerevisiae*, was cloned by PCR using the following primers;

```
EP-Promoter-F
(5'-GATCCTCGAGGGAGTTTGGCGCCCGTTTTTTC-3';
SEQ ID NO: 62)

EP-Promoter-R
(5'-GATCCCATGGTTGTAGATATGTCTTGTGTGTAAG-3';
SEQ ID NO: 63)
```

PCR reaction was carried out using TaKaRa ExTaq polymerase 2× premix, with *Y. lipolytica* genomic DNA as template (~100 ng). 1 μL each of 20 μM primers was added to a 50 μL PCR reaction mixture. Reaction condition was as follows: 94° C. for 2 min 30 sec followed by 30 cycles of 94° C. 30 sec, 55° C. 30 sec and 72° C. 1 min, and a final extension of 7 min at 72° C. The PCR product was purified using Qiagen PCR purification kit. Purified PCR product was digested with XhoI and NcoI, and ligated with a 6259 bp fragment resulting from a SalI and NcoI digestion of pZUF-MOD-1. This replaced the FBA-IN promoter in pZUF-MOD-1 with the EXP1 promoter. The resulting plasmid was named pEXP-MOD-1 (FIG. 5; Table 5).

TABLE 5

Description of Plasmid pEXP-MOD-1

| Restriction Enzyme Sites And Nucleotides Within SEQ ID NO: 64 pEXP-MOD-1 (7277 bp) | Description Of Fragment And Chimeric Gene Components |
|---|---|
| SalI/NcoI (6260-1) | 1017 bp *Y. lipolytica* EXP promoter |
| NcoI/NotI (1-239) | 238 bp part of the stuffer fragment (MCS) |

TABLE 5-continued

Description of Plasmid pEXP-MOD-1

Restriction Enzyme
Sites And
Nucleotides Within
SEQ ID NO: 64
pEXP-MOD-1 (7277 bp) | Description Of Fragment And Chimeric Gene Components

| | |
|---|---|
| NotI/BsiWI/ (239-556) | 316 bp fragment containing terminator region of *Y. lipolytica* PEX20 gene (GenBank ® AF054613) |
| SalI/PacI (4768-6260) | *Yarrowia* Ura3 gene (GenBank ® AJ306421; SEQ ID NO: 54) |

Construction of pZGN

Plasmid pZG4PR was digested with ClaI and PacI, and a ~12 kb fragment was isolated. Separately, pZG4PR was also digested with NcoI and PacI, and a 1.4 kb fragment containing the resveratrol synthase and the *Y. lipolytica* XPR2 terminator was isolated. Finally, plasmid pEXP-MOD-1 was digested with NcoI and ClaI to obtained a ~860 bp fragment containing the *Y. lipolytica* EXP promoter. The three DNA fragments were ligated together to form plasmid pZGN (FIG. 5), where the TEF promoter in plasmid pZG4PR was replaced with the more powerful EXP promoter of *Y. lipolytica* (SEQ ID NO: 61).

TABLE 6

Description of Plasmid pZGN

Restriction Enzyme
Sites And Nucleotides
Within SEQ ID NO: 66
pZGN (14213 bp) | Description Of Fragment And Chimeric Gene Components

| | |
|---|---|
| ClaI/NcoI (13375-1 complementary strand) | 838 bp fragment containing *Y. lipolytica* EXP promoter |
| NcoI/NotI (12193-13375, complementary strand) | 1182 bp resveratrol synthase (codon optimized) |
| (10487-11980) | *Yarrowia* Ura3 gene (GenBank ® AJ306421) |
| 2500-3494 (complementary strand) | 994 bp region containing the *Y. lipolytica* FBAIN promoter |
| 347-2497 (complementary strand) | 2150 bp Phenylalanine lyase (codon optimized) |
| 3535-4572 | 1037 bp *Y. lipolytica* GPAT promoter |
| 4574-6142 | 1568 bp coumaroyl-CoA ligase (codon optimized) |

Example 8

Integration of DNA Fragment Containing Multiple Resveratrol Biosynthesis Genes into the Genome of *Yarrowia lipolytica*

The plasmid pZGN was cut with BssHII/SphI and then used to transform a Ura⁻ derivative of *Y. lipolytica* ATCC# 20362, "20362U1", according to the method of Chen, D. C. et al. (Appl Microbiol Biotechnol., 48(2):232-235-(1997)).

Briefly, 20362U1 was streaked onto a YPD plate and grown at 30° C. for approximately 18 hr. Several large loopfuls of cells were scraped from the plate and resuspended in 1-mL of transformation buffer containing:

2.25 mL of 50% PEG, average MW 3350;
0.125 mL of 2 M Li acetate, pH 6.0;
0.125 mL of 2M DTT; and
50 μg shared salmon sperm DNA.

About 500 ng of plasmid DNA was incubated in 100 μL of resuspended cells, and maintained at 39° C. for 1 hr with vortex mixing at 15 min intervals. The cells were plated onto minimal media plates lacking uracil and maintained at 30° C. for 2 to 3 days. Individual colonies were patched on to minimal media without uracil. They were then screened for resveratrol production as described in Example 9.

Example 9

Production of Resveratrol from Tyrosine in *Yarrowia lipolytica* Cells Harboring Phenylalanine Ammonia Lyase, Coumaroyl-CoA Ligase and Resveratrol Synthase Three transformants from pZGN transformation of 20362U1 were grown individually in 50 mL of a medium containing 6.7 g/L yeast nitrogen base, 1 g/L proline, 20 g/L glucose, and 2 mM tyrosine at 30° C. for 3 days in the dark. Cells were harvested by centrifugation at 5,000 rpm for 10 min. Pelleted cells were resuspended in 2-mL ice cold methanol, mixed with equal volume of 0.5 mm glass beads, and shaken in a Biospec mini-beadbeater, at the setting of Homogenization, for 2 min. Three milliliters of methanol was added to the cell lysate. The whole mixture was shaken at 37° C. for 2 hr in the dark, followed by centrifugation for 2 min at 14,000 rpm to remove debris. The clarified supernatant was filtered through a 0.2 μM filter (Nylon Spin-X spin filter, CoStar, Corning Life Sciences, Acton, Mass.). The filtrates were concentrated in a Savant DNA 110 Speed Vac for 2 h to near complete dryness, re-dissolved in 250 μL 25 mM citrate-phosphate buffer, pH 5, containing 0.5 mg/mL β-glucosidase (Sigma catalog number G4511, isolated from almonds), and incubated at approximately 37° C. for 1 hr. The reaction mixture was extracted three times with 250 μL of ethyl acetate. The organic layers were combined and concentrated in Savant DNA 110 Speed Vac for 0.5 h to near complete dryness. Finally the sample was re-dissolved in 250 μL 50% acetonitrile and filtered through a 0.2 μM Nylon Spin-X spin filter (CoStar).

The filtered samples were analyzed for the presence of pHCA and resveratrol by HPLC, using an Agilent 1100 system (Agilent Technologies, Palo Alto, Calif.) with a Zorbax SB-$C_{18}$ column, 4.6×150 mm, 3.5 micron. The column was eluted with a gradient of 5% to 80% acetonitrile, in 0.5% TFA (trifluoroacetic acid) for 8 min, followed by 80% acetonitrile, 0.5% TFA for 2 min. Both pHCA and resveratrol are detected at 312 nm, with typical retention time of 5.4 min (pHCA) and 6.0 min (resveratrol). The amount of pHCA and resveratrol in the samples were calculated based on a comparison of peak area with known amounts of pure pHCA and resveratrol. Table 4 showed the levels of pHCA and resveratrol in the 4 cultures tested. Resveratrol was extracted from cell pellets, and the level is represented in the amount of resveratrol detected per liter of *Yarrowia* cells and % dry cell weight.

TABLE 7 p-HCA and Resveratrol Titer in pZGN Transformed *Y. lipolytica* 20362U1 cells.

| Sample | pHCA (mg/L) | Resveratrol (mg/L) | PHCA (% dcw) | Resveratrol (% dcw) |
|---|---|---|---|---|
| pZGN1 | 2.78 | 1.40 | 0.093 | 0.047 |
| pZGN2 | 2.63 | 1.29 | 0.088 | 0.043 |
| pZGN3 | 2.37 | 1.46 | 0.079 | 0.049 |

LC/MS analysis.

The presence of pHCA and resveratrol was further confirmed by Negative Ion Electrospray LCMS, using a Waters LCT Time of Flight mass spectrometer connected to a Waters Alliance 2790 LC system with an Agilent Zorbax SB-C18 column (2.1×150 mm). A gradient from 5% acetonitrile in $H_2O$ to 100% acetonitrile in 30 minutes, at a flow rate of 0.25 mL/minute was used to separate components in the samples. Both solvents contained 0.5% formic acid to sharpen the peaks eluding from the LC column. The mass spectrometer was set to scan from 60 to 800 Daltons in 0.9 seconds with a 0.1 second interscan delay.

Samples of pZGN transformed 20362U1 cells were analyzed as described above. The result of the analysis showed that both resveratrol and pHCA were present (FIG. 6). The presence of resveratrol was indicated by the peak at 10.51 min in the negative ion electrospray mass spectra, which contained a molecular ion of 227 Dalton, the same as resveratrol. The presence of pHCA was indicated by the peak at 7.84 min, with a molecular ion of 163 Dalton, same as pHCA. Thus, both resveratrol, and the intermediate pHCA, were present in the sample.

What is claimed is:

1. A method for the production of resveratrol comprising:
   a) providing an oleaginous microbial host cell comprising:
      1) at least one nucleic acid molecule encoding an enzyme having resveratrol synthase activity;
      2) a source of malonyl CoA and coumaroyl CoA;
   b) growing the oleaginous microbial host of (a) under conditions where malonyl CoA and coumaroyl CoA are reacted to form resveratrol glucoside, wherein the resveratrol glucoside is hydrolyzed to resveratrol; and
   c) optionally recovering the product of step (b).

2. A method according to claim 1 wherein the oleaginous microbial host cell comprises an enzyme having resveratrol glycosylating activity.

3. A method according to claim 1 wherein the oleaginous microbial host cell additionally comprises:
   a) at least one nucleic acid molecule encoding an enzyme having coumaroyl CoA ligase activity; and
   b) a source of p-hydroxycinnamic acid.

4. A method according to claim 3 wherein the oleaginous microbial host cell additionally comprises:
   a) at least one nucleic acid molecule encoding an enzyme having tyrosine ammonium lyase activity; and
   b) a source of tyrosine.

5. A method according to claim 3 wherein the oleaginous microbial host cell additionally comprises:
   a) at least one nucleic acid molecule encoding an enzyme having cinnamate-4- hydroxylase activity; and
   b) a source of cinnamic acid.

6. A method according to claim 5 wherein the oleaginous microbial host cell additionally comprises:
   a) at least one nucleic acid molecule encoding an enzyme having phenylalanine ammonium lyase activity; and
   b) a source of phenylalanine.

7. A method according to claim 1 wherein the oleaginous microbial host cell is selected from the group consisting of oleaginous algae, oleaginous fungi, and oleaginous yeast.

8. A method according to claim 7 wherein the oleaginous microbial host cell is a member of a genera selected from the group consisting of *Mortierella, Conidiobolus, Pythium, Phytophathora, Penicillium, Porphyridium, Coidosporium, Mucor, Fusarium, Aspergillus, Rhodotorula, Entomophthora, Yarrowia, Candida, Rhodosporidium, Cryptococcus, Trichosporon,* and *Lipomyces.*

9. A method according to claim 8 wherein the oleaginous microbial host cell is selected from the group consisting of *Rhodosporidium toruloides, Liopmyces starkeyii, Liopmyces lipoferus, Candida revkaufi, Candida pulcherrima, Candida tropicalis, Candida utilis, Trichosporon pullans, Trichosporon cutaneum, Rhodotorula glutinus, Rhodotorula graminis,* and *Yarrowia lipolytica.*

10. A method according to claim 1 wherein at the least one nucleic acid molecule encoding an enzyme having resveratrol synthase activity is isolated from an organism selected from the group consisting of *Vitis* sp., *Arachis* sp., *Cissus* sp, and *Parthenocissus* sp.

11. A method according to claim 3 wherein at the least one nucleic acid molecule encoding an enzyme having coumaroyl CoA ligase activity is; isolated from an organism selected from the group consisting of *Streptomyces* sp., *Allium* sp., *Populus* sp., *Oryza* sp., *Amorpha* sp., *Nicotiana* sp., *Pinus* sp., *Glycine* sp., *Arabidopsis* sp., *Rubus* sp., *Lithospermum* sp., and *Zea* sp.

12. A method according to claim 4 wherein at the least one nucleic acid molecule encoding an enzyme having tyrosine ammonium lyase activity; is isolated from an organism selected from the group consisting of *Rhodotorula* sp., *Amanita* sp., *Ustilago* sp., *Arabidopsis* sp., *Rubus* sp., *Medi-* cago sp, *Rehmannia* sp., *Lactuca* sp., *Petroselinium* sp., *Prunus* sp., *Lithospemum* sp., *Citrus* sp., *Rhodobacter* sp., and *Trichosporon* sp.

13. A method according to claim 5 wherein at the least one nucleic acid molecule encoding an enzyme having cinnamate-4-hydroxylase activity; is isolated from an organism selected from the group consisting of *Streptomyces* sp., *Allium* sp., *Populus* sp., *Oryza* sp., *Amorpha* sp., *Nicotiana* sp., *Pinus* sp., *Glycine* sp., *Arabidopsis* sp., *Rubus* sp., *Lithospermum* sp., and *Zea* sp.

14. A method according to claim 6 wherein at the least one nucleic acid molecule encoding an enzyme having phenylalanine ammonium lyase activity; is isolated from an organism selected from the group consisting of *Rhodotorula* sp., *Amanita* sp., *Ustilago* sp., *Arabidopsis* sp., *Rubus* sp., *Medicago* sp, *Rehmannia* sp., *Lactuca* sp., *Petroselinium* sp., *Prunus* sp., *Lithospernum* sp., *Citrus* sp., *Rhodobacter* sp., and *Trichosporon* sp.

15. A method according to claim 3 wherein the source of p-hydroxycinnamic acid is endogenous to the host cell.

16. A method according to claim 3 wherein the source of p-hydroxycinnamic acid is exogenous to the host cell.

17. A method according to claim 4 wherein the source of tyrosine is endogenous to the host cell.

18. A method according to claim 4 wherein the source of tyrosine is exogenous to the host cell.

19. A method according to claim 5 wherein the source of cinnamic acid is endogenous to the host cell.

20. A method according to claim 5 wherein the source of cinnamic acid is exogenous to the host cell.

21. A method according to claim 6 wherein the source of phenylalanine is endogenous to the host cell.

22. A method according to claim 6 wherein the source of phenylalanine is exogenous to the host cell.

23. A method according to claim 1 wherein resveratrol is produced at a concentration of at least 0.03 wt %.

24. A method according to claim 1 or 2 wherein resveratrol glucoside is produced at a concentration of at least 0.03 wt %.

25. A composition selected from the group consisting of antioxidants, anti-inflammatory agents, antifungal/antimicrobial agents, cosmetics, cosmeceuticals, nutritional/dietary supplements, feed additives, and pharmacological agents comprising 0.1 to 99 wt % recombinant oleaginous microbial biomass having at least 0.01 % (dry cell weight) resveratrol and/or resveratrol glucoside.

26. A method for the production of resveratrol comprising:
  a) providing an oleaginous microbial host cell that is a member of a genera selected from the group consisting of *Mortierella, Conidiobolus, Pythium, Phytophathora, Penicillium, Porphyridium, Coidosporium, Mucor, Fusarium, Aspergillus, Rhodotorula, Entomophthora, Yarrowia, Candida, Rhodosporidium, Cryptococcus, Trichosporon*, and *Lipomyces*, the oleaginous microbial host cell comprising:
    1) at least one nucleic acid molecule encoding an enzyme having resveratrol synthase activity;
    2) a source of malonyl CoA and coumaroyl CoA;
  b) growing the oleaginous microbial host of (a) under conditions where malonyl CoA and coumaroyl CoA are reacted to form a product selected from the group consisting of resveratrol and resveratrol glucoside; and
  c) optionally recovering the product of step (b).

27. A method according to claim 26 wherein the oleaginous microbial host cell is selected from the group consisting of *Rhodosporidium toruloides, Liopmyces starkeyii, Liopmyces lipoferus, Candida revkaufi, Candida puicherrima, Candida tropicalis, Candida utilis, Trichosporon pullans, Trichosporon cutaneum, Rhodotorula glutinus, Rhodotorula graminis*, and *Yarrowia lipolytica*.

28. A method for the production of resveratrol comprising:
  a) providing an oleaginous microbial host cell comprising:
    1) at least one nucleic acid molecule encoding an enzyme having resveratrol synthase activity;
    2) a source of malonyl CoA and coumaroyl CoA;
    3) at least one nucleic acid molecule encoding an enzyme having phenylalanine ammonium lyase activity, the enzyme having phenylalanine ammonium lyase activity is isolated from an organism selected from the group consisting of *Rhodotorula* sp., *Amanita* sp., *Ustilago* sp., *Arabidopsis* sp., *Rubus* sp., *Medicago* sp, *Rehmannia* sp., *Lactuca* sp., *Petroselinium* sp., *Prunus* sp., *Lithospernum* sp., *Citrus* sp., *Rhodobacter* sp., and *Trichosporon* sp.;
    4) a source of phenylalanine;
  b) growing the oleaginous microbial host of (a) under conditions where malonyl CoA and coumaroyl CoA are reacted to form a product selected from the group consisting of resveratrol and resveratrol glucoside; and
  c) optionally recovering the product of step (b).

29. A method for the production of resveratrol comprising:
  a) providing an oleaginous microbial host cell comprising:
    1) at least one nucleic acid molecule encoding an enzyme having resveratrol synthase activity;
    2) a source of malonyl CoA and coumaroyl CoA;
  b) growing the oleaginous microbial host of (a) under conditions where malonyl CoA and coumaroyl CoA are reacted to form a product selected from the group consisting of resveratrol and resveratrol glucoside, wherein resveratrol or resveratrol glucoside is produced at a concentration of at least 0.03 wt %; and
  c) optionally recovering the product of step (b).

30. A recombinant strain of *Yarrowia lipolytica* comprising at least one nucleic acid molecule encoding an enzyme having resveratrol synthase activity, and optionally at least one nucleic acid molecule encoding an enzyme having an activity selected from the group consisting of: coumaroyl CoA ligase, tyrosine ammonium lyase, cinnamate-4-hydroxylase and phenylalanine ammonium lyase, which produces a product selected from the group consisting of resveratrol and resveratrol glucoside.

* * * * *